United States Patent
Olsen et al.

(10) Patent No.: US 11,987,635 B2
(45) Date of Patent: *May 21, 2024

(54) ANTI-4-1BB ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Ole Olsen, Everett, WA (US); Dong Xia, Redmond, WA (US); David Jellyman, Duvall, WA (US); Brian Kovacevich, Snohomish, WA (US); Bill Brady, Bothell, MA (US); Blair Renshaw, Renton, WA (US); Zeren Gao, Redmond, WA (US); Yi Zhu, Chengdu (CN)

(73) Assignee: BAILI-BIO (CHENGDU) PHARMACEUTICAL CO., LTD., Chengdu (CN)

( * ) Notice: Subject to any disclaimer, the term of this patent is extended or adjusted under 35 U.S.C. 154(b) by 412 days.

This patent is subject to a terminal disclaimer.

(21) Appl. No.: 16/615,119

(22) PCT Filed: Jun. 22, 2018

(86) PCT No.: PCT/US2018/039155
§ 371 (c)(1),
(2) Date: Nov. 19, 2019

(87) PCT Pub. No.: WO2019/005638
PCT Pub. Date: Jan. 3, 2019

(65) Prior Publication Data
US 2021/0188989 A1 Jun. 24, 2021

Related U.S. Application Data

(60) Provisional application No. 62/551,032, filed on Aug. 28, 2017, provisional application No. 62/551,035, filed on Aug. 28, 2017, provisional application No. 62/551,065, filed on Aug. 28, 2017, provisional application No. 62/545,603, filed on Aug. 15, 2017, provisional application No. 62/524,554, filed on Jun. 25, 2017, provisional application No. 62/524,557, filed on Jun. 25, 2017, provisional application No. 62/524,558, filed on Jun. 25, 2017.

(51) Int. Cl.
*C07K 16/28* (2006.01)
*A61K 39/00* (2006.01)
*A61K 39/395* (2006.01)
*A61K 45/06* (2006.01)

(52) U.S. Cl.
CPC ...... *C07K 16/2878* (2013.01); *A61K 39/3955* (2013.01); *A61K 45/06* (2013.01); *C07K 16/2803* (2013.01); *A61K 2039/505* (2013.01); *C07K 2317/24* (2013.01); *C07K 2317/31* (2013.01); *C07K 2317/92* (2013.01)

(58) Field of Classification Search
None
See application file for complete search history.

(56) References Cited

FOREIGN PATENT DOCUMENTS

WO   WO 2016/106158   *   6/2016

* cited by examiner

*Primary Examiner* — Marianne P Allen
(74) *Attorney, Agent, or Firm* — Feng Wan

(57) ABSTRACT

The application provides anti-4-1BB monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

6 Claims, 9 Drawing Sheets

Specification includes a Sequence Listing.

FIGURE 1 Immunization schedule for rabbit cohorts no.1 and 2 with human 41BB or cynomolgus 41BB transiently transfected HEK293 cells.

| Day | Cohort | Antigen | Adjuvant |
|---|---|---|---|
| 0 | 1 | Human 41BB transfected 293 cells | Titermax |
| 7 | 1 | Cynomolgus 41BB transfected 293 cells | Alyhrodgel 2% + CpG 2007 |
| 14 | 1 | Human 41BB transfected 293 cells | Titermax |
| 21 | 1 | Cynomolgus 41BB transfected 293 cells | Alyhrodgel 2% + CpG 2007 |
| 27 | 1 | Serum collection | |
| 28 | 1 | Human 41BB transfected 293 cells | Titermax |
| 37 | 1 | Cynomolgus 41BB transfected 293 cells | Alyhrodgel 2% + CpG 2007 |
| 44 | 1 | Serum collection | |
| 44 | 1 | Human 41BB transfected 293 cells | Titermax |
| 51 | 1 | Cynomolgus 41BB transfected 293 cells | Alyhrodgel 2% + CpG 2007 |
| 58 | 1 | Human 41BB transfected 293 cells | Titermax |
| 62 | 1 | Serum collection | |

| Day | Cohort | Antigen | Adjuvant |
|---|---|---|---|
| 0 | 2 | Human 41BB transfected 293 cells | Complete Freund's |
| 7 | 2 | Cynomolgus 41BB transfected 293 cells | Alyhrodgel 2% + CpG 2007 |
| 14 | 2 | Human 41BB transfected 293 cells | Incomplete Freund's |
| 21 | 2 | Cynomolgus 41BB transfected 293 cells | Alyhrodgel 2% + CpG 2007 |
| 27 | 2 | Serum collection | |
| 28 | 2 | Human 41BB transfected 293 cells | Incomplete Freund's |
| 37 | 2 | Cynomolgus 41BB transfected 293 cells | Alyhrodgel 2% + CpG 2007 |
| 44 | 2 | Serum collection | |
| 44 | 2 | Human 41BB transfected 293 cells | Incomplete Freund's |
| 51 | 2 | Cynomolgus 41BB transfected 293 cells | Alyhrodgel 2% + CpG 2007 |
| 58 | 2 | Human 41BB transfected 293 cells | Titermax |
| 62 | 2 | Serum collection | |

FIGURE 2 41BB-specific rabbit IgG antibodies in B cell culture supernatant enhance activation of anti-CD3 activated human T cells and corresponding binding of chimeric rabbit/human IgG 41BB-specific antibodies rescued from the parental B cell culture wells to recombinant human and cynomolgus 41BB protein.

|  | Original BCC well ID | B cell culture supernatant | | Transfection Supernatant | |
|---|---|---|---|---|---|
|  |  | Proliferation | Gamma Interferon | Octet Binding to recombinant 41BB kdis(1/s) | |
|  |  | RLU | $OD_{450}$ | Human | Cynomolgus |
| 1 | 419D9 | 8.0E+07 | 2.2 | 6.3E-04 | 1.4E-03 |
| 2 | 418H5 | 8.9E+07 | 1.8 | 1.4E-03 | 1.6E-03 |
| 3 | 411H11 | 3.3E+07 | 2.2 | 1.0E-03 | 1.5E-03 |
| 4 | 413F3 | 1.8E+07 | 0.3 | 5.4E-04 | 7.9E-04 |
| 5 | 416G1 | 9.0E+07 | 2.0 | 1.4E-03 | 1.9E-03 |
| 6 | 416H5 | 7.8E+07 | 2.1 | 1.1E-02 | 3.2E-03 |
| 7 | 418E10 | 7.6E+07 | 1.5 | 1.1E-03 | 1.5E-03 |
| 8 | 418E4 | 9.4E+07 | 2.5 | 3.6E-03 | 5.0E-03 |
| 9 | 420H6 | 7.0E+07 | 2.5 | 9.4E-04 | 2.0E-03 |
| 10 | 459F1 | 3.2E+07 | 0.3 | 7.5E-04 | 7.5E-03 |
| 11 | 464C11 | 5.5E+07 | 1.0 | 4.5E-03 | 8.3E-03 |
| 12 | 470B6 | 1.4E+08 | 2.4 | 1.3E-03 | 1.2E-03 |
| 13 | 472E4 | 8.8E+07 | 1.9 | 1.1E-03 | 1.8E-03 |
| 14 | 418E8 | 9.8E+07 | 3.0 | 3.0E-03 | 3.6E-03 |
| 15 | 468C11 | 6.6E+07 | 2.2 | 2.7E-03 | 1.2E-03 |
| 16 | 470H2 | 5.5E+07 | 2.2 | 4.3E-03 | 6.9E-03 |
| 17 | 460C3 | 3.6E+07 | 0.3 | 6.7E-04 | 4.1E-03 |
| 18 | 413G3 | 2.4E+07 | 0.5 | 4.2E-04 | 7.9E-04 |
| 19 | 414A8 | 2.2E+07 | 0.4 | 2.9E-04 | 3.9E-04 |
| 20 | 415E8 | 5.4E+07 | 2.2 | 2.2E-03 | 5.8E-04 |
| 21 | 416G6 | 8.0E+07 | 2.5 | 7.0E-04 | 5.6E-03 |
| 22 | 416H7 | 8.1E+07 | 2.4 | 3.1E-03 | 2.5E-03 |
| 23 | 418H1 | 1.5E+08 | 2.4 | 1.4E-02 | 1.0E-02 |
| 24 | 420A11 | 7.6E+07 | 1.1 | 3.1E-03 | 1.1E-01 |
| 25 | 420G12 | 0.0E+00 | 2.2 | 1.4E-02 | 1.1E-03 |
| 26 | 459E8 | 4.4E+07 | 0.9 | 3.1E-04 | 6.4E-04 |
| 27 | 459H12 | 5.5E+07 | 2.2 | 1.4E-03 | 1.4E-03 |
| 28 | 464B12 | 7.5E+07 | 2.4 | 1.3E-03 | 6.4E-04 |
| 29 | 466G10 | 4.4E+07 | 0.3 | 2.8E-03 | 2.3E-03 |
| 30 | 468E5 | 0.0E+00 | 0.4 | 4.2E-04 | 1.1E-03 |
| 31 | 416F8 | 7.7E+07 | 1.8 | 4.3E-03 | 3.0E-03 |
| 32 | 420H5 | 8.1E+07 | 1.7 | 1.3E-03 | 2.3E-03 |
| 33 | 466F6 | 8.6E+07 | 1.7 | 2.1E-03 | 2.6E-03 |
| 34 | 470C6 | 8.1E+07 | 2.3 | 1.0E-03 | 1.4E-03 |

FIGURE 3 Chimeric rabbit/human IgG antibodies specific for 41BB enhance T cell activation, proliferation, and gamma interferon secretion.

First agonist assay

Proliferation (Fold change over background)

Concentration of 41BB-specific chimeric antibody [ng/ml]

| Original BCC well ID | Gamma-interferon EC$_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 18.9 | 2.9 | 2.4 | 2.2 | 2.7 | 2.5 | 1.8 | 1.4 | 1.5 | 1.4 | 1.3 | 1.0 |
| 413F3 | 11.3 | 1.4 | 1.4 | 1.3 | 1.2 | 1.5 | 1.3 | 1.1 | 1.1 | 1.0 | 1.1 | 1.0 |
| 413G3 | 23.7 | 1.3 | 1.4 | 1.3 | 1.4 | 1.3 | 1.2 | 1.0 | 1.0 | 1.1 | 0.9 | 1.0 |
| 414A8 | 90.3 | 1.1 | 1.5 | 1.2 | 1.4 | 1.4 | 1.2 | 1.2 | 1.1 | 1.2 | 1.1 | 1.0 |
| 415E8 | 10.3 | 1.7 | 1.6 | 1.8 | 1.8 | 1.5 | 1.4 | 1.2 | 1.0 | 1.0 | 1.0 | 1.0 |
| 416F8 | 7.3 | 1.3 | 1.6 | 1.6 | 1.8 | 1.6 | 2.2 | 1.3 | 1.1 | 1.2 | 1.2 | 1.0 |
| 416G1 | 11.9 | 1.3 | 1.6 | 1.1 | 1.5 | 1.6 | 1.0 | 1.0 | 1.1 | 1.1 | 1.0 | 1.0 |
| 416G6 | 7.3 | 1.5 | 1.8 | 1.8 | 1.8 | 1.9 | 1.8 | 1.7 | 1.1 | 1.1 | 1.1 | 1.0 |
| 416H5 | 39.1 | 1.5 | 1.6 | 1.5 | 1.6 | 1.5 | 1.2 | 1.0 | 1.0 | 1.0 | 1.1 | 1.0 |
| 416H7 | 17.1 | 1.9 | 1.9 | 2.3 | 2.6 | 1.9 | 1.7 | 1.2 | 1.3 | 1.2 | 1.2 | 1.0 |
| 418E10 | 20.9 | 1.6 | 1.6 | 1.7 | 1.7 | 1.8 | 1.3 | 1.0 | 0.8 | 1.0 | 1.0 | 1.0 |
| 418E4 | 24.4 | 2.3 | 1.6 | 1.5 | 1.5 | 1.5 | 1.8 | 1.0 | 1.1 | 0.8 | 0.9 | 1.0 |
| 418E8 | 5.6 | 1.7 | 1.5 | 1.5 | 1.5 | 1.6 | 1.6 | 1.5 | 1.3 | 1.2 | 1.0 | 1.0 |
| 418H1 | 28.9 | 1.7 | 1.6 | 1.9 | 1.8 | 1.7 | 1.4 | 1.0 | 1.3 | 1.1 | 1.1 | 1.0 |
| 418H5 | 25.5 | 1.6 | 1.4 | 1.8 | 2.0 | 1.9 | 1.1 | 1.1 | 1.1 | 1.1 | 1.1 | 1.0 |
| 419D9 | 17.6 | 1.1 | 1.6 | 1.7 | 1.8 | 1.8 | 1.3 | 1.0 | 1.1 | 1.1 | 1.1 | 1.0 |
| 420A11 | 23.8 | 1.4 | 1.4 | 1.6 | 1.6 | 1.6 | 1.2 | 0.9 | 0.7 | 0.9 | 0.9 | 1.0 |
| 420G12 | 5.7 | 1.6 | 1.9 | 1.6 | 1.6 | 1.7 | 1.6 | 1.4 | 1.3 | 1.2 | 1.1 | 1.0 |
| 420H5 | 5.2 | 1.6 | 1.9 | 2.1 | 2.2 | 2.2 | 2.2 | 1.7 | 1.4 | 1.5 | 1.3 | 1.0 |
| 420H6 | 17.1 | 1.2 | 1.8 | 2.0 | 2.0 | 2.0 | 1.4 | 1.3 | 1.1 | 1.3 | 1.2 | 1.0 |
| 459E8 | 71.9 | 1.1 | 1.3 | 1.2 | 1.5 | 1.3 | 1.1 | 1.1 | 1.1 | 1.1 | 1.1 | 1.0 |
| 459F1 | 23.7 | 1.6 | 1.9 | 2.2 | 2.3 | 2.3 | 1.5 | 1.5 | 1.4 | 1.3 | 1.3 | 1.0 |
| 459H12 | 8.4 | 1.1 | 1.3 | 1.3 | 1.4 | 1.3 | 1.4 | 0.9 | 0.8 | 1.0 | 1.0 | 1.0 |
| 460C3 | 8.8 | 1.4 | 1.7 | 1.9 | 2.6 | 1.7 | 1.6 | 1.4 | 1.1 | 1.0 | 1.2 | 1.0 |
| 464B12 | 18.1 | 1.9 | 1.8 | 2.0 | 1.9 | 1.7 | 1.3 | 1.0 | 1.0 | 1.0 | 1.1 | 1.0 |
| 464C11 | 25.3 | 1.2 | 1.4 | 1.5 | 1.5 | 1.6 | 1.3 | 1.6 | 1.1 | 1.1 | 1.1 | 1.0 |
| 466F6 | 8.8 | 1.7 | 1.7 | 1.8 | 1.9 | 2.1 | 1.5 | 1.3 | 1.1 | 1.2 | 1.0 | 1.0 |
| 466G10 | 11.1 | 2.5 | 2.1 | 2.5 | 2.3 | 1.9 | 2.1 | 1.4 | 1.3 | 1.3 | 1.3 | 1.0 |
| 468C11 | 12.4 | 1.8 | 1.9 | 1.9 | 1.9 | 1.8 | 1.5 | 1.2 | 1.1 | 1.0 | 1.1 | 1.0 |
| 468E5 | 22.7 | 0.9 | 1.3 | 1.2 | 1.4 | 1.5 | 1.2 | 1.4 | 1.1 | 1.1 | 1.2 | 1.0 |
| 470B6 | | | | | | | | | | | | |
| 470C6 | 6.9 | 2.3 | 2.5 | 2.4 | 2.8 | 2.8 | 2.4 | 1.7 | 1.6 | 1.4 | 1.4 | 1.0 |
| 470H2 | 10.5 | 1.4 | 1.6 | 1.7 | 1.7 | 1.9 | 1.6 | 1.5 | 1.1 | 0.9 | 1.1 | 1.0 |
| 472E4 | 14.1 | 1.9 | 1.4 | 1.5 | 1.5 | 1.5 | 1.3 | 0.9 | 1.0 | 0.9 | 1.0 | 1.0 |
| Positive control.1 | 14.1 | 1.9 | 1.9 | 2.1 | 2.7 | 2.7 | 1.7 | 1.3 | 1.1 | 1.0 | 1.1 | 1.0 |

FIGURE 3 (Continued)

Second agonist assay

Proliferation (Fold change over background)

Concentration of 41BB-specific chimeric antibody [ng/ml]

| Original BCC well ID | Gamma-interferon $EC_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 14.6 | 1.1 | 2.0 | 1.7 | 2.1 | 2.1 | 1.5 | 1.2 | 1.0 | 0.9 | 1.0 | 1.0 |
| 413F3 | 44.7 | 0.7 | 0.8 | 0.9 | 1.0 | 0.9 | 0.9 | 0.9 | 0.9 | 0.9 | 1.0 | 1.0 |
| 413G3 | 21.3 | 0.9 | 1.0 | 1.4 | 2.0 | 1.7 | 1.2 | 0.9 | 1.0 | 0.9 | 1.0 | 1.0 |
| 414A8 | 71.3 | 1.1 | 1.3 | 1.4 | 1.3 | 1.1 | 1.1 | 0.8 | 0.8 | 0.8 | 1.0 | 1.0 |
| 415E8 | 17.5 | 0.8 | 1.1 | 1.4 | 1.6 | 1.5 | 1.0 | 0.8 | 0.7 | 0.6 | 0.8 | 1.0 |
| 416F8 | 11.2 | 1.0 | 1.0 | 1.3 | 1.2 | 1.4 | 1.2 | 0.9 | 0.7 | 0.6 | 0.7 | 1.0 |
| 416G1 | 12.8 | 0.9 | 1.3 | 1.4 | 2.3 | 2.3 | 1.6 | 1.1 | 1.0 | 0.8 | 1.0 | 1.0 |
| 416G6 | 13.1 | 0.6 | 1.4 | 1.3 | 2.0 | 1.7 | 1.1 | 0.6 | 0.7 | 0.7 | 0.9 | 1.0 |
| 416H5 | 44.5 | 1.6 | 1.6 | 1.8 | 1.8 | 1.4 | 1.1 | 0.9 | 0.7 | 0.8 | 0.9 | 1.0 |
| 416H7 | 28.0 | 0.9 | 1.5 | 1.6 | 1.5 | 1.6 | 1.0 | 0.7 | 0.8 | 0.7 | 0.9 | 1.0 |
| 418E10 | 20.4 | 2.0 | 2.2 | 2.2 | 2.1 | 2.0 | 1.2 | 1.0 | 0.9 | 0.9 | 0.7 | 1.0 |
| 418E4 | 31.0 | 1.2 | 1.6 | 1.8 | 1.7 | 1.7 | 1.0 | 0.9 | 0.9 | 0.8 | 1.0 | 1.0 |
| 418E8 | 12.8 | 1.2 | 1.8 | 1.6 | 2.2 | 1.9 | 1.4 | 1.0 | 0.9 | 0.8 | 0.9 | 1.0 |
| 418H1 | 25.0 | 0.8 | 1.2 | 1.3 | 1.4 | 1.4 | 1.0 | 0.9 | 0.7 | 0.8 | 0.8 | 1.0 |
| 418H5 | 37.5 | 2.2 | 1.8 | 1.6 | 2.0 | 1.1 | 1.0 | 0.7 | 0.9 | 0.9 | 1.1 | 1.0 |
| 419D9 | 13.0 | 1.5 | 1.4 | 1.5 | 2.0 | 1.8 | 1.2 | 0.7 | 0.9 | 0.7 | 0.8 | 1.0 |
| 420A11 | 25.3 | 2.3 | 1.7 | 1.9 | 1.7 | 1.4 | 1.0 | 0.8 | 0.8 | 0.9 | 0.8 | 1.0 |
| 420G12 | 20.8 | 1.0 | 1.2 | 1.4 | 1.7 | 1.6 | 1.1 | 0.8 | 0.8 | 0.8 | 0.9 | 1.0 |
| 420H5 | 8.9 | 3.2 | 2.6 | 2.3 | 2.4 | 3.0 | 1.9 | 1.2 | 1.0 | 0.9 | 1.0 | 1.0 |
| 420H6 | 14.9 | 1.5 | 1.9 | 1.7 | 2.8 | 1.9 | 1.2 | 1.0 | 0.9 | 0.9 | 1.0 | 1.0 |
| 459E8 | 42.3 | 1.1 | 1.2 | 1.6 | 1.4 | 1.2 | 1.0 | 0.8 | 0.8 | 1.0 | 1.1 | 1.0 |
| 459F1 | 17.4 | 1.1 | 1.7 | 1.9 | 2.4 | 2.1 | 1.6 | 1.0 | 1.1 | 1.2 | 0.8 | 1.0 |
| 459H12 | 19.2 | 1.8 | 1.1 | 1.2 | 1.5 | 1.3 | 1.2 | 0.9 | 0.8 | 1.0 | 0.8 | 1.0 |
| 460C3 | 10.4 | 1.1 | 1.4 | 1.7 | 2.0 | 2.3 | 1.5 | 1.1 | 0.9 | 1.1 | 0.8 | 1.0 |
| 464B12 | 13.1 | 0.8 | 1.3 | 1.2 | 1.9 | 1.7 | 1.3 | 0.9 | 0.8 | 0.9 | 0.6 | 1.0 |
| 464C11 | 40.3 | 1.5 | 1.4 | 1.1 | 1.6 | 1.3 | 1.1 | 1.0 | 0.9 | 0.9 | 0.9 | 1.0 |
| 466F6 | 8.2 | 1.1 | 1.7 | 2.0 | 3.1 | 2.8 | 2.3 | 1.6 | 1.0 | 1.2 | 1.1 | 1.0 |
| 466G10 | 15.8 | 0.8 | 1.1 | 1.1 | 1.4 | 1.5 | 1.2 | 1.0 | 1.0 | 0.9 | 0.9 | 1.0 |
| 468C11 | 15.2 | 0.7 | 1.5 | 1.3 | 2.2 | 2.0 | 1.4 | 0.9 | 0.8 | 0.8 | 0.8 | 1.0 |
| 468E5 | 22.1 | 1.2 | 1.0 | 1.2 | 0.8 | 1.2 | 0.9 | 0.8 | 0.8 | 0.7 | 0.8 | 1.0 |
| 470B6 | 24.1 | 0.7 | 1.5 | 1.6 | 2.1 | 1.5 | 1.3 | 1.0 | 1.0 | 0.9 | 0.8 | 1.0 |
| 470C6 | 7.2 | 1.0 | 1.5 | 1.4 | 2.1 | 3.2 | 2.6 | 1.4 | 1.2 | 1.0 | 1.1 | 1.0 |
| 470H2 | 22.0 | 2.4 | 2.0 | 1.9 | 2.6 | 2.0 | 1.2 | 1.2 | 1.2 | 1.2 | 1.1 | 1.0 |
| 472E4 | 16.4 | 0.7 | 1.1 | 1.2 | 1.4 | 1.4 | 1.1 | 1.0 | 0.8 | 1.0 | 0.8 | 1.0 |
| Positive control.1 | 12.5 | 0.7 | 1.5 | 2.1 | 2.1 | 2.7 | 1.7 | 1.2 | 1.0 | 0.9 | 0.9 | 1.0 |

FIGURE 4 Octet analysis of dissociation rate for humanized 41BB-specific IgG antibodies.

| Antibody ID | Humanized Variant | Binding off-rate kdis(1/s) |
|---|---|---|
| 411H11 | VHv1VLv1 | 1.79E-03 |
| 413F3 | VHv1VLv1 | 2.24E-03 |
| 416F8 | VHv3VLv1 | 6.45E-03 |
| 416G1 | VHv1VLv1 | 1.66E-03 |
| 418E10 | VHv1VLv1 | 9.58E-04 |
| 418E4 | VHv1VLv1 | 2.77E-03 |
| 418H5 | VHv2VLv1 | 2.45E-03 |
| 419D9 | VHv3VLv3 | 2.84E-03 |
| 420H5 | VHv3VLv3 | 1.78E-03 |
| 420H6 | VHv1VLv1 | 1.28E-03 |
| 459F1 | VHv1VLv1 | 1.31E-03 |
| 460C3 | VHv1VLv1 | 7.28E-04 |
| 464C11 | VHv1VLv1 | 7.84E-04 |
| 466F6 | VHv2VLv5 | 2.54E-03 |
| 470B6 | VHv1VLv1 | 9.10E-04 |
| 470C6 | VHv3VLv3 | 1.83E-03 |
| 472E4 | VHv1VLv1 | 2.65E-03 |

FIGURE 5 Humanized 41BB-specific IgG antibodies enhance T cell activation, proliferation, and gamma interferon secretion.

Proliferation (Fold change over background)

Concentration of Humanized 41BB-specific antibody [ng/ml]

| Original BCC well ID | Gamma-interferon $EC_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 5.8 | 0.9 | 1.3 | 1.2 | 1.3 | 1.3 | 1.3 | 1.3 | 0.9 | 1.0 | 0.8 | 1.0 |
| 413F3 | 139.4 | 0.8 | 1.5 | 1.3 | 0.9 | 1.0 | 1.1 | 1.3 | 1.1 | 1.3 | 1.0 | 1.0 |
| 416F8 | 37.5 | 1.1 | 1.4 | 1.7 | 2.1 | 1.4 | 1.6 | 1.2 | 1.6 | 0.8 | 1.2 | 1.0 |
| 416G1 | 36.7 | 1.5 | 1.7 | 2.4 | 2.3 | 1.7 | 1.8 | 1.4 | 1.6 | 1.5 | 1.2 | 1.0 |
| 416H5 | - | 0.5 | 0.7 | 0.6 | 0.7 | 0.7 | 1.1 | 0.9 | 1.3 | 1.1 | 0.9 | 1.0 |
| 418E4 | 12.3 | 1.1 | 1.7 | 1.7 | 1.6 | 2.3 | 1.4 | 1.1 | 1.3 | 1.2 | 1.2 | 1.0 |
| 418E10 | 7.1 | 0.9 | 1.3 | 1.8 | 1.5 | 2.2 | 2.2 | 1.4 | 1.4 | 1.0 | 1.1 | 1.0 |
| 418H5 | 14.5 | 1.2 | 2.0 | 1.5 | 2.1 | 2.2 | 1.4 | 1.3 | 0.9 | 1.2 | 0.7 | 1.0 |
| 419D9 | 13 | 1.0 | 1.1 | 1.4 | 1.5 | 1.9 | 1.3 | 1.0 | 0.9 | 1.1 | 0.8 | 1.0 |
| 420H5 | 50.7 | 1.8 | 1.8 | 1.3 | 1.3 | 1.7 | 1.3 | 1.0 | 1.4 | 1.1 | 1.1 | 1.0 |
| 420H6 | 26 | 0.9 | 1.4 | 1.7 | 1.8 | 1.5 | 1.5 | 1.3 | 0.9 | 1.0 | 1.0 | 1.0 |
| 459F1 | 21.2 | 0.5 | 0.7 | 0.8 | 1.1 | 1.3 | 1.4 | 0.9 | 1.2 | 0.9 | 0.8 | 1.0 |
| 460C3 | 11.5 | 0.7 | 0.9 | 1.2 | 1.4 | 1.8 | 1.6 | 1.2 | 1.6 | 1.4 | 1.1 | 1.0 |
| 464C11 | 8.4 | 1.1 | 1.4 | 1.8 | 2.0 | 2.1 | 1.8 | 1.0 | 1.0 | 1.1 | 0.9 | 1.0 |
| 466F6 | 9.8 | 1.1 | 0.9 | 1.8 | 1.4 | 1.4 | 2.0 | 1.4 | 1.2 | 0.8 | 1.1 | 1.0 |
| 470B6 | 17.8 | 1.1 | 2.2 | 1.4 | 1.3 | 1.8 | 1.8 | 1.2 | 1.1 | 1.0 | 1.0 | 1.0 |
| 470C6 | 5.7 | 1.6 | 2.1 | 2.0 | 2.3 | 2.6 | 2.2 | 2.1 | 1.7 | 1.4 | 1.4 | 1.0 |
| 472E4 | 11.6 | 1.2 | 2.0 | 1.9 | 2.4 | 2.0 | 1.6 | 1.2 | 1.2 | 1.4 | 0.9 | 1.0 |
| Positive control.1 | 4.3 | 1.5 | 1.8 | 1.5 | 1.5 | 1.7 | 1.7 | 1.4 | 1.4 | 1.2 | 1.3 | 1.0 |

FIGURE 6 Serum from rabbits immunized with human or cynomolgus 41BB expressing HEK293's analyzed for 41BB-specific IgG antibody binding to parental CHO or human or cynomolgus 41BB-transfected CHO cells.
FIGURE 6_Panel A
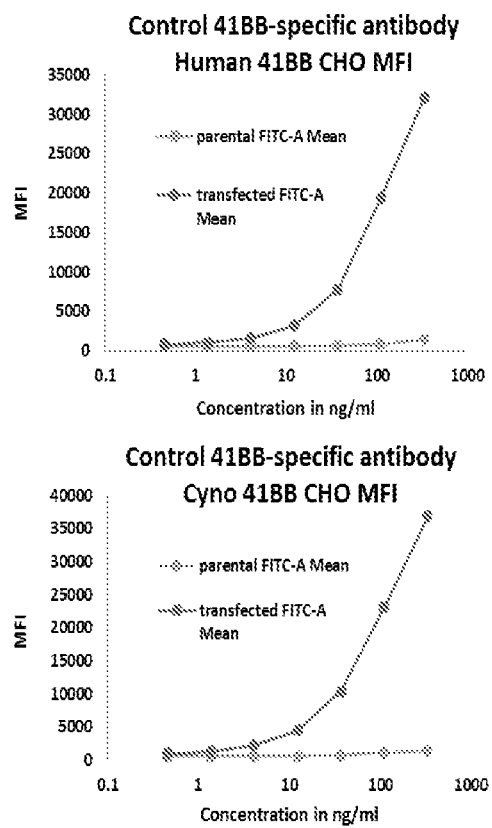

FIGURE 6_Panel B
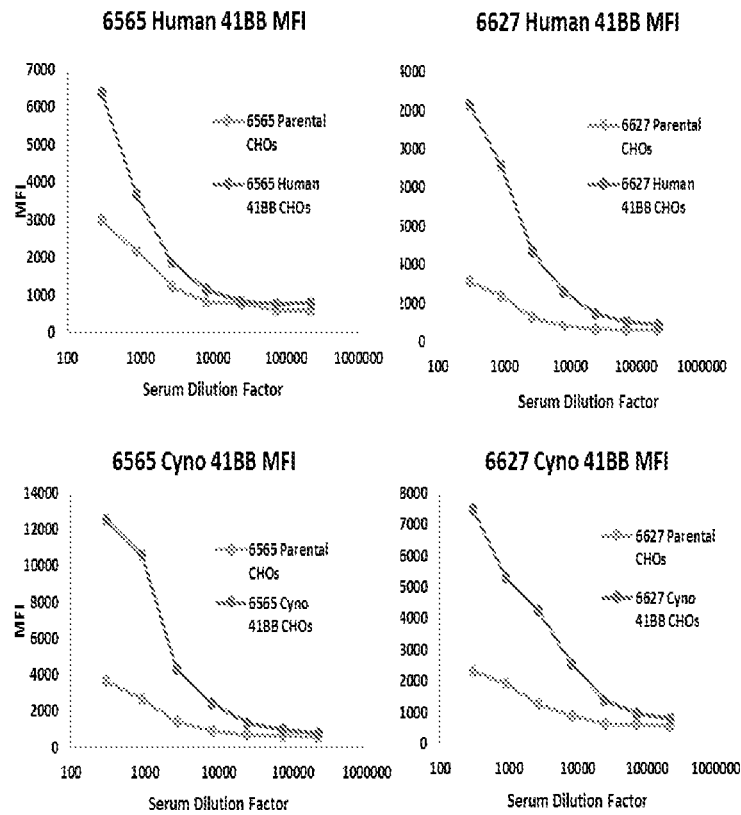
FIGURE6_Panel C
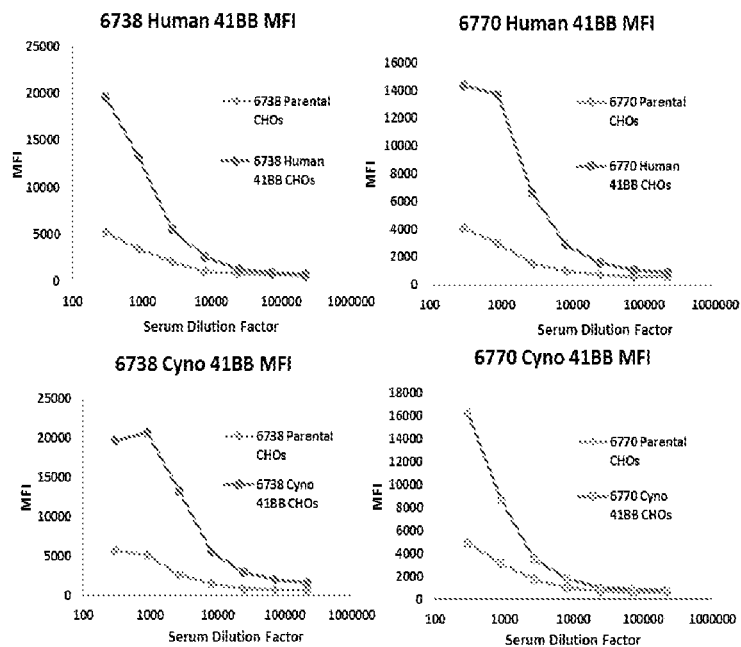

FIGURE 7 Correlation of 41BB-specific IgG antibody in B cell culture supernatant enhancement of Gamma interferon secretion versus proliferation of human T cells.
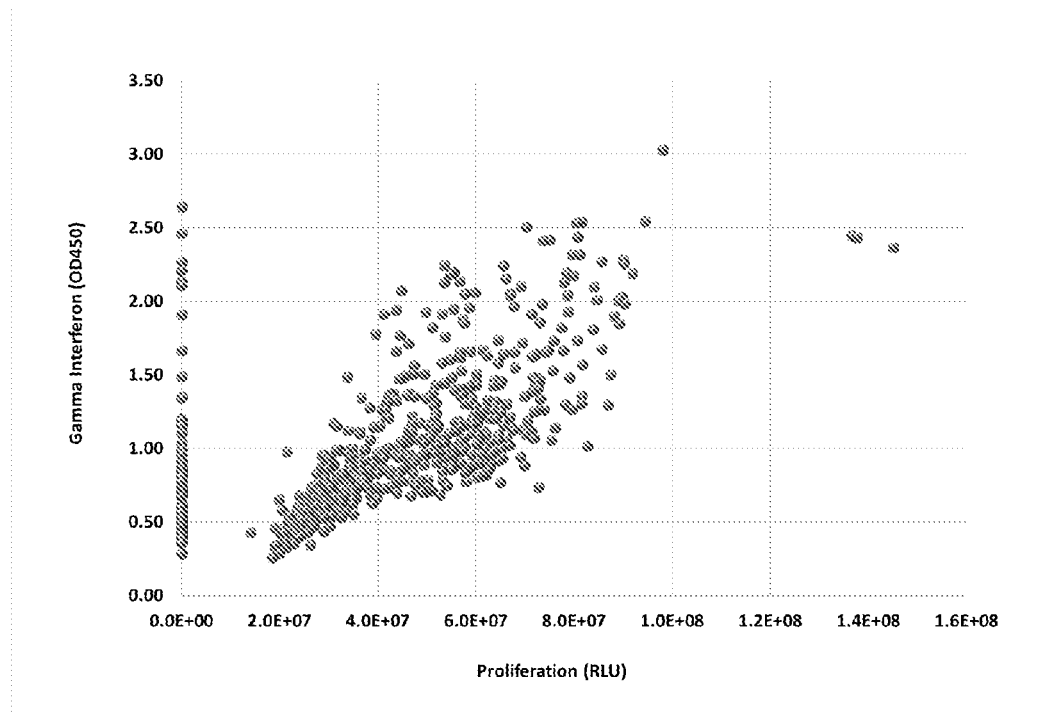

ANTI-4-1BB ANTIBODIES AND METHODS OF MAKING AND USING THEREOF

CROSS REFERENCE TO RELATED APPLICATIONS

This application claims the benefit of U.S. Provisional Patent Application No. 62/551,065, filed Aug. 28, 2017, U.S. Provisional Patent Application No. 62/551,032 filed Aug. 28, 2017, U.S. Provisional Patent Application No. 62/524,554 filed Jun. 25, 2017, U.S. Provisional Patent Application No. 62/524,557 filed Jun. 25, 2017, U.S. Provisional Patent Application No. 62/524,558 filed Jun. 25, 2017, U.S. Provisional Patent Application No. 62/545,603 filed Aug. 15, 2017, U.S. Provisional Patent Application No. 62/551,032 filed Aug. 28, 2017, and U.S. Provisional Patent Application No. 62/551,035 filed Aug. 28, 2017, the entire disclosures of which are expressly incorporated by reference herein.

SEQUENCE LISTING

The content of the ASCII text file of the sequence listing named "028 ST25", which is 409,337 bytes in size was created on Aug. 16, 2018 and electronically submitted via EFS-Web on Nov. 19, 2019, is incorporated herein by reference in its entirety.

TECHNICAL FIELD

The present disclosure generally relates to the technical field of antibodies, and more particularly relates to making and using anti-4-1BB antibodies, and applications of the antibodies in cancer treatment and therapy.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals that further influence the response of the T-cells. A secondary positive signal is required for full T-cell activation ((Lafferty et al., Ausl. J. Exp. Biol. Med. Sci. 53: 27-42 (1975)). Negative secondary signals can result in T-cell suppression and tolerance.

4-1BB is a co-stimulatory immune checkpoint molecule with the ability to active T cells. 4-1BB, also named as CD137, tumour necrosis factor receptor superfamily member 9 (TNFRSF9), and induced by lymphocyte activation (ILA), is a member of the tumour necrosis factor (TNF) receptor family. It has been reported that Crosslinking of CD137 enhances T cell proliferation, IL-2 secretion, survival and cytolytic activity. Further, it can enhance immune activity to eliminate tumours in mice.

Pfizer's Utomilumab (PF-05082566) targets 4-1BB, when in combination with Merck's Keytruda, stimulates a more intense immune system attack on cancers in a small clinical trial (https://www.reuters.com/article/us-health-cancer-pfizer-immunotherapy-idUSKCNOY92W2). And seven clinical trials of PF-05082566 are ongoing. (www.clinicaltrials.gov).

SUMMARY

The present disclosure provides, among others, anti-4-1BB monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

In one embodiment, an isolated monoclonal antibody (mAb) or antigen-binding fragment that binds specifically to human or cynomolgus 4-1BB is provided. In one embodiment, the isolated mAb or antigen-binding fragment include an amino acid sequence having a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, or SEQ ID NO:272. The percentage homology is not less than 70%, 80%, 90%, 95%, 98%, or 99%.

In one embodiment, the isolated mAb or antigen-binding fragment, has a binding affinity to human or cynomolgus 4-1BB with a Kd not greater than 30 nM, 40 nM, 50 nM, 60 nM, 70 nM, 80 nM, 90 nM, or 100 nM.

In one embodiment, the isolated mAb or antigen-binding fragment exhibits one or more functional properties such as, without limitation, high affinity binding to human or cynomolgus 4-1BB, inhibiting human or cynomolgus 4-1BB activity, induction of apoptosis, regulation of EGFR signalling pathway, upregulation of EMT genes, enhancing T cell activation, stimulating antibody response, reversing the suppressive function of an immunosuppressive cell, or a combination thereof. In one embodiment, the immunosuppressive cell comprises a regulatory cell. In one embodiment, the isolated mAb or antigen-binding fragment enhances T-cell activation via mechanisms or pathways including T-cell proliferation, IFN-γ and/or IL-2 secretion, or a combination thereof.

In one embodiment, the isolated mAb or antigen-binding fragment comprises a human framework region. In one embodiment, the isolated mAb or antigen-binding fragment is a humanized antibody, a chimeric antibody, or a recombinant antibody.

In one embodiment, the isolated mAb or antigen-binding fragment is an IgG. In one embodiment, the antigen-binding fragment is a Fv, a Fab, a F(ab')2, a scFV or a scFV2 fragment. In one embodiment, the isolated mAb is a bispecific antibody, tri-specific antibody, or multi-specific antibody.

In one embodiment, the isolated mAb or antigen-binding fragment may include an IgG1 heavy chain. In one embodiment, the IgG1 heavy chain comprises an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:95, SEQ ID NO:103, SEQ ID NO:111, SEQ ID NO:119, SEQ ID NO:127, SEQ ID NO:135, SEQ ID NO:143, SEQ ID NO:151, SEQ ID NO:159, SEQ ID NO:167, SEQ ID NO:175, SEQ ID NO:183, SEQ ID NO:191, SEQ ID NO:199, SEQ ID NO:207, SEQ ID NO:215, SEQ ID NO:223, SEQ ID NO:231, SEQ ID NO:239, SEQ ID NO:247, SEQ ID NO:255, SEQ ID NO:263, or SEQ ID NO:271. The percentage homology is not less than 70%, 80%, 90%, 95%, 98%, or 99%.

In one embodiment, the isolated mAb or antigen-binding fragment may include a kappa light chain. In one embodiment, the kappa light chain comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:91, SEQ ID NO:99, SEQ ID NO:107, SEQ ID NO:115, SEQ ID NO:123, SEQ ID NO:131, SEQ ID NO:139, SEQ ID NO:147, SEQ ID NO:155, SEQ ID NO:163, SEQ ID NO:171, SEQ ID NO:179, SEQ ID NO:187, SEQ ID NO:195, SEQ ID NO:203, SEQ ID NO:211, SEQ ID NO:219, SEQ ID NO:1 SEQ ID NO:227, SEQ ID NO:235, SEQ ID NO:243, SEQ ID NO:257, or SEQ ID NO:263. The percentage homology is not less than 70%, 80%, 90%, 95%, 98%, or 99%.

In one embodiment, the isolated mAb or antigen-binding fragment may include a variable light chain. In one embodiment, the variable light chain comprises an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:92, SEQ ID NO:100, SEQ ID NO:108, SEQ ID NO:116, SEQ ID NO:124, SEQ ID NO:132, SEQ ID NO:140, SEQ ID NO:148, SEQ ID NO:156, SEQ ID NO:164, SEQ ID NO:172, SEQ ID NO:180, SEQ ID NO:188, SEQ ID NO:196, SEQ ID NO:204, SEQ ID NO:212, SEQ ID NO:220, SEQ ID NO:228, SEQ ID NO:236, SEQ ID NO:244, SEQ ID NO:252, SEQ ID NO:260, or SEQ ID NO:268. The percentage homology is not less than 70%, 80%, 90%, 95%, 98%, or 99%.

In one embodiment, the isolated mAb or antigen-binding fragment may include a variable heavy chain. In one embodiment, the variable heavy chain comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:96, SEQ ID NO:104, SEQ ID NO:112, SEQ ID NO:120, SEQ ID NO:128, SEQ ID NO:136, SEQ ID NO:144, SEQ ID NO:152, SEQ ID NO:160, SEQ ID NO:168, SEQ ID NO:176, SEQ ID NO:184, SEQ ID NO:192, SEQ ID NO:200, SEQ ID NO:208, SEQ ID NO:216, SEQ ID NO:224, SEQ ID NO:232, SEQ ID NO:240, SEQ ID NO:248, SEQ ID NO:256, SEQ ID NO:264, or SEQ ID NO:272. The percentage homology is not less than 70%, 80%, 90%, 95%, 98%, or 99%.

The application further provides isolated nucleic acids encoding at least a portion of the isolated mAb or antigen-binding fragment disclosed herein. In one embodiments, the nucleic acid encodes an IgG1 heavy chain that includes an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:95, SEQ ID NO:103, SEQ ID NO:111, SEQ ID NO:119, SEQ ID NO:127, SEQ ID NO:135, SEQ ID NO:143, SEQ ID NO:151, SEQ ID NO:159, SEQ ID NO:167, SEQ ID NO:175, SEQ ID NO:183, SEQ ID NO:191, SEQ ID NO:199, SEQ ID NO:207, SEQ ID NO:215, SEQ ID NO:223, SEQ ID NO:231, SEQ ID NO:239, SEQ ID NO:247, SEQ ID NO:255, SEQ ID NO:263, or SEQ ID NO:271. In one embodiment, the nucleic acid encodes a kappa light chain that comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:91, SEQ ID NO:99, SEQ ID NO:107, SEQ ID NO:115, SEQ ID NO:123, SEQ ID NO:131, SEQ ID NO:139, SEQ ID NO:147, SEQ ID NO:155, SEQ ID NO:163, SEQ ID NO:171, SEQ ID NO:179, SEQ ID NO:187, SEQ ID NO:195, SEQ ID NO:203, SEQ ID NO:211, SEQ ID NO:219, SEQ ID NO:1 SEQ ID NO:227, SEQ ID NO:235, SEQ ID NO:243, SEQ ID NO:257, or SEQ ID NO:263. In one embodiment, the nucleic acid encodes a variable light chain that comprises an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:92, SEQ ID NO:100, SEQ ID NO:108, SEQ ID NO:116, SEQ ID NO:124, SEQ ID NO:132, SEQ ID NO:140, SEQ ID NO:148, SEQ ID NO:156, SEQ ID NO:164, SEQ ID NO:172, SEQ ID NO:180, SEQ ID NO:188, SEQ ID NO:196, SEQ ID NO:204, SEQ ID NO:212, SEQ ID NO:220, SEQ ID NO:228, SEQ ID NO:236, SEQ ID NO:244, SEQ ID NO:252, SEQ ID NO:260, or SEQ ID NO:268. In one embodiment, the nucleic acid encodes a variable heavy chain that comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:96, SEQ ID NO:104, SEQ ID NO:112, SEQ ID NO:120, SEQ ID NO:128, SEQ ID NO:136, SEQ ID NO:144, SEQ ID NO:152, SEQ ID NO:160, SEQ ID NO:168, SEQ ID NO:176, SEQ ID NO:184, SEQ ID NO:192, SEQ ID NO:200, SEQ ID NO:208, SEQ ID NO:216, SEQ ID NO:224, SEQ ID NO:232, SEQ ID NO:240, SEQ ID NO:248, SEQ ID NO:256, SEQ ID NO:264, or SEQ ID NO:272. The percentage homology is not less than 70%, 80%, 90%, 95%, 98%, or 99%.

In one embodiment, an expression vector is provided comprising at least one of the isolated nucleic acids described infra. In one embodiment, the expression vector is expressible in a cell.

In one embodiment, a host cell is provided, comprising at least one of the nucleic acids that is described infra. In one embodiment, a host cell is provided, comprising the expression vector described infra. In one embodiment, the host cell can be a prokaryotic cell or a eukaryotic cell.

The application further provides methods for producing the isolated mAb or antigen-binding fragment disclosed herein. In one embodiment, the method uses the host cell described above. In one embodiment, the method includes the steps of providing a host cell that contains an expression vector expressible in the host cell, wherein the expression vector comprises at least one of the nucleic acids that is described infra, and culturing the host cells to produce an antibody by the expression of the nucleic acids.

The application further provides an immuno-conjugate that comprises a drug unit or an imaging agent linked to an isolated mAb or antigen-binding fragment with the sequences disclosed herein through a linker. The linker may be cleavable or noncleavable. In one embodiment, the linker is a chemical linker. In one embodiment, the linker comprises a covalent bond such as an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly(ethylene glycol) linker. In one embodiment, the linker comprises a peptide bond.

In one embodiment, the drug unit in the immuno-conjugate comprises a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the therapeutic agent comprises an antibody, an enzyme, or a combination thereof. In one embodiment, the drug unit comprises a calicheamicin, ozogamicin, monomethyl auristatin E, emtansine, a derivative or a combination thereof.

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof. In one embodiment, the immune regulatory reagents activate or suppress immune cells, T cell, NK cell, B cell, macrophage, or dendritic cell.

In one embodiment, the imaging agent may be a radionuclide, a florescent agent, a quantum dots, or a combination thereof.

The application further provides pharmaceutical compositions. In one embodiment, a pharmaceutical composition comprises the isolated mAb or antigen-binding disclosed herein and a pharmaceutically acceptable carrier. In one embodiment, a pharmaceutical composition comprises the immuno-conjugate and pharmaceutically acceptable carrier.

In a further aspect, the application provides methods for treating cancer. In one embodiment, the method comprising administering to the subject an effective amount of the isolated mAb or antigen-binding fragment with the sequences disclosed herein. In one embodiment, the method includes directly injecting into the tumour site an effective amount of the monoclonal antibodies, the antigen-binding fragment thereof, and the immuno-conjugates and disclosed herein.

In some embodiments of the disclosure, the cancer has cells that express 4-1BB. Example cancer can be treated using the disclosed mAbs or their antigen-binding fragments include without limitation breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

In one embodiment, the method further includes co-administering an effective amount of a therapeutic agent. In one embodiment, the therapeutic agent can include an antibody, a chemotherapy agent, an enzyme, or a combination thereof. In one embodiment, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, calicheamicin, antimitotic agent, monomethyl auristatin E, emtansine, ozogamicin, or a derivative or a combination thereof.

The subject receiving the treatment may be a human. In one embodiment, a solution is provided that comprises an effective concentration of the isolated mAb or an antigen-binding disclosed herein, wherein the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 Immunization schedule for rabbit cohorts no. 1 and 2 with human 41BB or cynomolgus 41BB transiently transfected HEK293 cells.

FIG. 2 41BB-specific rabbit IgG antibodies in B cell culture supernatant enhance activation of anti-CD3 activated human T cells and corresponding binding of chimeric rabbit/human IgG 41BB-specific antibodies rescued from the parental B cell culture wells to recombinant human and cynomolgus 41BB protein.

FIG. 3 Chimeric rabbit/human IgG antibodies specific for 41BB enhance T cell activation, proliferation, and gamma interferon secretion.

FIG. 4. Octet analysis of dissociation rate for humanized 41BB-specific IgG antibodies.

FIG. 5. Humanized 41BB-specific IgG antibodies enhance T cell activation, proliferation, and gamma interferon secretion.

FIG. 6. Serum from rabbits immunized with human or cynomolgus 41BB expressing HEK293's analyzed for 41BB-specific IgG antibody binding to parental CHO or human or cynomolgus 41BB-transfected CHO cells.[

FIG. 7. Correlation of 41BB-specific IgG antibody in B cell culture supernatant enhancement of Gamma interferon secretion versus proliferation of human T cells.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, bispecific or multi-specific molecules, antibody-drug conjugates and/or immuno-conjugates composed from such antibodies or antigen binding fragments and pharmaceutical compositions containing the antibodies, bispecific or multi-specific molecules, antibody-drug conjugates and/or immuno-conjugates.

In one aspect, the disclosure provides isolated monoclonal antibodies that bind to human or cynomolgus 4-1BB. The antibodies may exhibit one or more desirable functional properties, such as high affinity binding to 4-1BB, the ability to enhance T cell activation including proliferation, IFN-γ and/or CD3+ T cell proliferation, IL-2 secretion, survival and cytolytic activity, the ability to stimulate antibody responses and/or the ability to reverse the suppressive function of immunosuppressive cells, such as T regulatory cells. In addition, the antibodies of the disclosure are derived from specific heavy and light chain amino acid sequences and/or structural features such as complementarity determining regions (CDRs) composed of specific amino acid sequences.

The term "antibody" is used in the broadest sense and specifically covers single monoclonal antibodies (including agonist and antagonist antibodies), antibody compositions with polyepitopic specificity, as well as antibody fragments (e.g., Fab, F(ab')2, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with cells transiently expressing human or cynomolgus 4-1BB on the cell surface. Rabbits are known to create antibodies of high affinity, diversity and specificity (Weber et al. Exp. Mol. Med. 49:e305). B cells from immunized animals were cultured in vitro and screened for the production of anti-4-1BB antibodies. The antibody variable genes were isolated using recombinant DNA techniques and the resulting antibodies were expressed recombinantly and further screened for desired features such as the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (4-1BB in this case). These fragments may be capable of the antigen-binding function and additional functions of the intact antibody. Examples of binding fragments include, but are not limited to, a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller subfragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about 10 M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In another aspect, the application provides pharmaceutical composition including the mAbs and their antigen-binding fragments disclosed herein. In one embodiment, the pharmaceutical composition includes the mAbs or their antigen-binding fragments and a pharmaceutically acceptable carrier. In one embodiment, the pharmaceutical composition includes the immuno-conjugate and a pharmaceutically acceptable carrier. Formulation of the pharmaceutical composition according to the disclosure can be accomplished according to standard methodology know to those of ordinary skill in the art.

The antibodies or immuno-conjugates according to the disclosure can be prepared in a physiologically acceptable formulation and may comprise a pharmaceutically acceptable carrier, diluent and/or excipient using known techniques. For example, the antibody according to the disclosure may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may comprise proteinaceous carriers such as, for example, serum albumin or immunoglobulin, particularly of human origin. Further biologically active agents may be present in the pharmaceutical composition of the disclosure dependent on the intended use. Proteinaceous pharmaceutically active matter may be present in amounts between 1 ng and 10 mg per dose. Generally, the regime of administration should be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

In a further aspect, the disclosure provide method for treating cancer using anti-4-1BB antibodies or other molecules containing the antigen-binding portion of an anti-4-1BB antibody. In one embodiment, the method is used to inhibit growth of tumour cells. In one embodiment, the method is used to stimulate a protective autoimmune response, to modify an immune response or to stimulate antigen-specific immune responses.

In one embodiment, the method for treating cancer includes administering to a subject in need of such treatment an effective amount of the mAbs, their antigen-binding fragments as disclosed herein. In one embodiment, the composition may be administered in combination with other compositions comprising a biologically active substance or compound. In one embodiment, the biologically active substance may include capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof.

The compositions of the present disclosure may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumour site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. For example, the composition may be administered by topical, oral, rectal, nasal, interdermal, intraperitoneal, or parenteral (for example, intravenous, subcutaneous, or intramuscular) routes. In one embodiment, administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

In one embodiment, the composition may be incorporated into sustained release matrices such as biodegradable polymers, the polymers being implanted in the vicinity of where delivery is desired, for example, at the site of a tumour. The method includes administration of a single dose, administration of repeated doses at predetermined time intervals, and sustained administration for a predetermined period of time.

It is known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

In one embodiment, the term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

Varieties of cancer may be treated using the mAbs, their antigen-binding fragments, and compositions disclosed herein. Example cancer including without limitation breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer. In one embodiment, the cancer may express 4-1BB genes. Inhibition of 4-1BB activity with anti-4-1BB monoclonal antibodies or antigen-binding fragment provides therapeutic effect. In one embodiment, administering a therapeutically effective amount of composition comprising anti-4-1BB monoclonal antibodies or antigen-binding fragment may cure, prevent, ameliorate, and delay the development or metastasis of cancers, through the effect of the drug unit.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure.

EXAMPLES

Example 1: Generation of Anti-4-1BB Antibodies

Monoclonal antibodies against human or cynomolgus 4-1BB were developed by immunizing New Zealand white rabbits. As shown in FIG. 1, animals were immunized with recombinant human embryonic kidney 293 (HEK) cells transiently transfected with human or cynomolgus 4-1BB mixed 1:1 v/v with Titermax Gold (Cohort 1) or Complete or incomplete Freund's adjuvant (Cohort 2) alternating with Alhydrogel 2% (Alum) plus CpG 2007 and were performed by subcutaneous injection. Blood samples were drawn at different timepoints during the immunization schedule as shown in FIG. 1. Serum which was drawn from all 4 animals on day 62 was analyzed for human or cynomolgus 4-1BB-specific IgG by FACS analysis as shown in FIG. 6. All 4 animals developed human or cynomolgus-specific IgG after immunization.

Antigen-specific B cells were labeled with biotinylated human and cynomolgus 4-1BB recombinant protein followed by streptavidin-alexafluor647 and then sorted into multiple 96 well tissue culture plates at 1 antigen-specific IgG+ B cell per well and cultured for 9 days to allow their differentiation into plasma cells and for secretion of antibodies. The supernatants from these B cell culture (BCC) plates were screened by ELISA and functional assay for the presence of 4-1BB-specific antibodies in the assays as listed below:

Binding to recombinant human and cynomolgus 4-1BB— IgG ELISA

Enhancement of CD3-induced T cell activation of purified human CD3+ T cells—detection of gamma interferon secretion by ELISA and quantitation of CD3+ T cell proliferation by alamar blue cell viability assay A total of 693 wells from the BCC plates had human and cynomolgus 4-1BB-specific IgG. The 4-1BB-specific antibody from these 693 BCC wells were then analyzed for agonist activity to enhance anti-CD3-induced activation of CD3+ human T cells. A fixed concentration of a control anti-human CD3-specific antibody was combined with a fixed concentration of 4-1BB-specific antibody from the BCC supernatants and then captured on and ELISA plate that was previously coated with a goat anti-rabbit IgG Fc polyclonal antibody. Purified human CD3+ T cells were added at 100,000 per each assay well and the plate was incubated for 5 days. On day 5 of the assay the contents of each assay well were collected and analyzed for the amount of gamma interferon secreted into the culture supernatant and for the number of CD3+ T cells in each assay well which is shown in FIG. 7. From these data the best 92 BCC wells were advanced to molecular rescue of the rabbit antibody heavy and light chain variable regions by RT-PCR.

On day 9 of B cell culture the supernatants were separated from the B cells and stored in a separate plate for later analysis. RNA later tissue storage reagent was added to each well in the B cell culture plate to preserve the RNA in the B cells for RT-PCR amplification of antibody variable regions. The set of 92 BCC wells were advanced to molecular "rescue" of the antibody variable regions. The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasmids generated from each well were transiently co-transfected to produce rabbit/human chimeric antibodies. Recombinant antibody supernatants were confirmed to contain antibodies specific for human and cynomolgus 4-1BB using bio-layer interferometry analysis on a ForteBio Octet Red 96 instrument. Anti-human Fc biosensors (Pall ForteBio) were used to capture antibodies in the supernatants. Association to human or cynomolgus 4-1BB was observed by real-time interferometry by placing the biosensors in wells containing recombinant human or cynomolgus 4-1BB extracellular domain protein. Dissociation was measured after transfer of the biosensors into wells containing 10× kinetics buffer (Pall ForteBio). The software provided by the manufacturer was used to analyze the interferometry data. A summary of the primary BCC screening data and the corresponding screening data for 34 recombinant chimeric rabbit/human IgG antibodies is shown in FIG. 2. From the original 92 BCC wells 34 chimeric antibodies were rescued and were shown to bind human and cynomolgus recombinant 4-1BB protein (FIG. 2)

The panel of 34 chimeric rabbit/human IgG antibodies specific for human and cynomolgus 4-1BB were then assayed for agonist activity which enhanced the anti-CD3-induced activation of human CD3+ T cells. As shown in FIG. 3, $EC_{50}$ for secretion of gamma interferon were calculated for each chimeric antibody as well as the fold-over-background of the enhancement of proliferation of human CD3+ T cells. Proliferation of human CD3+ T cells with anti-CD3 antibody alone, without additional 4-1BB antibody, is set to the background value of 1.0 and then the fold-over-background is calculated at different concentrations of the chimeric 4-1BB antibodies are tested. From these data 18 chimeric 4-1BB-specific antibodies were advanced to humanization.

From the panel of 34 chimeric rabbit/human IgG antibodies specific for human and cynomolgus 4-1BB that were advanced to humanization 18 were successfully humanized as shown in FIG. 4 where binding to human and recombinant 4-1BB by octet assay was performed. These 18 humanized antibodies specific for human or cynomolgus 4-1BB were then assayed for agonist activity which enhanced the anti-CD3-induced activation of human CD3+ T cells. As shown in FIG. 5, $EC_{50}$ for secretion of gamma interferon were calculated for each humanized antibody as well as the fold-over-background of the enhancement of proliferation of human CD3+ T cells. Proliferation of human CD3+ T cells with anti-CD3 antibody alone, without additional 4-1BB antibody, is set to the background value of 1.0 and then the fold-over-background is calculated at different concentrations of the humanized 4-1BB antibodies are tested. From these data 17 of the 18 humanized 4-113B-specific antibodies showed enhancement of anti-CD3-induced activation of human CD3+ T cells.

While the disclosure has been particularly shown and described as referenced to the embodiments thereof, those skilled in the art will understand that the foregoing and other changes in form and detail may be made therein without departing from the spirit and scope. All references cited or referred to in this disclosure are hereby incorporated by reference in their entireties.

```
SEQUENCE LISTING
411H11 CHIMERIC LIGHT CHAIN FULL-LENGTH NUCLEOTIDE SEQUENCE
                                                              SEQ ID NO: 1
GATGTTGTGATGACCCAGACTCCAGCCTCCGTGTCTGAACCTGTGAGAGCCACAGTCACCATCAAGTGCCAGGCCA

GTCAGAGCATTGGTGCTGATTTAGCCTGGTATCAGCAGAAACCAGGGCAGCCTCCCAAGCTCCTGATCTACAGGG

CATCCACTCTGGCCTCTGGGGTCCCATCGCGGTTCAGCGGCAGTGGATCTGGGACAGAGTTCACTCTCACCATCAG

CGACCTGGAGTGTGCCGATGCTGCCACTTACTACTGTCAATGTATTTATTATGGTACTGATGATGTCATATACCATA

CTTTCGGCGGAGGGACCGAGGTGGTGTTCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

411H11 CHIMERIC LIGHT CHAIN VARIABLE LIGHT CHAIN NUCLEOTIDE SEQUENCE
                                                              SEQ ID NO: 2
GATGTTGTGATGACCCAGACTCCAGCCTCCGTGTCTGAACCTGTGAGAGCCACAGTCACCATCAAGTGCCAGGCCA

GTCAGAGCATTGGTGCTGATTTAGCCTGGTATCAGCAGAAACCAGGGCAGCCTCCCAAGCTCCTGATCTACAGGG

CATCCACTCTGGCCTCTGGGGTCCCATCGCGGTTCAGCGGCAGTGGATCTGGGACAGAGTTCACTCTCACCATCAG

CGACCTGGAGTGTGCCGATGCTGCCACTTACTACTGTCAATGTATTTATTATGGTACTGATGATGTCATATACCATA

CTTTCGGCGGAGGGACCGAGGTGGTGTTCAAA

411H11 CHIMERIC LIGHT CHAIN FULL-LENGTH AMINO ACID SEQUENCE. HUMAN KAPPA CONSTANT
DOMAIN IS UNDERLINED
                                                              SEQ ID NO: 3
DVVMTQTPASVSEPVRATVTIKCQASQSIGADLAWYQQKPGQPPKLLIYRASTLASGVPSRFSGSGSGTEFTLTISDLEC

ADAATYYCQCIYYGTDDVIYHTFGGGTEVVFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

411H11 CHIMERIC LIGHT CHAIN VARIABLE LIGHT CHAIN AMINO ACID SEQUENCE. COMPIMENTARITY
DETERMINING REGIONS ARE UNDERLINED
                                                              SEQ ID NO: 4
DVVMTQTPASVSEPVRATVTIKCQASQSIGADLAWYQQKPGQPPKLLIYRASTLASGVPSRFSGSGSGTEFTLTISDLEC

ADAATYYCQCIYYGTDDVIYHTFGGGTEVVFK

411H11 CHIMERIC HEAVY CHAIN FULL-LENGTH NUCLEOTIDE SEQUENCE
                                                              SEQ ID NO: 5
CAGTCGGTGGAGGAGTCCGGGGGTCGCCTGGTCACGCCTGGGACACCCCTAACACTCACCTGCACAGTATCTGGA

TTCACCATCAGTAGCCACCACATGATCTGGGTCCGCCAGGCTCCAGGAGAGGGGCTGCAATACATCGGATTCATTA
```

-continued

ATGATGGTGACTATACATACTACACGAACTGGGCAAAAGGCCGATTCACCATCTCCAGAACCTCGACTACGGTGG

ACCTGAAAATGACCAGTCTGACAGCCGCGGACACGGCCACCTATTTCTGTGCCAGAGGGGTTGATGGTACTAGTT

ATCCTGGCTTGTGGGGCCCAGGCACCCTGGTCACCGTCTCGAGCGCTAGCACCAAGGGCCCATCGGTCTTCCCCCT

GGCACCCTCCTCCAAGAGCACCTCTGGGGGCACAGCGGCCCTGGGCTGCCTGGTCAAGGACTACTTCCCCGAACC

GGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACCCAGACCTACATCTGCAACGTGAAT

CACAAGCCCAGCAACACCAAGGTGGACAAGAGAGTTGAGCCCAAATCTTGTGACAAAACTCACACATGCCCACCG

TGCCCAGCACCTGAAGCCGCGGGGGCACCGTCAGTCTTCCTCTTCCCCCCAAAACCCAAGGACACCCTCATGATCT

CCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

411H11 CHIMERIC HEAVY CHAIN VARIABLE HEAVY CHAIN NUCLEOTIDE SEQUENCE
SEQ ID NO: 6

CAGTCGGTGGAGGAGTCCGGGGGTCGCCTGGTCACGCCTGGGACACCCCTAACACTCACCTGCACAGTATCTGGA

TTCACCATCAGTAGCCACCACATGATCTGGGTCCGCCAGGCTCCAGGAGAGGGGCTGCAATACATCGGATTCATTA

ATGATGGTGACTATACATACTACACGAACTGGGCAAAAGGCCGATTCACCATCTCCAGAACCTCGACTACGGTGG

ACCTGAAAATGACCAGTCTGACAGCCGCGGACACGGCCACCTATTTCTGTGCCAGAGGGGTTGATGGTACTAGTT

ATCCTGGCTTGTGGGGCCCAGGCACCCTGGTCACCGTCTCGAGC

411H11 CHIMERIC HEAVY CHAIN FULL-LENGTH AMINO ACID SEQUENCE. HUMAN GAMMA-1
CONSTANT DOMAIN IS UNDERLINED
SEQ ID NO: 7

QSVEESGGRLVTPGTPLTLTCTVSGFTISSHHMIWVRQAPGEGLQYIGFINDGDYTYYTNWAKGRFTISRTSTTVDLKM

TSLTAADTATYFCARGVDGTSYPGLWGPGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

411H11 CHIMERIC HEAVY CHAIN VARIABLE HEAVY CHAIN AMINO ACID SEQUENCE.
COMPLIMENTARITY DETERMINING REGIONS ARE UNDERLINED
SEQ ID NO: 8

QSVEESGGRLVTPGTPLTLTCTVSGFTISS<u>SHHMI</u>WVRQAPGEGLQYIG<u>FINDGDYTYYTNWAKG</u>RFTISRTSTTVDLKM

TSLTAADTATYFCAR<u>GVDGTSYPGLW</u>GPGTLVTVSS

413F3 CHIMERIC LIGHT CHAIN FULL-LENGTH NUCLEOTIDE SEQUENCE
SEQ ID NO: 9

GACGTCGTGATGACCCAGACTCCAGCCTCCGTGGAGGCAGCTGTGGGAGGCACAGTCACCATCAAGTGCCAGGC

CAGTCAGAGCATTTACAGCAATTTAGCCTGGTATCAGCAGAAACCAGGGCAGCCTCCCAAACTCCTAATCTATTCT

ACATCCACTCTGGCATCTGGGGTCCCATCGCGGTTCAGCGGCAGTGGATCCGGGACAGAGTTCACTCTCACCATCA

GCGACCTGGAGTGTGCCGATGCTGCCACTTACTACTGTCAAAACTATTATGGTAGTAGTACTGATAGTTATGGGAA

TCCTTTCGGCGGAGGCACCGAGGTGGTGTTCAAACGTACGGTGGCTGCACCATCTGTCTTCATCTTCCCGCCATCT

GATGAGCAGTTGAAATCTGGAACTGCCTCTGTTGTGTGCCTGCTGAATAACTTCTATCCCAGAGAGGCCAAAGTAC

AGTGGAAGGTGGATAACGCCCTCCAATCGGGTAACTCCCAGGAGAGTGTCACAGAGCAGGACAGCAAGGACAGC

ACCTACAGCCTCAGCAGCACCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGT

413F3 CHIMERIC LIGHT CHAIN VARIABLE LIGHT CHAIN NUCLEOTIDE SEQUENCE
SEQ ID NO: 10
GACGTCGTGATGACCCAGACTCCAGCCTCCGTGGAGGCAGCTGTGGGAGGCACAGTCACCATCAAGTGCCAGGC

CAGTCAGAGCATTTACAGCAATTTAGCCTGGTATCAGCAGAAACCAGGGCAGCCTCCCAAACTCCTAATCTATTCT

ACATCCACTCTGGCATCTGGGGTCCCATCGCGGTTCAGCGGCAGTGGATCCGGGACAGAGTTCACTCTCACCATCA

GCGACCTGGAGTGTGCCGATGCTGCCACTTACTACTGTCAAAACTATTATGGTAGTAGTACTGATAGTTATGGGAA

TCCTTTCGGCGGAGGCACCGAGGTGGTGTTCAAA

413F3 CHIMERIC LIGHT CHAIN FULL-LENGTH AMINO ACID SEQUENCE. HUMAN KAPPA CONSTANT
DOMAIN IS UNDERLINED
SEQ ID NO: 11
DVVMTQTPASVEAAVGGTVTIKCQASQSIYSNLAWYQQKPGQPPKLLIYSTSTLASGVPSRFSGSGSGTEFTLTISDLEC

ADAATYYCQNYYGSSTDSYGNPFGGGTEVVFKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

413F3 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 12
DVVMTQTPASVEAAVGGTVTIKCQASQSIYSNLAWYQQKPGQPPKLLIYSTSTLASGVPSRFSGSGSGTEFTLTISDLEC

ADAATYYCQNYYGSSTDSYGNPFGGGTEVVFK

413F3 CHIMERIC HEAVY CHAIN FULL-LENGTH NUCLEOTIDE SEQUENCE
SEQ ID NO: 13
CAGTCGCTGGAGGAGTCCGGGGGAGACCTGGTCAAGCCTGAGGGATCCCTGACACTCACCTGCACAGGCTCTGG

AATCGACTTCAGTAGCAACTACATGTGCTGGGTCCGCCAGGCTCCAGGGAAGGGGCTGGAGTGGATCGCATGCAT

TTATGGTGATAGTAGTGATAATAGTTACTCCGCGAGCTGGGCGAAAGGGCGATTCACCATCTCCAAAACCTCGTCG

ACCACGGTGACTCTGCAAATGACCAGTCTGACAGCCGCGGACACGGCCACCTATTTCTGTGCGAGATCTGGTTATA

GCTATTTAGGCTACTTTAACTTGTGGGGCCCAGGGACCCTGGTCACCGTCTCGAGCGCTAGCACCAAGGGCCCATC

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

413F3 CHIMERIC HEAVY CHAIN VARIABLE HEAVY CHAIN NUCLEOTIDE SEQUENCE
SEQ ID NO: 14
CAGTCGCTGGAGGAGTCCGGGGGAGACCTGGTCAAGCCTGAGGGATCCCTGACACTCACCTGCACAGGCTCTGG

AATCGACTTCAGTAGCAACTACATGTGCTGGGTCCGCCAGGCTCCAGGGAAGGGGCTGGAGTGGATCGCATGCAT

TTATGGTGATAGTAGTGATAATAGTTACTCCGCGAGCTGGGCGAAAGGGCGATTCACCATCTCCAAAACCTCGTCG

```
ACCACGGTGACTCTGCAAATGACCAGTCTGACAGCCGCGGACACGGCCACCTATTTCTGTGCGAGATCTGGTTATA

GCTATTTAGGCTACTTTAACTTGTGGGGCCCAGGGACCCTGGTCACCGTCTCGAGC
```

413F3 CHIMERIC HEAVY CHAIN FULL-LENGTH AMINO ACID SEQUENCE. HUMAN GAMMA-1 CONSTANT DOMAIN IS UNDERLINED

SEQ ID NO: 15

```
QSLEESGGDLVKPEGSLTLTCTGSGIDFSSNYMCWVRQAPGKGLEWIACIYGDSSDNSYSASWAKGRFTISKTSSTTVTL

QMTSLTAADTATYFCARSGYSYLGYFNLWGPGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG
```

413F3 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 16

```
QSLEESGGDLVKPEGSLTLTCTGSGIDFSSNYMCWVRQAPGKGLEWIACIYGDSSDNSYSASWAKGRFTISKTSSTTVTL

QMTSLTAADTATYFCARSGYSYLGYFNLWGPGTLVTVSS
```

416F8 CHIMERIC LIGHT CHAIN FULL-LENGTH NUCLEOTIDE SEQUENCE

SEQ ID NO: 17

```
GCGCAAGTGCTGACCCAGACTGCATCGTCCGTGTCTGCACCTGTGGGCGGCACAGTCACCATCAGTTGCCAGTCCA

GTCAGACTGTTTATAATAACAACTTGTTATCCTGGTATCAGCAGAAACCAGGGCAGCGTCCCAAGCTCCTGATCTA

TTATGCATCCACTCTGGCATTTGGGGTCCCATCGCGGTTCAAAGGCAGTGGATCTGGACAGAGTTCACTCTCACC

ATCAGCGACCTGGAGTGTGACGATGCTGCCACTTACTTCTGTCAAGGCGGTTATAGTGGTTGGATTTATGTTTTCG

GCGGAGGCACCGAGGTGGAGGTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT
```

416F8 CHIMERIC LIGHT CHAIN VARIABLE LIGHT CHAIN NUCLEOTIDE SEQUENCE

SEQ ID NO: 18

```
GCGCAAGTGCTGACCCAGACTGCATCGTCCGTGTCTGCACCTGTGGGCGGCACAGTCACCATCAGTTGCCAGTCCA

GTCAGACTGTTTATAATAACAACTTGTTATCCTGGTATCAGCAGAAACCAGGGCAGCGTCCCAAGCTCCTGATCTA

TTATGCATCCACTCTGGCATTTGGGGTCCCATCGCGGTTCAAAGGCAGTGGATCTGGACAGAGTTCACTCTCACC

ATCAGCGACCTGGAGTGTGACGATGCTGCCACTTACTTCTGTCAAGGCGGTTATAGTGGTTGGATTTATGTTTTCG

GCGGAGGCACCGAGGTGGAGGTCAAA
```

416F8 CHIMERIC LIGHT CHAIN FULL-LENGTH AMINO ACID SEQUENCE. HUMAN KAPPA CONSTANT DOMAIN IS UNDERLINED

SEQ ID NO: 19

```
AQVLTQTASSVSAPVGGTVTISCQSSQTVYNNNLLSWYQQKPGQRPKLLIYYASTLAFGVPSRFKGSGSGTEFTLTISDLE

CDDAATYFCQGGYSGWIYVFGGGTEVEVKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC
```

416F8 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 20

```
AQVLTQTASSVSAPVGGTVTISCQSSQTVYNNNLLSWYQQKPGQRPKLLIYYASTLAFGVPSRFKGSGSGTEFTLTISDLE

CDDAATYFCQGGYSGWIYVFGGGTEVEVK
```

416F8 CHIMERIC HEAVY CHAIN FULL-LENGTH NUCLEOTIDE SEQUENCE

SEQ ID NO: 21

```
CAGTCGCTGGAGGAGTCCGGGGGTCGCCTGGTCACGCCTGGGACACCCCTGACACTCACCTGCACAGCCTCTGGA

TTCTCCCTCAGTAACTACTACATGAACTGGGTCCGCCAGGCTCCAGGGAAGGGGCTGGAATACATCGGAATCATTA

GTAGTAGTGGTAGCGCATACTACGCGAGCTGGGCTAAAGGCCGATTCACCATCTCCAGAACCTCGACCACGGTGG
```

ACCTGAGAATCACCAGTCCGACAACCGAGGACACGGCCACCTATTTCTGTGCCAGAGGGGACTACGGCATGGACC

TCTGGGGCCAAGGGACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

416F8 CHIMERIC HEAVY CHAIN VARIABLE HEAVY CHAIN NUCLEOTIDE SEQUENCE
SEQ ID NO: 22
CAGTCGCTGGAGGAGTCCGGGGGTCGCCTGGTCACGCCTGGGACACCCCTGACACTCACCTGCACAGCCTCTGGA

TTCTCCCTCAGTAACTACTACATGAACTGGGTCCGCCAGGCTCCAGGGAAGGGGCTGGAATACATCGGAATCATTA

GTAGTAGTGGTAGCGCATACTACGCGAGCTGGGCTAAAGGCCGATTCACCATCTCCAGAACCTCGACCACGGTGG

ACCTGAGAATCACCAGTCCGACAACCGAGGACACGGCCACCTATTTCTGTGCCAGAGGGGACTACGGCATGGACC

TCTGGGGCCAAGGGACCCTGGTCACCGTCTCGAGC

416F8 CHIMERIC HEAVY CHAIN FULL-LENGTH AMINO ACID SEQUENCE. HUMAN GAMMA-1 CONSTANT
DOMAIN IS UNDERLINED
SEQ ID NO: 23
QSLEESGGRLVTPGTPLTLTCTASGFSLSNYYMNWVRQAPGKGLEYIGIISSSGSAYYASWAKGRFTISRTSTTVDLRITSP

TTEDTATYFCARGDYGMDLWGQGTLVTVSS<u>ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHTCPPCPAPEAAGAPSVFLFPPK

PKDTLMISRTPEVTCVVVDVSHEDPEVKFNWYVDGVEVHNAKTKPREEQYNSTYRVVSVLTVLHQDWLNGKEYKCAV

SNKALPAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG</u>

416F8 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 24
QSLEESGGRLVTPGTPLTLTCTASGFSLS<u>NYYMN</u>WVRQAPGKGLEYIGI<u>ISSSGSAYYASWAKG</u>RFTISRTSTTVDLRITSP

TTEDTATYFCAR<u>GDYGMDL</u>WGQGTLVTVSS

416G1 CHIMERIC LIGHT CHAIN FULL-LENGTH NUCLEOTIDE SEQUENCE
SEQ ID NO: 25
GACGTCGTGATGACCCAGACTCCAGCCTCCGTGTCTGAACCTGTGGGAGGCGCAGTCACCATCAAGTGCCAGGCC

AGTCAGAGCATTGGTAGTGATTTAGCCTGGTATCAGCAGAAACCAGGGCAGCCTCCCAAGCTCCTGATCTACAGG

GCATCCACTCTGGCATCTGGGGTCTCATCGCGGTTCAAAGGCAGTGGATCTGGGACAGAGTTCACTCTCACCATCA

GCGACCTGGAGTGTGCCGATGCTGCCACTTACTACTGTCAATGTATTTATTATGGTAGTGATGATGTCATATACCAT

ACTTTCGGCGGAGGGACCGAGGTGGTGGTCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

416G1 CHIMERIC LIGHT CHAIN VARIABLE LIGHT CHAIN NUCLEOTIDE SEQUENCE
SEQ ID NO: 26

```
CCTACAGCCTCAGCAGCACCCTGACGCTGAGCAAAGCAGACTACGAGAAACACAAAGTCTACGCCTGCGAAGTCA
CCCATCAGGGCCTGAGCTCGCCCGTCACAAAGAGCTTCAACAGGGGAGAGTGT
```

416G1 CHIMERIC LIGHT CHAIN VARIABLE LIGHT CHAIN NUCLEOTIDE SEQUENCE
SEQ ID NO: 26

```
GACGTCGTGATGACCCAGACTCCAGCCTCCGTGTCTGAACCTGTGGGAGGCGCAGTCACCATCAAGTGCCAGGCC
AGTCAGAGCATTGGTAGTGATTTAGCCTGGTATCAGCAGAAACCAGGGCAGCCTCCCAAGCTCCTGATCTACAGG
GCATCCACTCTGGCATCTGGGGTCTCATCGCGGTTCAAAGGCAGTGGATCTGGGACAGATTCACTCTCACCATCA
GCGACCTGGAGTGTGCCGATGCTGCCACTTACTACTGTCAATGTATTTATTATGGTAGTGATGATGTCATATACCAT
ACTTTCGGCGGAGGGACCGAGGTGGTGGTCAAA
```

416G1 CHIMERIC LIGHT CHAIN FULL-LENGTH AMINO ACID SEQUENCE. HUMAN KAPPA CONSTANT
DOMAIN IS UNDERLINED
SEQ ID NO: 27

DVVMTQTPASVSEPVGGAVTIKCQASQSIGSDLAWYQQKPGQPPKLLIYRASTLASGVSSRFKGSGSGTEFTLTISDLEC
ADAATYYCQCIYYGSDDVIYHTFGGGTEVVVK<u>RTVAAPSVFIFPPSDEQLKSGTASVVCLLNNFYPREAKVQWKVDNAL</u>
<u>QSGNSQESVTEQDSKDSTYSLSSTLTLSKADYEKHKVYACEVTHQGLSSPVTKSFNRGEC</u>

416G1 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 28

DVVMTQTPASVSEPVGGAVTIKC<u>QASQSIGSDLA</u>WYQQKPGQPPKLLIY<u>RASTLAS</u>GVSSRFKGSGSGTEFTLTISDLEC
ADAATYYC<u>QCIYYGSDDVIYHT</u>FGGGTEVVVK

416G1 CHIMERIC HEAVY CHAIN FULL-LENGTH NUCLEOTIDE SEQUENCE
SEQ ID NO: 29

```
CAGTCGGTGGAGGAGTCCGGGGGTCGCCTGGTCACGCCTGGGACACCCCTGACACTCACCTGCACAGTCTCTGGA
TTCACTATCAATAGCTACCACATGATCTGGGTCCGCCAGGCTCCAGGGGAGGGGCTGGAATACATCGGATTCATTA
ATGATGGTGGTTTCACATACTACGCGAGCTGGGCAAAAGGCCGATTTATCATCTCCAGAACCTCGACCACGGTGG
ATCTGAAAATGACCAGTCTGACAGTCGCGGACACGGCCACCTATTTCTGTGCCAGAGGGGTTGATGGTACTAGTT
ATCCTGACTTATGGGGCCCGGGCACCCTGGTCACCGTCTCGAGCGCTAGCACCAAGGGCCCATCGGTCTTCCCCCT
GGCACCCTCCTCCAAGAGCACCTCTGGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCTTCCCGGCTGTCCTACAGTCCTCAGG
ACTCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACCG
TGCCCAGCACCTGAAGCCGCGGGGGCACCGTCAGTCTTCCTCTTCCCCCCAAAACCCAAGGACACCCTCATGATCT
CCCGGACCCCTGAGGTCACATGCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCGCGGTCTCCAACAAAGCCC
TCCCAGCCCCCATCGAGAAAACCATCTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGGACTCCGACGGC
TCCTTCTTCCTCTATAGCAAGCTCACCGTGGACAAGAGCAGGTGGCAGCAGGGGAACGTCTTCTCATGCTCCGTGA
TGCATGAGGCTCTGCACAACCACTACACGCAGAAGAGCCTCTCCCTGTCTCGGGT
```

416G1 CHIMERIC HEAVY CHAIN VARIABLE HEAVY CHAIN NUCLEOTIDE SEQUENCE
SEQ ID NO: 30

```
CAGTCGGTGGAGGAGTCCGGGGGTCGCCTGGTCACGCCTGGGACACCCCTGACACTCACCTGCACAGTCTCTGGA
TTCACTATCAATAGCTACCACATGATCTGGGTCCGCCAGGCTCCAGGGGAGGGGCTGGAATACATCGGATTCATTA
ATGATGGTGGTTTCACATACTACGCGAGCTGGGCAAAAGGCCGATTTATCATCTCCAGAACCTCGACCACGGTGG
ATCTGAAAATGACCAGTCTGACAGTCGCGGACACGGCCACCTATTTCTGTGCCAGAGGGGTTGATGGTACTAGTT
ATCCTGACTTATGGGGCCCGGGCACCCTGGTCACCGTCTCGAGC
```

416G1 CHIMERIC HEAVY CHAIN FULL-LENGTH AMINO ACID SEQUENCE. HUMAN GAMMA-1 CONSTANT DOMAIN IS UNDERLINED

SEQ ID NO: 31

QSVEESGGRLVTPGTPLTLTCTVSGFTINSYHMIWVRQAPGEGLEYIGFINDGGFTYYASWAKGRFIISRTSTTVDLKMTS

LTVADTATYFCARGVDGTSYPDLWGPGTLVTVSS<u>ASTKGPSVFPLAPSSKSTSGGTAALGCLVKDYFPEPVTVSWNSGA</u>

<u>LTSGVHTFPAVLQSSGLYSLSSVVTVPSSSLGTQTYICNVNHKPSNTKVDKRVEPKSCDKTHTCPPCPAPEAAGAPSVFLF</u>

<u>PPKPKDTLMISRTPEVTCVVVDVSHEDPEVKFNWYVDGVEVHNAKTKPREEQYNSTYRVVSVLTVLHQDWLNGKEYK</u>

<u>CAVSNKALPAPIEKTISKAKGQPREPQVYTLPPSRDELTKNQVSLTCLVKGFYPSDIAVEWESNGQPENNYKTTPPVLDS</u>

<u>DGSFFLYSKLTVDKSRWQQGNVFSCSVMHEALHNHYTQKSLSLSPG</u>

416G1 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 32

QSVEESGGRLVTPGTPLTLTCTVSGFTINS<u>YHMI</u>WVRQAPGEGLEYIG<u>FINDGGFTYYASWAKG</u>RFIISRTSTTVDLKMTS

LTVADTATYFCAR<u>GVDGTSYPDL</u>WGPGTLVTVSS

418E10 CHIMERIC LIGHT CHAIN FULL-LENGTH NUCLEOTIDE SEQUENCE

SEQ ID NO: 33

GCCCTGGTGATGACCCAGACTCCATCCCCTGTGTCTGCGGCTGTGGGAGGCACAGTCACCATCAACTGCCAGGCC

AGTCAGAGCATTGGTAGTAACTTGAACTGGTATCAGCAGAAACCAGGGCAGCCTCCCAAGCTCCTGATTTATTATG

TATCCACTCTGGCATCTGGGGTCCCATCGCGGTTCAAAGGCAGTGGATCTGGGACAGAGTACACTCTCACCATCAG

CGGCGTGCAGTGTGACGATGCTGCCACTTACTACTGCCTAGGTGTTTGGAATTATTGGGGTGATGACGGTACTGCT

TTCGGCGGAGGCACCGAGGTGGAGGTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418E10 CHIMERIC LIGHT CHAIN VARIABLE LIGHT CHAIN NUCLEOTIDE SEQUENCE

SEQ ID NO: 34

GCCCTGGTGATGACCCAGACTCCATCCCCTGTGTCTGCGGCTGTGGGAGGCACAGTCACCATCAACTGCCAGGCC

AGTCAGAGCATTGGTAGTAACTTGAACTGGTATCAGCAGAAACCAGGGCAGCCTCCCAAGCTCCTGATTTATTATG

TATCCACTCTGGCATCTGGGGTCCCATCGCGGTTCAAAGGCAGTGGATCTGGGACAGAGTACACTCTCACCATCAG

CGGCGTGCAGTGTGACGATGCTGCCACTTACTACTGCCTAGGTGTTTGGAATTATTGGGGTGATGACGGTACTGCT

TTCGGCGGAGGCACCGAGGTGGAGGTCAAA

418E10 CHIMERIC LIGHT CHAIN FULL-LENGTH AMINO ACID SEQUENCE. HUMAN KAPPA CONSTANT DOMAIN IS UNDERLINED

SEQ ID NO: 35

ALVMTQTPSPVSAAVGGTVTINCQASQSIGSNLNWYQQKPGQPPKLLIYYVSTLASGVPSRFKGSGSGTEYTLTISGVQ

CDDAATYYCLGVWNYWGDDGTAFGGGTEVEVK<u>RTVAAPSVFIFPPSDEQLKSGTASVVCLLNNFYPREAKVQWKVD</u>

<u>NALQSGNSQESVTEQDSKDSTYSLSSTLTLSKADYEKHKVYACEVTHQGLSSPVTKSFNRGEC</u>

418E10 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 36

ALVMTQTPSPVSAAVGGTVTINC<u>QASQSIGSNLN</u>WYQQKPGQPPKLLIY<u>YVSTLAS</u>GVPSRFKGSGSGTEYTLTISGVQ

CDDAATYYC<u>LGVWNYWGDDGTA</u>FGGGTEVEVK

418E10 CHIMERIC HEAVY CHAIN FULL-LENGTH NUCLEOTIDE SEQUENCE

SEQ ID NO: 37

CAGTCGCTGGAGGAGTCCGGGGGTCGCCTGGTCACGCCTGGGACACCCCTGACACTCACCTGCACAGCCTCTGAT

TTCTCCCTCAGTACCTATTATATGAGCTGGGTCCGCCAGGCTCCAGGGAAGGGGCTGGAGTGGATCGGAAGTATT

TATGATAGTGGTGCCGCATACTACGCGACCTGGGCGAAGGGCCGATTCACCATCTCCAGAACGTCGACCACGGTG

GATCTGAGAATGACCAGTCTGACAGCCGCGGACACGGCCACCTATTTCTGTGCCAGAGATCCTATTAATAATGCCA

```
TCTGGGGCCAAGGGACCCTCGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT
```

418E10 CHIMERIC HEAVY CHAIN VARIABLE HEAVY CHAIN NUCLEOTIDE SEQUENCE
SEQ ID NO: 38
```
CAGTCGCTGGAGGAGTCCGGGGGTCGCCTGGTCACGCCTGGGACACCCCTGACACTCACCTGCACAGCCTCTGAT

TTCTCCCTCAGTACCTATTATATGAGCTGGGTCCGCCAGGCTCCAGGGAAGGGGCTGGAGTGGATCGGAAGTATT

TATGATAGTGGTGCCGCATACTACGCGACCTGGGCGAAGGGCCGATTCACCATCTCCAGAACGTCGACCACGGTG

GATCTGAGAATGACCAGTCTGACAGCCGCGGACACGGCCACCTATTTCTGTGCCAGAGATCCTATTAATAATGCCA

TCTGGGGCCAAGGGACCCTCGTCACCGTCTCGAGC
```

418E10 CHIMERIC HEAVY CHAIN FULL-LENGTH AMINO ACID SEQUENCE. HUMAN GAMMA-1
CONSTANT DOMAIN IS UNDERLINED
SEQ ID NO: 39
QSLEESGGRLVTPGTPLTLTCTASDFSLSTYYMSWVRQAPGKGLEWIGSIYDSGAAYYATWAKGRFTISRTSTTVDLRM

TSLTAADTATYFCARDPINNAIWGQGTLVTVSSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKRVEPKSCDKTHTCPPCPAPEAAGAPSVFLFPP

KPKDTLMISRTPEVTCVVVDVSHEDPEVKFNWYVDGVEVHNAKTKPREEQYNSTYRVVSVLTVLHQDWLNGKEYKCA

VSNKALPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

418E10 CHIMERIC HEAVY CHAIN VARIABLE HEAVY CHAIN AMINO ACID SEQUENCE.
COMPLIMENTARITY DETERMINING REGIONS ARE UNDERLINED
SEQ ID NO: 40
QSLEESGGRLVTPGTPLTLTCTASDFSLSTYYMSWVRQAPGKGLEWIGSIYDSGAAYYATWAKGRFTISRTSTTVDLRM

TSLTAADTATYFCARDPINNAIWGQGTLVTVSS

418E4 CHIMERIC LIGHT CHAIN FULL-LENGTH NUCLEOTIDE SEQUENCE
SEQ ID NO: 41
```
GCCCTGGTGATGACCCAGACTCCATCCCCTGTGTCTGCGGCTGTGGGAGGCACAGTCACCATCAACTGCCAGGCC

AGTCAGAGTATTGCTACTAACTTGAACTGGTATCAGCAGAAACCAGGGCAGCCTCCCAAGCTCCTGATCTATTATA

CATCCAGTCTGGCATCTGGGGTCCCATCGCGGTTCAGCGGCAGTGGATCTGGCACAGAGTTCACTCTCACCATCAG

CGGTGTGCAGTGTGACGATGCTGCCACTTACTACTGCCAGGTGTTTGGAATTATTGGGGTGATGATGGTACTGCT

TTCGGCGGAGGGACCGAGGTGGAGTTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT
```

418E4 CHIMERIC LIGHT CHAIN VARIABLE LIGHT CHAIN NUCLEOTIDE SEQUENCE

SEQ ID NO: 42

GCCCTGGTGATGACCCAGACTCCATCCCCTGTGTCTGCGGCTGTGGGAGGCACAGTCACCATCAACTGCCAGGCC

AGTCAGAGTATTGCTACTAACTTGAACTGGTATCAGCAGAAACCAGGGCAGCCTCCCAAGCTCCTGATCTATTATA

CATCCAGTCTGGCATCTGGGGTCCCATCGCGGTTCAGCGGCAGTGGATCTGGCACAGAGTTCACTCTCACCATCAG

CGGTGTGCAGTGTGACGATGCTGCCACTTACTACTGCCTAGGTGTTTGGAATTATTGGGGTGATGATGGTACTGCT

TTCGGCGGAGGGACCGAGGTGGAGTTCAAA

418E4 CHIMERIC LIGHT CHAIN FULL-LENGTH AMINO ACID SEQUENCE. HUMAN KAPPA CONSTANT
DOMAIN IS UNDERLINED

SEQ ID NO: 43

ALVMTQTPSPVSAAVGGTVTINCQASQSIATNLNWYQQKPGQPPKLLIYYTSSLASGVPSRFSGSGSGTEFTLTISGVQC

DDAATYYCLGVWNYWGDDGTAFGGGTEVEFK<u>RTVAAPSVFIFPPSDEQLKSGTASVVCLLNNFYPREAKVQWKVDN</u>

<u>ALQSGNSQESVTEQDSKDSTYSLSSTLTLSKADYEKHKVYACEVTHQGLSSPVTKSFNRGEC</u>

418E4 CHIMERIC LIGHT CHAIN VARIABLE LIGHT CHAIN AMINO ACID SEQUENCE. COMPIMENTARITY
DETERMINING REGIONS ARE UNDERLINED

SEQ ID NO: 44

ALVMTQTPSPVSAAVGGTVTINCQ<u>ASQSIATNLN</u>WYQQKPGQPPKLLIY<u>YTSSLAS</u>GVPSRFSGSGSGTEFTLTISGVQC

DDAATYYC<u>LGVWNYWGDDGTA</u>FGGGTEVEFK

418E4 CHIMERIC HEAVY CHAIN FULL-LENGTH NUCLEOTIDE SEQUENCE

SEQ ID NO: 45

CAGTCGCTGGAGGAGTCCGGGGGTCGCCTGGTCACGCCTGGGACACCCCTGACACTCACCTGCACAGCCTCTGAA

TTCTCCCTCAGTAGCTACTACATGAGCTGGGTCCGCCAGGCTCCAGGGAAGGGGCTGGAATGGATCGGAAGTATT

TATGCTAGTGGTAGCGCATACTACGCGAGTTGGGCGAAGGGCCGATTCACCATCTCCAGAACGTCGACCACGGTG

GATCTGAAAATGACCAGTCTGACAGCCGCGGACACGGCCACCTATTTCTGTGTCAGAGATCCTATTAACAATGACA

TCTGGGGCCCAGGCACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

418E4 CHIMERIC HEAVY CHAIN VARIABLE HEAVY CHAIN NUCLEOTIDE SEQUENCE

SEQ ID NO: 46

CAGTCGCTGGAGGAGTCCGGGGGTCGCCTGGTCACGCCTGGGACACCCCTGACACTCACCTGCACAGCCTCTGAA

TTCTCCCTCAGTAGCTACTACATGAGCTGGGTCCGCCAGGCTCCAGGGAAGGGGCTGGAATGGATCGGAAGTATT

TATGCTAGTGGTAGCGCATACTACGCGAGTTGGGCGAAGGGCCGATTCACCATCTCCAGAACGTCGACCACGGTG

GATCTGAAAATGACCAGTCTGACAGCCGCGGACACGGCCACCTATTTCTGTGTCAGAGATCCTATTAACAATGACA

TCTGGGGCCCAGGCACCCTGGTCACCGTCTCGAGC

418E4 CHIMERIC HEAVY CHAIN FULL-LENGTH AMINO ACID SEQUENCE. HUMAN GAMMA-1 CONSTANT DOMAIN IS UNDERLINED
SEQ ID NO: 47

QSLEESGGRLVTPGTPLTLTCTASEFSLSSYYMSWVRQAPGKGLEWIGSIYASGSAYYASWAKGRFTISRTSTTVDLKMT

SLTAADTATYFCVRDPINNDIWGPGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHTCPPCPAPEAAGAPSVFLFPPK

PKDTLMISRTPEVTCVVVDVSHEDPEVKFNWYVDGVEVHNAKTKPREEQYNSTYRVVSVLTVLHQDWLNGKEYKCAV

SNKALPAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG

418E4 CHIMERIC HEAVY CHAIN VARIABLE HEAVY CHAIN AMINO ACID SEQUENCE. COMPLIMENTARITY DETERMINING REGIONS ARE UNDERLINED
SEQ ID NO: 48

QSLEESGGRLVTPGTPLTLTCTASEFSLSSYYMSWVRQAPGKGLEWIGSIYASGSAYYASWAKGRFTISRTSTTVDLKMT

SLTAADTATYFCVRDPINNDIWGPGTLVTVSS

418H5 CHIMERIC LIGHT CHAIN FULL-LENGTH NUCLEOTIDE SEQUENCE
SEQ ID NO: 49

GCCCAAGTGCTGACCCAGACTCCAGCCTCCGTGTCTGCAACTGTGGGAAGCACAGTCACCATCAGTTGCCAGTCCA

GTCCGAGTGTTTATAAGAACAACCAATTAGCCTGGTATCAGCAGAAACCAGGGCAGCCTCCCAAACTCCTGATCTA

TCTGGCATCTACTCTGGCATCTGGGGTCCCATCGCGGTTCAAAGGCAGTGGATCTGGGACAGAGTTCACTCTCACC

ATCAGCGACCTGGAGTGTGCCGATGCTGCCACTTACTACTGTGCAGGCGGTTATAGTAGTAGTAGTGATACTGCTT

TCGGCGGAGGGACCGAGGTGGAGGTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418H5 CHIMERIC LIGHT CHAIN VARIABLE LIGHT CHAIN NUCLEOTIDE SEQUENCE
SEQ ID NO: 50

GCCCAAGTGCTGACCCAGACTCCAGCCTCCGTGTCTGCAACTGTGGGAAGCACAGTCACCATCAGTTGCCAGTCCA

GTCCGAGTGTTTATAAGAACAACCAATTAGCCTGGTATCAGCAGAAACCAGGGCAGCCTCCCAAACTCCTGATCTA

TCTGGCATCTACTCTGGCATCTGGGGTCCCATCGCGGTTCAAAGGCAGTGGATCTGGGACAGAGTTCACTCTCACC

ATCAGCGACCTGGAGTGTGCCGATGCTGCCACTTACTACTGTGCAGGCGGTTATAGTAGTAGTAGTGATACTGCTT

TCGGCGGAGGGACCGAGGTGGAGGTCAAA

418H5 CHIMERIC LIGHT CHAIN FULL-LENGTH AMINO ACID SEQUENCE. HUMAN KAPPA CONSTANT DOMAIN IS UNDERLINED
SEQ ID NO: 51

AQVLTQTPASVSATVGSTVTISCQSSPSVYKNNQLAWYQQKPGQPPKLLIYLASTLASGVPSRFKGSGSGTEFTLTISDLE

CADAATYYCAGGYSSSSDTAFGGGTEVEVKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

418H5 CHIMERIC LIGHT CHAIN VARIABLE LIGHT CHAIN AMINO ACID SEQUENCE. COMPIMENTARITY DETERMINING REGIONS ARE UNDERLINED
SEQ ID NO: 52

AQVLTQTPASVSATVGSTVTISCQSSPSVYKNNQLAWYQQKPGQPPKLLIYLASTLASGVPSRFKGSGSGTEFTLTISDLE

CADAATYYCAGGYSSSSDTAFGGGTEVEVK

418H5 CHIMERIC HEAVY CHAIN FULL-LENGTH NUCLEOTIDE SEQUENCE
SEQ ID NO: 53

CAGTCGCTGGAGGAGTCCGGGGGTCGCCTGGTCACGCCTGGGACACCCCTGACACTCACCTGCACAGTCTCTGGA

ATCGACCTCAGTGCCTACCACATGAGCTGGGTCCGCCAGGCTCCAGGGAAGGGGCTGGAATACATCGGAATGATT

GGTAGTAGTGGTACCATACACTACGCGAACTGGGCGAAAGGCCGATTCACCATCTCCAAAACCTCGACCACGGTG

GATCTGAAAATCACCAGTCCGACAACCGAGGACACGGCCACCTATTTCTGTGCCAGGGACAGTTATAATAGTGATT

ATGCCTTTAACTTATGGGGCCCAGGGACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418H5 CHIMERIC HEAVY CHAIN VARIABLE HEAVY CHAIN NUCLEOTIDE SEQUENCE
                                                              SEQ ID NO: 54
CAGTCGCTGGAGGAGTCCGGGGGTCGCCTGGTCACGCCTGGGACACCCCTGACACTCACCTGCACAGTCTCTGGA

ATCGACCTCAGTGCCTACCACATGAGCTGGGTCCGCCAGGCTCCAGGGAAGGGGCTGGAATACATCGGAATGATT

GGTAGTAGTGGTACCATACACTACGCGAACTGGGCGAAAGGCCGATTCACCATCTCCAAAACCTCGACCACGGTG

GATCTGAAAATCACCAGTCCGACAACCGAGGACACGGCCACCTATTTCTGTGCCAGGGACAGTTATAATAGTGATT

ATGCCTTTAACTTATGGGGCCCAGGGACCCTGGTCACCGTCTCGAGC

418H5 CHIMERIC HEAVY CHAIN FULL-LENGTH AMINO ACID SEQUENCE. HUMAN GAMMA-1 CONSTANT
DOMAIN IS UNDERLINED
                                                              SEQ ID NO: 55
QSLEESGGRLVTPGTPLTLTCTVSGIDLSAYHMSWVRQAPGKGLEYIGMIGSSGTIHYANWAKGRFTISKTSTTVDLKITS

PTTEDTATYFCARDSYNSDYAFNLWGPGTLVTVSS<u>ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKSCDKTHTCPPCPAPEAAGAPSVFL

FPPKPKDTLMISRTPEVTCVVVDVSHEDPEVKFNWYVDGVEVHNAKTKPREEQYNSTYRVVSVLTVLHQDWLNGKEY

KCAVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG</u>

418H5 CHIMERIC HEAVY CHAIN VARIABLE HEAVY CHAIN AMINO ACID SEQUENCE. COMPLIMENTARITY
DETERMINING REGIONS ARE UNDERLINED
                                                              SEQ ID NO: 56
QSLEESGGRLVTPGTPLTLTCTVSGIDLS<u>AYHMS</u>WVRQAPGKGLEYIG<u>MIGSSGTIHYANWAKG</u>RFTISKTSTTVDLKITS

PTTEDTATYFCARD<u>SYNSDYAFN</u>LWGPGTLVTVSS

419D9 CHIMERIC LIGHT CHAIN FULL-LENGTH NUCLEOTIDE SEQUENCE
                                                              SEQ ID NO: 57
GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTATCCTGGTATCAGCAGAAACCAGGGCAGCCTCCCAAGCGCCTGATCTATTC

TGCATCCACTCTGGCATCTGGGGTCCCATCGCGGTTCAAAGGCAGTGGATCTGGGACACAGTTCACTCTCACCATC

AGCGACCTGGAGTGTGACGATGCTGCCACTTACTACTGTGCAGGCGGTTATAATACTGTTACTGATACTTTTGCTTT

CGGCAGAGGCACCGAGGTGGAGGTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

419D9 CHIMERIC LIGHT CHAIN VARIABLE LIGHT CHAIN NUCLEOTIDE SEQUENCE

SEQ ID NO: 58

GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTATCCTGGTATCAGCAGAAACCAGGGCAGCCTCCCAAGCGCCTGATCTATTC

TGCATCCACTCTGGCATCTGGGGTCCCATCGCGGTTCAAAGGCAGTGGATCTGGGACACAGTTCACTCTCACCATC

AGCGACCTGGAGTGTGACGATGCTGCCACTTACTACTGTGCAGGCGGTTATAATACTGTTACTGATACTTTTGCTTT

CGGCAGAGGCACCGAGGTGGAGGTCAAA

419D9 CHIMERIC LIGHT CHAIN FULL-LENGTH AMINO ACID SEQUENCE. HUMAN KAPPA CONSTANT
DOMAIN IS UNDERLINED

SEQ ID NO: 59

AQVLTQTASPVSAAVGGTVTINCQSSQSVYSNWLSWYQQKPGQPPKRLIYSASTLASGVPSRFKGSGSGTQFTLTISDL

ECDDAATYYCAGGYNTVTDTFAFGRGTEVEVK<u>RTVAAPSVFIFPPSDEQLKSGTASVVCLLNNFYPREAKVQWKVDNA</u>

<u>LQSGNSQESVTEQDSKDSTYSLSSTLTLSKADYEKHKVYACEVTHQGLSSPVTKSFNRGEC</u>

419D9 CHIMERIC LIGHT CHAIN VARIABLE LIGHT CHAIN AMINO ACID SEQUENCE. COMPIMENTARITY
DETERMINING REGIONS ARE UNDERLINED

SEQ ID NO: 60

AQVLTQTASPVSAAVGGTVTINC<u>QSSQSVYSNWLS</u>WYQQKPGQPPKRLIY<u>SASTLAS</u>GVPSRFKGSGSGTQFTLTISDL

ECDDAATYYC<u>AGGYNTVTDTFAF</u>GRGTEVEVK

419D9 CHIMERIC HEAVY CHAIN FULL-LENGTH NUCLEOTIDE SEQUENCE

SEQ ID NO: 61

CAGTCGTTGGAGGAGTCCGGGGGAGACCTGGTCAAGCCTGGGGCATCCCTGACACTCACCTGCACAGCCTCTGGA

TTCTCCTTCAGTAGCAGGCACTACATGTGTTGGGTCCGCCAGGCTCCAGGGGAGGGGCTGGAGTGGATCGCATGC

ATTTATACTGGTAGTAGTGGTACTCCTCACTACGCGAGCTGGGCGAAAGGCCGATTCACCATCTCCCAAACCTCGT

CGACCACGGTGACTCTGCAAATGACCAGTCTGACAGCCGCGGACACGGCCACCTATTTCTGTTCGAGCGAAGGTA

ACCTGTGGGGCCCAGGCACCCTGGTCACCGTCTCGAGCGCTAGCACCAAGGGCCCATCGGTCTTCCCCCTGGCACC

CTCCTCCAAGAGCACCTCTGGGGGCACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAGC

CCAGCAACACCAAGGTGGACAAGAGAGTTGAGCCCAAATCTTGTGACAAAACTCACACATGCCCACCGTGCCCAG

CACCTGAAGCCGCGGGGCACCGTCAGTCTTCCTCTTCCCCCCAAAACCCAAGGACACCCTCATGATCTCCCGGAC

CCCTGAGGTCACATGCGTGGTGGTGGACGTGAGCCACGAAGACCCTGAGGTCAAGTTCAACTGGTACGTGGACG

GCGTGGAGGTGCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCGCGGTCTCCAACAAAGCCCTCCCAGCC

CCCATCGAGAAAACCATCTCCAAAGCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCCGACGGCTCCTTCTTC

CTCTATAGCAAGCTCACCGTGGACAAGAGCAGGTGGCAGCAGGGGAACGTCTTCTCATGCTCCGTGATGCATGAG

GCTCTGCACAACCACTACACGCAGAAGAGCCTCTCCCTGTCTCCGGGT

419D9 CHIMERIC HEAVY CHAIN VARIABLE HEAVY CHAIN NUCLEOTIDE SEQUENCE

SEQ ID NO: 62

CAGTCGTTGGAGGAGTCCGGGGGAGACCTGGTCAAGCCTGGGGCATCCCTGACACTCACCTGCACAGCCTCTGGA

TTCTCCTTCAGTAGCAGGCACTACATGTGTTGGGTCCGCCAGGCTCCAGGGGAGGGGCTGGAGTGGATCGCATGC

ATTTATACTGGTAGTAGTGGTACTCCTCACTACGCGAGCTGGGCGAAAGGCCGATTCACCATCTCCCAAACCTCGT

CGACCACGGTGACTCTGCAAATGACCAGTCTGACAGCCGCGGACACGGCCACCTATTTCTGTTCGAGCGAAGGTA

ACCTGTGGGGCCCAGGCACCCTGGTCACCGTCTCGAGC

419D9 CHIMERIC HEAVY CHAIN FULL-LENGTH AMINO ACID SEQUENCE. HUMAN GAMMA-1 CONSTANT
DOMAIN IS UNDERLINED
SEQ ID NO: 63
QSLEESGGDLVKPGASLTLTCTASGFSFSSRHYMCWVRQAPGEGLEWIACIYTGSSGTPHYASWAKGRFTISQTSSTTV

TLQMTSLTAADTATYFCSSEGNLWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

419D9 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 64
QSLEESGGDLVKPGASLTLTCTASGFSFSSRHYMCWVRQAPGEGLEWIACIYTGSSGTPHYASWAKGRFTISQTSSTTV

TLQMTSLTAADTATYFCSSEGNLWGPGTLVTVSS

420H5 CHIMERIC LIGHT CHAIN FULL-LENGTH NUCLEOTIDE SEQUENCE
SEQ ID NO: 65
GCCCTTGTGATGACCCAGACTCCAGCCTCCGTGTCTGCAGCTGTGGGAGGCACAGTCACCATCAATTGCCAGGCCA

GTGAGGACATTGATACCTATTTAGCCTGGTATCAGCAGAAACCAGGGCAGCCTCCCAAGCTCCTGATCTTTTATGC

ATCCGATCTGGCATCTGGGGTCCCATCGCGGTTCAAAGGCAGTGGATCTGGGACAGAGTTCACTCTCACCATCAGC

GGTGTGCAGTGTGACGATGCTGCCACTTACTACTGTCAAGGCGGTTACTATACTAGTAGTGCTGATACGAGGGGT

GCTTTCGGCGGAGGCACCGAGGTGGTGGTCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

CCTACAGCCTCAGCAGCACCCTGACGCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAGTGT

420H5 CHIMERIC LIGHT CHAIN VARIABLE LIGHT CHAIN NUCLEOTIDE SEQUENCE
SEQ ID NO: 66
GCCCTTGTGATGACCCAGACTCCAGCCTCCGTGTCTGCAGCTGTGGGAGGCACAGTCACCATCAATTGCCAGGCCA

GTGAGGACATTGATACCTATTTAGCCTGGTATCAGCAGAAACCAGGGCAGCCTCCCAAGCTCCTGATCTTTTATGC

ATCCGATCTGGCATCTGGGGTCCCATCGCGGTTCAAAGGCAGTGGATCTGGGACAGAGTTCACTCTCACCATCAGC

GGTGTGCAGTGTGACGATGCTGCCACTTACTACTGTCAAGGCGGTTACTATACTAGTAGTGCTGATACGAGGGGT

GCTTTCGGCGGAGGCACCGAGGTGGTGGTCAAA

420H5 CHIMERIC LIGHT CHAIN FULL-LENGTH AMINO ACID SEQUENCE. HUMAN KAPPA CONSTANT
DOMAIN IS UNDERLINED
SEQ ID NO: 67
ALVMTQTPASVSAAVGGTVTINCQASEDIDTYLAWYQQKPGQPPKLLIFYASDLASGVPSRFKGSGSGTEFTLTISGVQC

DDAATYYCQGGYYTSSADTRGAFGGGTEVVVKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

420H5 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 68
ALVMTQTPASVSAAVGGTVTINCQASEDIDTYLAWYQQKPGQPPKLLIFYASDLASGVPSRFKGSGSGTEFTLTISGVQC

DDAATYYCQGGYYTSSADTRGAFGGGTEVVVK

420H5 CHIMERIC HEAVY CHAIN FULL-LENGTH NUCLEOTIDE SEQUENCE
SEQ ID NO: 69
CAGTCGTTGGAGGAGTCCGGGGGAGACCTGGTCAAGCCTGGGGCATCCCTGACACTCACCTGCACAGCCTCTGGA

TTCTCCTTCAGTAGCAACTACTGGATATGCTGGGTCCGCCAGGCTCCAGGGAAGGGGCTGGAGTGGATCGCATGC

ATTTATGTTGGTAGTAGTGGTGACACTTACTACGCGAGCTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

-continued

```
GTAGTTATTATATGTTTAACTTGTGGGGCCAGGGGACCCTGGTCACCGTCTCGAGCGCTAGCACCAAGGGCCCATC

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT
```

420H5 CHIMERIC HEAVY CHAIN VARIABLE HEAVY CHAIN NUCLEOTIDE SEQUENCE
SEQ ID NO: 70

```
CAGTCGTTGGAGGAGTCCGGGGGAGACCTGGTCAAGCCTGGGGCATCCCTGACACTCACCTGCACAGCCTCTGGA

TTCTCCTTCAGTAGCAACTACTGGATATGCTGGGTCCGCCAGGCTCCAGGGAAGGGGCTGGAGTGGATCGCATGC

ATTTATGTTGGTAGTAGTGGTGACACTTACTACGCGAGCTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGGACCCTGGTCACCGTCTCGAGC
```

420H5 CHIMERIC HEAVY CHAIN FULL-LENGTH AMINO ACID SEQUENCE. HUMAN GAMMA-1 CONSTANT DOMAIN IS UNDERLINED
SEQ ID NO: 71

QSLEESGGDLVKPGASLTLTCTASGFSFSSNYWICWVRQAPGKGLEWIACIYVGSSGDTYYASWAKGRFTISKTSSTTVT

LQMTSLTAADTATYFCARDSSSYYMFNLWGQGTLVTVSS<u>ASTKGPSVFPLAPSSKSTSGGTAALGCLVKDYFPEPVTVS</u>

<u>WNSGALTSGVHTFPAVLQSSGLYSLSSVVTVPSSSLGTQTYICNVNHKPSNTKVDKRVEPKSCDKTHTCPPCPAPEAAG</u>

<u>APSVFLFPPKPKDTLMISRTPEVTCVVVDVSHEDPEVKFNWYVDGVEVHNAKTKPREEQYNSTYRVVSVLTVLHQDWL</u>

<u>NGKEYKCAVSNKALPAPIEKTISKAKGQPREPQVYTLPPSRDELTKNQVSLTCLVKGFYPSDIAVEWESNGQPENNYKTT</u>

<u>PPVLDSDGSFFLYSKLTVDKSRWQQGNVFSCSVMHEALHNHYTQKSLSLSPG</u>

420H5 CHIMERIC HEAVY CHAIN VARIABLE HEAVY CHAIN AMINO ACID SEQUENCE. COMPLIMENTARITY DETERMINING REGIONS ARE UNDERLINED
SEQ ID NO: 72

QSLEESGGDLVKPGASLTLTCTASGFSFS<u>SNYWIC</u>WVRQAPGKGLEWIAC<u>IYVGSSGDTYYASWAKG</u>RFTISKTSSTTVT

LQMTSLTAADTATYFCARD<u>SSSYYMFNL</u>WGQGTLVTVSS

420H6 CHIMERIC LIGHT CHAIN FULL-LENGTH NUCLEOTIDE SEQUENCE
SEQ ID NO: 73

```
GCTCAAGTGCTGACCCAGACTGCATCGCCCGTGTCTGCCGCTGTGGGAGGCACAGTCACCATCAACTGCCAGGCC

AGTCAGAGTGTTTATAGTAACTGGTTATCCTGGTATCAGCAGAAACCAGGGCAGCCTCCCAAGCGCCTGATCTATT

CTGCATCCACTCTGGCATCTGGGGTCCCATCGCGGTTCAAAGGCAGTGGATCTGGGACACAGTTCACTCTCACCAT

TAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT
```

420H6 CHIMERIC LIGHT CHAIN VARIABLE LIGHT CHAIN NUCLEOTIDE SEQUENCE
SEQ ID NO: 74
GCTCAAGTGCTGACCCAGACTGCATCGCCCGTGTCTGCCGCTGTGGGAGGCACAGTCACCATCAACTGCCAGGCC

AGTCAGAGTGTTTATAGTAACTGGTTATCCTGGTATCAGCAGAAACCAGGGCAGCCTCCCAAGCGCCTGATCTATT

CTGCATCCACTCTGGCATCTGGGGTCCCATCGCGGTTCAAAGGCAGTGGATCTGGGACACAGTTCACTCTCACCAT

TAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAA

420H6 CHIMERIC LIGHT CHAIN FULL-LENGTH AMINO ACID SEQUENCE. HUMAN KAPPA CONSTANT
DOMAIN IS UNDERLINED
SEQ ID NO: 75
AQVLTQTASPVSAAVGGTVTINCQASQSVYSNWLSWYQQKPGQPPKRLIYSASTLASGVPSRFKGSGSGTQFTLTISDL

ECDDAATYYCAGGYNTVIDTFAFGGGTEVEFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

420H6 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 76
AQVLTQTASPVSAAVGGTVTINCQASQSVYSNWLSWYQQKPGQPPKRLIYSASTLASGVPSRFKGSGSGTQFTLTISDL

ECDDAATYYCAGGYNTVIDTFAFGGGTEVEFK

420H6 CHIMERIC HEAVY CHAIN FULL-LENGTH NUCLEOTIDE SEQUENCE
SEQ ID NO: 77
CAGCAGCAGCTGGAGGAGTCCGGGGGAGGCCTGGTCAAGCCTGGAGGAACCCTGACACTCACCTGCAAAGCCTC

TGGAATTGACTTCAGTAGTAGTTACTACATGTGCTGGGTCCGCCAGGCTCCAGGGGAGGGGCTGGAGTGGATCGC

ATGCATTTATACTGGTGGTAGTGGTACTCCTCACTACGCGAGCTGGGCGAAAGGCCGATTCACCATCTCCCAAACC

TCGTCGACCACGGTGACTCTGCAAATGACCAGTCTGACAGCCGCGGACACGGCCACCTATTTCTGTGCGAGAGAA

GGTAGCCTGTGGGGCCAGGGCACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

420H6 CHIMERIC HEAVY CHAIN VARIABLE HEAVY CHAIN NUCLEOTIDE SEQUENCE
SEQ ID NO: 78
CAGCAGCAGCTGGAGGAGTCCGGGGGAGGCCTGGTCAAGCCTGGAGGAACCCTGACACTCACCTGCAAAGCCTC

TGGAATTGACTTCAGTAGTAGTTACTACATGTGCTGGGTCCGCCAGGCTCCAGGGGAGGGGCTGGAGTGGATCGC

ATGCATTTATACTGGTGGTAGTGGTACTCCTCACTACGCGAGCTGGGCGAAAGGCCGATTCACCATCTCCCAAACC

TCGTCGACCACGGTGACTCTGCAAATGACCAGTCTGACAGCCGCGGACACGGCCACCTATTTCTGTGCGAGAGAA

GGTAGCCTGTGGGGCCAGGGCACCCTGGTCACCGTCTCGAGC

420H6 CHIMERIC HEAVY CHAIN FULL-LENGTH AMINO ACID SEQUENCE. HUMAN GAMMA-1 CONSTANT DOMAIN IS UNDERLINED

SEQ ID NO: 79

QQQLEESGGGLVKPGGTLTLTCKASGIDFSSSYYMCWVRQAPGEGLEWIACIYTGGSGTPHYASWAKGRFTISQTSSTT

VTLQMTSLTAADTATYFCAREGSLWGQGTLVTVSS<u>ASTKGPSVFPLAPSSKSTSGGTAALGCLVKDYFPEPVTVSWNSG</u>

<u>ALTSGVHTFPAVLQSSGLYSLSSVVTVPSSSLGTQTYICNVNHKPSNTKVDKRVEPKSCDKTHTCPPCPAPEAAGAPSVFL</u>

<u>FPPKPKDTLMISRTPEVTCVVVDVSHEDPEVKFNWYVDGVEVHNAKTKPREEQYNSTYRVVSVLTVLHQDWLNGKEY</u>

<u>KCAVSNKALPAPIEKTISKAKGQPREPQVYTLPPSRDELTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPG</u>

420H6 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 80

QQQLEESGGGLVKPGGTLTLTCKASGIDFS<u>SSYYMC</u>WVRQAPGEGLEWIA<u>CIYTGGSGTPHYASWAKG</u>RFTISQTSSTT

VTLQMTSLTAADTATYFCAR<u>EGS</u>LWGQGTLVTVSS

459F1 CHIMERIC LIGHT CHAIN FULL-LENGTH NUCLEOTIDE SEQUENCE

SEQ ID NO: 81

GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTCTCCTGGTATCAGCAGAAACCAGGGCAGCCTCCCAAGCTCCTGATCTATTCT

GCATCCACTCTGGCATCTGGGGTCCCCTCGCGGTTTAAAGGCAGTGGATCTGGGACACAGTTCACTCTCACCATCA

GCGACCTGGAGTGTGACGATGCTGCCACTTACTACTGTGCAGGCGGTTACAATACTGTAACTGATACTTTTGCTTTC

GGCGGAGGCACCGAGGTGGAGTTCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

459F1 CHIMERIC LIGHT CHAIN VARIABLE LIGHT CHAIN NUCLEOTIDE SEQUENCE

SEQ ID NO: 82

GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTCTCCTGGTATCAGCAGAAACCAGGGCAGCCTCCCAAGCTCCTGATCTATTCT

GCATCCACTCTGGCATCTGGGGTCCCCTCGCGGTTTAAAGGCAGTGGATCTGGGACACAGTTCACTCTCACCATCA

GCGACCTGGAGTGTGACGATGCTGCCACTTACTACTGTGCAGGCGGTTACAATACTGTAACTGATACTTTTGCTTTC

GGCGGAGGCACCGAGGTGGAGTTCAAA

459F1 CHIMERIC LIGHT CHAIN FULL-LENGTH AMINO ACID SEQUENCE. HUMAN KAPPA CONSTANT DOMAIN IS UNDERLINED

SEQ ID NO: 83

AQVLTQTASPVSAAVGGTVTINCQSSQSVYSNWFSWYQQKPGQPPKLLIYSASTLASGVPSRFKGSGSGTQFTLTISDLE

CDDAATYYCAGGYNTVTDTFAFGGGTEVEFK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

459F1 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 84

AQVLTQTASPVSAAVGGTVTINC<u>QSSQSVYSNWFS</u>WYQQKPGQPPKLLIY<u>SASTLAS</u>GVPSRFKGSGSGTQFTLTISDLE

CDDAATYYC<u>AGGYNTVTDTFAF</u>GGGTEVEFK

459F1 CHIMERIC HEAVY CHAIN FULL-LENGTH NUCLEOTIDE SEQUENCE

SEQ ID NO: 85

GAGTCGTTGGAGGAGTCCGGGGGAGACCTGGTCAAGCCTGGGGCATCCCTGACACTCACCTGCACAGCCTCTGG

AATCGACTTCAGTAGGAGATACTACATGTGCTGGGTCCGCCAGGCTCCAGGGAAGGGGCTGGAGTGGATCGCAT

GCATGTATACTGGTAGCCGCGATACTCCTCACTACGCGAGCTGGGCGAAAGGCCGGTTCACCATCTCCCAAACCTC

GTCGACCACGGTGACTCTGCAAATGACCAGTCTGACAGCCGCGGACACGGCCACCTATTTCTGTGCGAGAGAAGG

```
TAACCTGTGGGGCCCGGGGACCCTGGTCACCGTCTCGAGCGCTAGCACCAAGGGCCCATCGGTCTTCCCCCTGGC
ACCCTCCTCCAAGAGCACCTCTGGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACTCACACATGCCCACCGTGC
CCAGCACCTGAAGCCGCGGGGGCACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCGCGGTCTCCAACAAAGCCCTCC
CAGCCCCCATCGAGAAAACCATCTCCAAAGCCAAAGGGCAGCCCCGAGAACCACAGGTGTACACCCTGCCCCCAT
CCCGGGATGAGCTGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTCCGACGGCTCC
TTCTTCCTCTATAGCAAGCTCACCGTGGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCGGGT
```

459F1 CHIMERIC HEAVY CHAIN VARIABLE HEAVY CHAIN NUCLEOTIDE SEQUENCE
SEQ ID NO: 86
```
GAGTCGTTGGAGGAGTCCGGGGGAGACCTGGTCAAGCCTGGGGCATCCCTGACACTCACCTGCACAGCCTCTGG
AATCGACTTCAGTAGGAGATACTACATGTGCTGGGTCCGCCAGGCTCCAGGGAAGGGGCTGGAGTGGATCGCAT
GCATGTATACTGGTAGCCGCGATACTCCTCACTACGCGAGCTGGGCGAAAGGCCGGTTCACCATCTCCCAAACCTC
GTCGACCACGGTGACTCTGCAAATGACCAGTCTGACAGCCGCGGACACGGCCACCTATTTCTGTGCGAGAGAAGG
TAACCTGTGGGGCCCGGGGACCCTGGTCACCGTCTCGAGC
```

459F1 CHIMERIC HEAVY CHAIN FULL-LENGTH AMINO ACID SEQUENCE. HUMAN GAMMA-1 CONSTANT
DOMAIN IS UNDERLINED
SEQ ID NO: 87
ESLEESGGDLVKPGASLTLTCTASGIDFSRRYYMCWVRQAPGKGLEWIACMYTGSRDTPHYASWAKGRFTISQTSSTTV
TLQMTSLTAADTATYFCAREGNLWGPGTLVTVSS<u>ASTKGPSVFPLAPSSKSTSGGTAALGCLVKDYFPEPVTVSWNSGA</u>
<u>LTSGVHTFPAVLQSSGLYSLSSVVTVPSSSLGTQTYICNVNHKPSNTKVDKRVEPKSCDKTHTCPPCPAPEAAGAPSVFLF</u>
<u>PPKPKDTLMISRTPEVTCVVVDVSHEDPEVKFNWYVDGVEVHNAKTKPREEQYNSTYRVVSVLTVLHQDWLNGKEYK</u>
<u>CAVSNKALPAPIEKTISKAKGQPREPQVYTLPPSRDELTKNQVSLTCLVKGFYPSDIAVEWESNGQPENNYKTTPPVLDS</u>
<u>DGSFFLYSKLTVDKSRWQQGNVFSCSVMHEALHNHYTQKSLSLSPG</u>

459F1 CHIMERIC HEAVY CHAIN VARIABLE HEAVY CHAIN AMINO ACID SEQUENCE. COMPLIMENTARITY
DETERMINING REGIONS ARE UNDERLINED
SEQ ID NO: 88
ESLEESGGDLVKPGASLTLTCTASGIDFS<u>RRYYMC</u>WVRQAPGKGLEWIA<u>CMYTGSRDTPHYASWAKG</u>RFTISQTSSTTV
TLQMTSLTAADTATYFCAR<u>EGNL</u>WGPGTLVTVSS

460C3 CHIMERIC LIGHT CHAIN FULL-LENGTH NUCLEOTIDE SEQUENCE
SEQ ID NO: 89
```
GCCCAAGTGCTGACCCAGACTCCATCGTCCGTGTCTGCAGCTGTGGGAGGCACAGTCAGCATCAGTTGCCAGTCC
AGTCAGAGTGTTTATAGTAACTGGTTCTCCTGGTATCAGCAGAAACCAGGGCAGCCTCCCAAGCTCCTGATCTATT
CTGCATCCACTCTGGCATCTGGGGTCCCCTCGCGGTTTAAAGGCAGTGGATCTGGGACACAGTTCACTCTCACCAT
CAGCGACCTGGAGTGTGACGATGCTGCCACTTACTACTGTGCAGGCGGTTACAATACTGTTATTGATACTTTTGCTT
TCGGCGGAGGCACCGAGGTGGAGTTCAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGCAAGGACAGCACCTA
CAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGT
```

460C3 CHIMERIC LIGHT CHAIN VARIABLE LIGHT CHAIN NUCLEOTIDE SEQUENCE
SEQ ID NO: 90
GCCCAAGTGCTGACCCAGACTCCATCGTCCGTGTCTGCAGCTGTGGGAGGCACAGTCAGCATCAGTTGCCAGTCC

AGTCAGAGTGTTTATAGTAACTGGTTCTCCTGGTATCAGCAGAAACCAGGGCAGCCTCCCAAGCTCCTGATCTATT

CTGCATCCACTCTGGCATCTGGGGTCCCCTCGCGGTTTAAAGGCAGTGGATCTGGGACACAGTTCACTCTCACCAT

CAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAA

460C3 CHIMERIC LIGHT CHAIN FULL-LENGTH AMINO ACID SEQUENCE. HUMAN KAPPA CONSTANT
DOMAIN IS UNDERLINED
SEQ ID NO: 91
AQVLTQTPSSVSAAVGGTVSISCQSSQSVYSNWFSWYQQKPGQPPKLLIYSASTLASGVPSRFKGSGSGTQFTLTISDLE

CDDAATYYCAGGYNTVIDTFAFGGGTEVEFKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

460C3 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 92
AQVLTQTPSSVSAAVGGTVSISCQSSQSVYSNWFSWYQQKPGQPPKLLIYSASTLASGVPSRFKGSGSGTQFTLTISDLE

CDDAATYYCAGGYNTVIDTFAFGGGTEVEFK

460C3 CHIMERIC HEAVY CHAIN FULL-LENGTH NUCLEOTIDE SEQUENCE
SEQ ID NO: 93
CAGTCGTTGGAGGAGTCCGGGGGAGACCTGGTCAAGCCTGGGGCATCCCTGACACTCACCTGCACAGCCTCTGGA

ATCGACTTCAGTAGGAGATACTACATGTGCTGGGTCCGCCAGGCTCCAGGGAAGGGGCTGGAGTGGATCGCATG

CATATATACTGGTAGCCGCGATACTCCTCACTACGCGAGCTGGGCGAAAGGCCGATTCACCATCTCCCAAACCTCG

TCGACCACGGTGACTCTGCAAATGACCAGTCTGACAGCCGCGGACACGGCCACCTATTTCTGTGCGAGAGAAGGT

AGCCTGTGGGGCCAGGGCACCCTGGTCACCGTCTCGAGCGCTAGCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCGGTG

ACGGTGTCGTGGAACTCAGGCGCCCTGACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAGACCTACATCTGCAACGTGAATCACAA

GCCCAGCAACACCAAGGTGGACAAGAGAGTTGAGCCCAAATCTTGTGACAAAACTCACACATGCCCACCGTGCCC

AGCACCTGAAGCCGCGGGGGCACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACAACAGCACGTACCGTGTGGTCAGC

GTCCTCACCGTCCTGCACCAGGACTGGCTGAATGGCAAGGAGTACAAGTGCGCGGTCTCCAACAAAGCCCTCCCA

GCCCCCATCGAGAAAACCATCTCCAAAGCCAAAGGGCAGCCCCGAGAACCACAGGTGTACACCCTGCCCCCATCC

CGGGATGAGCTGACCAAGAACCAGGTCAGCCTGACCTGCCTGGTCAAAGGCTTCTATCCCAGCGACATCGCCGTG

GAGTGGGAGAGCAATGGGCAGCCGGAGAACAACTACAAGACCACGCCTCCCGTGCTGGACTCCGACGGCTCCTT

CTTCCTCTATAGCAAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGGGT

460C3 CHIMERIC HEAVY CHAIN VARIABLE HEAVY CHAIN NUCLEOTIDE SEQUENCE
SEQ ID NO: 94
CAGTCGTTGGAGGAGTCCGGGGGAGACCTGGTCAAGCCTGGGGCATCCCTGACACTCACCTGCACAGCCTCTGGA

ATCGACTTCAGTAGGAGATACTACATGTGCTGGGTCCGCCAGGCTCCAGGGAAGGGGCTGGAGTGGATCGCATG

CATATATACTGGTAGCCGCGATACTCCTCACTACGCGAGCTGGGCGAAAGGCCGATTCACCATCTCCCAAACCTCG

TCGACCACGGTGACTCTGCAAATGACCAGTCTGACAGCCGCGGACACGGCCACCTATTTCTGTGCGAGAGAAGGT

AGCCTGTGGGGCCAGGGCACCCTGGTCACCGTCTCGAGC

460C3 CHIMERIC HEAVY CHAIN FULL-LENGTH AMINO ACID SEQUENCE. HUMAN GAMMA-1 CONSTANT DOMAIN IS UNDERLINED

SEQ ID NO: 95

QSLEESGGDLVKPGASLTLTCTASGIDFSRRYYMCWVRQAPGKGLEWIACIYTGSRDTPHYASWAKGRFTISQTSSTTV

TLQMTSLTAADTATYFCAREGSLWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

460C3 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 96

QSLEESGGDLVKPGASLTLTCTASGIDFSRRYYMCWVRQAPGKGLEWIACIYTGSRDTPHYASWAKGRFTISQTSSTTV

TLQMTSLTAADTATYFCAREGSLWGQGTLVTVSS

464D11 CHIMERIC LIGHT CHAIN FULL-LENGTH NUCLEOTIDE SEQUENCE

SEQ ID NO: 97

GCGCAAGTGCTGACCCAGACTCCATCGCCTGTGTCTGCAGCTGTGGGAGGCACAGTCACCATCAATTGCCAGTCCA

GTCAGAGTGTTTATAGTAACAGCTTCTTATCCTGGTATCAGCAGAAACCAGGGCAGCCTCCCAAGCGCCTGATCTA

TTCTGCATCCGATCTGGCATCTGGGGTCCCATCGCGGTTCAAAGGCAGTGGATCTGGGACACAGTTCACTCTCACC

ATCAGCGACCTGGAGTGTGACGATGCTGCCACTTACTACTGTGCAGGCGTTTATAGTGATAATACTTATGTTTTCG

GCGGAGGCACCGAGGTGGAGTTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

464D11 CHIMERIC LIGHT CHAIN VARIABLE LIGHT CHAIN NUCLEOTIDE SEQUENCE

SEQ ID NO: 98

GCGCAAGTGCTGACCCAGACTCCATCGCCTGTGTCTGCAGCTGTGGGAGGCACAGTCACCATCAATTGCCAGTCCA

GTCAGAGTGTTTATAGTAACAGCTTCTTATCCTGGTATCAGCAGAAACCAGGGCAGCCTCCCAAGCGCCTGATCTA

TTCTGCATCCGATCTGGCATCTGGGGTCCCATCGCGGTTCAAAGGCAGTGGATCTGGGACACAGTTCACTCTCACC

ATCAGCGACCTGGAGTGTGACGATGCTGCCACTTACTACTGTGCAGGCGTTTATAGTGATAATACTTATGTTTTCG

GCGGAGGCACCGAGGTGGAGTTCAAA

464D11 CHIMERIC LIGHT CHAIN FULL-LENGTH AMINO ACID SEQUENCE. HUMAN KAPPA CONSTANT DOMAIN IS UNDERLINED

SEQ ID NO: 99

AQVLTQTPSPVSAAVGGTVTINCQSSQSVYSNSFLSWYQQKPGQPPKRLIYSASDLASGVPSRFKGSGSGTQFTLTISDL

ECDDAATYYCAGVYSDNTYVFGGGTEVEFKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

464D11 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 100

AQVLTQTPSPVSAAVGGTVTINCQSSQSVYSNSFLSWYQQKPGQPPKRLIYSASDLASGVPSRFKGSGSGTQFTLTISDL

ECDDAATYYCAGVYSDNTYVFGGGTEVEFK

464D11 CHIMERIC HEAVY CHAIN FULL-LENGTH NUCLEOTIDE SEQUENCE

SEQ ID NO: 101

CAGTCGGTGGAGGAGTCCGGCGGTCGCCTGGTAAAGCCTGACGAATCCCTGACACTCACCTGCACAGCCTCTGGA

TTCTCCCTCAGTCACTACTGGATGACTTGGGTCCGACAGGCTCCAGGGAAGGGACTGGAATACATCGGATTCATTA

ATGTTGGTGGTGACACATCTTACGCGAGCTGGTCGAAAGGCCGATTCACCATCTCCAAGGCCTCGACCACGGTGG

ATCTGAAGATCAGTAGTCTGACAACCGAGGACACGGCCACCTATTTCTGTGGCAGAGGTGGTCTGACTTTTGGTTG

-continued

GGACTTGTGGGGCCCAGGGACCCTCGTCACCGTCTCGAGCGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTTCCCCGAACCGGT

GACGGTGTCGTGGAACTCAGGCGCCCTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCACCGTGC

CCAGCACCTGAAGCCGCGGGGGCACCGTCAGTCTTCCTCTTCCCCCCAAAACCCAAGGACACCCTCATGATCTCCC

GGACCCCTGAGGTCACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCGCGGTCTCCAACAAAGCCCTCC

CAGCCCCCATCGAGAAAACCATCTCCAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAAGGCTTCTATCCCAGCGACATCGCCG

TGGAGTGGGAGAGCAATGGGCAGCCGGAGAACAACTACAAGACCACGCCTCCCGTGCTGGACTCCGACGGCTCC

TTCTTCCTCTATAGCAAGCTCACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGT

464D11 CHIMERIC HEAVY CHAIN VARIABLE HEAVY CHAIN NUCLEOTIDE SEQUENCE
SEQ ID NO: 102
CAGTCGGTGGAGGAGTCCGGCGGTCGCCTGGTAAAGCCTGACGAATCCCTGACACTCACCTGCACAGCCTCTGGA

TTCTCCCTCAGTCACTACTGGATGACTTGGGTCCGACAGGCTCCAGGGAAGGGACTGGAATACATCGGATTCATTA

ATGTTGGTGGTGACACATCTTACGCGAGCTGGTCGAAAGGCCGATTCACCATCTCCAAGGCCTCGACCACGGTGG

ATCTGAAGATCAGTAGTCTGACAACCGAGGACACGGCCACCTATTTCTGTGGCAGAGGTGGTCTGACTTTTGGTTG

GGACTTGTGGGGCCCAGGGACCCTCGTCACCGTCTCGAGC

464D11 CHIMERIC HEAVY CHAIN FULL-LENGTH AMINO ACID SEQUENCE. HUMAN GAMMA-1
CONSTANT DOMAIN IS UNDERLINED
SEQ ID NO: 103
QSVEESGGRLVKPDESLTLTCTASGFSLSHYWMTWVRQAPGKGLEYIGFINVGGDTSYASWSKGRFTISKASTTVDLKIS

SLTTEDTATYFCGRGGLTFGWDLWGPGTLVTVSSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKSCDKTHTCPPCPAPEAAGAPSVFL

FPPKPKDTLMISRTPEVTCVVVDVSHEDPEVKFNWYVDGVEVHNAKTKPREEQYNSTYRVVSVLTVLHQDWLNGKEY

KCAVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

464D11 CHIMERIC HEAVY CHAIN VARIABLE HEAVY CHAIN AMINO ACID SEQUENCE.
COMPLIMENTARITY DETERMINING REGIONS ARE UNDERLINED
SEQ ID NO: 104
QSVEESGGRLVKPDESLTLTCTASGFSLSHYWMTWVRQAPGKGLEYIGFINVGGDTSYASWSKGRFTISKASTTVDLKIS

SLTTEDTATYFCGRGGLTFGWDLWGPGTLVTVSS

466F6 CHIMERIC LIGHT CHAIN FULL-LENGTH NUCLEOTIDE SEQUENCE
SEQ ID NO: 105
GATGTTGTGATGACCCAGACTCCAGCCTCCGTGTCTGAACCTGTGGGAGGCACAGTCACCATCAAGTGCCAGGCC

AGTCAGAACATTAGGACTTACTTATCCTGGTATCAGCAGAAACCAGGGCAGCGTCCCAAGCTCCTGATCTATGCTG

CAGCCAATCTGGCATCTGGGGTCCCATCGCGGTTCAGTGGCAGTAGATCTGGGACAGAGTTCACTCTCACCATCAG

CGACCTGGAGTGTGCCGATGCTGCCACTTACTATTGTCAGTGTACCTATCTTGGTACTGATTATGTTGGCGGTGCTT

TCGGCGGAGGCACCGAGGTGGAGTTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

-continued

466F6 CHIMERIC LIGHT CHAIN VARIABLE LIGHT CHAIN NUCLEOTIDE SEQUENCE
SEQ ID NO: 106
GATGTTGTGATGACCCAGACTCCAGCCTCCGTGTCTGAACCTGTGGGAGGCACAGTCACCATCAAGTGCCAGGCC

AGTCAGAACATTAGGACTTACTTATCCTGGTATCAGCAGAAACCAGGGCAGCGTCCCAAGCTCCTGATCTATGCTG

CAGCCAATCTGGCATCTGGGGTCCCATCGCGGTTCAGTGGCAGTAGATCTGGGACAGAGTTCACTCTCACCATCAG

CGACCTGGAGTGTGCCGATGCTGCCACTTACTATTGTCAGTGTACCTATCTTGGTACTGATTATGTTGGCGGTGCTT

TCGGCGGAGGCACCGAGGTGGAGTTCAAA

466F6 CHIMERIC LIGHT CHAIN FULL-LENGTH AMINO ACID SEQUENCE. HUMAN KAPPA CONSTANT
DOMAIN IS UNDERLINED
SEQ ID NO: 107
DVVMTQTPASVSEPVGGTVTIKCQASQNIRTYLSWYQQKPGQRPKLLIYAAANLASGVPSRFSGSRSGTEFTLTISDLEC

ADAATYYCQCTYLGTDYVGGAFGGGTEVEFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

466F6 CHIMERIC LIGHT CHAIN VARIABLE LIGHT CHAIN AMINO ACID SEQUENCE. COMPIMENTARITY
DETERMINING REGIONS ARE UNDERLINED
SEQ ID NO: 108
DVVMTQTPASVSEPVGGTVTIKCQASQNIRTYLSWYQQKPGQRPKLLIYAAANLASGVPSRFSGSRSGTEFTLTISDLEC

ADAATYYCQCTYLGTDYVGGAFGGGTEVEFK

466F6 CHIMERIC HEAVY CHAIN FULL-LENGTH NUCLEOTIDE SEQUENCE
SEQ ID NO: 109
CGGTCGCTGGAGGAGTCCGGGGGTCGCCTGGTCACGCCTGGGACACCCCTGACACTCACCTGCACAGCCTCTGGA

TTCACCATCAGTAGCTACCACATGCAGTGGGTCCGCCAGGCTCCAGGGAAGGGGCTGGAATACATCGGAACCATT

AGTAGTGGTGGTAATGTATACTACGCGAGCTGGGCGAGAGGCCGATTCACCATCTCCAGACCCTCGTCGACCACG

GTGGATCTGAAGATGACCAGTCTGACAACCGAGGACACGGCCACCTATTTCTGTGCCAGAGACTCTGGTTATAGT

GATCCTATGTGGGGCCCGGGCACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

466F6 CHIMERIC HEAVY CHAIN VARIABLE HEAVY CHAIN NUCLEOTIDE SEQUENCE
SEQ ID NO: 110
CGGTCGCTGGAGGAGTCCGGGGGTCGCCTGGTCACGCCTGGGACACCCCTGACACTCACCTGCACAGCCTCTGGA

TTCACCATCAGTAGCTACCACATGCAGTGGGTCCGCCAGGCTCCAGGGAAGGGGCTGGAATACATCGGAACCATT

AGTAGTGGTGGTAATGTATACTACGCGAGCTGGGCGAGAGGCCGATTCACCATCTCCAGACCCTCGTCGACCACG

GTGGATCTGAAGATGACCAGTCTGACAACCGAGGACACGGCCACCTATTTCTGTGCCAGAGACTCTGGTTATAGT

GATCCTATGTGGGGCCCGGGCACCCTGGTCACCGTCTCGAGC

466F6 CHIMERIC HEAVY CHAIN FULL-LENGTH AMINO ACID SEQUENCE. HUMAN GAMMA-1 CONSTANT DOMAIN IS UNDERLINED

SEQ ID NO: 111

RSLEESGGRLVTPGTPLTLTCTASGFTISSYHMQWVRQAPGKGLEYIGTISSGGNVYYASWARGRFTISRPSSTTVDLKM

TSLTTEDTATYFCARDSGYSDPMWGPGTLVTVSS<u>ASTKGPSVFPLAPSSKSTSGGTAALGCLVKDYFPEPVTVSWNSGA</u>

<u>LTSGVHTFPAVLQSSGLYSLSSVVTVPSSSLGTQTYICNVNHKPSNTKVDKRVEPKSCDKTHTCPPCPAPEAAGAPSVFLF</u>

<u>PPKPKDTLMISRTPEVTCVVVDVSHEDPEVKFNWYVDGVEVHNAKTKPREEQYNSTYRVVSVLTVLHQDWLNGKEYK</u>

<u>CAVSNKALPAPIEKTISKAKGQPREPQVYTLPPSRDELTKNQVSLTCLVKGFYPSDIAVEWESNGQPENNYKTTPPVLDS</u>

<u>DGSFFLYSKLTVDKSRWQQGNVFSCSVMHEALHNHYTQKSLSLSPG</u>

466F6 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 112

RSLEESGGRLVTPGTPLTLTCTASGFTIS<u>SYHMQ</u>WVRQAPGKGLEYIG<u>TISSGGNVYYASWARG</u>RFTISRPSSTTVDLKM

TSLTTEDTATYFCAR<u>DSGYSDPM</u>WGPGTLVTVSS

470B6 CHIMERIC LIGHT CHAIN FULL-LENGTH NUCLEOTIDE SEQUENCE

SEQ ID NO: 113

GCAGCCGTGCTGACCCAGACACCATCGCCCGTGTCTGCAGCTGTGGGAGGCACAGTCACCATCAGTTGCCAGTCC

AGTCAGAGTGTTTATAGTAACAACCAATTATCCTGGTTTCAGCAGAAATCAGGGCAGCCTCCCAAGCTCCTGATCT

ATGATGCATCCAATCTGGCATCTGGGGTCCCATCACGGTTCAGCGGCAGTGGATCTGGGACACAGTTCACTCTCAC

CATCAGCAGCGTGCAGTGTGACGATGCTGCCACTTACCACTGTCTAGGCGGTAGTGATGATGATGGTGATATTGCT

TTCGGCGGAGGCACCGAGGTGGTGTTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

470B6 CHIMERIC LIGHT CHAIN VARIABLE LIGHT CHAIN NUCLEOTIDE SEQUENCE

SEQ ID NO: 114

GCAGCCGTGCTGACCCAGACACCATCGCCCGTGTCTGCAGCTGTGGGAGGCACAGTCACCATCAGTTGCCAGTCC

AGTCAGAGTGTTTATAGTAACAACCAATTATCCTGGTTTCAGCAGAAATCAGGGCAGCCTCCCAAGCTCCTGATCT

ATGATGCATCCAATCTGGCATCTGGGGTCCCATCACGGTTCAGCGGCAGTGGATCTGGGACACAGTTCACTCTCAC

CATCAGCAGCGTGCAGTGTGACGATGCTGCCACTTACCACTGTCTAGGCGGTAGTGATGATGATGGTGATATTGCT

TTCGGCGGAGGCACCGAGGTGGTGTTCAAA

470B6 CHIMERIC LIGHT CHAIN FULL-LENGTH AMINO ACID SEQUENCE. HUMAN KAPPA CONSTANT DOMAIN IS UNDERLINED

SEQ ID NO: 115

AAVLTQTPSPVSAAVGGTVTISCQSSQSVYSNNQLSWFQQKSGQPPKLLIYDASNLASGVPSRFSGSGSGTQFTLTISSV

QCDDAATYHCLGGSDDDGDIAFGGGTEVVFK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

470B6 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 116

AAVLTQTPSPVSAAVGGTVTISC<u>QSSQSVYSNNQLS</u>WFQQKSGQPPKLLIY<u>DASNLAS</u>GVPSRFSGSGSGTQFTLTISSV

QCDDAATYHC<u>LGGSDDDGDIA</u>FGGGTEVVFK

470B6 CHIMERIC HEAVY CHAIN FULL-LENGTH NUCLEOTIDE SEQUENCE

SEQ ID NO: 117

CAGTCACTGGAGGAGTCCGGGGGTCGCCTGGTCACGCCTGGGACACCCCTGACACTCACCTGCACAGCCTCTGGA

TTCTCCCTCAGTAGCTACTACATGAGCTGGGTCCGCCAGGCTCCAGGGAAGGGACTGGAATGGATCGGAAGTATT

TATGGTAGTGGTGCCGCATACTACGCGAGCTGGGCGAAAGGCCGATTCACCATCTCCAGAACGTCGACCACGGTG

GATCTGAAAATGACCAGTCTGACAGCCGCGGACACGGCCACCTATTTCTGTGCCAGAGATCCTATTAACAATGCCA

-continued

```
TGTGGGGCCCAGGCACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

470B6 CHIMERIC HEAVY CHAIN VARIABLE HEAVY CHAIN NUCLEOTIDE SEQUENCE
                                                                        SEQ ID NO: 118
CAGTCACTGGAGGAGTCCGGGGGTCGCCTGGTCACGCCTGGGACACCCCTGACACTCACCTGCACAGCCTCTGGA

TTCTCCCTCAGTAGCTACTACATGAGCTGGGTCCGCCAGGCTCCAGGGAAGGGACTGGAATGGATCGGAAGTATT

TATGGTAGTGGTGCCGCATACTACGCGAGCTGGGCGAAAGGCCGATTCACCATCTCCAGAACGTCGACCACGGTG

GATCTGAAAATGACCAGTCTGACAGCCGCGGACACGGCCACCTATTTCTGTGCCAGAGATCCTATTAACAATGCCA

TGTGGGGCCCAGGCACCCTGGTCACCGTCTCGAGC

470B6 CHIMERIC HEAVY CHAIN FULL-LENGTH AMINO ACID SEQUENCE. HUMAN GAMMA-1 CONSTANT
DOMAIN IS UNDERLINED
                                                                        SEQ ID NO: 119
QSLEESGGRLVTPGTPLTLTCTASGFSLSSYYMSWVRQAPGKGLEWIGSIYGSGAAYYASWAKGRFTISRTSTTVDLKMT

SLTAADTATYFCARDPINNAMWGPGTLVTVSSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKRVEPKSCDKTHTCPPCPAPEAAGAPSVFLFPP

KPKDTLMISRTPEVTCVVVDVSHEDPEVKFNWYVDGVEVHNAKTKPREEQYNSTYRVVSVLTVLHQDWLNGKEYKCA

VSNKALPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

470B6 CHIMERIC HEAVY CHAIN VARIABLE HEAVY CHAIN AMINO ACID SEQUENCE. COMPLIMENTARITY
DETERMINING REGIONS ARE UNDERLINED
                                                                        SEQ ID NO: 120
QSLEESGGRLVTPGTPLTLTCTASGFSLSSYYMSWVRQAPGKGLEWIGSIYGSGAAYYASWAKGRFTISRTSTTVDLKMT

SLTAADTATYFCARDPINNAMWGPGTLVTVSS

470C6 CHIMERIC LIGHT CHAIN FULL-LENGTH NUCLEOTIDE SEQUENCE
                                                                        SEQ ID NO: 121
GCCCTTGTGATGACCCAGACTCCAGCCTCCGTGTCTGCAGCTGTGGGAGGCACAGTCACCATCAATTGCCAGGCCA

GTGAGGACATTGATAACTATTTAGCCTGGTATCAGCAGAAACCAGGGCAGCCTCCCAAGCTCCTGATCTTTTATGC

ATCCGATCTGGCATCTGGGGTCCCATCGCGGTTCTCAGGCAGTGGATCTGGGACACAGTTCACTCTCACCATCAGC

GGTGTGCAGTGTGACGATGCTGCCACTTACTACTGTCAAGGCGGTTACTATACTAGTAGTACTGATACGAGGGGT

GCTTTCGGCGGAGGCACCGAGGTGGTGGTCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

CCTACAGCCTCAGCAGCACCCTGACGCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAGTGT
```

470C6 CHIMERIC LIGHT CHAIN VARIABLE LIGHT CHAIN NUCLEOTIDE SEQUENCE

SEQ ID NO: 122

GCCCTTGTGATGACCCAGACTCCAGCCTCCGTGTCTGCAGCTGTGGGAGGCACAGTCACCATCAATTGCCAGGCCA

GTGAGGACATTGATAACTATTTAGCCTGGTATCAGCAGAAACCAGGGCAGCCTCCCAAGCTCCTGATCTTTTATGC

ATCCGATCTGGCATCTGGGGTCCCATCGCGGTTCTCAGGCAGTGGATCTGGGACACAGTTCACTCTCACCATCAGC

GGTGTGCAGTGTGACGATGCTGCCACTTACTACTGTCAAGGCGGTTACTATACTAGTAGTACTGATACGAGGGGT

GCTTTCGGCGGAGGCACCGAGGTGGTGGTCAAA

470C6 CHIMERIC LIGHT CHAIN FULL-LENGTH AMINO ACID SEQUENCE. HUMAN KAPPA CONSTANT
DOMAIN IS UNDERLINED

SEQ ID NO: 123

ALVMTQTPASVSAAVGGTVTINCQASEDIDNYLAWYQQKPGQPPKLLIFYASDLASGVPSRFSGSGSGTQFTLTISGVQ

CDDAATYYCQGGYYTSSTDTRGAFGGGTEVVVK<u>RTVAAPSVFIFPPSDEQLKSGTASVVCLLNNFYPREAKVQWKVDN</u>

<u>ALQSGNSQESVTEQDSKDSTYSLSSTLTLSKADYEKHKVYACEVTHQGLSSPVTKSFNRGEC</u>

470C6 CHIMERIC LIGHT CHAIN VARIABLE LIGHT CHAIN AMINO ACID SEQUENCE. COMPIMENTARITY
DETERMINING REGIONS ARE UNDERLINED

SEQ ID NO: 124

ALVMTQTPASVSAAVGGTVTINC<u>QASEDIDNYLA</u>WYQQKPGQPPKLLIF<u>YASDLAS</u>GVPSRFSGSGSGTQFTLTISGVQ

CDDAATYYC<u>QGGYYTSSTDTRGA</u>FGGGTEVVVK

470C6 CHIMERIC HEAVY CHAIN FULL-LENGTH NUCLEOTIDE SEQUENCE

SEQ ID NO: 125

CAGTCATTGGAGGAGGCCGGGGGAGACCTGGTCAAGCCTGGGGCATCCCTGACACTCACCTGCACAGCCTCTGGC

TTCTCCTTCACTAGCAGCTACTACATGTGCTGGGTCCGCCAGGCTCCAGGGAAGGGGCTGGAGTGGATCGCATGC

ATTTATACTGGTAGTAGTGGTAGCACTTACTACGCGAACTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGCACCCTCGTCACCGTCTCGAGCGCTAGCACCAAGGGCCCATC

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

470C6 CHIMERIC HEAVY CHAIN VARIABLE HEAVY CHAIN NUCLEOTIDE SEQUENCE

SEQ ID NO: 126

CAGTCATTGGAGGAGGCCGGGGGAGACCTGGTCAAGCCTGGGGCATCCCTGACACTCACCTGCACAGCCTCTGGC

TTCTCCTTCACTAGCAGCTACTACATGTGCTGGGTCCGCCAGGCTCCAGGGAAGGGGCTGGAGTGGATCGCATGC

ATTTATACTGGTAGTAGTGGTAGCACTTACTACGCGAACTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGCACCCTCGTCACCGTCTCGAGC

470C6 CHIMERIC HEAVY CHAIN FULL-LENGTH AMINO ACID SEQUENCE. HUMAN GAMMA-1 CONSTANT DOMAIN IS UNDERLINED

SEQ ID NO: 127

QSLEEAGGDLVKPGASLTLTCTASGFSFTSSYYMCWVRQAPGKGLEWIACIYTGSSGSTYYANWAKGRFTISKTSSTTVT

LQMTSLTAADTATYFCARDSSSYYMFNLWGQGTLVTVSS<u>ASTKGPSVFPLAPSSKSTSGGTAALGCLVKDYFPEPVTVS</u>

<u>WNSGALTSGVHTFPAVLQSSGLYSLSSVVTVPSSSLGTQTYICNVNHKPSNTKVDKRVEPKSCDKTHTCPPCPAPEAAG</u>

<u>APSVFLFPPKPKDTLMISRTPEVTCVVVDVSHEDPEVKFNWYVDGVEVHNAKTKPREEQYNSTYRVVSVLTVLHQDWL</u>

<u>NGKEYKCAVSNKALPAPIEKTISKAKGQPREPQVYTLPPSRDELTKNQVSLTCLVKGFYPSDIAVEWESNGQPENNYKTT</u>

<u>PPVLDSDGSFFLYSKLTVDKSRWQQGNVFSCSVMHEALHNHYTQKSLSLSPG</u>

470C6 CHIMERIC HEAVY CHAIN VARIABLE HEAVY CHAIN AMINO ACID SEQUENCE. COMPLIMENTARITY DETERMINING REGIONS ARE UNDERLINED

SEQ ID NO: 128

QSLEEAGGDLVKPGASLTLTCTASGFSFT<u>SSYYMC</u>WVRQAPGKGLEWIAC<u>IYTGSSGSTYYANWAK</u>GRFTISKTSSTTVT

LQMTSLTAADTATYFCAR<u>DSSSYYMFN</u>LWGQGTLVTVSS

472E4 CHIMERIC LIGHT CHAIN FULL-LENGTH NUCLEOTIDE SEQUENCE

SEQ ID NO: 129

GCAGCCGTGCTGACCCAGACTCCATCTTCCACGTCTGCAGCTGTGGGAGGCACAGTCACCATCAGTTGCCAGTCCA

GTCAGAGTGTTTATAATAACAATGCTTTAGCCTGGTATCAGAAAAAACCAGGACAGCCTCCCAAGCTCCTGATCTA

TTTGGCTTCCACTCTGGCATCTGGGGTCCCATCGCGGTTCAGCGGCAGTGGATCTGGGACACAGTTCACTCTCACC

ATCAGCGACCTGGAGTGTGACGATGCTGCCACTTATTATTGTCTAGGTGTTTATAATGATGATGTTGATAATGGTTT

CGGCGGAGGCACCGAGGTGGTGTTCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

472E4 CHIMERIC LIGHT CHAIN VARIABLE LIGHT CHAIN NUCLEOTIDE SEQUENCE

SEQ ID NO: 130

GCAGCCGTGCTGACCCAGACTCCATCTTCCACGTCTGCAGCTGTGGGAGGCACAGTCACCATCAGTTGCCAGTCCA

GTCAGAGTGTTTATAATAACAATGCTTTAGCCTGGTATCAGAAAAAACCAGGACAGCCTCCCAAGCTCCTGATCTA

TTTGGCTTCCACTCTGGCATCTGGGGTCCCATCGCGGTTCAGCGGCAGTGGATCTGGGACACAGTTCACTCTCACC

ATCAGCGACCTGGAGTGTGACGATGCTGCCACTTATTATTGTCTAGGTGTTTATAATGATGATGTTGATAATGGTTT

CGGCGGAGGCACCGAGGTGGTGTTCAAA

472E4 CHIMERIC LIGHT CHAIN FULL-LENGTH AMINO ACID SEQUENCE. HUMAN KAPPA CONSTANT DOMAIN IS UNDERLINED

SEQ ID NO: 131

AAVLTQTPSSTSAAVGGTVTISCQSSQSVYNNNALAWYQKKPGQPPKLLIYLASTLASGVPSRFSGSGSGTQFTLTISDLE

CDDAATYYCLGVYNDDVDNGFGGGTEVVFK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

472E4 CHIMERIC LIGHT CHAIN VARIABLE LIGHT CHAIN AMINO ACID SEQUENCE. COMPIMENTARITY DETERMINING REGIONS ARE UNDERLINED

SEQ ID NO: 132

AAVLTQTPSSTSAAVGGTVTISC<u>QSSQSVYNNNALA</u>WYQKKPGQPPKLLIY<u>LASTLAS</u>GVPSRFSGSGSGTQFTLTISDLE

CDDAATYYC<u>LGVYNDDVDN</u>GFGGGTEVVFK

472E4 CHIMERIC HEAVY CHAIN FULL-LENGTH NUCLEOTIDE SEQUENCE

SEQ ID NO: 133

CAGTCGCTGGAGGAGTCCGGGGGTCGCCTGGTCACGCCTGGAGGATCCCTGACACTCACCTGCACCGTCTCTGGA

TTCTCCCTCAATAACAATGCAATAAGCTGGGTCCGCCAGGCTCCAGGGAAGGGGCTGGAATGGGTTGCAATCATA

CAAAATACTGGTACCACAGACTACGCGAGGTGGGCGAAAGGCCGATTCACCATCTCCAAAACCTCGACCACGGTG

GATTTGAAAATCAACAGTCCGACAACCGAGGACACGGCCACCTATTTCTGTGGCAGAGGGTATGGTTTTGAGTCG

```
GAGCTTGTCATCTGGGGCCCGGGCACCCTGGTCACCGTCTCGAGCGCTAGCACCAAGGGCCCATCGGTCTTCCCCC

TGGCACCCTCCTCCAAGAGCACCTCTGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGCACCCAGACCTACATCTGCAACGTGAA

TCACAAGCCCAGCAACACCAAGGTGGACAAGAGAGTTGAGCCCAAATCTTGTGACAAAACTCACACATGCCCACC

GTGCCCAGCACCTGAAGCCGCGGGGGCACCGTCAGTCTTCCTCTTCCCCCCAAAACCCAAGGACACCCTCATGATC

TCCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT
```

472E4 CHIMERIC HEAVY CHAIN VARIABLE HEAVY CHAIN NUCLEOTIDE SEQUENCE
SEQ ID NO: 134

```
CAGTCGCTGGAGGAGTCCGGGGGTCGCCTGGTCACGCCTGGAGGATCCCTGACACTCACCTGCACCGTCTCTGGA

TTCTCCCTCAATAACAATGCAATAAGCTGGGTCCGCCAGGCTCCAGGGAAGGGGCTGGAATGGGTTGCAATCATA

CAAAATACTGGTACCACAGACTACGCGAGGTGGGCGAAAGGCCGATTCACCATCTCCAAAACCTCGACCACGGTG

GATTTGAAAATCAACAGTCCGACAACCGAGGACACGGCCACCTATTTCTGTGGCAGAGGGTATGGTTTTGAGTCG

GAGCTTGTCATCTGGGGCCCGGGCACCCTGGTCACCGTCTCGAGC
```

472E4 CHIMERIC HEAVY CHAIN FULL-LENGTH AMINO ACID SEQUENCE. HUMAN GAMMA-1 CONSTANT DOMAIN IS UNDERLINED
SEQ ID NO: 135

QSLEESGGRLVTPGGSLTLTCTVSGFSLNNNAISWVRQAPGKGLEWVAIIQNTGTTDYARWAKGRFTISKTSTTVDLKIN

SPTTEDTATYFCGRGYGFESELVIWGPGTLVTVSS<u>ASTKGPSVFPLAPSSKSTSGGTAALGCLVKDYFPEPVTVSWNSGA</u>

<u>LTSGVHTFPAVLQSSGLYSLSSVVTVPSSSLGTQTYICNVNHKPSNTKVDKRVEPKSCDKTHTCPPCPAPEAAGAPSVFLF</u>

<u>PPKPKDTLMISRTPEVTCVVVDVSHEDPEVKFNWYVDGVEVHNAKTKPREEQYNSTYRVVSVLTVLHQDWLNGKEYK</u>

<u>CAVSNKALPAPIEKTISKAKGQPREPQVYTLPPSRDELTKNQVSLTCLVKGFYPSDIAVEWESNGQPENNYKTTPPVLDS</u>

<u>DGSFFLYSKLTVDKSRWQQGNVFSCSVMHEALHNHYTQKSLSLSPG</u>

472E4 CHIMERIC HEAVY CHAIN VARIABLE HEAVY CHAIN AMINO ACID SEQUENCE. COMPLIMENTARITY DETERMINING REGIONS ARE UNDERLINED
SEQ ID NO: 136

QSLEESGGRLVTPGGSLTLTCTVSGFSLN<u>NNAIS</u>WVRQAPGKGLEWVAI<u>IQNTGTTDYARWAKG</u>RFTISKTSTTVDLKIN

SPTTEDTATYFCGR<u>GYGFESELVI</u>WGPGTLVTVSS

411H11 HUMANIZED LIGHT CHAIN FULL-LENGTH NUCLEOTIDE SEQUENCE
SEQ ID NO: 137

```
GACGTTGTGATGACCCAGTCTCCATCTTCCGTGTCTGCATCTGTAGGAGACAGAGTCACCATCACCTGTCAGGCCA

GTCAGAGCATTGGTGCTGATTTAGCCTGGTATCAGCAGAAACCAGGGAAAGCCCCTAAGCTCCTGATCTATAGGG

CATCCACTCTGGCCTCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAAGCTATTTATTATGGTACTGATGATGTCATATACCATA

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT
```

411H11 HUMANIZED LIGHT CHAIN VARIABLE LIGHT CHAIN NUCLEOTIDE SEQUENCE

SEQ ID NO: 138

GACGTTGTGATGACCCAGTCTCCATCTTCCGTGTCTGCATCTGTAGGAGACAGAGTCACCATCACCTGTCAGGCCA

GTCAGAGCATTGGTGCTGATTTAGCCTGGTATCAGCAGAAACCAGGGAAAGCCCCTAAGCTCCTGATCTATAGGG

CATCCACTCTGGCCTCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAAGCTATTTATTATGGTACTGATGATGTCATATACCATA

CTTTCGGCGGAGGGACCAAGGTGGAGATCAAA

411H11 HUMANIZED LIGHT CHAIN FULL-LENGTH AMINO ACID SEQUENCE. HUMAN KAPPA CONSTANT
DOMAIN IS UNDERLINED

SEQ ID NO: 139

DVVMTQSPSSVSASVGDRVTITCQASQSIGADLAWYQQKPGKAPKLLIYRASTLASGVPSRFSGSGSGTDFTLTISSLQP

EDFATYYCQAIYYGTDDVIYHTFGGGTKVEIK<u>RTVAAPSVFIFPPSDEQLKSGTASVVCLLNNFYPREAKVQWKVDNALQ</u>

<u>SGNSQESVTEQDSKDSTYSLSSTLTLSKADYEKHKVYACEVTHQGLSSPVTKSFNRGEC</u>

411H11 HUMANIZED LIGHT CHAIN VARIABLE LIGHT CHAIN AMINO ACID SEQUENCE.
COMPIMENTARITY DETERMINING REGIONS ARE UNDERLINED

SEQ ID NO: 140

DVVMTQSPSSVSASVGDRVTITC<u>QASQSIGADLA</u>WYQQKPGKAPKLLIY<u>RASTLAS</u>GVPSRFSGSGSGTDFTLTISSLQP

EDFATYYC<u>QAIYYGTDDVIYHT</u>FGGGTKVEIK

411H11 HUMANIZED HEAVY CHAIN FULL-LENGTH NUCLEOTIDE SEQUENCE

SEQ ID NO: 141

GAGGTGCAGCTGGTGGAGTCTGGGGGAGGCTTGGTCCAGCCTGGGGGGTCCCTGAGACTCTCCTGTGCAGCCTC

TGGATTCACCATCAGTAGCCACCACATGATCTGGGTCCGCCAGGCTCCAGGGAAGGGGCTGCAATACATCGGATT

CATTAATGATGGTGACTATACATACTACACGAACTCCGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGGCTTGTGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

411H11 HUMANIZED HEAVY CHAIN VARIABLE HEAVY CHAIN NUCLEOTIDE SEQUENCE

SEQ ID NO: 142

GAGGTGCAGCTGGTGGAGTCTGGGGGAGGCTTGGTCCAGCCTGGGGGGTCCCTGAGACTCTCCTGTGCAGCCTC

TGGATTCACCATCAGTAGCCACCACATGATCTGGGTCCGCCAGGCTCCAGGGAAGGGGCTGCAATACATCGGATT

CATTAATGATGGTGACTATACATACTACACGAACTCCGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGGCTTGTGGGGCCAGGGAACCCTGGTCACCGTCTCGAGC

411H11 HUMANIZED HEAVY CHAIN FULL-LENGTH AMINO ACID SEQUENCE. HUMAN GAMMA-1 CONSTANT DOMAIN IS UNDERLINED

SEQ ID NO: 143

EVQLVESGGGLVQPGGSLRLSCAASGFTISSHHMIWVRQAPGKGLQYIGFINDGDYTYYTNSAKGRFTISRDNSKNTLYL

QMNSLRAEDTAVYYCARGVDGTSYPGLWGQGTLVTVSS<u>ASTKGPSVFPLAPSSKSTSGGTAALGCLVKDYFPEPVTVS</u>

<u>WNSGALTSGVHTFPAVLQSSGLYSLSSVVTVPSSSLGTQTYICNVNHKPSNTKVDKRVEPKSCDKTHTCPPCPAPEAAG</u>

<u>APSVFLFPPKPKDTLMISRTPEVTCVVVDVSHEDPEVKFNWYVDGVEVHNAKTKPREEQYNSTYRVVSVLTVLHQDWL</u>

<u>NGKEYKCAVSNKALPAPIEKTISKAKGQPREPQVYTLPPSRDELTKNQVSLTCLVKGFYPSDIAVEWESNGQPENNYKTT</u>

<u>PPVLDSDGSFFLYSKLTVDKSRWQQGNVFSCSVMHEALHNHYTQKSLSLSPG</u>

411H11 HUMANIZED HEAVY CHAIN VARIABLE HEAVY CHAIN AMINO ACID SEQUENCE. COMPLIMENTARITY DETERMINING REGIONS ARE UNDERLINED

SEQ ID NO: 144

EVQLVESGGGLVQPGGSLRLSCAASGFTIS<u>SHHMI</u>WVRQAPGKGLQYIG<u>FINDGDYTYYTNSAK</u>GRFTISRDNSKNTLYL

QMNSLRAEDTAVYYCAR<u>GVDGTSYPGL</u>WGQGTLVTVSS

413F3 HUMANIZED LIGHT CHAIN FULL-LENGTH NUCLEOTIDE SEQUENCE

SEQ ID NO: 145

GACATCCAGATGACCCAGTCTCCATCCTCCCTGTCTGCATCTGTAGGAGACAGAGTCACCATCACTTGCCAGGCCA

GTCAGAGCATTTACAGCAATTTAGCCTGGTATCAGCAGAAACCAGGGAAAGTTCCTAAGCTCCTGATCTATTCTAC

ATCCACTCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAACTATTATGGTAGTAGTACTGATAGTTATGGGAATC

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

413F3 HUMANIZED LIGHT CHAIN VARIABLE LIGHT CHAIN NUCLEOTIDE SEQUENCE

SEQ ID NO: 146

GACATCCAGATGACCCAGTCTCCATCCTCCCTGTCTGCATCTGTAGGAGACAGAGTCACCATCACTTGCCAGGCCA

GTCAGAGCATTTACAGCAATTTAGCCTGGTATCAGCAGAAACCAGGGAAAGTTCCTAAGCTCCTGATCTATTCTAC

ATCCACTCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAACTATTATGGTAGTAGTACTGATAGTTATGGGAATC

CTTTCGGCGGAGGGACCAAGGTGGAGATCAAA

413F3 HUMANIZED LIGHT CHAIN FULL-LENGTH AMINO ACID SEQUENCE. HUMAN KAPPA CONSTANT DOMAIN IS UNDERLINED

SEQ ID NO: 147

DIQMTQSPSSLSASVGDRVTITCQASQSIYSNLAWYQQKPGKVPKLLIYSTSTLASGVPSRFSGSGSGTDFTLTISSLQPED

VATYYCQNYYGSSTDSYGNPFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

413F3 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 148

DIQMTQSPSSLSASVGDRVTITC<u>QASQSIYSNLA</u>WYQQKPGKVPKLLIY<u>STSTLAS</u>GVPSRFSGSGSGTDFTLTISSLQPED

VATYYC<u>QNYYGSSTDSYGNPF</u>GGGTKVEIK

413F3 HUMANIZED HEAVY CHAIN FULL-LENGTH NUCLEOTIDE SEQUENCE

SEQ ID NO: 149

GAGGTGCAGCTGGTGGAGTCTGGGGGAGGCTTGGTCCAGCCTGGGGGGTCCCTGAGACTCTCCTGTGCAGCCTC

TGGAATCGACTTCAGTAGCAACTACATGTGCTGGGTCCGCCAGGCTCCAGGGAAGGGGCTGGAGTGGATCGCAT

GCATTTATGGTGATAGTAGTGATAATAGTTACTCCGCGAGCTCCGCTAAAGGCAGATTCACCATCTCCAGAGACAA

TTCCAAGAACACGCTGTATCTTCAAATGAACAGCCTGAGAGCCGAGGACACGGCTGTGTATTACTGTGCGAGATCT

-continued

```
GGTTATAGCTATTTAGGCTACTTTAACTTGTGGGGCCAGGGAACCCTGGTCACCGTCTCGAGCGCTAGCACCAAGG

GCCCATCGGTCTTCCCCCTGGCACCCTCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

ACTCACACATGCCCACCGTGCCCAGCACCTGAAGCCGCGGGGGCACCGTCAGTCTTCCTCTTCCCCCCAAAACCCA

AGGACACCCTCATGATCTCCCGGACCCCTGAGGTCACATGCGTGGTGGTGGACGTGAGCCACGAAGACCCTGAGG

TCAAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGCGCG

GTCTCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGT
```

413F3 HUMANIZED HEAVY CHAIN VARIABLE HEAVY CHAIN NUCLEOTIDE SEQUENCE
SEQ ID NO: 150
```
GAGGTGCAGCTGGTGGAGTCTGGGGGAGGCTTGGTCCAGCCTGGGGGGTCCCTGAGACTCTCCTGTGCAGCCTC

TGGAATCGACTTCAGTAGCAACTACATGTGCTGGGTCCGCCAGGCTCCAGGGAAGGGGCTGGAGTGGATCGCAT

GCATTTATGGTGATAGTAGTGATAATAGTTACTCCGCGAGCTCCGCTAAAGGCAGATTCACCATCTCCAGAGACAA

TTCCAAGAACACGCTGTATCTTCAAATGAACAGCCTGAGAGCCGAGGACACGGCTGTGTATTACTGTGCGAGATCT

GGTTATAGCTATTTAGGCTACTTTAACTTGTGGGGCCAGGGAACCCTGGTCACCGTCTCGAGC
```

413F3 HUMANIZED HEAVY CHAIN FULL-LENGTH AMINO ACID SEQUENCE. HUMAN GAMMA-1
CONSTANT DOMAIN IS UNDERLINED
SEQ ID NO: 151
EVQLVESGGGLVQPGGSLRLSCAASGIDFSSNYMCWVRQAPGKGLEWIACIYGDSSDNSYSASSAKGRFTISRDNSKNT

LYLQMNSLRAEDTAVYYCARSGYSYLGYFNLWGQGTLVTVSS<u>ASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG</u>

413F3 HUMANIZED HEAVY CHAIN VARIABLE HEAVY CHAIN AMINO ACID SEQUENCE.
COMPLIMENTARITY DETERMINING REGIONS ARE UNDERLINED
SEQ ID NO: 152
EVQLVESGGGLVQPGGSLRLSCAASGIDFS<u>SNYMC</u>WVRQAPGKGLEWIA<u>CIYGDSSDNSYSASSAKG</u>RFTISRDNSKNT

LYLQMNSLRAEDTAVYYCARS<u>GYSYLGYFNL</u>WGQGTLVTVSS

416F8 HUMANIZED LIGHT CHAIN FULL-LENGTH NUCLEOTIDE SEQUENCE
SEQ ID NO: 153
```
GACATCCAGATGACCCAGTCTCCATCCTCCCTGTCTGCATCTGTAGGAGACAGAGTCACCATCACTTGCCAGTCCA

GTCAGACTGTTTATAATAACAACTTGTTATCCTGGTATCAGCAGAAACCAGGGAAAGTTCCTAAGCTCCTGATCTAT

TATGCATCCACTCTGGCATTTGGGGTCCCATCTCGGTTCAGTGGCAGTGGATCTGGGACAGATTTCACTCTCACCAT

CAGCAGCCTGCAGCCTGAAGATGTTGCAACTTATTACTGTCAAGGCGGTTATAGTGGTTGGATTTATGTTTTCGGC

GGAGGGACCAAGGTGGAGATCAAACGTACGGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAGCACCTACAGC

CTCAGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGT
```

416F8 HUMANIZED LIGHT CHAIN VARIABLE LIGHT CHAIN NUCLEOTIDE SEQUENCE
SEQ ID NO: 154
GACATCCAGATGACCCAGTCTCCATCCTCCCTGTCTGCATCTGTAGGAGACAGAGTCACCATCACTTGCCAGTCCA

GTCAGACTGTTTATAATAACAACTTGTTATCCTGGTATCAGCAGAAACCAGGGAAAGTTCCTAAGCTCCTGATCTAT

TATGCATCCACTCTGGCATTTGGGGTCCCATCTCGGTTCAGTGGCAGTGGATCTGGGACAGATTTCACTCTCACCAT

CAGCAGCCTGCAGCCTGAAGATGTTGCAACTTATTACTGTCAAGGCGGTTATAGTGGTTGGATTTATGTTTTCGGC

GGAGGGACCAAGGTGGAGATCAAA

416F8 HUMANIZED LIGHT CHAIN FULL-LENGTH AMINO ACID SEQUENCE. HUMAN KAPPA CONSTANT
DOMAIN IS UNDERLINED
SEQ ID NO: 155
DIQMTQSPSSLSASVGDRVTITCQSSQTVYNNNLLSWYQQKPGKVPKLLIYYASTLAFGVPSRFSGSGSGTDFTLTISSLQ

PEDVATYYCQGGYSGWIYVFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

416F8 HUMANIZED LIGHT CHAIN VARIABLE LIGHT CHAIN AMINO ACID SEQUENCE. COMPIMENTARITY
DETERMINING REGIONS ARE UNDERLINED
SEQ ID NO: 156
DIQMTQSPSSLSASVGDRVTITC<u>QSSQTVYNNNLLS</u>WYQQKPGKVPKLLIY<u>YASTLAF</u>GVPSRFSGSGSGTDFTLTISSLQ

PEDVATYYC<u>QGGYSGWIYV</u>FGGGTKVEIK

416F8 HUMANIZED HEAVY CHAIN FULL-LENGTH NUCLEOTIDE SEQUENCE
SEQ ID NO: 157
CAGTCGCTGGTGGAGTCTGGGGGAGGCTTGGTCCAGCCTGGGGGGTCCCTGAGACTCTCCTGTGCAGCCTCTGGA

TTCTCCCTCAGTAACTACTACATGAACTGGGTCCGCCAGGCTCCAGGGAAGGGGCTGGAGTACATCGGAATCATT

AGTAGTAGTGGTAGCGCATACTACGCGAGCTCCGCTAAAGGCAGATTCACCATCTCCAGAGACAATTCCAAGAAC

ACGCTGTATCTTCAAATGAACAGCCTGAGAGCCGAGGACACGGCTGTGTATTACTGTGCGAGAGGGGACTACGGC

ATGGACCTCTGGGGCCAGGGAACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

416F8 HUMANIZED HEAVY CHAIN VARIABLE HEAVY CHAIN NUCLEOTIDE SEQUENCE
SEQ ID NO: 158
CAGTCGCTGGTGGAGTCTGGGGGAGGCTTGGTCCAGCCTGGGGGGTCCCTGAGACTCTCCTGTGCAGCCTCTGGA

TTCTCCCTCAGTAACTACTACATGAACTGGGTCCGCCAGGCTCCAGGGAAGGGGCTGGAGTACATCGGAATCATT

AGTAGTAGTGGTAGCGCATACTACGCGAGCTCCGCTAAAGGCAGATTCACCATCTCCAGAGACAATTCCAAGAAC

ACGCTGTATCTTCAAATGAACAGCCTGAGAGCCGAGGACACGGCTGTGTATTACTGTGCGAGAGGGGACTACGGC

ATGGACCTCTGGGGCCAGGGAACCCTGGTCACCGTCTCGAGC

416F8 HUMANIZED HEAVY CHAIN FULL-LENGTH AMINO ACID SEQUENCE. HUMAN GAMMA-1 CONSTANT DOMAIN IS UNDERLINED

SEQ ID NO: 159

QSLVESGGGLVQPGGSLRLSCAASGFSLSNYYMNWVRQAPGKGLEYIGIISSSGSAYYASSAKGRFTISRDNSKNTLYLQ

MNSLRAEDTAVYYCARGDYGMDLWGQGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

416F8 HUMANIZED HEAVY CHAIN VARIABLE HEAVY CHAIN AMINO ACID SEQUENCE. COMPLIMENTARITY DETERMINING REGIONS ARE UNDERLINED

SEQ ID NO: 160

QSLVESGGGLVQPGGSLRLSCAASGFSLS<u>NYYMN</u>WVRQAPGKGLEYIGI<u>ISSSGSAYYASSAKG</u>RFTISRDNSKNTLYLQ

MNSLRAEDTAVYYCAR<u>GDYGMDL</u>WGQGTLVTVSS

416G1 HUMANIZED LIGHT CHAIN FULL-LENGTH NUCLEOTIDE SEQUENCE

SEQ ID NO: 161

GACGTTGTGATGACCCAGTCTCCATCTTCCGTGTCTGCATCTGTAGGAGACAGAGTCACCATCACCTGTCAGGCCA

GTCAGAGCATTGGTAGTGATTTAGCCTGGTATCAGCAGAAACCAGGGAAAGCCCCTAAGCTCCTGATCTATAGGG

CATCCACTCTGGCATCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAATCCATTTATTATGGTAGTGATGATGTCATATACCATA

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

416G1 HUMANIZED LIGHT CHAIN VARIABLE LIGHT CHAIN NUCLEOTIDE SEQUENCE

SEQ ID NO: 162

GACGTTGTGATGACCCAGTCTCCATCTTCCGTGTCTGCATCTGTAGGAGACAGAGTCACCATCACCTGTCAGGCCA

GTCAGAGCATTGGTAGTGATTTAGCCTGGTATCAGCAGAAACCAGGGAAAGCCCCTAAGCTCCTGATCTATAGGG

CATCCACTCTGGCATCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAATCCATTTATTATGGTAGTGATGATGTCATATACCATA

CTTTCGGCGGAGGGACCAAGGTGGAGATCAAA

416G1 HUMANIZED LIGHT CHAIN FULL-LENGTH AMINO ACID SEQUENCE. HUMAN KAPPA CONSTANT DOMAIN IS UNDERLINED

SEQ ID NO: 163

DVVMTQSPSSVSASVGDRVTITCQASQSIGSDLAWYQQKPGKAPKLLIYRASTLASGVPSRFSGSGSGTDFTLTISSLQPE

DFATYYCQSIYYGSDDVIYHTFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

416G1 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 164

DVVMTQSPSSVSASVGDRVTITC<u>QASQSIGSDLA</u>WYQQKPGKAPKLLIY<u>RASTLAS</u>GVPSRFSGSGSGTDFTLTISSLQPE

DFATYYC<u>QSIYYGSDDVIYHT</u>FGGGTKVEIK

416G1 HUMANIZED HEAVY CHAIN FULL-LENGTH NUCLEOTIDE SEQUENCE

SEQ ID NO: 165

GAGGTGCAGCTGGTGGAGTCTGGGGGAGGCTTGGTCCAGCCTGGGGGGTCCCTGAGACTCTCCTGTGCAGCCTC

TGGATTCACTATCAATAGCTACCACATGATCTGGGTCCGCCAGGCTCCAGGGAAGGGGCTGGAGTACATCGGATT

CATTAATGATGGTGGTTTCACATACTACGCGAGCTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

```
GGTACTAGTTATCCTGACTTATGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

416G1 HUMANIZED HEAVY CHAIN VARIABLE HEAVY CHAIN NUCLEOTIDE SEQUENCE
                                                                  SEQ ID NO: 166
GAGGTGCAGCTGGTGGAGTCTGGGGGAGGCTTGGTCCAGCCTGGGGGGTCCCTGAGACTCTCCTGTGCAGCCTC

TGGATTCACTATCAATAGCTACCACATGATCTGGGTCCGCCAGGCTCCAGGGAAGGGGCTGGAGTACATCGGATT

CATTAATGATGGTGGTTTCACATACTACGCGAGCTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGACTTATGGGGCCAGGGAACCCTGGTCACCGTCTCGAGC

416G1 HUMANIZED HEAVY CHAIN FULL-LENGTH AMINO ACID SEQUENCE. HUMAN GAMMA-1
CONSTANT DOMAIN IS UNDERLINED
                                                                  SEQ ID NO: 167
EVQLVESGGGLVQPGGSLRLSCAASGFTINSYHMIWVRQAPGKGLEYIGFINDGGFTYYASSAKGRFTISRDNSKNTLYL

QMNSLRAEDTAVYYCARGVDGTSYPDLWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

416G1 HUMANIZED HEAVY CHAIN VARIABLE HEAVY CHAIN AMINO ACID SEQUENCE.
COMPLIMENTARITY DETERMINING REGIONS ARE UNDERLINED
                                                                  SEQ ID NO: 168
EVQLVESGGGLVQPGGSLRLSCAASGFTINSYHMIWVRQAPGKGLEYIGFINDGGFTYYASSAKGRFTISRDNSKNTLYL

QMNSLRAEDTAVYYCARGVDGTSYPDLWGQGTLVTVSS

418E10 HUMANIZED LIGHT CHAIN FULL-LENGTH NUCLEOTIDE SEQUENCE
                                                                  SEQ ID NO: 169
GACATCCAGATGACCCAGTCTCCTTCCACCCTGTCTGCATCTGTAGGAGACAGAGTCACCATCACTTGCCAGGCCA

GTCAGAGCATTGGTAGTAACTTGAACTGGTATCAGCAGAAACCAGGGAAAGCCCCTAAGCTCCTGATCTATTATGT

ATCCACTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGACGGTACTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT
```

418E10 HUMANIZED LIGHT CHAIN VARIABLE LIGHT CHAIN NUCLEOTIDE SEQUENCE
SEQ ID NO: 170

GACATCCAGATGACCCAGTCTCCTTCCACCCTGTCTGCATCTGTAGGAGACAGAGTCACCATCACTTGCCAGGCCA

GTCAGAGCATTGGTAGTAACTTGAACTGGTATCAGCAGAAACCAGGGAAAGCCCCTAAGCTCCTGATCTATTATGT

ATCCACTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGACGGTACTGCTTTT

CGGCGGAGGGACCAAGGTGGAGATCAAA

418E10 HUMANIZED LIGHT CHAIN FULL-LENGTH AMINO ACID SEQUENCE. HUMAN KAPPA CONSTANT
DOMAIN IS UNDERLINED
SEQ ID NO: 171

DIQMTQSPSTLSASVGDRVTITCQASQSIGSNLNWYQQKPGKAPKLLIYYVSTLASGVPSRFSGSGSGTEFTLTISSLQPD

DFATYYCLGVWNYWGDDGTAFGGGTKVEIK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

418E10 HUMANIZED LIGHT CHAIN VARIABLE LIGHT CHAIN AMINO ACID SEQUENCE.
COMPIMENTARITY DETERMINING REGIONS ARE UNDERLINED
SEQ ID NO: 172

DIQMTQSPSTLSASVGDRVTITC<u>QASQSIGSNLN</u>WYQQKPGKAPKLLIY<u>YVSTLAS</u>GVPSRFSGSGSGTEFTLTISSLQPD

DFATYYC<u>LGVWNYWGDDGTA</u>FGGGTKVEIK

418E10 HUMANIZED HEAVY CHAIN FULL-LENGTH NUCLEOTIDE SEQUENCE
SEQ ID NO: 173

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTACCTATTATATGAGCTGGGTCCGCCAGGCTCCAGGGAAGGGGCTGGAGTGGATCGGAAG

TATTTATGATAGTGGTGCCGCATACTACGCGACCTCCGCGAAGGGCAGATTCACCATCTCCAGAGACAATTCCAAG

AACACGCTGTATCTTCAAATGAACAGCCTGAGAGCCGAGGACACGGCTGTGTATTACTGTGCGAGAGATCCTATT

AATAATGCCATCTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418E10 HUMANIZED HEAVY CHAIN VARIABLE HEAVY CHAIN NUCLEOTIDE SEQUENCE
SEQ ID NO: 174

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTACCTATTATATGAGCTGGGTCCGCCAGGCTCCAGGGAAGGGGCTGGAGTGGATCGGAAG

TATTTATGATAGTGGTGCCGCATACTACGCGACCTCCGCGAAGGGCAGATTCACCATCTCCAGAGACAATTCCAAG

AACACGCTGTATCTTCAAATGAACAGCCTGAGAGCCGAGGACACGGCTGTGTATTACTGTGCGAGAGATCCTATT

AATAATGCCATCTGGGGCCAGGGAACCCTGGTCACCGTCTCGAGC

418E10 HUMANIZED HEAVY CHAIN FULL-LENGTH AMINO ACID SEQUENCE. HUMAN GAMMA-1 CONSTANT DOMAIN IS UNDERLINED

SEQ ID NO: 175

EVQLVESGGGLVQPGGSLRLSCAASGFSLSTYYMSWVRQAPGKGLEWIGSIYDSGAAYYATSAKGRFTISRDNSKNTLY

LQMNSLRAEDTAVYYCARDPINNAIWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

418E10 HUMANIZED HEAVY CHAIN VARIABLE HEAVY CHAIN AMINO ACID SEQUENCE. COMPLIMENTARITY DETERMINING REGIONS ARE UNDERLINED

SEQ ID NO: 176

EVQLVESGGGLVQPGGSLRLSCAASGFSLSTYYMSWVRQAPGKGLEWIGSIYDSGAAYYATSAKGRFTISRDNSKNTLY

LQMNSLRAEDTAVYYCARDPINNAIWGQGTLVTVSS

418E4 HUMANIZED LIGHT CHAIN FULL-LENGTH NUCLEOTIDE SEQUENCE

SEQ ID NO: 177

GACATCCAGATGACCCAGTCTCCTTCCACCCTGTCTGCATCTGTAGGAGACAGAGTCACCATCACTTGCCAGGCCA

GTCAGAGTATTGCTACTAACTTGAACTGGTATCAGCAGAAACCAGGGAAAGCCCCTAAGCTCCTGATCTATTATAC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

418E4 HUMANIZED LIGHT CHAIN VARIABLE LIGHT CHAIN NUCLEOTIDE SEQUENCE

SEQ ID NO: 178

GACATCCAGATGACCCAGTCTCCTTCCACCCTGTCTGCATCTGTAGGAGACAGAGTCACCATCACTTGCCAGGCCA

GTCAGAGTATTGCTACTAACTTGAACTGGTATCAGCAGAAACCAGGGAAAGCCCCTAAGCTCCTGATCTATTATAC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGCTTT

CGGCGGAGGGACCAAGGTGGAGATCAAA

418E4 HUMANIZED LIGHT CHAIN FULL-LENGTH AMINO ACID SEQUENCE. HUMAN KAPPA CONSTANT DOMAIN IS UNDERLINED

SEQ ID NO: 179

DIQMTQSPSTLSASVGDRVTITCQASQSIATNLNWYQQKPGKAPKLLIYYTSSLASGVPSRFSGSGSGTEFTLTISSLQPD

DFATYYCLGVWNYWGDDGTAFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

418E4 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 180

DIQMTQSPSTLSASVGDRVTITCQASQSIATNLNWYQQKPGKAPKLLIYYTSSLASGVPSRFSGSGSGTEFTLTISSLQPD

DFATYYCLGVWNYWGDDGTAFGGGTKVEIK

418E4 HUMANIZED HEAVY CHAIN FULL-LENGTH NUCLEOTIDE SEQUENCE

SEQ ID NO: 181

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGCTAGTGGTAGCGCATACTACGCGAGTTCCGCGAAGGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

```
TAACAATGACATCTGGGGCCAGGGAACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418E4 HUMANIZED HEAVY CHAIN VARIABLE HEAVY CHAIN NUCLEOTIDE SEQUENCE
                                                         SEQ ID NO: 182
GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGCTAGTGGTAGCGCATACTACGCGAGTTCCGCGAAGGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGACATCTGGGGCCAGGGAACCCTGGTCACCGTCTCGAGC

418E4 HUMANIZED HEAVY CHAIN FULL-LENGTH AMINO ACID SEQUENCE. HUMAN GAMMA-1
CONSTANT DOMAIN IS UNDERLINED
                                                         SEQ ID NO: 183
EVQLVESGGGLVQPGGSLRLSCAASGFSLSSYYMSWVRQAPGKGLEWIGSIYASGSAYYASSAKGRFTISRDNSKNTLYL

QMNSLRAEDTAVYYCARDPINNDIWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

418E4 HUMANIZED HEAVY CHAIN VARIABLE HEAVY CHAIN AMINO ACID SEQUENCE.
COMPLIMENTARITY DETERMINING REGIONS ARE UNDERLINED
                                                         SEQ ID NO: 184
EVQLVESGGGLVQPGGSLRLSCAASGFSLSSYYMSWVRQAPGKGLEWIGSIYASGSAYYASSAKGRFTISRDNSKNTLYL

QMNSLRAEDTAVYYCARDPINNDIWGQGTLVTVSS

418H5 HUMANIZED LIGHT CHAIN FULL-LENGTH NUCLEOTIDE SEQUENCE
                                                         SEQ ID NO: 185
GACATCCAGATGACCCAGTCTCCATCTTCCGTGTCTGCATCTGTAGGAGACAGAGTCACCATCACTTGTCAGTCCA

GTCCGAGTGTTTATAAGAACAACCAATTAGCCTGGTATCAGCAGAAACCAGGGAAAGCCCCTAAGCTCCTGATCTA

TCTGGCATCTACTCTGGCATCTGGGGTCCCATCAAGGTTCAGCGGCAGTGGATCTGGGACAGATTTCACTCTCACC

ATCAGCAGCCTGCAGCCTGAAGATTTTGCAACTTACTATTGTGCAGGCGGTTATAGTAGTAGTAGTGATACTGCTT

TCGGCGGAGGGACCAAGGTGGAGATCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT
```

418H5 HUMANIZED LIGHT CHAIN VARIABLE LIGHT CHAIN NUCLEOTIDE SEQUENCE
SEQ ID NO: 186
GACATCCAGATGACCCAGTCTCCATCTTCCGTGTCTGCATCTGTAGGAGACAGAGTCACCATCACTTGTCAGTCCA

GTCCGAGTGTTTATAAGAACAACCAATTAGCCTGGTATCAGCAGAAACCAGGGAAAGCCCCTAAGCTCCTGATCTA

TCTGGCATCTACTCTGGCATCTGGGGTCCCATCAAGGTTCAGCGGCAGTGGATCTGGGACAGATTTCACTCTCACC

ATCAGCAGCCTGCAGCCTGAAGATTTTGCAACTTACTATTGTGCAGGCGGTTATAGTAGTAGTAGTGATACTGCTT

TCGGCGGAGGGACCAAGGTGGAGATCAAA

418H5 HUMANIZED LIGHT CHAIN FULL-LENGTH AMINO ACID SEQUENCE. HUMAN KAPPA CONSTANT
DOMAIN IS UNDERLINED
SEQ ID NO: 187
DIQMTQSPSSVSASVGDRVTITCQSSPSVYKNNQLAWYQQKPGKAPKLLIYLASTLASGVPSRFSGSGSGTDFTLTISSLQ

PEDFATYYCAGGYSSSSDTAFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

418H5 HUMANIZED LIGHT CHAIN VARIABLE LIGHT CHAIN AMINO ACID SEQUENCE. COMPIMENTARITY
DETERMINING REGIONS ARE UNDERLINED
SEQ ID NO: 188
DIQMTQSPSSVSASVGDRVTITC<u>QSSPSVYKNNQLA</u>WYQQKPGKAPKLLIY<u>LASTLAS</u>GVPSRFSGSGSGTDFTLTISSLQ

PEDFATYYC<u>AGGYSSSSDTAFGGGTKVEIK</u>

418H5 HUMANIZED HEAVY CHAIN FULL-LENGTH NUCLEOTIDE SEQUENCE
SEQ ID NO: 189
GAGGTGCAGCTGGTGGAGTCTGGGGGAGGCTTGGTCCAGCCTGGGGGGTCCCTGAGACTCTCCTGTACAGCCTC

TGGAATCGACCTCAGTGCCTACCACATGAGCTGGGTCCGCCAGGCTCCAGGGAAGGGGCTGGAGTACATCGGGA

TGATTGGTAGTAGTGGTACCATACACTACGCGAACTCCGCGAAAGGCAGATTCACCATCTCCAAAGACAATACCAA

GAACACGGTGGATCTTCAAATGAACAGCCTGAGAGCCGAGGACACGGCTGTGTATTACTGTGCGAGAGACAGTT

ATAATAGTGATTATGCCTTTAACTTATGGGGCCAGGGAACCCTGGTCACCGTCTCGAGCGCTAGCACCAAGGGCCC

ATCGGTCTTCCCCCTGGCACCCTCCTCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTCCAGCAGCTTGGGCACCCAGACCTACA

TCTGCAACGTGAATCACAAGCCCAGCAACACCAAGGTGGACAAGAGAGTTGAGCCCAAATCTTGTGACAAAACTC

ACACATGCCCACCGTGCCCAGCACCTGAAGCCGCGGGGGCACCGTCAGTCTTCCTCTTCCCCCCAAAACCCAAGGA

CACCCTCATGATCTCCCGGACCCCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTACAAGTGCGCGGTCT

CCAACAAAGCCCTCCCAGCCCCCATCGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTGACCTGCCTGGTCAAAGGCTTCTATCC

CAGCGACATCGCCGTGGAGTGGGAGAGCAATGGGCAGCCGGAGAACAACTACAAGACCACGCCTCCCGTGCTGG

ACTCCGACGGCTCCTTCTTCCTCTATAGCAAGCTCACCGTGGACAAGAGCAGGTGGCAGCAGGGGAACGTCTTCTC

ATGCTCCGTGATGCATGAGGCTCTGCACAACCACTACACGCAGAAGAGCCTCTCCCTGTCTCCGGGT

418H5 HUMANIZED HEAVY CHAIN VARIABLE HEAVY CHAIN NUCLEOTIDE SEQUENCE
SEQ ID NO: 190
GAGGTGCAGCTGGTGGAGTCTGGGGGAGGCTTGGTCCAGCCTGGGGGGTCCCTGAGACTCTCCTGTACAGCCTC

TGGAATCGACCTCAGTGCCTACCACATGAGCTGGGTCCGCCAGGCTCCAGGGAAGGGGCTGGAGTACATCGGGA

TGATTGGTAGTAGTGGTACCATACACTACGCGAACTCCGCGAAAGGCAGATTCACCATCTCCAAAGACAATACCAA

GAACACGGTGGATCTTCAAATGAACAGCCTGAGAGCCGAGGACACGGCTGTGTATTACTGTGCGAGAGACAGTT

ATAATAGTGATTATGCCTTTAACTTATGGGGCCAGGGAACCCTGGTCACCGTCTCGAGC

418H5 HUMANIZED HEAVY CHAIN FULL-LENGTH AMINO ACID SEQUENCE. HUMAN GAMMA-1
CONSTANT DOMAIN IS UNDERLINED

SEQ ID NO: 191

EVQLVESGGGLVQPGGSLRLSCTASGIDLSAYHMSWVRQAPGKGLEYIGMIGSSGTIHYANSAKGRFTISKDNTKNTVD

LQMNSLRAEDTAVYYCARDSYNSDYAFNLWGQGTLVTVSS<u>ASTKGPSVFPLAPSSKSTSGGTAALGCLVKDYFPEPVTV</u>

<u>SWNSGALTSGVHTFPAVLQSSGLYSLSSVVTVPSSSLGTQTYICNVNHKPSNTKVDKRVEPKSCDKTHTCPPCPAPEAA</u>

<u>GAPSVFLFPPKPKDTLMISRTPEVTCVVVDVSHEDPEVKFNWYVDGVEVHNAKTKPREEQYNSTYRVVSVLTVLHQDW</u>

<u>LNGKEYKCAVSNKALPAPIEKTISKAKGQPREPQVYTLPPSRDELTKNQVSLTCLVKGFYPSDIAVEWESNGQPENNYKT</u>

<u>TPPVLDSDGSFFLYSKLTVDKSRWQQGNVFSCSVMHEALHNHYTQKSLSLSPG</u>

418H5 HUMANIZED HEAVY CHAIN VARIABLE HEAVY CHAIN AMINO ACID SEQUENCE.
COMPLIMENTARITY DETERMINING REGIONS ARE UNDERLINED

SEQ ID NO: 192

EVQLVESGGGLVQPGGSLRLSCTASGIDLS<u>AYHMS</u>WVRQAPGKGLEYIG<u>MIGSSGTIHYANSAK</u>GRFTISKDNTKNTVD

LQMNSLRAEDTAVYYCAR<u>DSYNSDYAFNL</u>WGQGTLVTVSS

419D9 HUMANIZED LIGHT CHAIN FULL-LENGTH NUCLEOTIDE SEQUENCE

SEQ ID NO: 193

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTATCCTGGTATCAGCAGAAACCAGGGAAAGCCCCTAAGAGACTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTATAATACTGTTACTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

419D9 HUMANIZED LIGHT CHAIN VARIABLE LIGHT CHAIN NUCLEOTIDE SEQUENCE

SEQ ID NO: 194

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTATCCTGGTATCAGCAGAAACCAGGGAAAGCCCCTAAGAGACTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTATAATACTGTTACTGATACTTTTGCTTT

CGGCGGAGGGACCAAGGTGGAGATCAAA

419D9 HUMANIZED LIGHT CHAIN FULL-LENGTH AMINO ACID SEQUENCE. HUMAN KAPPA CONSTANT
DOMAIN IS UNDERLINED

SEQ ID NO: 195

DIQMTQSPSTLSASVGDRVTITCQSSQSVYSNWLSWYQQKPGKAPKRLIYSASTLASGVPSRFSGSGSGTEFTLTISSLQP

DDFATYYCAGGYNTVTDTFAFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

419D9 HUMANIZED LIGHT CHAIN VARIABLE LIGHT CHAIN AMINO ACID SEQUENCE. COMPIMENTARITY
DETERMINING REGIONS ARE UNDERLINED

SEQ ID NO: 196

DIQMTQSPSTLSASVGDRVTITC<u>QSSQSVYSNWLS</u>WYQQKPGKAPKRLIY<u>SASTLAS</u>GVPSRFSGSGSGTEFTLTISSLQP

DDFATYYC<u>AGGYNTVTDTFAF</u>GGGTKVEIK

419D9 HUMANIZED HEAVY CHAIN FULL-LENGTH NUCLEOTIDE SEQUENCE

SEQ ID NO: 197

GAGGTGCAGCTGTTGGAGTCTGGGGGAGGCTTGGTACAGCCTGGGGGGTCCCTGAGACTCTCCTGTACAGCCTCT

GGATTCTCCTTCAGTAGCAGGCACTACATGTGTTGGGTCCGCCAGGCTCCAGGGAAGGGGCTGGAGTGGATCGCA

TGCATTTATACTGGTAGTAGTGGTACTCCTCACTACGCGAGCTCCGCGAAAGGCCGGTTCACCATCTCCCAAGACA

ATTCCAAGAACACGGTGACTCTGCAAATGAACAGCCTGAGAGCCGAGGACACGGCCGTATATTACTGTGCGAGAG

-continued

AAGGTAACCTGTGGGGCCAGGGAACCCTGGTCACCGTCTCGAGCGCTAGCACCAAGGGCCCATCGGTCTTCCCCC

TGGCACCCTCCTCCAAGAGCACCTCTGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGCACCCAGACCTACATCTGCAACGTGAA

TCACAAGCCCAGCAACACCAAGGTGGACAAGAGAGTTGAGCCCAAATCTTGTGACAAAACTCACACATGCCCACC

GTGCCCAGCACCTGAAGCCGCGGGGGCACCGTCAGTCTTCCTCTTCCCCCCAAAACCCAAGGACACCCTCATGATC

TCCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

419D9 HUMANIZED HEAVY CHAIN VARIABLE HEAVY CHAIN NUCLEOTIDE SEQUENCE
SEQ ID NO: 198
GAGGTGCAGCTGTTGGAGTCTGGGGGAGGCTTGGTACAGCCTGGGGGGTCCCTGAGACTCTCCTGTACAGCCTCT

GGATTCTCCTTCAGTAGCAGGCACTACATGTGTTGGGTCCGCCAGGCTCCAGGGAAGGGGCTGGAGTGGATCGCA

TGCATTTATACTGGTAGTAGTGGTACTCCTCACTACGCGAGCTCCGCGAAAGGCCGGTTCACCATCTCCCAAGACA

ATTCCAAGAACACGGTGACTCTGCAAATGAACAGCCTGAGAGCCGAGGACACGGCCGTATATTACTGTGCGAGAG

AAGGTAACCTGTGGGGCCAGGGAACCCTGGTCACCGTCTCGAGC

419D9 HUMANIZED HEAVY CHAIN FULL-LENGTH AMINO ACID SEQUENCE. HUMAN GAMMA-1
CONSTANT DOMAIN IS UNDERLINED
SEQ ID NO: 199
EVQLLESGGGLVQPGGSLRLSCTASGFSFSSRHYMCWVRQAPGKGLEWIACIYTGSSGTPHYASSAKGRFTISQDNSKN

TVTLQMNSLRAEDTAVYYCAREGNLWGQGTLVTVSS<u>ASTKGPSVFPLAPSSKSTSGGTAALGCLVKDYFPEPVTVSWN</u>

<u>SGALTSGVHTFPAVLQSSGLYSLSSVVTVPSSSLGTQTYICNVNHKPSNTKVDKRVEPKSCDKTHTCPPCPAPEAAGAPS</u>

<u>VFLFPPKPKDTLMISRTPEVTCVVVDVSHEDPEVKFNWYVDGVEVHNAKTKPREEQYNSTYRVVSVLTVLHQDWLNG</u>

<u>KEYKCAVSNKALPAPIEKTISKAKGQPREPQVYTLPPSRDELTKNQVSLTCLVKGFYPSDIAVEWESNGQPENNYKTTPP</u>

<u>VLDSDGSFFLYSKLTVDKSRWQQGNVFSCSVMHEALHNHYTQKSLSLSPG</u>

419D9 HUMANIZED HEAVY CHAIN VARIABLE HEAVY CHAIN AMINO ACID SEQUENCE.
COMPLIMENTARITY DETERMINING REGIONS ARE UNDERLINED
SEQ ID NO: 200
EVQLLESGGGLVQPGGSLRLSCTASGFSFS<u>SRHYMC</u>WVRQAPGKGLEWIAC<u>IYTGSSGTPHYASSAKG</u>RFTISQDNSKN

TVTLQMNSLRAEDTAVYYCAR<u>EGNLW</u>GQGTLVTVSS

420H5 HUMANIZED LIGHT CHAIN FULL-LENGTH NUCLEOTIDE SEQUENCE
SEQ ID NO: 201
GCCCTTGTGATGACCCAGTCTCCTTCCACCCTGTCTGCATCTGTAGGAGACAGAGTCACCATCAATTGCCAGGCCA

GTGAGGACATTGATACCTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTGCTGATACGAGGGGTG

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

420H5 HUMANIZED LIGHT CHAIN VARIABLE LIGHT CHAIN NUCLEOTIDE SEQUENCE

SEQ ID NO: 202

GCCCTTGTGATGACCCAGTCTCCTTCCACCCTGTCTGCATCTGTAGGAGACAGAGTCACCATCAATTGCCAGGCCA

GTGAGGACATTGATACCTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTGCTGATACGAGGGGTG

CTTTCGGCGGAGGGACCAAGGTGGAGATCAAA

420H5 HUMANIZED LIGHT CHAIN FULL-LENGTH AMINO ACID SEQUENCE. HUMAN KAPPA CONSTANT DOMAIN IS UNDERLINED

SEQ ID NO: 203

ALVMTQSPSTLSASVGDRVTINCQASEDIDTYLAWYQQKPGKAPKLLIFYASDLASGVPSRFSGSGSGTEFTLTISSLQPD

DFATYYCQGGYYTSSADTRGAFGGGTKVEIK<u>RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC</u>

420H5 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 204

ALVMTQSPSTLSASVGDRVTINC<u>QASEDIDTYLA</u>WYQQKPGKAPKLLIF<u>YASDLAS</u>GVPSRFSGSGSGTEFTLTISSLQPD

DFATYYC<u>QGGYYTSSADTRGA</u>FGGGTKVEIK

420H5 HUMANIZED HEAVY CHAIN FULL-LENGTH NUCLEOTIDE SEQUENCE

SEQ ID NO: 205

CAGTCGCTGGTGGAGTCTGGGGGAGGCTTGGTACAGCCTGGGGGGTCCCTGAGACTCTCCTGTGCAGCCTCTGG

ATTCTCCTTCAGTAGCAACTACTGGATATGCTGGGTCCGCCAGGCTCCAGGGAAGGGGCTGGAGTGGATCGCATG

CATTTATGTTGGTAGTAGTGGTGACACTTACTACGCGAGCTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGCACCCAGACCTA

CATCTGCAACGTGAATCACAAGCCCAGCAACACCAAGGTGGACAAGAGAGTTGAGCCCAAATCTTGTGACAAAAC

TCACACATGCCCACCGTGCCCAGCACCTGAAGCCGCGGGGGCACCGTCAGTCTTCCTCTTCCCCCCAAAACCCAAG

GACACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTGCGCGG

TCTCCAACAAAGCCCTCCCAGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCTCCCTGTCTCCGGGT

420H5 HUMANIZED HEAVY CHAIN VARIABLE HEAVY CHAIN NUCLEOTIDE SEQUENCE

SEQ ID NO: 206

CAGTCGCTGGTGGAGTCTGGGGGAGGCTTGGTACAGCCTGGGGGGTCCCTGAGACTCTCCTGTGCAGCCTCTGG

ATTCTCCTTCAGTAGCAACTACTGGATATGCTGGGTCCGCCAGGCTCCAGGGAAGGGGCTGGAGTGGATCGCATG

CATTTATGTTGGTAGTAGTGGTGACACTTACTACGCGAGCTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGC

420H5 HUMANIZED HEAVY CHAIN FULL-LENGTH AMINO ACID SEQUENCE. HUMAN GAMMA-1
CONSTANT DOMAIN IS UNDERLINED

SEQ ID NO: 207

QSLVESGGGLVQPGGSLRLSCAASGFSFSSNYWICWVRQAPGKGLEWIACIYVGSSGDTYYASSAKGRFTISRDNSKNT

LYLQMNSLRAEDTAVYYCARDSSSYYMFNLWGQGTLVTVSS<u>ASTKGPSVFPLAPSSKSTSGGTAALGCLVKDYFPEPVT</u>

<u>VSWNSGALTSGVHTFPAVLQSSGLYSLSSVVTVPSSSLGTQTYICNVNHKPSNTKVDKRVEPKSCDKTHTCPPCPAPEAA</u>

<u>GAPSVFLFPPKPKDTLMISRTPEVTCVVVDVSHEDPEVKFNWYVDGVEVHNAKTKPREEQYNSTYRVVSVLTVLHQDW</u>

<u>LNGKEYKCAVSNKALPAPIEKTISKAKGQPREPQVYTLPPSRDELTKNQVSLTCLVKGFYPSDIAVEWESNGQPENNYKT</u>

<u>TPPVLDSDGSFFLYSKLTVDKSRWQQGNVFSCSVMHEALHNHYTQKSLSLSPG</u>

420H5 HUMANIZED HEAVY CHAIN VARIABLE HEAVY CHAIN AMINO ACID SEQUENCE.
COMPLIMENTARITY DETERMINING REGIONS ARE UNDERLINED

SEQ ID NO: 208

QSLVESGGGLVQPGGSLRLSCAASGFSFS<u>SNYWIC</u>WVRQAPGKGLEWIAC<u>IYVGSSGDTYYASSAKG</u>RFTISRDNSKNT

LYLQMNSLRAEDTAVYYCAR<u>DSSSYYMFNL</u>WGQGTLVTVSS

420H6 HUMANIZED LIGHT CHAIN FULL-LENGTH NUCLEOTIDE SEQUENCE

SEQ ID NO: 209

GACATCCAGATGACCCAGTCTCCTTCCACCCTGTCTGCATCTGTAGGAGACAGAGTCACCATCACTTGCCAGGCCA

GTCAGAGTGTTTATAGTAACTGGTTATCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAATTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

420H6 HUMANIZED LIGHT CHAIN VARIABLE LIGHT CHAIN NUCLEOTIDE SEQUENCE

SEQ ID NO: 210

GACATCCAGATGACCCAGTCTCCTTCCACCCTGTCTGCATCTGTAGGAGACAGAGTCACCATCACTTGCCAGGCCA

GTCAGAGTGTTTATAGTAACTGGTTATCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAATTGATACTTTTGCTTT

CGGCGGAGGGACCAAGGTGGAGATCAAA

420H6 HUMANIZED LIGHT CHAIN FULL-LENGTH AMINO ACID SEQUENCE. HUMAN KAPPA CONSTANT
DOMAIN IS UNDERLINED

SEQ ID NO: 211

DIQMTQSPSTLSASVGDRVTITCQASQSVYSNWLSWYQQKPGKAPKLLIYSASTLASGVPSRFSGSGSGTEFTLTISSLQP

DDFATYYCAGGYNTVIDTFAFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

420H6 HUMANIZED LIGHT CHAIN VARIABLE LIGHT CHAIN AMINO ACID SEQUENCE. COMPIMENTARITY
DETERMINING REGIONS ARE UNDERLINED

SEQ ID NO: 212

DIQMTQSPSTLSASVGDRVTITC<u>QASQSVYSNWLS</u>WYQQKPGKAPKLLIY<u>SASTLAS</u>GVPSRFSGSGSGTEFTLTISSLQP

DDFATYYC<u>AGGYNTVIDTFAF</u>GGGTKVEIK

420H6 HUMANIZED HEAVY CHAIN FULL-LENGTH NUCLEOTIDE SEQUENCE

SEQ ID NO: 213

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGTAGTTACTACATGTGCTGGGTCCGCCAGGCTCCAGGGAAGGGGCTGGAGTGGATCGC

ATGCATTTATACTGGTGGTAGTGGTACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

420H6 HUMANIZED HEAVY CHAIN VARIABLE HEAVY CHAIN NUCLEOTIDE SEQUENCE
SEQ ID NO: 214
GAGGTGCAGCTGTTGGAGTCTGGGGGAGGCTTGGTACAGCCTGGGGGGTCCCTGAGACTCTCCTGTGCAGCCTCT

GGAATCGACTTCAGTAGTAGTTACTACATGTGCTGGGTCCGCCAGGCTCCAGGGAAGGGGCTGGAGTGGATCGC

ATGCATTTATACTGGTGGTAGTGGTACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGC

420H6 HUMANIZED HEAVY CHAIN FULL-LENGTH AMINO ACID SEQUENCE. HUMAN GAMMA-1
CONSTANT DOMAIN IS UNDERLINED
SEQ ID NO: 215
EVQLLESGGGLVQPGGSLRLSCAASGIDFSSSYYMCWVRQAPGKGLEWIACIYTGGSGTPHYASSAKGRFTISRDNSKN

TLYLQMNSLRAEDTAVYYCAREGSLWGQGTLVTVSS<u>ASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG</u>

420H6 HUMANIZED HEAVY CHAIN VARIABLE HEAVY CHAIN AMINO ACID SEQUENCE.
COMPLIMENTARITY DETERMINING REGIONS ARE UNDERLINED
SEQ ID NO: 216
EVQLLESGGGLVQPGGSLRLSCAASGIDFS<u>SSYYMC</u>WVRQAPGKGLEWIA<u>CIYTGGSGTPHYASSAKG</u>RFTISRDNSKN

TLYLQMNSLRAEDTAVYYCAR<u>EGSLWGQGTLVTVSS

459F1 HUMANIZED LIGHT CHAIN FULL-LENGTH NUCLEOTIDE SEQUENCE
SEQ ID NO: 217
GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAACTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

459F1 HUMANIZED LIGHT CHAIN VARIABLE LIGHT CHAIN NUCLEOTIDE SEQUENCE

SEQ ID NO: 218

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAACTGATACTTTTGCTTT

CGGCGGAGGGACCAAGGTGGAGATCAAA

459F1 HUMANIZED LIGHT CHAIN FULL-LENGTH AMINO ACID SEQUENCE. HUMAN KAPPA CONSTANT DOMAIN IS UNDERLINED

SEQ ID NO: 219

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVTDTFAFGGGTKVEIK<u>RTVAAPSVFIFPPSDEQLKSGTASVVCLLNNFYPREAKVQWKVDNALQS</u>

<u>GNSQESVTEQDSKDSTYSLSSTLTLSKADYEKHKVYACEVTHQGLSSPVTKSFNRGEC</u>

459F1 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 220

DIQMTQSPSTLSASVGDRVTITC<u>QSSQSVYSNWFS</u>WYQQKPGKAPKLLIY<u>SASTLAS</u>GVPSRFSGSGSGTEFTLTISSLQP

DDFATYYC<u>AGGYNTVTDTFAF</u>GGGTKVEIK

459F1 HUMANIZED HEAVY CHAIN FULL-LENGTH NUCLEOTIDE SEQUENCE

SEQ ID NO: 221

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATGTATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAACCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

459F1 HUMANIZED HEAVY CHAIN VARIABLE HEAVY CHAIN NUCLEOTIDE SEQUENCE

SEQ ID NO: 222

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATGTATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAACCTGTGGGGCCAGGGAACCCTGGTCACCGTCTCGAGC

459F1 HUMANIZED HEAVY CHAIN FULL-LENGTH AMINO ACID SEQUENCE. HUMAN GAMMA-1
CONSTANT DOMAIN IS UNDERLINED

SEQ ID NO: 223

EVQLLESGGGLVQPGGSLRLSCAASGIDFSRRYYMCWVRQAPGKGLEWIACMYTGSRDTPHYASSAKGRFTISRDNSK

NTLYLQMNSLRAEDTAVYYCAREGNLWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKRVEPKSCDKTHTCPPCPAPEAAGAP

SVFLFPPKPKDTLMISRTPEVTCVVVDVSHEDPEVKFNWYVDGVEVHNAKTKPREEQYNSTYRVVSVLTVLHQDWLNG

KEYKCAVSNKALPAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

459F1 HUMANIZED HEAVY CHAIN VARIABLE HEAVY CHAIN AMINO ACID SEQUENCE.
COMPLIMENTARITY DETERMINING REGIONS ARE UNDERLINED

SEQ ID NO: 224

EVQLLESGGGLVQPGGSLRLSCAASGIDFSRRYYMCWVRQAPGKGLEWIACMYTGSRDTPHYASSAKGRFTISRDNSK

NTLYLQMNSLRAEDTAVYYCAREGNLWGQGTLVTVSS

460C3 HUMANIZED LIGHT CHAIN FULL-LENGTH NUCLEOTIDE SEQUENCE

SEQ ID NO: 225

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTTATTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

460C3 HUMANIZED LIGHT CHAIN VARIABLE LIGHT CHAIN NUCLEOTIDE SEQUENCE

SEQ ID NO: 226

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTTATTGATACTTTTGCTTT

CGGCGGAGGGACCAAGGTGGAGATCAAA

460C3 HUMANIZED LIGHT CHAIN FULL-LENGTH AMINO ACID SEQUENCE. HUMAN KAPPA CONSTANT
DOMAIN IS UNDERLINED

SEQ ID NO: 227

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVIDTFAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

460C3 HUMANIZED LIGHT CHAIN VARIABLE LIGHT CHAIN AMINO ACID SEQUENCE. COMPIMENTARITY
DETERMINING REGIONS ARE UNDERLINED

SEQ ID NO: 228

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVIDTFAFGGGTKVEIK

460C3 HUMANIZED HEAVY CHAIN FULL-LENGTH NUCLEOTIDE SEQUENCE

SEQ ID NO: 229

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATATATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

```
GAAGGTAGCCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT
```

460C3 HUMANIZED HEAVY CHAIN VARIABLE HEAVY CHAIN NUCLEOTIDE SEQUENCE
SEQ ID NO: 230

```
GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATATATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGC
```

460C3 HUMANIZED HEAVY CHAIN FULL-LENGTH AMINO ACID SEQUENCE. HUMAN GAMMA-1
CONSTANT DOMAIN IS UNDERLINED
SEQ ID NO: 231

EVQLLESGGGLVQPGGSLRLSCAASGIDFSRRYYMCWVRQAPGKGLEWIACIYTGSRDTPHYASSAKGRFTISRDNSKN

TLYLQMNSLRAEDTAVYYCAREGSLWGQGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

460C3 HUMANIZED HEAVY CHAIN VARIABLE HEAVY CHAIN AMINO ACID SEQUENCE.
COMPLIMENTARITY DETERMINING REGIONS ARE UNDERLINED
SEQ ID NO: 232

EVQLLESGGGLVQPGGSLRLSCAASGIDFS<u>RRYYMC</u>WVRQAPGKGLEWIA<u>CIYTGSRDTPHYASSAKG</u>RFTISRDNSKN

TLYLQMNSLRAEDTAVYYCAR<u>EGSLWGQGTLVTVSS</u>

464C11 HUMANIZED LIGHT CHAIN FULL-LENGTH NUCLEOTIDE SEQUENCE
SEQ ID NO: 233

```
GACATCCAGATGACCCAGTCTCCTTCCACCCTGTCTGCATCTGTAGGAGACAGAGTCACCATCACTTGCCAGTCCA

GTCAGAGTGTTTATAGTAACAGCTTCTTATCCTGGTATCAGCAGAAACCAGGGAAAGCCCCTAAGCTCCTGATCTA

TTCTGCATCCGATCGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCGCAGGCGTTTATAGTGATAATACTTATGTTTTCGG

CGGAGGGACCAAGGTGGAGATCAAACGTACGGTGGCTGCACCATCTGTCTTCATCTTCCCGCCATCTGATGAGCA

GTTGAAATCTGGAACTGCCTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGCAAGGACAGCACCTACAG

CCTCAGCAGCACCCTGACGCTGAGCAAAGCAGACTACGAGAAACACAAAGTCTACGCCTGCGAAGTCACCCATCA

GGGCCTGAGCTCGCCCGTCACAAAGAGCTTCAACAGGGGAGAGTGT
```

464C11 HUMANIZED LIGHT CHAIN VARIABLE LIGHT CHAIN NUCLEOTIDE SEQUENCE
SEQ ID NO: 234

GACATCCAGATGACCCAGTCTCCTTCCACCCTGTCTGCATCTGTAGGAGACAGAGTCACCATCACTTGCCAGTCCA

GTCAGAGTGTTTATAGTAACAGCTTCTTATCCTGGTATCAGCAGAAACCAGGGAAAGCCCCTAAGCTCCTGATCTA

TTCTGCATCCGATCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCGCAGGCGTTTATAGTGATAATACTTATGTTTTCGG

CGGAGGGACCAAGGTGGAGATCAAA

464C11 HUMANIZED LIGHT CHAIN FULL-LENGTH AMINO ACID SEQUENCE. HUMAN KAPPA CONSTANT DOMAIN IS UNDERLINED
SEQ ID NO: 235

DIQMTQSPSTLSASVGDRVTITCQSSQSVYSNSFLSWYQQKPGKAPKLLIYSASDLASGVPSRFSGSGSGTEFTLTISSLQP

DDFATYYCAGVYSDNTYVFGGGTKVEIKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

464C11 HUMANIZED LIGHT CHAIN VARIABLE LIGHT CHAIN AMINO ACID SEQUENCE. COMPIMENTARITY DETERMINING REGIONS ARE UNDERLINED
SEQ ID NO: 236

DIQMTQSPSTLSASVGDRVTITCQSSQSVYSNSFLSWYQQKPGKAPKLLIYSASDLASGVPSRFSGSGSGTEFTLTISSLQP

DDFATYYCAGVYSDNTYVFGGGTKVEIK

464C11 HUMANIZED HEAVY CHAIN FULL-LENGTH NUCLEOTIDE SEQUENCE
SEQ ID NO: 237

GAGGTGCAGCTGGTGGAGTCTGGGGGAGGCTTGGTACAGCCAGGGCCGTCCCTGAGACTCTCCTGTACAGCTTCT

GGATTCTCCCTCAGTCACTACTGGATGACTTGGGTCCGCCAGGCTCCAGGGAAGGGGCTGGAGTACATCGGATTC

ATTAATGTTGGTGGTGACACATCTTACGCGAGCTCTGTGAAAGGCAGATTCACCATCTCAAGAGATGATTCCAAAA

GCATCGCCTATCTGCAAATGAACAGCCTGAAAACCGAGGACACAGCCGTGTATTACTGTGGCAGAGGTGGTCTGA

CTTTTGGTTGGGACTTGTGGGGCCAGGGAACCCTGGTCACCGTCTCGAGCGCTAGCACCAAGGGCCCATCGGTCT

TCCCCCTGGCACCCTCCTCCAAGAGCACCTCTGGGGGCACAGCGGCCCTGGGCTGCCTGGTCAAGGACTACTTCC

CGAACCGGTGACGGTGTCGTGGAACTCAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAGAGTTGAGCCCAAATCTTGTGACAAAACTCACACATGC

CCACCGTGCCCAGCACCTGAAGCCGCGGGGGCACCGTCAGTCTTCCTCTTCCCCCCAAAACCCAAGGACACCCTCA

TGATCTCCCGGACCCCTGAGGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCAGTACAACAGCACGTACCG

TGTGGTCAGCGTCCTCACCGTCCTGCACCAGGACTGGCTGAATGGCAAGGAGTACAAGTGCGCGGTCTCCAACAA

AGCCCTCCCAGCCCCCATCGAGAAAACCATCTCCAAAGCCAAAGGGCAGCCCCGAGAACCACAGGTGTACACCCT

GCCCCCATCCCGGGATGAGCTGACCAAGAACCAGGTCAGCCTGACCTGCCTGGTCAAAGGCTTCTATCCCAGCGA

CATCGCCGTGGAGTGGGAGAGCAATGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCTCCGGGT

464C11 HUMANIZED HEAVY CHAIN VARIABLE HEAVY CHAIN NUCLEOTIDE SEQUENCE
SEQ ID NO: 238

GAGGTGCAGCTGGTGGAGTCTGGGGGAGGCTTGGTACAGCCAGGGCCGTCCCTGAGACTCTCCTGTACAGCTTCT

GGATTCTCCCTCAGTCACTACTGGATGACTTGGGTCCGCCAGGCTCCAGGGAAGGGGCTGGAGTACATCGGATTC

ATTAATGTTGGTGGTGACACATCTTACGCGAGCTCTGTGAAAGGCAGATTCACCATCTCAAGAGATGATTCCAAAA

GCATCGCCTATCTGCAAATGAACAGCCTGAAAACCGAGGACACAGCCGTGTATTACTGTGGCAGAGGTGGTCTGA

CTTTTGGTTGGGACTTGTGGGGCCAGGGAACCCTGGTCACCGTCTCGAGC

464C11 HUMANIZED HEAVY CHAIN FULL-LENGTH AMINO ACID SEQUENCE. HUMAN GAMMA-1 CONSTANT DOMAIN IS UNDERLINED

SEQ ID NO: 239

EVQLVESGGGLVQPGPSLRLSCTASGFSLSHYWMTWVRQAPGKGLEYIGFINVGGDTSYASSVKGRFTISRDDSKSIAYL

QMNSLKTEDTAVYYCGRGGLTFGWDLWGQGTLVTVSS<u>ASTKGPSVFPLAPSSKSTSGGTAALGCLVKDYFPEPVTVSW</u>

<u>NSGALTSGVHTFPAVLQSSGLYSLSSVVTVPSSSLGTQTYICNVNHKPSNTKVDKRVEPKSCDKTHTCPPCPAPEAAGAP</u>

<u>SVFLFPPKPKDTLMISRTPEVTCVVVDVSHEDPEVKFNWYVDGVEVHNAKTKPREEQYNSTYRVVSVLTVLHQDWLNG</u>

<u>KEYKCAVSNKALPAPIEKTISKAKGQPREPQVYTLPPSRDELTKNQVSLTCLVKGFYPSDIAVEWESNGQPENNYKTTPP</u>

<u>VLDSDGSFFLYSKLTVDKSRWQQGNVFSCSVMHEALHNHYTQKSLSLSPG</u>

464C11 HUMANIZED HEAVY CHAIN VARIABLE HEAVY CHAIN AMINO ACID SEQUENCE. COMPLIMENTARITY DETERMINING REGIONS ARE UNDERLINED

SEQ ID NO: 240

EVQLVESGGGLVQPGPSLRLSCTASGFSLS<u>HYWMT</u>WVRQAPGKGLEYIG<u>FINVGGDTSYASS</u>VKGRFTISRDDSKSIAYL

QMNSLKTEDTAVYYCGR<u>GGLTFGWDL</u>WGQGTLVTVSS

466F6 HUMANIZED LIGHT CHAIN FULL-LENGTH NUCLEOTIDE SEQUENCE

SEQ ID NO: 241

GACGTTGTGATGACCCAGTCTCCATCTTCCGTGTCTGCATCTGTAGGAGACAGAGTCACCATCACCTGTCAGGCCA

GTCAGAACATTAGGACTTACTTATCCTGGTATCAGCAGAAACCAGGGAAAGCCCCTAAGCTCCTGATCTATGCTGC

AGCCAATCTGGCATCTGGGGTCCCATCAAGGTTCAGCGGCAGTGGATCTGGGACAGATTTCACTCTCACCATCAGC

GACCTGGAGCCTGGCGATGCTGCAACTTACTATTGTCAGTCTACCTATCTTGGTACTGATTATGTTGGCGGTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

466F6 HUMANIZED LIGHT CHAIN VARIABLE LIGHT CHAIN NUCLEOTIDE SEQUENCE

SEQ ID NO: 242

GACGTTGTGATGACCCAGTCTCCATCTTCCGTGTCTGCATCTGTAGGAGACAGAGTCACCATCACCTGTCAGGCCA

GTCAGAACATTAGGACTTACTTATCCTGGTATCAGCAGAAACCAGGGAAAGCCCCTAAGCTCCTGATCTATGCTGC

AGCCAATCTGGCATCTGGGGTCCCATCAAGGTTCAGCGGCAGTGGATCTGGGACAGATTTCACTCTCACCATCAGC

GACCTGGAGCCTGGCGATGCTGCAACTTACTATTGTCAGTCTACCTATCTTGGTACTGATTATGTTGGCGGTGCTTT

CGGCGGAGGGACCAAGGTGGAGATCAAA

466F6 HUMANIZED LIGHT CHAIN FULL-LENGTH AMINO ACID SEQUENCE. HUMAN KAPPA CONSTANT DOMAIN IS UNDERLINED

SEQ ID NO: 243

DVVMTQSPSSVSASVGDRVTITCQASQNIRTYLSWYQQKPGKAPKLLIYAAANLASGVPSRFSGSGSGTDFTLTISDLEP

GDAATYYCQSTYLGTDYVGGAFGGGTKVEIK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

466F6 HUMANIZED LIGHT CHAIN VARIABLE LIGHT CHAIN AMINO ACID SEQUENCE. COMPIMENTARITY DETERMINING REGIONS ARE UNDERLINED

SEQ ID NO: 244

DVVMTQSPSSVSASVGDRVTITC<u>QASQNIRTYLS</u>WYQQKPGKAPKLLIY<u>AAANLAS</u>GVPSRFSGSGSGTDFTLTISDLEP

GDAATYYC<u>QSTYLGTDYVGGA</u>FGGGTKVEIK

466F6 HUMANIZED HEAVY CHAIN FULL-LENGTH NUCLEOTIDE SEQUENCE

SEQ ID NO: 245

CGGTCGCTGGTGGAGTCTGGGGGAGGCTTGGTCCAGCCTGGGGGGTCCCTGAGACTCTCCTGTACAGCCTCTGGA

TTCACCATCAGTAGCTACCACATGCAGTGGGTCCGCCAGGCTCCAGGGAAGGGGCTGGAGTACATCGGAACCATT

AGTAGTGGTGGTAATGTATACTACGCGAGCTCCGCGAGAGGCAGATTCACCATCTCCAGACCCTCGTCCAAGAAC

ACGGTGGATCTTCAAATGAACAGCCTGAGAGCCGAGGACACGGCTGTGTATTACTGTGCGAGAGACTCTGGTTAT

```
AGTGATCCTATGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT
```

466F6 HUMANIZED HEAVY CHAIN VARIABLE HEAVY CHAIN NUCLEOTIDE SEQUENCE
SEQ ID NO: 246
```
CGGTCGCTGGTGGAGTCTGGGGGAGGCTTGGTCCAGCCTGGGGGGTCCCTGAGACTCTCCTGTACAGCCTCTGGA

TTCACCATCAGTAGCTACCACATGCAGTGGGTCCGCCAGGCTCCAGGGAAGGGGCTGGAGTACATCGGAACCATT

AGTAGTGGTGGTAATGTATACTACGCGAGCTCCGCGAGAGGCAGATTCACCATCTCCAGACCCTCGTCCAAGAAC

ACGGTGGATCTTCAAATGAACAGCCTGAGAGCCGAGGACACGGCTGTGTATTACTGTGCGAGAGACTCTGGTTAT

AGTGATCCTATGTGGGGCCAGGGAACCCTGGTCACCGTCTCGAGC
```

466F6 HUMANIZED HEAVY CHAIN FULL-LENGTH AMINO ACID SEQUENCE. HUMAN GAMMA-1
CONSTANT DOMAIN IS UNDERLINED
SEQ ID NO: 247
RSLVESGGGLVQPGGSLRLSCTASGFTISSYHMQWVRQAPGKGLEYIGTISSGGNVYYASSARGRFTISRPSSKNTVDLQ

MNSLRAEDTAVYYCARDSGYSDPMWGQGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

466F6 HUMANIZED HEAVY CHAIN VARIABLE HEAVY CHAIN AMINO ACID SEQUENCE.
COMPLIMENTARITY DETERMINING REGIONS ARE UNDERLINED
SEQ ID NO: 248
RSLVESGGGLVQPGGSLRLSCTASGFTIS<u>SYHMQ</u>WVRQAPGKGLEYIGT<u>ISSGGNVYYASSARG</u>RFTISRPSSKNTVDLQ

MNSLRAEDTAVYYCAR<u>DSGYSDPM</u>WGQGTLVTVSS

470B6 HUMANIZED LIGHT CHAIN FULL-LENGTH NUCLEOTIDE SEQUENCE
SEQ ID NO: 249
```
GACATCCAGATGACCCAGTCTCCTTCCACCCTGTCTGCATCTGTAGGAGACAGAGTCACCATCACTTGCCAGGCCA

GTCAGAGCATTAGTACTAACTTGAACTGGTATCAGCAGAAACCAGGGAAAGCCCCTAAGCTCCTGATCTATTATGC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGATTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT
```

470B6 HUMANIZED LIGHT CHAIN VARIABLE LIGHT CHAIN NUCLEOTIDE SEQUENCE

SEQ ID NO: 250

GACATCCAGATGACCCAGTCTCCTTCCACCCTGTCTGCATCTGTAGGAGACAGAGTCACCATCACTTGCCAGGCCA

GTCAGAGCATTAGTACTAACTTGAACTGGTATCAGCAGAAACCAGGGAAAGCCCCTAAGCTCCTGATCTATTATGC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGATTT

CGGCGGAGGGACCAAGGTGGAGATCAAA

470B6 HUMANIZED LIGHT CHAIN FULL-LENGTH AMINO ACID SEQUENCE. HUMAN KAPPA CONSTANT
DOMAIN IS UNDERLINED

SEQ ID NO: 251

DIQMTQSPSTLSASVGDRVTITCQASQSISTNLNWYQQKPGKAPKLLIYYASSLASGVPSRFSGSGSGTEFTLTISSLQPD

DFATYYCLGVWNYWGDDGTDFGGGTKVEIK<u>RTVAAPSVFIFPPSDEQLKSGTASVVCLLNNFYPREAKVQWKVDNAL</u>

<u>QSGNSQESVTEQDSKDSTYSLSSTLTLSKADYEKHKVYACEVTHQGLSSPVTKSFNRGEC</u>

470B6 HUMANIZED LIGHT CHAIN VARIABLE LIGHT CHAIN AMINO ACID SEQUENCE. COMPIMENTARITY
DETERMINING REGIONS ARE UNDERLINED

SEQ ID NO: 252

DIQMTQSPSTLSASVGDRVTITC<u>QASQSISTNLN</u>WYQQKPGKAPKLLIY<u>YASSLAS</u>GVPSRFSGSGSGTEFTLTISSLQPD

DFATYYC<u>LGVWNYWGDDGTDF</u>GGGTKVEIK

470B6 HUMANIZED HEAVY CHAIN FULL-LENGTH NUCLEOTIDE SEQUENCE

SEQ ID NO: 253

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGGTAGTGGTGCCGCATACTACGCGAGCTCCGCTAAAGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGCCATGTGGGGCCAGGGAACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

470B6 HUMANIZED HEAVY CHAIN VARIABLE HEAVY CHAIN NUCLEOTIDE SEQUENCE

SEQ ID NO: 254

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGGTAGTGGTGCCGCATACTACGCGAGCTCCGCTAAAGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGCCATGTGGGGCCAGGGAACCCTGGTCACCGTCTCGAGC

470B6 HUMANIZED HEAVY CHAIN FULL-LENGTH AMINO ACID SEQUENCE. HUMAN GAMMA-1
CONSTANT DOMAIN IS UNDERLINED

SEQ ID NO: 255

EVQLVESGGGLVQPGGSLRLSCAASGFSLSSYYMSWVRQAPGKGLEWIGSIYGSGAAYYASSAKGRFTISRDNSKNTLY

LQMNSLRAEDTAVYYCARDPINNAMWGQGTLVTVSS<u>ASTKGPSVFPLAPSSKSTSGGTAALGCLVKDYFPEPVTVSW</u>

<u>NSGALTSGVHTFPAVLQSSGLYSLSSVVTVPSSSLGTQTYICNVNHKPSNTKVDKRVEPKSCDKTHTCPPCPAPEAAGAP</u>

<u>SVFLFPPKPKDTLMISRTPEVTCVVVDVSHEDPEVKFNWYVDGVEVHNAKTKPREEQYNSTYRVVSVLTVLHQDWLNG</u>

<u>KEYKCAVSNKALPAPIEKTISKAKGQPREPQVYTLPPSRDELTKNQVSLTCLVKGFYPSDIAVEWESNGQPENNYKTTPP</u>

<u>VLDSDGSFFLYSKLTVDKSRWQQGNVFSCSVMHEALHNHYTQKSLSLSPG</u>

470B6 HUMANIZED HEAVY CHAIN VARIABLE HEAVY CHAIN AMINO ACID SEQUENCE.
COMPLIMENTARITY DETERMINING REGIONS ARE UNDERLINED

SEQ ID NO: 256

EVQLVESGGGLVQPGGSLRLSCAASGFSLS<u>SYYMS</u>WVRQAPGKGLEWIGS<u>IYGSGAAYYASSAKG</u>RFTISRDNSKNTLY

LQMNSLRAEDTAVYYCAR<u>DPINNAM</u>WGQGTLVTVSS

470C6 HUMANIZED LIGHT CHAIN FULL-LENGTH NUCLEOTIDE SEQUENCE

SEQ ID NO: 257

GCCCTTGTGATGACCCAGTCTCCTTCCACCCTGTCTGCATCTGTAGGAGACAGAGTCACCATCAATTGCCAGGCCA

GTGAGGACATTGATAACTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTACTGATACGAGGGGTG

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

470C6 HUMANIZED LIGHT CHAIN VARIABLE LIGHT CHAIN NUCLEOTIDE SEQUENCE

SEQ ID NO: 258

GCCCTTGTGATGACCCAGTCTCCTTCCACCCTGTCTGCATCTGTAGGAGACAGAGTCACCATCAATTGCCAGGCCA

GTGAGGACATTGATAACTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTACTGATACGAGGGGTG

CTTTCGGCGGAGGGACCAAGGTGGAGATCAAA

470C6 HUMANIZED LIGHT CHAIN FULL-LENGTH AMINO ACID SEQUENCE. HUMAN KAPPA CONSTANT
DOMAIN IS UNDERLINED

SEQ ID NO: 259

ALVMTQSPSTLSASVGDRVTINCQASEDIDNYLAWYQQKPGKAPKLLIFYASDLASGVPSRFSGSGSGTEFTLTISSLQPD

DFATYYCQGGYYTSSTDTRGAFGGGTKVEIK<u>RTVAAPSVFIFPPSDEQLKSGTASVVCLLNNFYPREAKVQWKVDNALQ</u>

<u>SGNSQESVTEQDSKDSTYSLSSTLTLSKADYEKHKVYACEVTHQGLSSPVTKSFNRGEC</u>

470C6 HUMANIZED LIGHT CHAIN VARIABLE LIGHT CHAIN AMINO ACID SEQUENCE. COMPIMENTARITY
DETERMINING REGIONS ARE UNDERLINED

SEQ ID NO: 260

ALVMTQSPSTLSASVGDRVTINC<u>QASEDIDNYLA</u>WYQQKPGKAPKLLIF<u>YASDLAS</u>GVPSRFSGSGSGTEFTLTISSLQPD

DFATYYC<u>QGGYYTSSTDTRG</u>AFGGGTKVEIK

470C6 HUMANIZED HEAVY CHAIN FULL-LENGTH NUCLEOTIDE SEQUENCE

SEQ ID NO: 261

CAGTCGCTGGTGGAGTCTGGGGGAGGCTTGGTACAGCCTGGGGGGTCCCTGAGACTCTCCTGTGCAGCCTCTGG

ATTCTCCTTCACTAGCAGCTACTACATGTGCTGGGTCCGCCAGGCTCCAGGGAAGGGGCTGGAGTGGATCGCATG

CATTTATACTGGTAGTAGTGGTAGCACTTACTACGCGAACTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

-continued
AGTAGTAGTTATTATATGTTTAACTTGTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGCACCCAGACCTA

CATCTGCAACGTGAATCACAAGCCCAGCAACACCAAGGTGGACAAGAGAGTTGAGCCCAAATCTTGTGACAAAAC

TCACACATGCCCACCGTGCCCAGCACCTGAAGCCGCGGGGGCACCGTCAGTCTTCCTCTTCCCCCCAAAACCCAAG

GACACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTGCGCGG

TCTCCAACAAAGCCCTCCCAGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCTCCCTGTCTCCGGGT

470C6 HUMANIZED HEAVY CHAIN VARIABLE HEAVY CHAIN NUCLEOTIDE SEQUENCE
                                                          SEQ ID NO: 262
CAGTCGCTGGTGGAGTCTGGGGGAGGCTTGGTACAGCCTGGGGGGTCCCTGAGACTCTCCTGTGCAGCCTCTGG

ATTCTCCTTCACTAGCAGCTACTACATGTGCTGGGTCCGCCAGGCTCCAGGGAAGGGGCTGGAGTGGATCGCATG

CATTTATACTGGTAGTAGTGGTAGCACTTACTACGCGAACTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGC

470C6 HUMANIZED HEAVY CHAIN FULL-LENGTH AMINO ACID SEQUENCE. HUMAN GAMMA-1
CONSTANT DOMAIN IS UNDERLINED
                                                          SEQ ID NO: 263
QSLVESGGGLVQPGGSLRLSCAASGFSFTSSYYMCWVRQAPGKGLEWIACIYTGSSGSTYYANSAKGRFTISRDNSKNT

LYLQMNSLRAEDTAVYYCARDSSSYYMFNLWGQGTLVTVSS<u>ASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG</u>

470C6 HUMANIZED HEAVY CHAIN VARIABLE HEAVY CHAIN AMINO ACID SEQUENCE.
COMPLIMENTARITY DETERMINING REGIONS ARE UNDERLINED
                                                          SEQ ID NO: 264
QSLVESGGGLVQPGGSLRLSCAASGFSFTS<u>SYYMC</u>WVRQAPGKGLEWIA<u>CIYTGSSGSTYYANSAKG</u>RFTISRDNSKNT

LYLQMNSLRAEDTAVYYCAR<u>DSSSYYMFNL</u>WGQGTLVTVSS

472E4 HUMANIZED LIGHT CHAIN FULL-LENGTH NUCLEOTIDE SEQUENCE
                                                          SEQ ID NO: 265
GACATCCAGATGACCCAGTCTCCATCCTCCCTGTCTGCATCTGTAGGAGACAGAGTCACCATCACTTGCCAGTCCA

GTCAGAGTGTTTATAATAACAATGCTTTAGCCTGGTATCAGCAGAAACCAGGGAAAGTTCCTAAGCTCCTGATCTA

TTTGGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTCTAGGTGTTTATAATGATGATGTTGATAATGGTTTC

GGCGGAGGGACCAAGGTGGAGATCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

472E4 HUMANIZED LIGHT CHAIN VARIABLE LIGHT CHAIN NUCLEOTIDE SEQUENCE
SEQ ID NO: 266
GACATCCAGATGACCCAGTCTCCATCCTCCCTGTCTGCATCTGTAGGAGACAGAGTCACCATCACTTGCCAGTCCA

GTCAGAGTGTTTATAATAACAATGCTTTAGCCTGGTATCAGCAGAAACCAGGGAAAGTTCCTAAGCTCCTGATCTA

TTTGGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTCTAGGTGTTTATAATGATGATGTTGATAATGGTTTC

GGCGGAGGGACCAAGGTGGAGATCAAA

472E4 HUMANIZED LIGHT CHAIN FULL-LENGTH AMINO ACID SEQUENCE. HUMAN KAPPA CONSTANT
DOMAIN IS UNDERLINED
SEQ ID NO: 267
DIQMTQSPSSLSASVGDRVTITCQSSQSVYNNNALAWYQQKPGKVPKLLIYLASTLASGVPSRFSGSGSGTDFTLTISSLQ

PEDVATYYCLGVYNDDVDNGFGGGTKVEIK<u>RTVAAPSVFIFPPSDEQLKSGTASVVCLLNNFYPREAKVQWKVDNALQ</u>

<u>SGNSQESVTEQDSKDSTYSLSSTLTLSKADYEKHKVYACEVTHQGLSSPVTKSFNRGEC</u>

472E4 HUMANIZED LIGHT CHAIN VARIABLE LIGHT CHAIN AMINO ACID SEQUENCE. COMPIMENTARITY
DETERMINING REGIONS ARE UNDERLINED
SEQ ID NO: 268
DIQMTQSPSSLSASVGDRVTITC<u>QSSQSVYNNNALA</u>WYQQKPGKVPKLLIY<u>LASTLAS</u>GVPSRFSGSGSGTDFTLTISSLQ

PEDVATYYC<u>LGVYNDDVDNG</u>FGGGTKVEIK

472E4 HUMANIZED HEAVY CHAIN FULL-LENGTH NUCLEOTIDE SEQUENCE
SEQ ID NO: 269
GAGGTGCAGCTGGTGGAGTCTGGGGGAGGCTTGGTCCAGCCTGGGGGGTCCCTGAGACTCTCCTGTGCAGCCTC

TGGATTCTCCCTCAATAACAATGCAATAAGCTGGGTCCGCCAGGCTCCAGGGAAGGGGCTGGAGTGGGTTGCAAT

CATACAAAATACTGGTACCACAGACTACGCGAGGTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGTATGGT

TTTGAGTCGGAGCTTGTCATCTGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

472E4 HUMANIZED HEAVY CHAIN VARIABLE HEAVY CHAIN NUCLEOTIDE SEQUENCE
SEQ ID NO: 270
GAGGTGCAGCTGGTGGAGTCTGGGGGAGGCTTGGTCCAGCCTGGGGGGTCCCTGAGACTCTCCTGTGCAGCCTC

TGGATTCTCCCTCAATAACAATGCAATAAGCTGGGTCCGCCAGGCTCCAGGGAAGGGGCTGGAGTGGGTTGCAAT

CATACAAAATACTGGTACCACAGACTACGCGAGGTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGTATGGT

TTTGAGTCGGAGCTTGTCATCTGGGGCCAGGGAACCCTGGTCACCGTCTCGAGC

472E4 HUMANIZED HEAVY CHAIN FULL-LENGTH AMINO ACID SEQUENCE. HUMAN GAMMA-1
CONSTANT DOMAIN IS UNDERLINED

SEQ ID NO: 271

EVQLVESGGGLVQPGGSLRLSCAASGFSLNNNAISWVRQAPGKGLEWVAIIQNTGTTDYARSAKGRFTISRDNSKNTLY

LQMNSLRAEDTAVYYCARGYGFESELVIWGQGTLVTVSS<u>ASTKGPSVFPLAPSSKSTSGGTAALGCLVKDYFPEPVTVS</u>

<u>WNSGALTSGVHTFPAVLQSSGLYSLSSVVTVPSSSLGTQTYICNVNHKPSNTKVDKRVEPKSCDKTHTCPPCPAPEAAG</u>

<u>APSVFLFPPKPKDTLMISRTPEVTCVVVDVSHEDPEVKFNWYVDGVEVHNAKTKPREEQYNSTYRVVSVLTVLHQDWL</u>

<u>NGKEYKCAVSNKALPAPIEKTISKAKGQPREPQVYTLPPSRDELTKNQVSLTCLVKGFYPSDIAVEWESNGQPENNYKTT</u>

<u>PPVLDSDGSFFLYSKLTVDKSRWQQGNVFSCSVMHEALHNHYTQKSLSLSPG</u>

472E4 HUMANIZED HEAVY CHAIN VARIABLE HEAVY CHAIN AMINO ACID SEQUENCE.
COMPLIMENTARITY DETERMINING REGIONS ARE UNDERLINED

SEQ ID NO: 272

EVQLVESGGGLVQPGGSLRLSCAASGFSLN<u>NNAI</u>SWVRQAPGKGLEWVA<u>IIQNTGTTDYARSAK</u>GRFTISRDNSKNTLY

LQMNSLRAEDTAVYYCA<u>RGYGFESELVI</u>WGQGTLVTVSS

---

What is claimed is:

1. An isolated monoclonal antibody (mAb) or antigen-binding fragment thereof that binds specifically to human or cynomolgus 4-1BB, comprising a variable light chain comprising SEQ ID NO:244, and a variable heavy chain comprising SEQ ID NO:248.

2. The isolated mAb or antigen-binding fragment thereof according to claim 1, wherein the isolated mAb is an IgG, a humanized antibody, a chimeric antibody, a recombinant antibody, a bispecific antibody, tri-specific antibody, or multi-specific antibody.

3. An isolated mAb or antigen-binding fragment thereof having a binding specificity to human or cynomolgus 4-1BB, comprising a light chain and a heavy chain, wherein the isolated mAb or antigen-binding fragment thereof comprises amino acids 24-34 of SEQ ID NO: 244 as complementarity determining region (CDR) 1, amino acids 50-56 of SEQ ID NO: 244 as CDR2, and amino acids 89-101 of SEQ ID NO: 244 as CDR3 of the light chain, and amino acids 30-34 of SEQ ID NO: 248 as CDR1, amino acids 49-64 of SEQ ID NO: 248 as CDR2, and amino acids 97-104 of SEQ ID NO: 248 as CDR3 of the heavy chain.

4. The isolated mAb or antigen-binding fragment thereof according to claim 1, wherein the antigen-binding fragment is a Fv, a Fab, a F(ab')2, a scFV or a scFV2 fragment.

5. A pharmaceutical composition, comprising the isolated mAb or antigen-binding fragment thereof of claim 1 or 3 and a pharmaceutically acceptable carrier.

6. The pharmaceutical composition of claim 5, further comprising a radioisotope, a radionuclide, a toxin, a therapeutic agent, a chemotherapeutic agent or a combination thereof.

* * * * *

SEQUENCE LISTING

<160> NUMBER OF SEQ ID NOS: 272

<210> SEQ ID NO 1
<211> LENGTH: 657
<212> TYPE: DNA
<213> ORGANISM: Artificial Sequence
<220> FEATURE:
<223> OTHER INFORMATION: synthesized

<400> SEQUENCE: 1

```
gatgttgtga tgacccagac tccagcctcc gtgtctgaac ctgtgagagc cacagtcacc      60
atcaagtgcc aggccagtca gagcattggt gctgatttag cctggtatca gcagaaacca     120
gggcagcctc ccaagctcct gatctacagg gcatccactc tggcctctgg ggtcccatcg     180
cggttcagcg gcagtggatc tgggacagag ttcactctca ccatcagcga cctggagtgt     240
gccgatgctg ccacttacta ctgtcaatgt atttattatg gtactgatga tgtcatatac     300
catactttcg gcggagggac cgaggtggtg ttcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt        657
```

<210> SEQ ID NO 2
<211> LENGTH: 336
<212> TYPE: DNA
<213> ORGANISM: Artificial Sequence
<220> FEATURE:
<223> OTHER INFORMATION: synthesized

<400> SEQUENCE: 2

```
gatgttgtga tgacccagac tccagcctcc gtgtctgaac ctgtgagagc cacagtcacc      60
atcaagtgcc aggccagtca gagcattggt gctgatttag cctggtatca gcagaaacca     120
gggcagcctc ccaagctcct gatctacagg gcatccactc tggcctctgg ggtcccatcg     180
cggttcagcg gcagtggatc tgggacagag ttcactctca ccatcagcga cctggagtgt     240
gccgatgctg ccacttacta ctgtcaatgt atttattatg gtactgatga tgtcatatac     300
```
catactttcg gcggagggac cgaggtggtg ttcaaa    336

<210> SEQ ID NO 3
<211> LENGTH: 219
<212> TYPE: PRT
<213> ORGANISM: Artificial Sequence
<220> FEATURE:
<223> OTHER INFORMATION: synthesized

<400> SEQUENCE: 3

Asp Val Val Met Thr Gln Thr Pro Ala Ser Val Ser Glu Pro Val Arg
1               5                   10                  15

Ala Thr Val Thr Ile Lys Cys Gln Ala Ser Gln Ser Ile Gly Ala Asp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Ile Tyr Tyr Gly Thr Asp
                85                  90                  95

Asp Val Ile Tyr His Thr Phe Gly Gly Gly Thr Glu Val Val Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 4
<211> LENGTH: 112
<212> TYPE: PRT
<213> ORGANISM: Artificial Sequence
<220> FEATURE:
<223> OTHER INFORMATION: synthesized

<400> SEQUENCE: 4

Asp Val Val Met Thr Gln Thr Pro Ala Ser Val Ser Glu Pro Val Arg
1               5                   10                  15

Ala Thr Val Thr Ile Lys Cys Gln Ala Ser Gln Ser Ile Gly Ala Asp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Ile Tyr Tyr Gly Thr Asp
                85                  90                  95

Asp Val Ile Tyr His Thr Phe Gly Gly Gly Thr Glu Val Val Phe Lys
            100                 105                 110

<210> SEQ ID NO 5
<211> LENGTH: 1332
<212> TYPE: DNA
<213> ORGANISM: Artificial Sequence
<220> FEATURE:
<223> OTHER INFORMATION: synthesized

<400> SEQUENCE: 5
cagtcggtgg aggagtccgg gggtcgcctg gtcacgcctg gacacccct aacactcacc      60
tgcacagtat ctggattcac catcagtagc caccacatga tctgggtccg ccaggctcca    120
ggagagggc tgcaatacat cggattcatt aatgatggtg actatacata ctacacgaac    180
tgggcaaaag gccgattcac catctccaga acctcgacta cggtggacct gaaaatgacc    240
agtctgacag ccgcggacac ggccacctat ttctgtgcca gaggggttga tggtactagt    300
tatcctggct tgtggggccc aggcaccctg gtcaccgtct cgagcgctag caccaagggc    360
ccatcggtct tccccctggc accctcctcc aagagcacct ctggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaagccgcgg ggcaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcgcg    960
gtctccaaca aagccctccc agcccccatc gagaaaacca tctccaaagc caaagggcag   1020
ccccgagaac cacaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gt                                                       1332

<210> SEQ ID NO 6
<211> LENGTH: 345
<212> TYPE: DNA
<213> ORGANISM: Artificial Sequence
<220> FEATURE:
<223> OTHER INFORMATION: synthesized

<400> SEQUENCE: 6
cagtcggtgg aggagtccgg gggtcgcctg gtcacgcctg gacacccct aacactcacc      60
tgcacagtat ctggattcac catcagtagc caccacatga tctgggtccg ccaggctcca    120
ggagagggc tgcaatacat cggattcatt aatgatggtg actatacata ctacacgaac    180

```
tgggcaaaag gccgattcac catctccaga acctcgacta cggtggacct gaaaatgacc    240
agtctgacag ccgcggacac ggccacctat ttctgtgcca gagggggtga tggtactagt    300
tatcctggct tgtggggccc aggcaccctg gtcaccgtct cgagc                    345
```

```
<210> SEQ ID NO 7
<211> LENGTH: 444
<212> TYPE: PRT
<213> ORGANISM: Artificial Sequence
<220> FEATURE:
<223> OTHER INFORMATION: synthesized

<400> SEQUENCE: 7
```

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Thr Ile Ser Ser His His
            20                  25                  30

Met Ile Trp Val Arg Gln Ala Pro Gly Glu Gly Leu Gln Tyr Ile Gly
        35                  40                  45

Phe Ile Asn Asp Gly Asp Tyr Thr Tyr Tyr Thr Asn Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Ala Ala Asp Thr Ala Thr Tyr Phe Cys Ala Arg Gly Val
                85                  90                  95

Asp Gly Thr Ser Tyr Pro Gly Leu Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335
```

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 8
<211> LENGTH: 115
<212> TYPE: PRT
<213> ORGANISM: Artificial Sequence
<220> FEATURE:
<223> OTHER INFORMATION: synthesized

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Val Ser Gly Phe Thr Ile Ser Ser His His
            20                  25                  30

Met Ile Trp Val Arg Gln Ala Pro Gly Glu Gly Leu Gln Tyr Ile Gly
        35                  40                  45

Phe Ile Asn Asp Gly Asp Tyr Thr Tyr Tyr Thr Asn Trp Ala Lys Gly
    50                  55                  60

Arg Phe Thr Ile Ser Arg Thr Ser Thr Val Asp Leu Lys Met Thr
65                  70                  75                  80

Ser Leu Thr Ala Ala Asp Thr Ala Thr Tyr Phe Cys Ala Arg Gly Val
                85                  90                  95

Asp Gly Thr Ser Tyr Pro Gly Leu Trp Gly Pro Gly Thr Leu Val Thr
            100                 105                 110

Val Ser Ser
        115

<210> SEQ ID NO 9
<211> LENGTH: 657
<212> TYPE: DNA
<213> ORGANISM: Artificial Sequence
<220> FEATURE:
<223> OTHER INFORMATION: synthesized

<400> SEQUENCE: 9
gacgtcgtga tgacccagac tccagcctcc gtggaggcag ctgtgggagg cacagtcacc      60
atcaagtgcc aggccagtca gagcatttac agcaatttag cctggtatca gcagaaacca     120
gggcagcctc ccaaactcct aatctattct acatccactc tggcatctgg ggtcccatcg     180
cggttcagcg gcagtggatc cgggacagag ttcactctca ccatcagcga cctggagtgt     240
gccgatgctg ccacttacta ctgtcaaaac tattatggta gtagtactga tagttatggg     300 aatccttttcg gcggaggcac cgaggtggtg ttcaaacgta cggtggctgc accatctgtc     360
ttcatcttcc cgccatctga tgagcagttg aaatctggaa ctgcctctgt tgtgtgcctg     420

```
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaagagct tcaacagggg agagtgt        657

<210> SEQ ID NO 10
<211> LENGTH: 336
<212> TYPE: DNA
<213> ORGANISM: Artificial Sequence
<220> FEATURE:
<223> OTHER INFORMATION: synthesized

<400> SEQUENCE: 10
gacgtcgtga tgacccagac tccagcctcc gtggaggcag ctgtgggagg cacagtcacc     60
atcaagtgcc aggccagtca gagcatttac agcaatttag cctggtatca gcagaaacca    120
gggcagcctc ccaaactcct aatctattct acatccactc tggcatctgg ggtcccatcg    180
cggttcagcg gcagtggatc cggacagag ttcactctca ccatcagcga cctggagtgt     240
gccgatgctg ccacttacta ctgtcaaaac tattatggta gtagtactga tagttatggg    300
aatcctttcg gcggaggcac cgaggtggtg ttcaaa                              336

<210> SEQ ID NO 11
<211> LENGTH: 219
<212> TYPE: PRT
<213> ORGANISM: Artificial Sequence
<220> FEATURE:
<223> OTHER INFORMATION: synthesized

<400> SEQUENCE: 11

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Lys Pro Gly Gln Pro Pro Lys Leu Leu Ile
        35                  40                  45

Tyr Ser Thr Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Gly Ser Ser Thr
                85                  90                  95

Asp Ser Tyr Gly Asn Pro Phe Gly Gly Thr Glu Val Val Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 12
<211> LENGTH: 112
<212> TYPE: PRT
<213> ORGANISM: Artificial Sequence
<220> FEATURE:
<223> OTHER INFORMATION: synthesized

<400> SEQUENCE: 12

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Lys Pro Gly Gln Pro Pro Lys Leu Leu Ile
        35                  40                  45

Tyr Ser Thr Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Gly Ser Ser Thr
                85                  90                  95

Asp Ser Tyr Gly Asn Pro Phe Gly Gly Gly Thr Glu Val Val Phe Lys
            100                 105                 110
```

<210> SEQ ID NO 13
<211> LENGTH: 1344
<212> TYPE: DNA
<213> ORGANISM: Artificial Sequence
<220> FEATURE:
<223> OTHER INFORMATION: synthesized

<400> SEQUENCE: 13

```
cagtcgctgg aggagtccgg gggagacctg gtcaagcctg agggatccct gacactcacc      60
tgcacaggct ctggaatcga cttcagtagc aactacatgt gctgggtccg ccaggctcca     120
gggaaggggc tggagtggat cgcatgcatt tatggtgata gtagtgataa tagttactcc     180
gcgagctggg cgaaagggcg attcaccatc tccaaaacct cgtcgaccac ggtgactctg     240
caaatgacca gtctgacagc cgcggacacg gccacctatt tctgtgcgag atctggttat     300
agctatttag ctactttaaa cttgtggggc cagggaccct ggtcaccgtc tcgagcgct     360 agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagccgc ggggggcaccg     720 tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgcg cggtctccaa caaagccctc ccagccccca tcgagaaaac catctccaaa    1020
gccaaagggc agccccgaga accacaggtg tacaccctgc ccccatcccg ggatgagctg    1080
```

```
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggt                                         1344
```

<210> SEQ ID NO 14
<211> LENGTH: 357
<212> TYPE: DNA
<213> ORGANISM: Artificial Sequence
<220> FEATURE:
<223> OTHER INFORMATION: synthesized

<400> SEQUENCE: 14

```
cagtcgctgg aggagtccgg gggagacctg gtcaagcctg agggatccct gacactcacc    60
tgcacaggct ctggaatcga cttcagtagc aactacatgt gctgggtccg ccaggctcca   120
gggaaggggc tggagtggat cgcatgcatt tatggtgata gtagtgataa tagttactcc   180
gcgagctggg cgaaagggcg attcaccatc tccaaaacct cgtcgaccac ggtgactctg   240
caaatgacca gtctgacagc cgcggacacg gccacctatt tctgtgcgag atctggttat   300
agctatttag ctactttaa cttgtggggc cagggaccc tggtcaccgt ctcgagc       357
```

<210> SEQ ID NO 15
<211> LENGTH: 448
<212> TYPE: PRT
<213> ORGANISM: Artificial Sequence
<220> FEATURE:
<223> OTHER INFORMATION: synthesized

<400> SEQUENCE: 15

```
Gln Ser Leu Glu Glu Ser Gly Gly Asp Leu Val Lys Pro Glu Gly Ser
1               5                   10                  15

Leu Thr Leu Thr Cys Thr Gly Ser Gly Ile Asp Phe Ser Ser Asn Tyr
            20                  25                  30

Met Cys Trp Val Arg Gln Ala Pro Gly Lys Gly Leu Glu Trp Ile Ala
        35                  40                  45

Cys Ile Tyr Gly Asp Ser Asp Asn Ser Tyr Ser Ala Ser Trp Ala
    50                  55                  60

Lys Gly Arg Phe Thr Ile Ser Lys Thr Ser Ser Thr Val Thr Leu
65                  70                  75                  80

Gln Met Thr Ser Leu Thr Ala Ala Asp Thr Ala Thr Tyr Phe Cys Ala
                85                  90                  95

Arg Ser Gly Tyr Ser Tyr Leu Ala Tyr Phe Asn Leu Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 16
<211> LENGTH: 119
<212> TYPE: PRT
<213> ORGANISM: Artificial Sequence
<220> FEATURE:
<223> OTHER INFORMATION: synthesized

<400> SEQUENCE: 16

Gln Ser Leu Glu Glu Ser Gly Gly Asp Leu Val Lys Pro Glu Gly Ser
1               5                   10                  15

Leu Thr Leu Thr Cys Thr Gly Ser Gly Ile Asp Phe Ser Ser Asn Tyr
            20                  25                  30

Met Cys Trp Val Arg Gln Ala Pro Gly Lys Gly Leu Glu Trp Ile Ala
        35                  40                  45

Cys Ile Tyr Gly Asp Ser Ser Asp Asn Ser Tyr Ser Ala Ser Trp Ala
    50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
            85                  90                  95

Arg Ser Gly Tyr Ser Tyr Leu Gly Tyr Phe Asn Leu Trp Gly Pro Gly
            100                 105                 110

```
Thr Leu Val Thr Val Ser Ser
        115
```

<210> SEQ ID NO 17
<211> LENGTH: 651
<212> TYPE: DNA
<213> ORGANISM: Artificial Sequence
<220> FEATURE:
<223> OTHER INFORMATION: synthesized

<400> SEQUENCE: 17

```
gcgcaagtgc tgacccagac tgcatcgtcc gtgtctgcac ctgtgggcgg cacagtcacc    60
atcagttgcc agtccagtca gactgtttat aataacaact tgttatcctg gtatcagcag   120
aaaccagggc agcgtcccaa gctcctgatc tattatgcat ccactctggc atttggggtc   180
ccatcgcggt tcaaaggcag tggatctggg acagagttca ctctcaccat cagcgacctg   240
gagtgtgacg atgctgccac ttacttctgt caaggcggtt atagtggttg gatttatgtt   300
ttcggcggag gcaccgaggt ggaggtcaaa cgtacggtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg t            651
```

<210> SEQ ID NO 18
<211> LENGTH: 330
<212> TYPE: DNA
<213> ORGANISM: Artificial Sequence
<220> FEATURE:
<223> OTHER INFORMATION: synthesized

<400> SEQUENCE: 18

```
gcgcaagtgc tgacccagac tgcatcgtcc gtgtctgcac ctgtgggcgg cacagtcacc    60
atcagttgcc agtccagtca gactgtttat aataacaact tgttatcctg gtatcagcag   120
aaaccagggc agcgtcccaa gctcctgatc tattatgcat ccactctggc atttggggtc   180
ccatcgcggt tcaaaggcag tggatctggg acagagttca ctctcaccat cagcgacctg   240
gagtgtgacg atgctgccac ttacttctgt caaggcggtt atagtggttg gatttatgtt   300
ttcggcggag gcaccgaggt ggaggtcaaa                                    330
```

<210> SEQ ID NO 19
<211> LENGTH: 217
<212> TYPE: PRT
<213> ORGANISM: Artificial Sequence
<220> FEATURE:
<223> OTHER INFORMATION: synthesized

<400> SEQUENCE: 19

```
Ala Gln Val Leu Thr Gln Thr Ala Ser Ser Val Ser Ala Pro Val Gly
1               5                   10                  15
Gly Thr Val Thr Ile Ser Cys Gln Ser Ser Gln Thr Val Tyr Asn Asn
            20                  25                  30
Asn Leu Leu Ser Trp Tyr Gln Gln Lys Pro Gly Gln Arg Pro Lys Leu
        35                  40                  45
Leu Ile Tyr Tyr Ala Ser Thr Leu Ala Phe Gly Val Pro Ser Arg Phe
    50                  55                  60
```

Lys Gly Ser Gly Ser Gly Thr Glu Phe Thr Leu Thr Ile Ser Asp Leu
65                  70                  75                  80

Glu Cys Asp Asp Ala Ala Thr Tyr Phe Cys Gln Gly Gly Tyr Ser Gly
                85                  90                  95

Trp Ile Tyr Val Phe Gly Gly Gly Thr Glu Val Glu Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 20
<211> LENGTH: 110
<212> TYPE: PRT
<213> ORGANISM: Artificial Sequence
<220> FEATURE:
<223> OTHER INFORMATION: synthesized

<400> SEQUENCE: 20

Ala Gln Val Leu Thr Gln Thr Ala Ser Ser Val Ser Ala Pro Val Gly
1               5                   10                  15

Gly Thr Val Thr Ile Ser Cys Gln Ser Ser Gln Thr Val Tyr Asn Asn
            20                  25                  30

Asn Leu Leu Ser Trp Tyr Gln Gln Lys Pro Gly Gln Arg Pro Lys Leu
        35                  40                  45

Leu Ile Tyr Tyr Ala Ser Thr Leu Ala Phe Gly Val Pro Ser Arg Phe
    50                  55                  60

Lys Gly Ser Gly Ser Gly Thr Glu Phe Thr Leu Thr Ile Ser Asp Leu
65                  70                  75                  80

Glu Cys Asp Asp Ala Ala Thr Tyr Phe Cys Gln Gly Gly Tyr Ser Gly
                85                  90                  95

Trp Ile Tyr Val Phe Gly Gly Gly Thr Glu Val Glu Val Lys
            100                 105                 110

<210> SEQ ID NO 21
<211> LENGTH: 1323
<212> TYPE: DNA
<213> ORGANISM: Artificial Sequence
<220> FEATURE:
<223> OTHER INFORMATION: synthesized

<400> SEQUENCE: 21
cagtcgctgg aggagtccgg gggtcgcctg gtcacgcctg ggacacccct gacactcacc      60
tgcacagcct ctggattctc cctcagtaac tactacatga actgggtccg ccaggctcca     120
gggaaggggc tggaatacat cggaatcatt agtagtagtg gtagcgcata ctacgcgagc     180
tgggctaaag gccgattcac catctccaga acctcgacca cggtggacct gagaatcacc     240

```
agtccgacaa ccgaggacac ggccacctat ttctgtgcca gaggggacta cggcatggac    300
ctctggggcc aagggaccct ggtcaccgtc tcgagcgcta gcaccaaggg cccatcggtc    360
ttccccctgg caccctcctc aagagcacc tctgggggca cagcggccct gggctgcctg     420
gtcaaggact acttccccga accggtgacg gtgtcgtgga actcaggcgc cctgaccagc    480
ggcgtgcaca ccttcccggc tgtcctacag tcctcaggac tctactccct cagcagcgtg    540
gtgaccgtgc cctccagcag cttgggcacc cagacctaca tctgcaacgt gaatcacaag    600
cccagcaaca ccaaggtgga caagagagtt gagcccaaat cttgtgacaa aactcacaca    660
tgcccaccgt gcccagcacc tgaagccgcg ggggcaccgt cagtcttcct cttccccca    720 aaacccaagg acaccctcat gatctcccgg acccctgagg tcacatgcgt ggtggtggac    780
gtgagccacg aagaccctga ggtcaagttc aactggtacg tggacggcgt ggaggtgcat    840
aatgccaaga caaagccgcg ggaggagcag tacaacagca cgtaccgtgt ggtcagcgtc    900
ctcaccgtcc tgcaccagga ctggctgaat ggcaaggagt acaagtgcgc ggtctccaac    960
aaagccctcc cagcccccat cgagaaaacc atctccaaag ccaaagggca gccccgagaa    1020
ccacaggtgt acaccctgcc cccatcccgg gatgagctga ccaagaacca ggtcagcctg    1080
acctgcctgt tcaaaggctt ctatcccagc gacatcgccg tggagtggga gagcaatggg    1140
cagccggaga acaactacaa gaccacgcct cccgtgctgg actccgacgg ctccttcttc    1200
ctctatagca agctcaccgt ggacaagagc aggtggcagc aggggaacgt cttctcatgc    1260
tccgtgatgc atgaggctct gcacaaccac tacacgcaga agagcctctc cctgtctccg    1320
ggt                                                                  1323
```

<210> SEQ ID NO 22
<211> LENGTH: 336
<212> TYPE: DNA
<213> ORGANISM: Artificial Sequence
<220> FEATURE:
<223> OTHER INFORMATION: synthesized

<400> SEQUENCE: 22

```
cagtcgctgg aggagtccgg gggtcgcctg gtcacgcctg gacacccct gacactcacc      60 tgcacagcct ctggattctc cctcagtaac tactacatga actgggtccg ccaggctcca    120
gggaaggggc tggaatacat cggaatcatt agtagtagtg gtagcgcata ctacgcgagc    180
tgggctaaag gccgattcac catctccaga acctcgacca cggtggacct gagaatcacc    240
agtccgacaa ccgaggacac ggccacctat ttctgtgcca gaggggacta cggcatggac    300
ctctggggcc aagggaccct ggtcaccgtc tcgagc                              336
```

<210> SEQ ID NO 23
<211> LENGTH: 441
<212> TYPE: PRT
<213> ORGANISM: Artificial Sequence
<220> FEATURE:
<223> OTHER INFORMATION: synthesized

<400> SEQUENCE: 23

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Asn Trp Val Arg Gln Ala Pro Gly Lys Gly Leu Glu Tyr Ile Gly
        35                  40                  45
```

```
Ile Ile Ser Ser Ser Gly Ser Ala Tyr Tyr Ala Ser Trp Ala Lys Gly
 50                  55                  60

Arg Phe Thr Ile Ser Arg Thr Ser Thr Thr Val Asp Leu Arg Ile Thr
 65                  70                  75                  80

Ser Pro Thr Thr Glu Asp Thr Ala Thr Tyr Phe Cys Ala Arg Gly Asp
                 85                  90                  95

Tyr Gly Met Asp Leu Trp Gly Gln Gly Thr Leu Val Thr Val Ser Ser
             100                 105                 110

Ala Ser Thr Lys Gly Pro Ser Val Phe Pro Leu Ala Pro Ser Ser Lys
             115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Arg Val Glu Pro Lys Ser Cys Asp Lys Thr His Thr Cys Pro Pro Cys
210                 215                 220

Pro Ala Pro Glu Ala Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Ala Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
            435                 440

<210> SEQ ID NO 24
<211> LENGTH: 112
<212> TYPE: PRT
```

<213> ORGANISM: Artificial Sequence
<220> FEATURE:
<223> OTHER INFORMATION: synthesized

<400> SEQUENCE: 24

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Asn Trp Val Arg Gln Ala Pro Gly Lys Gly Leu Glu Tyr Ile Gly
        35                  40                  45

Ile Ile Ser Ser Ser Gly Ser Ala Tyr Tyr Ala Ser Trp Ala Lys Gly
    50                  55                  60

Arg Phe Thr Ile Ser Arg Thr Ser Thr Thr Val Asp Leu Arg Ile Thr
65                  70                  75                  80

Ser Pro Thr Thr Glu Asp Thr Ala Thr Tyr Phe Cys Ala Arg Gly Asp
                85                  90                  95

Tyr Gly Met Asp Leu Trp Gly Gln Gly Thr Leu Val Thr Val Ser Ser
            100                 105                 110
```

<210> SEQ ID NO 25
<211> LENGTH: 657
<212> TYPE: DNA
<213> ORGANISM: Artificial Sequence
<220> FEATURE:
<223> OTHER INFORMATION: synthesized

<400> SEQUENCE: 25

```
gacgtcgtga tgacccagac tccagcctcc gtgtctgaac ctgtgggagg cgcagtcacc    60
atcaagtgcc aggccagtca gagcattggt agtgatttag cctggtatca gcagaaacca   120
gggcagcctc ccaagctcct gatctacagg gcatccactc tggcatctgg ggtctcatcg   180
cggttcaaag gcagtggatc tgggacagag ttcactctca ccatcagcga cctggagtgt   240
gccgatgctg ccacttacta ctgtcaatgt atttattatg gtagtgatga tgtcatatac   300
catactttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 26
<211> LENGTH: 336
<212> TYPE: DNA
<213> ORGANISM: Artificial Sequence
<220> FEATURE:
<223> OTHER INFORMATION: synthesized

<400> SEQUENCE: 26

```
gacgtcgtga tgacccagac tccagcctcc gtgtctgaac ctgtgggagg cgcagtcacc    60
atcaagtgcc aggccagtca gagcattggt agtgatttag cctggtatca gcagaaacca   120
gggcagcctc ccaagctcct gatctacagg gcatccactc tggcatctgg ggtctcatcg   180
cggttcaaag gcagtggatc tgggacagag ttcactctca ccatcagcga cctggagtgt   240
gccgatgctg ccacttacta ctgtcaatgt atttattatg gtagtgatga tgtcatatac   300
```

```
catactttcg gcggagggac cgaggtggtg gtcaaa                                336
```

<210> SEQ ID NO 27
<211> LENGTH: 219
<212> TYPE: PRT
<213> ORGANISM: Artificial Sequence
<220> FEATURE:
<223> OTHER INFORMATION: synthesized

<400> SEQUENCE: 27

```
Asp Val Val Met Thr Gln Thr Pro Ala Ser Val Ser Glu Pro Val Gly
1               5                   10                  15

Gly Ala Val Thr Ile Lys Cys Gln Ala Ser Gln Ser Ile Gly Ser Asp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Ile Tyr Tyr Gly Ser Asp
                85                  90                  95

Asp Val Ile Tyr His Thr Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 28
<211> LENGTH: 112
<212> TYPE: PRT
<213> ORGANISM: Artificial Sequence
<220> FEATURE:
<223> OTHER INFORMATION: synthesized

<400> SEQUENCE: 28

```
Asp Val Val Met Thr Gln Thr Pro Ala Ser Val Ser Glu Pro Val Gly
1               5                   10                  15

Gly Ala Val Thr Ile Lys Cys Gln Ala Ser Gln Ser Ile Gly Ser Asp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80
```

Ala Asp Ala Ala Thr Tyr Tyr Cys Gln Cys Ile Tyr Tyr Gly Ser Asp
             85                  90                  95

Asp Val Ile Tyr His Thr Phe Gly Gly Gly Thr Glu Val Val Lys
            100                 105                 110

<210> SEQ ID NO 29
<211> LENGTH: 1332
<212> TYPE: DNA
<213> ORGANISM: Artificial Sequence
<220> FEATURE:
<223> OTHER INFORMATION: synthesized

<400> SEQUENCE: 29
cagtcggtgg aggagtccgg gggtcgcctg gtcacgcctg ggacacccct gacactcacc      60
tgcacagtct ctggattcac tatcaatagc taccacatga tctgggtccg ccaggctcca     120
ggggaggggc tggaatacat cggattcatt aatgatggtg gtttcacata ctacgcgagc     180
tgggcaaaag gccgatttat catctccaga acctcgacca cggtggatct gaaaatgacc     240
agtctgacag tcgcggacac ggccacctat ttctgtgcca gaggggttga tggtactagt     300
tatcctgact tatggggccc gggcacccta gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagcccctcc cagcccccatc gagaaaacca tctccaaagc caagggcag   1020 ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                       1332

<210> SEQ ID NO 30
<211> LENGTH: 345
<212> TYPE: DNA
<213> ORGANISM: Artificial Sequence
<220> FEATURE:
<223> OTHER INFORMATION: synthesized

<400> SEQUENCE: 30
cagtcggtgg aggagtccgg gggtcgcctg gtcacgcctg ggacacccct gacactcacc      60
tgcacagtct ctggattcac tatcaatagc taccacatga tctgggtccg ccaggctcca     120
ggggaggggc tggaatacat cggattcatt aatgatggtg gtttcacata ctacgcgagc     180
tgggcaaaag gccgatttat catctccaga acctcgacca cggtggatct gaaaatgacc     240

-continued

```
agtctgacag tcgcggacac ggccacctat ttctgtgcca gaggggttga tggtactagt    300
tatcctgact tatggggccc gggcaccctg gtcaccgtct cgagc                    345
```

<210> SEQ ID NO 31
<211> LENGTH: 444
<212> TYPE: PRT
<213> ORGANISM: Artificial Sequence
<220> FEATURE:
<223> OTHER INFORMATION: synthesized

<400> SEQUENCE: 31

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Thr Ile Asn Ser Tyr His
            20                  25                  30

Met Ile Trp Val Arg Gln Ala Pro Gly Glu Gly Leu Glu Tyr Ile Gly
        35                  40                  45

Phe Ile Asn Asp Gly Gly Phe Thr Tyr Tyr Ala Ser Trp Ala Lys Gly
    50                  55                  60

Arg Phe Ile Ile Ser Arg Thr Ser Thr Thr Val Asp Leu Lys Met Thr
65                  70                  75                  80

Ser Leu Thr Val Ala Asp Thr Ala Thr Tyr Phe Cys Ala Arg Gly Val
                85                  90                  95

Asp Gly Thr Ser Tyr Pro Asp Leu Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

```
            340             345             350
Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
                435                 440

<210> SEQ ID NO 32
<211> LENGTH: 115
<212> TYPE: PRT
<213> ORGANISM: Artificial Sequence
<220> FEATURE:
<223> OTHER INFORMATION: synthesized

<400> SEQUENCE: 32

Gln Ser Val Glu Glu Ser Gly Gly Arg Leu Val Thr Pro Gly Thr Pro
1               5                   10                  15

Leu Thr Leu Thr Cys Thr Val Ser Gly Phe Thr Ile Asn Ser Tyr His
                20                  25                  30

Met Ile Trp Val Arg Gln Ala Pro Gly Glu Gly Leu Glu Tyr Ile Gly
            35                  40                  45

Phe Ile Asn Asp Gly Gly Phe Thr Tyr Tyr Ala Ser Trp Ala Lys Gly
    50                  55                  60

Arg Phe Ile Ile Ser Arg Thr Ser Thr Thr Val Asp Leu Lys Met Thr
65                  70                  75                  80

Ser Leu Thr Val Ala Asp Thr Ala Thr Tyr Phe Cys Ala Arg Gly Val
                85                  90                  95

Asp Gly Thr Ser Tyr Pro Asp Leu Trp Gly Pro Gly Thr Leu Val Thr
            100                 105                 110

Val Ser Ser
        115

<210> SEQ ID NO 33
<211> LENGTH: 654
<212> TYPE: DNA
<213> ORGANISM: Artificial Sequence
<220> FEATURE:
<223> OTHER INFORMATION: synthesized

<400> SEQUENCE: 33
gccctggtga tgacccagac tccatcccct gtgtctgcgg ctgtgggagg cacagtcacc       60
atcaactgcc aggccagtca gagcattggt agtaacttga actggtatca gcagaaacca      120
gggcagcctc ccaagctcct gatttattat gtatccactc tggcatctgg ggtcccatcg      180
cggttcaaag gcagtggatc tgggacagag tacactctca ccatcagcgg cgtgcagtgt      240
gacgatgctg ccacttacta ctgcctaggt gtttggaatt attggggtga tgacggtact      300
gctttcggcg gaggcaccga ggtggaggtc aaacgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
```

```
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt          654
```

<210> SEQ ID NO 34
<211> LENGTH: 333
<212> TYPE: DNA
<213> ORGANISM: Artificial Sequence
<220> FEATURE:
<223> OTHER INFORMATION: synthesized

<400> SEQUENCE: 34

```
gccctggtga tgacccagac tccatcccct gtgtctgcgg ctgtgggagg cacagtcacc    60
atcaactgcc aggccagtca gagcattggt agtaacttga actggtatca gcagaaacca   120
gggcagcctc ccaagctcct gatttattat gtatccactc tggcatctgg ggtcccatcg   180
cggttcaaag gcagtggatc tgggacagag tacactctca ccatcagcgg cgtgcagtgt   240
gacgatgctg ccacttacta ctgcctaggt gtttggaatt attggggtga tgacggtact   300
gctttcggcg gaggcaccga ggtggaggtc aaa                                333
```

<210> SEQ ID NO 35
<211> LENGTH: 218
<212> TYPE: PRT
<213> ORGANISM: Artificial Sequence
<220> FEATURE:
<223> OTHER INFORMATION: synthesized

<400> SEQUENCE: 35

```
Ala Leu Val Met Thr Gln Thr Pro Ser Pro Val Ser Ala Ala Val Gly
1               5                   10                  15

Gly Thr Val Thr Ile Asn Cys Gln Ala Ser Gln Ser Ile Gly Ser Asn
            20                  25                  30

Leu Asn Trp Tyr Gln Gln Lys Pro Gly Gln Pro Pro Lys Leu Leu Ile
        35                  40                  45

Tyr Tyr Val Ser Thr Leu Ala Ser Gly Val Pro Ser Arg Phe Lys Gly
50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Leu Gly Val Trp Asn Tyr Trp Gly
                85                  90                  95

Asp Asp Gly Thr Ala Phe Gly Gly Gly Thr Glu Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

<210> SEQ ID NO 36
<211> LENGTH: 111
<212> TYPE: PRT
<213> ORGANISM: Artificial Sequence
<220> FEATURE:
<223> OTHER INFORMATION: synthesized

<400> SEQUENCE: 36

```
Ala Leu Val Met Thr Gln Thr Pro Ser Pro Val Ser Ala Ala Val Gly
1               5                   10                  15

Gly Thr Val Thr Ile Asn Cys Gln Ala Ser Gln Ser Ile Gly Ser Asn
            20                  25                  30

Leu Asn Trp Tyr Gln Gln Lys Pro Gly Gln Pro Pro Lys Leu Leu Ile
        35                  40                  45

Tyr Tyr Val Ser Thr Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Leu Gly Val Trp Asn Tyr Trp Gly
                85                  90                  95

Asp Asp Gly Thr Ala Phe Gly Gly Gly Thr Glu Val Glu Val Lys
                100                 105                 110
```

<210> SEQ ID NO 37
<211> LENGTH: 1323
<212> TYPE: DNA
<213> ORGANISM: Artificial Sequence
<220> FEATURE:
<223> OTHER INFORMATION: synthesized

<400> SEQUENCE: 37

| | | | | | |
|---|---|---|---|---|---|
| cagtcgctgg | aggagtccgg | gggtcgcctg | gtcacgcctg | ggacacccct | gacactcacc | 60 |
| tgcacagcct | ctgatttctc | cctcagtacc | tattatatga | gctgggtccg | ccaggctcca | 120 |
| gggaaggggc | tggagtggat | cggaagtatt | tatgatagtg | gtgccgcata | ctacgcgacc | 180 |
| tgggcgaagg | gccgattcac | catctccaga | acgtcgacca | cggtggatct | gagaatgacc | 240 |
| agtctgacag | ccgcggacac | ggccacctat | ttctgtgcca | gagatcctat | taataatgcc | 300 |
| atctggggcc | aagggaccct | cgtcaccgtc | tcgagcgcta | gcaccaaggg | cccatcggtc | 360 |
| ttccccctgg | caccctcctc | caagagcacc | tctgggggca | cagcggccct | gggctgcctg | 420 |
| gtcaaggact | acttccccga | accggtgacg | gtgtcgtgga | actcaggcgc | cctgaccagc | 480 |
| ggcgtgcaca | ccttcccggc | tgtcctacag | tcctcaggac | tctactccct | cagcagcgtg | 540 |
| gtgaccgtgc | cctccagcag | cttgggcacc | cagacctaca | tctgcaacgt | gaatcacaag | 600 |
| cccagcaaca | ccaaggtgga | caagagagtt | gagcccaaat | cttgtgacaa | aactcacaca | 660 |
| tgcccaccgt | gcccagcacc | tgaagccgcg | gggcaccgt | cagtcttcct | cttccccca | 720 |
| aaacccaagg | acaccctcat | gatctcccgg | acccctgagg | tcacatgcgt | ggtggtggac | 780 |
| gtgagccacg | aagaccctga | ggtcaagttc | aactggtacg | tggacggcgt | ggaggtgcat | 840 |
| aatgccaaga | caaagccgcg | ggaggagcag | tacaacagca | cgtaccgtgt | ggtcagcgtc | 900 |
| ctcaccgtcc | tgcaccagga | ctggctgaat | ggcaaggagt | acaagtgcgc | ggtctccaac | 960 |
| aaagccctcc | cagcccccat | cgagaaaacc | atctccaaag | ccaagggca | gccccgagaa | 1020 |
| ccacaggtgt | acaccctgcc | cccatcccgg | gatgagctga | ccaagaacca | ggtcagcctg | 1080 |

```
acctgcctgg tcaaaggctt ctatcccagc gacatcgccg tggagtggga gagcaatggg   1140
cagccggaga caactacaa gaccacgcct cccgtgctgg actccgacgg ctccttcttc    1200
ctctatagca agctcaccgt ggacaagagc aggtggcagc aggggaacgt cttctcatgc   1260
tccgtgatgc atgaggctct gcacaaccac tacacgcaga gagcctctc cctgtctccg    1320 ggt                                                                  1323
```

<210> SEQ ID NO 38
<211> LENGTH: 336
<212> TYPE: DNA
<213> ORGANISM: Artificial Sequence
<220> FEATURE:
<223> OTHER INFORMATION: synthesized

<400> SEQUENCE: 38

```
cagtcgctgg aggagtccgg gggtcgcctg gtcacgcctg ggacacccct gacactcacc    60
tgcacagcct ctgatttctc cctcagtacc tattatatga gctgggtccg ccaggctcca   120
gggaaggggc tggagtggat cggaagtatt tatgatagtg gtgccgcata ctacgcgacc   180
tgggcgaagg gccgattcac catctccaga acgtcgacca cggtggatct gagaatgacc   240
agtctgacag ccgcggacac ggccacctat ttctgtgcca gagatcctat taataatgcc   300
atctggggcc aagggaccct cgtcaccgtc tcgagc                             336
```

<210> SEQ ID NO 39
<211> LENGTH: 441
<212> TYPE: PRT
<213> ORGANISM: Artificial Sequence
<220> FEATURE:
<223> OTHER INFORMATION: synthesized

<400> SEQUENCE: 39

```
Gln Ser Leu Glu Glu Ser Gly Gly Arg Leu Val Thr Pro Gly Thr Pro
1               5                   10                  15

Leu Thr Leu Thr Cys Thr Ala Ser Asp Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ser Ile Tyr Asp Ser Gly Ala Ala Tyr Tyr Ala Thr Trp Ala Lys Gly
    50                  55                  60

Arg Phe Thr Ile Ser Arg Thr Ser Thr Val Asp Leu Arg Met Thr
65                  70                  75                  80

Ser Leu Thr Ala Ala Asp Thr Ala Thr Tyr Phe Cys Ala Arg Asp Pro
                85                  90                  95

Ile Asn Asn Ala Ile Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
```

```
            195                 200                 205
Arg Val Glu Pro Lys Ser Cys Asp Lys Thr His Thr Cys Pro Pro Cys
210                 215                 220

Pro Ala Pro Glu Ala Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Ala Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 40
<211> LENGTH: 112
<212> TYPE: PRT
<213> ORGANISM: Artificial Sequence
<220> FEATURE:
<223> OTHER INFORMATION: synthesized

<400> SEQUENCE: 40

Gln Ser Leu Glu Glu Ser Gly Gly Arg Leu Val Thr Pro Gly Thr Pro
1               5                   10                  15

Leu Thr Leu Thr Cys Thr Ala Ser Asp Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ser Ile Tyr Asp Ser Gly Ala Ala Tyr Tyr Ala Thr Trp Ala Lys Gly
    50                  55                  60

Arg Phe Thr Ile Ser Arg Thr Ser Thr Val Asp Leu Arg Met Thr
65                  70                  75                  80

Ser Leu Thr Ala Ala Asp Thr Ala Thr Tyr Phe Cys Ala Arg Asp Pro
                85                  90                  95

Ile Asn Asn Ala Ile Trp Gly Gln Gly Thr Leu Val Thr Val Ser Ser
            100                 105                 110
```

<210> SEQ ID NO 41
<211> LENGTH: 654
<212> TYPE: DNA
<213> ORGANISM: Artificial Sequence
<220> FEATURE:
<223> OTHER INFORMATION: synthesized

<400> SEQUENCE: 41

```
gccctggtga tgacccagac tccatcccct gtgtctgcgg ctgtgggagg cacagtcacc      60
atcaactgcc aggccagtca gagtattgct actaacttga actggtatca gcagaaacca     120
gggcagcctc ccaagctcct gatctattat acatccagtc tggcatctgg ggtcccatcg     180
cggttcagcg gcagtggatc tggcacagag ttcactctca ccatcagcgg tgtgcagtgt     240
gacgatgctg ccacttacta ctgcctaggt gtttggaatt attggggtga tgatggtact     300
gctttcggcg agggaccga ggtggagttc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600
acccatcagg gcctgagctc gcccgtcaca aagagcttca caggggaga gtgt            654
```

<210> SEQ ID NO 42
<211> LENGTH: 333
<212> TYPE: DNA
<213> ORGANISM: Artificial Sequence
<220> FEATURE:
<223> OTHER INFORMATION: synthesized

<400> SEQUENCE: 42

```
gccctggtga tgacccagac tccatcccct gtgtctgcgg ctgtgggagg cacagtcacc      60
atcaactgcc aggccagtca gagtattgct actaacttga actggtatca gcagaaacca     120
gggcagcctc ccaagctcct gatctattat acatccagtc tggcatctgg ggtcccatcg     180
cggttcagcg gcagtggatc tggcacagag ttcactctca ccatcagcgg tgtgcagtgt     240
gacgatgctg ccacttacta ctgcctaggt gtttggaatt attggggtga tgatggtact     300
gctttcggcg agggaccga ggtggagttc aaa                                   333
```

<210> SEQ ID NO 43
<211> LENGTH: 218
<212> TYPE: PRT
<213> ORGANISM: Artificial Sequence
<220> FEATURE:
<223> OTHER INFORMATION: synthesized

<400> SEQUENCE: 43

```
Ala Leu Val Met Thr Gln Thr Pro Ser Pro Val Ser Ala Ala Val Gly
1               5                  10                  15
Gly Thr Val Thr Ile Asn Cys Gln Ala Ser Gln Ser Ile Ala Thr Asn
            20                  25                  30
Leu Asn Trp Tyr Gln Gln Lys Pro Gly Gln Pro Pro Lys Leu Leu Ile
        35                  40                  45
Tyr Tyr Thr Ser Ser Leu Ala Ser Gly Val Pro Ser Arg Phe Ser Gly
    50                  55                  60
Ser Gly Ser Gly Thr Glu Phe Thr Leu Thr Ile Ser Gly Val Gln Cys
65                  70                  75                  80
Asp Asp Ala Ala Thr Tyr Tyr Cys Leu Gly Val Trp Asn Tyr Trp Gly
```

```
            85                  90                  95
Asp Asp Gly Thr Ala Phe Gly Gly Thr Glu Val Glu Phe Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                    180                 185                 190

His Lys Val Tyr Ala Cys Glu Val Thr His Gln Gly Leu Ser Ser Pro
                    195                 200                 205

Val Thr Lys Ser Phe Asn Arg Gly Glu Cys
                    210                 215

<210> SEQ ID NO 44
<211> LENGTH: 111
<212> TYPE: PRT
<213> ORGANISM: Artificial Sequence
<220> FEATURE:
<223> OTHER INFORMATION: synthesized

<400> SEQUENCE: 44

Ala Leu Val Met Thr Gln Thr Pro Ser Pro Val Ser Ala Ala Val Gly
1               5                   10                  15

Gly Thr Val Thr Ile Asn Cys Gln Ala Ser Gln Ser Ile Ala Thr Asn
                20                  25                  30

Leu Asn Trp Tyr Gln Gln Lys Pro Gly Gln Pro Pro Lys Leu Leu Ile
            35                  40                  45

Tyr Tyr Thr Ser Ser Leu Ala Ser Gly Val Pro Ser Arg Phe Ser Gly
        50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Leu Gly Val Trp Asn Tyr Trp Gly
                85                  90                  95

Asp Asp Gly Thr Ala Phe Gly Gly Thr Glu Val Glu Phe Lys
            100                 105                 110

<210> SEQ ID NO 45
<211> LENGTH: 1323
<212> TYPE: DNA
<213> ORGANISM: Artificial Sequence
<220> FEATURE:
<223> OTHER INFORMATION: synthesized

<400> SEQUENCE: 45
cagtcgctgg aggagtccgg gggtcgcctg gtcacgcctg ggacacccct gacactcacc      60
tgcacagcct ctgaattctc cctcagtagc tactacatga gctgggtccg ccaggctcca    120
gggaaggggc tggaatggat cggaagtatt tatgctagtg gtagcgcata ctacgcgagt    180
tgggcgaagg gccgattcac catctccaga acgtcgacca cggtggatct gaaaatgacc    240
agtctgacag ccgcggacac ggccacctat ttctgtgtca gagatcctat taacaatgac    300
atctggggcc aggcaccct ggtcaccgtc tcgagcgcta gcaccaaggg cccatcggtc    360
```

```
ttcccccctgg caccctcctc caagagcacc tctgggggca cagcggccct gggctgcctg    420
gtcaaggact acttccccga accggtgacg gtgtcgtgga actcaggcgc cctgaccagc    480
ggcgtgcaca ccttcccggc tgtcctacag tcctcaggac tctactccct cagcagcgtg    540
gtgaccgtgc cctccagcag cttgggcacc cagacctaca tctgcaacgt gaatcacaag    600
cccagcaaca ccaaggtgga caagagagtt gagcccaaat cttgtgacaa aactcacaca    660
tgcccaccgt gcccagcacc tgaagccgcg ggggcaccgt cagtcttcct cttccccccca    720 aaacccaagg acaccctcat gatctcccgg acccctgagg tcacatgcgt ggtggtggac    780
gtgagccacg aagaccctga ggtcaagttc aactggtacg tggacggcgt ggaggtgcat    840
aatgccaaga caaagccgcg ggaggagcag tacaacagca cgtaccgtgt ggtcagcgtc    900
ctcaccgtcc tgcaccagga ctggctgaat ggcaaggagt acaagtgcgc ggtctccaac    960
aaagccctcc cagcccccat cgagaaaacc atctccaaag ccaaagggca gccccgagaa   1020
ccacaggtgt acaccctgcc cccatcccgg gatgagctga ccaagaacca ggtcagcctg   1080
acctgcctgg tcaaaggctt ctatcccagc gacatcgccg tggagtggga gagcaatggg   1140
cagccggaga acaactacaa gaccacgcct cccgtgctgg actccgacgg ctccttcttc   1200
ctctatagca agctcaccgt ggacaagagc aggtggcagc aggggaacgt cttctcatgc   1260
tccgtgatgc atgaggctct gcacaaccac tacacgcaga agagcctctc cctgtctccg   1320
ggt                                                                  1323

<210> SEQ ID NO 46
<211> LENGTH: 336
<212> TYPE: DNA
<213> ORGANISM: Artificial Sequence
<220> FEATURE:
<223> OTHER INFORMATION: synthesized

<400> SEQUENCE: 46
cagtcgctgg aggagtccgg gggtcgcctg gtcacgcctg gacaccccct gacactcacc     60
tgcacagcct ctgaattctc cctcagtagc tactacatga gctgggtccg ccaggctcca    120
gggaaggggc tggaatggat cggaagtatt tatgctagtg gtagcgcata ctacgcgagt    180
tgggcgaagg gccgattcac catctccaga acgtcgacca cggtggatct gaaaatgacc    240
agtctgacag ccgcggacac ggccacctat ttctgtgtca gagatcctat taacaatgac    300
atctggggcc aggcaccct ggtcaccgtc tcgagc                                336

<210> SEQ ID NO 47
<211> LENGTH: 441
<212> TYPE: PRT
<213> ORGANISM: Artificial Sequence
<220> FEATURE:
<223> OTHER INFORMATION: synthesized

<400> SEQUENCE: 47

Gln Ser Leu Glu Glu Ser Gly Gly Arg Leu Val Thr Pro Gly Thr Pro
1               5                   10                  15

Leu Thr Leu Thr Cys Thr Ala Ser Glu Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Ser Ile Tyr Ala Ser Gly Ser Ala Tyr Tyr Ala Ser Trp Ala Lys Gly
    50                  55                  60

Arg Phe Thr Ile Ser Arg Thr Ser Thr Thr Val Asp Leu Lys Met Thr
```

```
                65                  70                  75                  80
Ser Leu Thr Ala Ala Asp Thr Ala Thr Tyr Phe Cys Val Arg Asp Pro
                    85                  90                  95
Ile Asn Asn Asp Ile Trp Gly Pro Gly Thr Leu Val Thr Val Ser Ser
                    100                 105                 110
Ala Ser Thr Lys Gly Pro Ser Val Phe Pro Leu Ala Pro Ser Ser Lys
                    115                 120                 125
Ser Thr Ser Gly Gly Thr Ala Ala Leu Gly Cys Leu Val Lys Asp Tyr
            130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                    165                 170                 175
Leu Ser Ser Val Val Thr Val Pro Ser Ser Ser Leu Gly Thr Gln Thr
                    180                 185                 190
Tyr Ile Cys Asn Val Asn His Lys Pro Ser Asn Thr Lys Val Asp Lys
                    195                 200                 205
Arg Val Glu Pro Lys Ser Cys Asp Lys Thr His Thr Cys Pro Pro Cys
            210                 215                 220
Pro Ala Pro Glu Ala Ala Gly Ala Pro Ser Val Phe Leu Phe Pro Pro
225                 230                 235                 240
Lys Pro Lys Asp Thr Leu Met Ile Ser Arg Thr Pro Glu Val Thr Cys
                    245                 250                 255
Val Val Val Asp Val Ser His Glu Asp Pro Glu Val Lys Phe Asn Trp
                    260                 265                 270
Tyr Val Asp Gly Val Glu Val His Asn Ala Lys Thr Lys Pro Arg Glu
                    275                 280                 285
Glu Gln Tyr Asn Ser Thr Tyr Arg Val Val Ser Val Leu Thr Val Leu
            290                 295                 300
His Gln Asp Trp Leu Asn Gly Lys Glu Tyr Lys Cys Ala Val Ser Asn
305                 310                 315                 320
Lys Ala Leu Pro Ala Pro Ile Glu Lys Thr Ile Ser Lys Ala Lys Gly
                    325                 330                 335
Gln Pro Arg Glu Pro Gln Val Tyr Thr Leu Pro Pro Ser Arg Asp Glu
                    340                 345                 350
Leu Thr Lys Asn Gln Val Ser Leu Thr Cys Leu Val Lys Gly Phe Tyr
                    355                 360                 365
Pro Ser Asp Ile Ala Val Glu Trp Glu Ser Asn Gly Gln Pro Glu Asn
            370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                    405                 410                 415
Val Phe Ser Cys Ser Val Met His Glu Ala Leu His Asn His Tyr Thr
                    420                 425                 430
Gln Lys Ser Leu Ser Leu Ser Pro Gly
            435                 440

<210> SEQ ID NO 48
<211> LENGTH: 112
<212> TYPE: PRT
<213> ORGANISM: Artificial Sequence
<220> FEATURE:
<223> OTHER INFORMATION: synthesized
```

<400> SEQUENCE: 48

Gln Ser Leu Glu Glu Ser Gly Gly Arg Leu Val Thr Pro Gly Thr Pro
1               5                   10                  15

Leu Thr Leu Thr Cys Thr Ala Ser Glu Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Ser Ile Tyr Ala Ser Gly Ser Ala Tyr Tyr Ala Ser Trp Ala Lys Gly
    50                  55                  60

Arg Phe Thr Ile Ser Arg Thr Ser Thr Val Asp Leu Lys Met Thr
65                  70                  75                  80

Ser Leu Thr Ala Ala Asp Thr Ala Thr Tyr Phe Cys Val Arg Asp Pro
                85                  90                  95

Ile Asn Asn Asp Ile Trp Gly Pro Gly Thr Leu Val Thr Val Ser Ser
            100                 105                 110

<210> SEQ ID NO 49
<211> LENGTH: 654
<212> TYPE: DNA
<213> ORGANISM: Artificial Sequence
<220> FEATURE:
<223> OTHER INFORMATION: synthesized

<400> SEQUENCE: 49
gcccaagtgc tgacccagac tccagcctcc gtgtctgcaa ctgtgggaag cacagtcacc      60
atcagttgcc agtccagtcc gagtgtttat aagaacaacc aattagcctg gtatcagcag     120
aaaccagggc agcctcccaa actcctgatc tatctggcat ctactctggc atctggggtc     180
ccatcgcggt tcaaaggcag tggatctggg acagagttca ctctcaccat cagcgacctg     240
gagtgtgccg atgctgccac ttactactgt gcaggcggtt atagtagtag tagtgatact     300
gctttcggcg agggaccgag gtggaggtca aacgtacgg tggctgcacc atctgtcttc      360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgt            654

<210> SEQ ID NO 50
<211> LENGTH: 333
<212> TYPE: DNA
<213> ORGANISM: Artificial Sequence
<220> FEATURE:
<223> OTHER INFORMATION: synthesized

<400> SEQUENCE: 50
gcccaagtgc tgacccagac tccagcctcc gtgtctgcaa ctgtgggaag cacagtcacc      60
atcagttgcc agtccagtcc gagtgtttat aagaacaacc aattagcctg gtatcagcag     120
aaaccagggc agcctcccaa actcctgatc tatctggcat ctactctggc atctggggtc     180
ccatcgcggt tcaaaggcag tggatctggg acagagttca ctctcaccat cagcgacctg     240
gagtgtgccg atgctgccac ttactactgt gcaggcggtt atagtagtag tagtgatact     300
gctttcggcg agggaccga ggtggaggtc aaa                                    333

<210> SEQ ID NO 51

<211> LENGTH: 218
<212> TYPE: PRT
<213> ORGANISM: Artificial Sequence
<220> FEATURE:
<223> OTHER INFORMATION: synthesized

<400> SEQUENCE: 51

```
Ala Gln Val Leu Thr Gln Thr Pro Ala Ser Val Ser Ala Thr Val Gly
1               5                   10                  15

Ser Thr Val Thr Ile Ser Cys Gln Ser Ser Pro Ser Val Tyr Lys Asn
            20                  25                  30

Asn Gln Leu Ala Trp Tyr Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Glu Phe Thr Leu Thr Ile Ser Asp Leu
65                  70                  75                  80

Glu Cys Ala Asp Ala Ala Thr Tyr Tyr Cys Ala Gly Gly Tyr Ser Ser
                85                  90                  95

Ser Ser Asp Thr Ala Phe Gly Gly Gly Thr Glu Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 52
<211> LENGTH: 111
<212> TYPE: PRT
<213> ORGANISM: Artificial Sequence
<220> FEATURE:
<223> OTHER INFORMATION: synthesized

<400> SEQUENCE: 52

```
Ala Gln Val Leu Thr Gln Thr Pro Ala Ser Val Ser Ala Thr Val Gly
1               5                   10                  15

Ser Thr Val Thr Ile Ser Cys Gln Ser Ser Pro Ser Val Tyr Lys Asn
            20                  25                  30

Asn Gln Leu Ala Trp Tyr Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Glu Phe Thr Leu Thr Ile Ser Asp Leu
65                  70                  75                  80

Glu Cys Ala Asp Ala Ala Thr Tyr Tyr Cys Ala Gly Gly Tyr Ser Ser
                85                  90                  95

Ser Ser Asp Thr Ala Phe Gly Gly Gly Thr Glu Val Glu Val Lys
            100                 105                 110
```

<210> SEQ ID NO 53
<211> LENGTH: 1335
<212> TYPE: DNA
<213> ORGANISM: Artificial Sequence
<220> FEATURE:
<223> OTHER INFORMATION: synthesized

<400> SEQUENCE: 53

```
cagtcgctgg aggagtccgg gggtcgcctg gtcacgcctg ggacacccct gacactcacc      60
tgcacagtct ctggaatcga cctcagtgcc taccacatga gctgggtccg ccaggctcca     120
gggaaggggc tggaatacat cggaatgatt ggtagtagtg gtaccataca ctacgcgaac     180
tgggcgaaag gccgattcac catctccaaa acctcgacca cggtggatct gaaaatcacc     240
agtccgacaa ccgaggacac ggccacctat ttctgtgcca gggacagtta taatagtgat     300
tatgccttta acttatgggg cccagggacc ctggtcaccg tctcgagcgc tagcaccaag     360
ggcccatcgg tcttccccct ggcacccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaagccg cggggggcacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctatag caagctcacc gtggacaaga gcaggtggca gcaggggaac    1260
gtcttctcat gctccgtgat gcatgaggct ctgcacaacc actacacgca gaagagcctc    1320
tccctgtctc cgggt                                                    1335
```

<210> SEQ ID NO 54
<211> LENGTH: 348
<212> TYPE: DNA
<213> ORGANISM: Artificial Sequence
<220> FEATURE:
<223> OTHER INFORMATION: synthesized

<400> SEQUENCE: 54

```
cagtcgctgg aggagtccgg gggtcgcctg gtcacgcctg ggacacccct gacactcacc      60
tgcacagtct ctggaatcga cctcagtgcc taccacatga gctgggtccg ccaggctcca     120
gggaaggggc tggaatacat cggaatgatt ggtagtagtg gtaccataca ctacgcgaac     180
tgggcgaaag gccgattcac catctccaaa acctcgacca cggtggatct gaaaatcacc     240
agtccgacaa ccgaggacac ggccacctat ttctgtgcca gggacagtta taatagtgat     300
tatgccttta acttatgggg cccagggacc ctggtcaccg tctcgagc                 348
```

<210> SEQ ID NO 55
<211> LENGTH: 445
<212> TYPE: PRT
<213> ORGANISM: Artificial Sequence
<220> FEATURE:
<223> OTHER INFORMATION: synthesized

<400> SEQUENCE: 55

```
Gln Ser Leu Glu Glu Ser Gly Gly Arg Leu Val Thr Pro Gly Thr Pro
1               5                   10                  15
Leu Thr Leu Thr Cys Thr Val Ser Gly Ile Asp Leu Ser Ala Tyr His
                20                  25                  30
Met Ser Trp Val Arg Gln Ala Pro Gly Lys Gly Leu Glu Tyr Ile Gly
            35                  40                  45
Met Ile Gly Ser Ser Gly Thr Ile His Tyr Ala Asn Trp Ala Lys Gly
        50                  55                  60
Arg Phe Thr Ile Ser Lys Thr Ser Thr Val Asp Leu Lys Ile Thr
65                  70                  75                  80
Ser Pro Thr Thr Glu Asp Thr Ala Thr Tyr Phe Cys Ala Arg Asp Ser
                85                  90                  95
Tyr Asn Ser Asp Tyr Ala Phe Asn Leu Trp Gly Pro Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Ala Ala Gly Ala Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Ala Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 56
<211> LENGTH: 116
<212> TYPE: PRT
<213> ORGANISM: Artificial Sequence
<220> FEATURE:
<223> OTHER INFORMATION: synthesized

<400> SEQUENCE: 56

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ala Tyr His
            20                  25                  30

Met Ser Trp Val Arg Gln Ala Pro Gly Lys Gly Leu Glu Tyr Ile Gly
        35                  40                  45

Met Ile Gly Ser Ser Gly Thr Ile His Tyr Ala Asn Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Asp Ser
                85                  90                  95

Tyr Asn Ser Asp Tyr Ala Phe Asn Leu Trp Gly Pro Gly Thr Leu Val
            100                 105                 110

Thr Val Ser Ser
        115

<210> SEQ ID NO 57
<211> LENGTH: 654
<212> TYPE: DNA
<213> ORGANISM: Artificial Sequence
<220> FEATURE:
<223> OTHER INFORMATION: synthesized

<400> SEQUENCE: 57
gctcaagtgc tgacccagac tgcatcgccc gtgtctgccg ctgtgggagg cacagtcacc      60
atcaactgcc agtccagtca gagtgtttat agtaactggt tatcctggta tcagcagaaa    120
ccagggcagc ctcccaagcg cctgatctat tctgcatcca ctctggcatc tggggtccca    180
tcgcggttca aaggcagtgg atctgggaca cagttcactc tcaccatcag cgacctggag    240
tgtgacgatg ctgccactta ctactgtgca ggcggttata atactgttac tgatactttt    300
gctttcggca gaggcaccga ggtggaggtc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc      600 acccatcagg gcctgagctc gcccgtcaca aagagcttca acaggggaga gtgt      654

<210> SEQ ID NO 58
<211> LENGTH: 333
<212> TYPE: DNA
<213> ORGANISM: Artificial Sequence
<220> FEATURE:
<223> OTHER INFORMATION: synthesized

<400> SEQUENCE: 58
gctcaagtgc tgacccagac tgcatcgccc gtgtctgccg ctgtgggagg cacagtcacc      60
atcaactgcc agtccagtca gagtgtttat agtaactggt tatcctggta tcagcagaaa      120
ccagggcagc ctcccaagcg cctgatctat tctgcatcca ctctggcatc tggggtccca      180
tcgcggttca aaggcagtgg atctgggaca cagttcactc tcaccatcag cgacctggag      240
tgtgacgatg ctgccactta ctactgtgca ggcggttata atactgttac tgatactttt      300
gctttcggca gaggcaccga ggtggaggtc aaa      333

<210> SEQ ID NO 59
<211> LENGTH: 218
<212> TYPE: PRT
<213> ORGANISM: Artificial Sequence
<220> FEATURE:
<223> OTHER INFORMATION: synthesized

<400> SEQUENCE: 59

Ala Gln Val Leu Thr Gln Thr Ala Ser Pro Val Ser Ala Ala Val Gly
1               5                   10                  15

Gly Thr Val Thr Ile Asn Cys Gln Ser Ser Gln Ser Val Tyr Ser Asn
            20                  25                  30

Trp Leu Ser Trp Tyr Gln Gln Lys Pro Gly Gln Pro Pro Lys Arg Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Thr Asp Thr Phe Ala Phe Gly Arg Gly Thr Glu Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 60

<211> LENGTH: 111
<212> TYPE: PRT
<213> ORGANISM: Artificial Sequence
<220> FEATURE:
<223> OTHER INFORMATION: synthesized

<400> SEQUENCE: 60

```
Ala Gln Val Leu Thr Gln Thr Ala Ser Pro Val Ser Ala Ala Val Gly
 1               5                  10                  15

Gly Thr Val Thr Ile Asn Cys Gln Ser Ser Gln Ser Val Tyr Ser Asn
            20                  25                  30

Trp Leu Ser Trp Tyr Gln Gln Lys Pro Gly Gln Pro Pro Lys Arg Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Thr Asp Thr Phe Ala Phe Gly Arg Gly Thr Glu Val Glu Val Lys
            100                 105                 110
```

<210> SEQ ID NO 61
<211> LENGTH: 1326
<212> TYPE: DNA
<213> ORGANISM: Artificial Sequence
<220> FEATURE:
<223> OTHER INFORMATION: synthesized

<400> SEQUENCE: 61

```
cagtcgttgg aggagtccgg gggagacctg gtcaagcctg gggcatccct gacactcacc      60
tgcacagcct ctggattctc cttcagtagc aggcactaca tgtgttgggt ccgccaggct     120
ccagggagg ggctggagtg gatcgcatgc atttatactg gtagtagtgg tactcctcac      180
tacgcgagct gggcgaaagg ccgattcacc atctcccaaa cctcgtcgac acggtgact      240
ctgcaaatga ccagtctgac agccgcggac acggccacct atttctgttc gagcgaaggt     300
aacctgtggg gcccaggcac cctggtcacc gtctcgagcg ctagcaccaa gggcccatcg     360
gtcttccccc tggcaccctc ctccaagagc acctctgggg gcacagcggc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaga gttgagccca atcttgtga caaaactcac      660
acatgcccac cgtgcccagc acctgaagcc gcggggcac cgtcagtctt cctcttcccc      720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg cgcggtctcc     960
aacaaagccc tcccagcccc catcgagaaa accatctcca agccaaagg gcagccccga    1020
gaaccacagg tgtacaccct gcccccatcc cgggatgagc tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
```

```
ttcctctata gcaagctcac cgtggacaag agcaggtggc agcagggaa cgtcttctca    1260 tgctccgtga tgcatgaggc tctgcacaac cactacacgc agaagagcct ctccctgtct   1320
ccgggt                                                              1326
```

<210> SEQ ID NO 62
<211> LENGTH: 339
<212> TYPE: DNA
<213> ORGANISM: Artificial Sequence
<220> FEATURE:
<223> OTHER INFORMATION: synthesized

<400> SEQUENCE: 62

```
cagtcgttgg aggagtccgg gggagacctg gtcaagcctg ggcatccct gacactcacc     60 tgcacagcct ctggattctc cttcagtagc aggcactaca tgtgttgggt ccgccaggct   120
ccaggggagg ggctggagtg gatcgcatgc atttatactg gtagtagtgg tactcctcac   180
tacgcgagct gggcgaaagg ccgattcacc atctcccaaa cctcgtcgac acggtgact    240 ctgcaaatga ccagtctgac agccgcggac acggccacct atttctgttc gagcgaaggt   300
aacctgtggg gcccaggcac cctggtcacc gtctcgagc                          339
```

<210> SEQ ID NO 63
<211> LENGTH: 442
<212> TYPE: PRT
<213> ORGANISM: Artificial Sequence
<220> FEATURE:
<223> OTHER INFORMATION: synthesized

<400> SEQUENCE: 63

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Arg His
            20                  25                  30

Tyr Met Cys Trp Val Arg Gln Ala Pro Gly Glu Gly Leu Glu Trp Ile
        35                  40                  45

Ala Cys Ile Tyr Thr Gly Ser Ser Gly Thr Pro His Tyr Ala Ser Trp
    50                  55                  60

Ala Lys Gly Arg Phe Thr Ile Ser Gln Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ser Ser Glu Gly Asn Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220
```

Cys Pro Ala Pro Glu Ala Ala Gly Ala Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
            435                 440

<210> SEQ ID NO 64
<211> LENGTH: 113
<212> TYPE: PRT
<213> ORGANISM: Artificial Sequence
<220> FEATURE:
<223> OTHER INFORMATION: synthesized

<400> SEQUENCE: 64

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Arg His
            20                  25                  30

Tyr Met Cys Trp Val Arg Gln Ala Pro Gly Glu Gly Leu Glu Trp Ile
        35                  40                  45

Ala Cys Ile Tyr Thr Gly Ser Ser Gly Thr Pro His Tyr Ala Ser Trp
    50                  55                  60

Ala Lys Gly Arg Phe Thr Ile Ser Gln Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ser Ser Glu Gly Asn Leu Trp Gly Pro Gly Thr Leu Val Thr Val Ser
            100                 105                 110

Ser

<210> SEQ ID NO 65
<211> LENGTH: 657

```
<212> TYPE: DNA
<213> ORGANISM: Artificial Sequence
<220> FEATURE:
<223> OTHER INFORMATION: synthesized

<400> SEQUENCE: 65
gcccttgtga tgacccagac tccagcctcc gtgtctgcag ctgtgggagg cacagtcacc    60
atcaattgcc aggccagtga ggacattgat acctatttag cctggtatca gcagaaacca   120
gggcagcctc ccaagctcct gatcttttat gcatccgatc tggcatctgg ggtcccatcg   180
cggttcaaag gcagtggatc tgggacagag ttcactctca ccatcagcgg tgtgcagtgt   240
gacgatgctg ccacttacta ctgtcaaggc ggttactata ctagtagtgc tgatacgagg   300
ggtgctttcg gcggaggcac cgaggtggtg gtcaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657

<210> SEQ ID NO 66
<211> LENGTH: 336
<212> TYPE: DNA
<213> ORGANISM: Artificial Sequence
<220> FEATURE:
<223> OTHER INFORMATION: synthesized

<400> SEQUENCE: 66
gcccttgtga tgacccagac tccagcctcc gtgtctgcag ctgtgggagg cacagtcacc    60
atcaattgcc aggccagtga ggacattgat acctatttag cctggtatca gcagaaacca   120
gggcagcctc ccaagctcct gatcttttat gcatccgatc tggcatctgg ggtcccatcg   180
cggttcaaag gcagtggatc tgggacagag ttcactctca ccatcagcgg tgtgcagtgt   240
gacgatgctg ccacttacta ctgtcaaggc ggttactata ctagtagtgc tgatacgagg   300
ggtgctttcg gcggaggcac cgaggtggtg gtcaaa                             336

<210> SEQ ID NO 67
<211> LENGTH: 219
<212> TYPE: PRT
<213> ORGANISM: Artificial Sequence
<220> FEATURE:
<223> OTHER INFORMATION: synthesized

<400> SEQUENCE: 67

Ala Leu Val Met Thr Gln Thr Pro Ala Ser Val Ser Ala Ala Val Gly
1               5                   10                  15

Gly Thr Val Thr Ile Asn Cys Gln Ala Ser Glu Asp Ile Asp Thr Tyr
            20                  25                  30

Leu Ala Trp Tyr Gln Gln Lys Pro Gly Gln Pro Pro Lys Leu Leu Ile
        35                  40                  45

Phe Tyr Ala Ser Asp Leu Ala Ser Gly Val Pro Ser Arg Phe Lys Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Gly Gly Tyr Tyr Thr Ser Ser
                85                  90                  95
```

```
Ala Asp Thr Arg Gly Ala Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 68
<211> LENGTH: 112
<212> TYPE: PRT
<213> ORGANISM: Artificial Sequence
<220> FEATURE:
<223> OTHER INFORMATION: synthesized

<400> SEQUENCE: 68

```
Ala Leu Val Met Thr Gln Thr Pro Ala Ser Val Ser Ala Ala Val Gly
1               5                   10                  15

Gly Thr Val Thr Ile Asn Cys Gln Ala Ser Glu Asp Ile Asp Thr Tyr
            20                  25                  30

Leu Ala Trp Tyr Gln Gln Lys Pro Gly Gln Pro Pro Lys Leu Leu Ile
        35                  40                  45

Phe Tyr Ala Ser Asp Leu Ala Ser Gly Val Pro Ser Arg Phe Lys Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Gly Tyr Tyr Thr Ser Ser
                85                  90                  95

Ala Asp Thr Arg Gly Ala Phe Gly Gly Gly Thr Glu Val Val Val Lys
            100                 105                 110
```

<210> SEQ ID NO 69
<211> LENGTH: 1344
<212> TYPE: DNA
<213> ORGANISM: Artificial Sequence
<220> FEATURE:
<223> OTHER INFORMATION: synthesized

<400> SEQUENCE: 69

```
cagtcgttgg aggagtccgg gggagacctg gtcaagcctg ggcatccct gacactcacc      60 tgcacagcct ctggattctc cttcagtagc aactactgga tatgctgggt ccgccaggct    120
ccagggaagg ggctggagtg gatcgcatgc atttatgttg gtagtagtgg tgacacttac    180
tacgcgagct gggcgaaagg ccgattcacc atctccaaaa cctcgtcgac acggtgact    240 ctgcaaatga ccagtctgac agccgcggac acggccacct atttctgtgc gagagatagt    300
agtagttatt atatgtttaa cttgtggggc caggggaccc tggtcaccgt ctcgagcgct    360
agcaccaagg gcccatcggt cttccccctg gcaccctcct ccaagagcac ctctggggc    420
```

```
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagccgc ggggggcaccg    720 tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgcg cggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggt                                          1344
```

<210> SEQ ID NO 70
<211> LENGTH: 357
<212> TYPE: DNA
<213> ORGANISM: Artificial Sequence
<220> FEATURE:
<223> OTHER INFORMATION: synthesized

<400> SEQUENCE: 70

```
cagtcgttgg aggagtccgg gggagacctg gtcaagcctg ggcatccct gacactcacc     60 tgcacagcct ctggattctc cttcagtagc aactactgga tatgctgggt ccgccaggct   120
ccagggaagg ggctggagtg gatcgcatgc atttatgttg gtagtagtgg tgacacttac   180
tacgcgagct gggcgaaagg ccgattcacc atctccaaaa cctcgtcgac cacggtgact   240
ctgcaaatga ccagtctgac agccgcggac acggccacct atttctgtgc gagagatagt   300
agtagttatt atatgtttaa cttgtggggc caggggaccc tggtcaccgt ctcgagc     357
```

<210> SEQ ID NO 71
<211> LENGTH: 448
<212> TYPE: PRT
<213> ORGANISM: Artificial Sequence
<220> FEATURE:
<223> OTHER INFORMATION: synthesized

<400> SEQUENCE: 71

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Trp
    50                  55                  60

Ala Lys Gly Arg Phe Thr Ile Ser Lys Thr Ser Ser Thr Val Thr
65                  70                  75                  80

```
Leu Gln Met Thr Ser Leu Thr Ala Ala Asp Thr Ala Thr Tyr Phe Cys
                 85                  90                  95
Ala Arg Asp Ser Ser Tyr Tyr Met Phe Asn Leu Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Ala Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

<210> SEQ ID NO 72
<211> LENGTH: 119
<212> TYPE: PRT
<213> ORGANISM: Artificial Sequence
<220> FEATURE:
<223> OTHER INFORMATION: synthesized

<400> SEQUENCE: 72

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Tyr
                20                  25                  30

Trp Ile Cys Trp Val Arg Gln Ala Pro Gly Lys Gly Leu Glu Trp Ile
            35                  40                  45

Ala Cys Ile Tyr Val Gly Ser Ser Gly Asp Thr Tyr Tyr Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ser Ser Ser Tyr Tyr Met Phe Asn Leu Trp Gly Gln Gly
            100                 105                 110

Thr Leu Val Thr Val Ser Ser
        115

<210> SEQ ID NO 73
<211> LENGTH: 427
<212> TYPE: DNA
<213> ORGANISM: Artificial Sequence
<220> FEATURE:
<223> OTHER INFORMATION: synthesized

<400> SEQUENCE: 73
tagcgacctg gagtgtgacg atgctgccac ttactactgt gcaggcggtt acaatactgt      60
tattgatact tttgctttcg gcggaggcac cgaggtggag ttcaaacgta cggtggctgc     120
accatctgtc ttcatcttcc cgccatctga tgagcagttg aaatctggaa ctgcctctgt     180
tgtgtgcctg ctgaataact ctatcccag agaggccaaa gtacagtgga aggtggataa      240
cgccctccaa tcgggtaact cccaggagag tgtcacagag caggacagca aggacagcac     300
ctacagcctc agcagcaccc tgacgctgag caaagcagac tacgagaaac acaaagtcta    360
cgcctgcgaa gtcaccccatc agggcctgag ctcgcccgtc acaaagagct tcaacagggg    420
agagtgt                                                              427

<210> SEQ ID NO 74
<211> LENGTH: 333
<212> TYPE: DNA
<213> ORGANISM: Artificial Sequence
<220> FEATURE:
<223> OTHER INFORMATION: synthesized

<400> SEQUENCE: 74
gctcaagtgc tgacccagac tgcatcgccc gtgtctgccg ctgtgggagg cacagtcacc      60
atcaactgcc aggccagtca gagtgtttat agtaactggt atcctggta tcagcagaaa     120 ccagggcagc ctcccaagcg cctgatctat tctgcatcca ctctggcatc tggggtccca    180
tcgcggttca aaggcagtgg atctgggaca cagttcactc tcaccattag cgacctggag    240
tgtgacgatg ctgccactta ctactgtgca ggcggttaca atactgttat tgataccttt    300
gctttcggcg gaggcaccga ggtggagttc aaa                                 333

<210> SEQ ID NO 75
<211> LENGTH: 218
<212> TYPE: PRT
<213> ORGANISM: Artificial Sequence
<220> FEATURE:
<223> OTHER INFORMATION: synthesized

<400> SEQUENCE: 75

Ala Gln Val Leu Thr Gln Thr Ala Ser Pro Val Ser Ala Ala Val Gly
1               5                   10                  15

Gly Thr Val Thr Ile Asn Cys Gln Ala Ser Gln Ser Val Tyr Ser Asn
                20                  25                  30

Trp Leu Ser Trp Tyr Gln Gln Lys Pro Gly Gln Pro Pro Lys Arg Leu
            35                  40                  45

Ile Tyr Ser Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Ile Asp Thr Phe Ala Phe Gly Gly Thr Glu Val Glu Phe Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
145             130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 76
<211> LENGTH: 111
<212> TYPE: PRT
<213> ORGANISM: Artificial Sequence
<220> FEATURE:
<223> OTHER INFORMATION: synthesized

<400> SEQUENCE: 76

Ala Gln Val Leu Thr Gln Thr Ala Ser Pro Val Ser Ala Ala Val Gly
1               5                   10                  15

Gly Thr Val Thr Ile Asn Cys Gln Ala Ser Gln Ser Val Tyr Ser Asn
                20                  25                  30

Trp Leu Ser Trp Tyr Gln Gln Lys Pro Gly Gln Pro Pro Lys Arg Leu
            35                  40                  45

Ile Tyr Ser Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Ile Asp Thr Phe Ala Phe Gly Gly Gly Thr Glu Val Glu Phe Lys
                100                 105                 110

<210> SEQ ID NO 77
<211> LENGTH: 1329

<212> TYPE: DNA
<213> ORGANISM: Artificial Sequence
<220> FEATURE:
<223> OTHER INFORMATION: synthesized

<400> SEQUENCE: 77

```
cagcagcagc tggaggagtc cggggagggc ctggtcaagc ctggaggaac cctgacactc      60
acctgcaaag cctctggaat tgacttcagt agtagttact acatgtgctg ggtccgccag     120
gctccagggg aggggctgga gtggatcgca tgcatttata ctggtggtag tggtactcct     180
cactacgcga gctgggcgaa aggccgattc accatctccc aaacctcgtc gaccacggtg     240
actctgcaaa tgaccagtct gacagccgcg gacacggcca cctatttctg tgcgagagaa     300
ggtagcctgt ggggccaggg caccctggtc accgtctcga gcgctagcac caagggccca     360
tcggtcttcc cctggcacc ctcctccaag agcacctctg gggcacagc ggccctgggc        420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg gcacccaga cctacatctg caacgtgaat        600
cacaagccca gcaacaccaa ggtggacaag agagttgagc ccaaatcttg tgacaaaact     660
cacacatgcc caccgtgccc agcacctgaa gccgcggggg gaccgtcagt cttcctcttc     720
cccccaaaac ccaaggacac cctcatgatc tcccggaccc ctgaggtcac atgcgtggtg     780
gtggacgtga gccacgaaga ccctgaggtc aagttcaact ggtacgtgga cggcgtggag     840
gtgcataatg ccaagacaaa gccgcgggag gagcagtaca acagcacgta ccgtgtggtc     900
agcgtcctca ccgtcctgca ccaggactgg ctgaatggca aggagtacaa gtgcgcggtc     960
tccaacaaag ccctcccagc ccccatcgag aaaaccatct ccaaagccaa agggcagccc    1020
cgagaaccac aggtgtacac cctgccccca tcccgggatg agctgaccaa gaaccaggtc    1080
agcctgacct gcctggtcaa aggcttctat cccagcgaca tcgccgtgga gtgggagagc    1140
aatgggcagc cggagaacaa ctacaagacc acgcctcccg tgctggactc cgacggctcc    1200
ttcttcctct atagcaagct caccgtggac aagagcaggt ggcagcaggg gaacgtcttc    1260
tcatgctccg tgatgcatga ggctctgcac aaccactaca cgcagaagag cctctccctg    1320
tctccgggt                                                            1329
```

<210> SEQ ID NO 78
<211> LENGTH: 342
<212> TYPE: DNA
<213> ORGANISM: Artificial Sequence
<220> FEATURE:
<223> OTHER INFORMATION: synthesized

<400> SEQUENCE: 78

```
cagcagcagc tggaggagtc cggggagggc ctggtcaagc ctggaggaac cctgacactc      60
acctgcaaag cctctggaat tgacttcagt agtagttact acatgtgctg ggtccgccag     120
gctccagggg aggggctgga gtggatcgca tgcatttata ctggtggtag tggtactcct     180
cactacgcga gctgggcgaa aggccgattc accatctccc aaacctcgtc gaccacggtg     240
actctgcaaa tgaccagtct gacagccgcg gacacggcca cctatttctg tgcgagagaa     300
ggtagcctgt ggggccaggg caccctggtc accgtctcga gc                        342
```

<210> SEQ ID NO 79
<211> LENGTH: 443
<212> TYPE: PRT

<213> ORGANISM: Artificial Sequence
<220> FEATURE:
<223> OTHER INFORMATION: synthesized

<400> SEQUENCE: 79

```
Gln Gln Gln Leu Glu Glu Ser Gly Gly Gly Leu Val Lys Pro Gly Gly
1               5                   10                  15

Thr Leu Thr Leu Thr Cys Lys Ala Ser Gly Ile Asp Phe Ser Ser Ser
            20                  25                  30

Tyr Tyr Met Cys Trp Val Arg Gln Ala Pro Gly Glu Gly Leu Glu Trp
        35                  40                  45

Ile Ala Cys Ile Tyr Thr Gly Ser Gly Thr Pro His Tyr Ala Ser
    50                  55                  60

Trp Ala Lys Gly Arg Phe Thr Ile Ser Gln Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Glu Gly Ser Leu Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Ala Ala Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
```

```
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
        435                 440
```

<210> SEQ ID NO 80
<211> LENGTH: 114
<212> TYPE: PRT
<213> ORGANISM: Artificial Sequence
<220> FEATURE:
<223> OTHER INFORMATION: synthesized

<400> SEQUENCE: 80

```
Gln Gln Gln Leu Glu Glu Ser Gly Gly Gly Leu Val Lys Pro Gly Gly
1               5                   10                  15
Thr Leu Thr Leu Thr Cys Lys Ala Ser Gly Ile Asp Phe Ser Ser Ser
            20                  25                  30
Tyr Tyr Met Cys Trp Val Arg Gln Ala Pro Gly Glu Gly Leu Glu Trp
        35                  40                  45
Ile Ala Cys Ile Tyr Thr Gly Gly Ser Gly Thr Pro His Tyr Ala Ser
    50                  55                  60
Trp Ala Lys Gly Arg Phe Thr Ile Ser Gln Thr Ser Ser Thr Thr Val
65                  70                  75                  80
Thr Leu Gln Met Thr Ser Leu Thr Ala Ala Asp Thr Ala Thr Tyr Phe
            85                  90                  95
Cys Ala Arg Glu Gly Ser Leu Trp Gly Gln Gly Thr Leu Val Thr Val
        100                 105                 110
Ser Ser
```

<210> SEQ ID NO 81
<211> LENGTH: 654
<212> TYPE: DNA
<213> ORGANISM: Artificial Sequence
<220> FEATURE:
<223> OTHER INFORMATION: synthesized

<400> SEQUENCE: 81

```
gctcaagtgc tgacccagac tgcatcgccc gtgtctgccg ctgtgggagg cacagtcacc      60
atcaactgcc agtccagtca gagtgtttat agtaactggt tgtcctggta tcagcagaaa    120
ccagggcagc ctcccaagct cctgatctat tctgcatcca ctctggcatc tggggtcccc    180
tcgcggttta aaggcagtgg atctgggaca cagttcactc tcaccatcag cgacctggag    240
tgtgacgatg ctgccactta ctactgtgca ggcggttaca atactgtaac tgatactttt    300
gctttcggcg gaggcaccga ggtggagttc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600
acccatcagg gcctgagctc gcccgtcaca aagagcttca caggggaga gtgt           654
```

<210> SEQ ID NO 82
<211> LENGTH: 333

```
<212> TYPE: DNA
<213> ORGANISM: Artificial Sequence
<220> FEATURE:
<223> OTHER INFORMATION: synthesized

<400> SEQUENCE: 82
gctcaagtgc tgacccagac tgcatcgccc gtgtctgccg ctgtgggagg cacagtcacc    60
atcaactgcc agtccagtca gagtgtttat agtaactggt tctcctggta tcagcagaaa   120
ccagggcagc ctcccaagct cctgatctat tctgcatcca ctctggcatc tggggtcccc   180
tcgcggttta aaggcagtgg atctgggaca cagttcactc tcaccatcag cgacctggag   240
tgtgacgatg ctgccactta ctactgtgca ggcggttaca atactgtaac tgatactttt   300
gctttcggcg gaggcaccga ggtggagttc aaa                                 333

<210> SEQ ID NO 83
<211> LENGTH: 218
<212> TYPE: PRT
<213> ORGANISM: Artificial Sequence
<220> FEATURE:
<223> OTHER INFORMATION: synthesized

<400> SEQUENCE: 83

Ala Gln Val Leu Thr Gln Thr Ala Ser Pro Val Ser Ala Ala Val Gly
 1               5                  10                  15

Gly Thr Val Thr Ile Asn Cys Gln Ser Ser Gln Ser Val Tyr Ser Asn
                20                  25                  30

Trp Phe Ser Trp Tyr Gln Gln Lys Pro Gly Gln Pro Pro Lys Leu Leu
            35                  40                  45

Ile Tyr Ser Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Leu Glu
 65                  70                  75                  80

Cys Asp Asp Ala Ala Thr Tyr Tyr Cys Ala Gly Gly Tyr Asn Thr Val
                85                  90                  95

Thr Asp Thr Phe Ala Phe Gly Gly Thr Glu Val Glu Phe Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 84
<211> LENGTH: 111
<212> TYPE: PRT
<213> ORGANISM: Artificial Sequence
<220> FEATURE:
<223> OTHER INFORMATION: synthesized
```

<400> SEQUENCE: 84

| Ala | Gln | Val | Leu | Thr | Gln | Thr | Ala | Ser | Pro | Val | Ser | Ala | Ala | Val | Gly |
|---|---|---|---|---|---|---|---|---|---|---|---|---|---|---|---|
| 1 | | | | 5 | | | | | 10 | | | | | 15 | |

| Gly | Thr | Val | Thr | Ile | Asn | Cys | Gln | Ser | Ser | Gln | Ser | Val | Tyr | Ser | Asn |
|---|---|---|---|---|---|---|---|---|---|---|---|---|---|---|---|
| | | | 20 | | | | | 25 | | | | | 30 | | |

| Trp | Phe | Ser | Trp | Tyr | Gln | Gln | Lys | Pro | Gly | Gln | Pro | Pro | Lys | Leu | Leu |
|---|---|---|---|---|---|---|---|---|---|---|---|---|---|---|---|
| | | 35 | | | | | 40 | | | | | 45 | | | |

| Ile | Tyr | Ser | Ala | Ser | Thr | Leu | Ala | Ser | Gly | Val | Pro | Ser | Arg | Phe | Lys |
|---|---|---|---|---|---|---|---|---|---|---|---|---|---|---|---|
| | 50 | | | | | 55 | | | | | 60 | | | | |

| Gly | Ser | Gly | Ser | Gly | Thr | Gln | Phe | Thr | Leu | Thr | Ile | Ser | Asp | Leu | Glu |
|---|---|---|---|---|---|---|---|---|---|---|---|---|---|---|---|
| 65 | | | | | 70 | | | | | 75 | | | | | 80 |

| Cys | Asp | Asp | Ala | Ala | Thr | Tyr | Tyr | Cys | Ala | Gly | Gly | Tyr | Asn | Thr | Val |
|---|---|---|---|---|---|---|---|---|---|---|---|---|---|---|---|
| | | | | 85 | | | | | 90 | | | | | 95 | |

| Thr | Asp | Thr | Phe | Ala | Phe | Gly | Gly | Gly | Thr | Glu | Val | Glu | Phe | Lys |
|---|---|---|---|---|---|---|---|---|---|---|---|---|---|---|
| | | | 100 | | | | | 105 | | | | | 110 | |

<210> SEQ ID NO 85
<211> LENGTH: 1326
<212> TYPE: DNA
<213> ORGANISM: Artificial Sequence
<220> FEATURE:
<223> OTHER INFORMATION: synthesized

<400> SEQUENCE: 85

| | |
|---|---|
| gagtcgttgg aggagtccgg gggagacctg gtcaagcctg ggcatccct gacactcacc | 60 |
| tgcacagcct ctggaatcga cttcagtagg agatactaca tgtgctgggt ccgccaggct | 120 |
| ccagggaagg ggctggagtg gatcgcatgc atgtatactg gtagccgcga tactcctcac | 180 |
| tacgcgagct gggcgaaagg ccggttcacc atctcccaaa cctcgtcgac cacggtgact | 240 |
| ctgcaaatga ccagtctgac agccgcggac acggccacct atttctgtgc gagagaaggt | 300 |
| aacctgtggg gccgggggac cctggtcacc gtctcgagcg ctagcaccaa gggcccatcg | 360 |
| gtcttccccc tggcaccctc ctccaagagc acctctgggg gcacagcggc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag gactctactc cctcagcagc | 540 |
| gtggtgaccg tgccctccag cagcttgggc acccagacct acatctgcaa cgtgaatcac | 600 |
| aagcccagca acaccaaggt ggacaagaga gttgagccca atcttgtga caaaactcac | 660 |
| acatgcccac cgtgcccagc acctgaagcc gcggggcac cgtcagtctt cctcttcccc | 720 |
| ccaaaaccca aggacaccct catgatctcc cggacccctg aggtcacatg cgtggtggtg | 780 |
| gacgtgagcc acgaagaccc tgaggtcaag ttcaactggt acgtggacgg cgtggaggtg | 840 |
| cataatgcca agacaaagcc gcgggaggag cagtacaaca gcacgtaccg tgtggtcagc | 900 |
| gtcctcaccg tcctgcacca ggactggctg aatggcaagg agtacaagtg cgcggtctcc | 960 |
| aacaaagccc tcccagcccc catcgagaaa accatctcca agccaaagg gcagccccga | 1020 |
| gaaccacagg tgtacaccct gcccccatcc cgggatgagc tgaccaagaa ccaggtcagc | 1080 |
| ctgacctgcc tggtcaaagg cttctatccc agcgacatcg ccgtggagtg ggagagcaat | 1140 |
| gggcagccgg agaacaacta caagaccacg cctcccgtgc tggactccga cggctccttc | 1200 |
| ttcctctata gcaagctcac cgtggacaag agcaggtggc agcaggggaa cgtcttctca | 1260 |
| tgctccgtga tgcatgaggc tctgcacaac cactacacgc agaagagcct ctccctgtct | 1320 |
| ccgggt | 1326 |

<210> SEQ ID NO 86
<211> LENGTH: 339
<212> TYPE: DNA
<213> ORGANISM: Artificial Sequence
<220> FEATURE:
<223> OTHER INFORMATION: synthesized

<400> SEQUENCE: 86

```
gagtcgttgg aggagtccgg gggagacctg gtcaagcctg gggcatccct gacactcacc    60
tgcacagcct ctggaatcga cttcagtagg agatactaca tgtgctgggt ccgccaggct   120
ccagggaagg ggctggagtg gatcgcatgc atgtatactg gtagccgcga tactcctcac   180
tacgcgagct gggcgaaagg ccggttcacc atctcccaaa cctcgtcgac cacggtgact   240
ctgcaaatga ccagtctgac agccgcggac acggccacct atttctgtgc gagagaaggt   300
aacctgtggg gcccggggac cctggtcacc gtctcgagc                           339
```

<210> SEQ ID NO 87
<211> LENGTH: 442
<212> TYPE: PRT
<213> ORGANISM: Artificial Sequence
<220> FEATURE:
<223> OTHER INFORMATION: synthesized

<400> SEQUENCE: 87

```
Glu Ser Leu Glu Glu Ser Gly Gly Asp Leu Val Lys Pro Gly Ala Ser
1               5                   10                  15

Leu Thr Leu Thr Cys Thr Ala Ser Gly Ile Asp Phe Ser Arg Arg Tyr
                20                  25                  30

Tyr Met Cys Trp Val Arg Gln Ala Pro Gly Lys Gly Leu Glu Trp Ile
            35                  40                  45

Ala Cys Met Tyr Thr Gly Ser Arg Asp Thr Pro His Tyr Ala Ser Trp
        50                  55                  60

Ala Lys Gly Arg Phe Thr Ile Ser Gln Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Gly Asn Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
210                 215                 220

Cys Pro Ala Pro Glu Ala Ala Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

Cys Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
    275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
            435                 440

<210> SEQ ID NO 88
<211> LENGTH: 113
<212> TYPE: PRT
<213> ORGANISM: Artificial Sequence
<220> FEATURE:
<223> OTHER INFORMATION: synthesized

<400> SEQUENCE: 88

Glu Ser Leu Glu Glu Ser Gly Gly Asp Leu Val Lys Pro Gly Ala Ser
1               5                   10                  15

Leu Thr Leu Thr Cys Thr Ala Ser Gly Ile Asp Phe Ser Arg Arg Tyr
            20                  25                  30

Tyr Met Cys Trp Val Arg Gln Ala Pro Gly Lys Gly Leu Glu Trp Ile
        35                  40                  45

Ala Cys Met Tyr Thr Gly Ser Arg Asp Thr Pro His Tyr Ala Ser Trp
    50                  55                  60

Ala Lys Gly Arg Phe Thr Ile Ser Gln Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Gly Asn Leu Trp Gly Pro Gly Thr Leu Val Thr Val Ser
            100                 105                 110

Ser

<210> SEQ ID NO 89
<211> LENGTH: 654
<212> TYPE: DNA
<213> ORGANISM: Artificial Sequence
<220> FEATURE:
<223> OTHER INFORMATION: synthesized

<400> SEQUENCE: 89

```
gcccaagtgc tgacccagac tccatcgtcc gtgtctgcag ctgtgggagg cacagtcagc      60
atcagttgcc agtccagtca gagtgtttat agtaactggt tctcctggta tcagcagaaa     120
ccagggcagc ctcccaagct cctgatctat tctgcatcca ctctggcatc tggggtcccc     180
tcgcggttta aaggcagtgg atctgggaca cagttcactc tcaccatcag cgacctggag     240
tgtgacgatg ctgccactta ctactgtgca ggcggttaca atactgttat tgatactttt     300
gctttcggcg gaggcaccga ggtggagttc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600 acccatcagg gcctgagctc gcccgtcaca aagagcttca caggggaga gtgt            654
```

<210> SEQ ID NO 90
<211> LENGTH: 333
<212> TYPE: DNA
<213> ORGANISM: Artificial Sequence
<220> FEATURE:
<223> OTHER INFORMATION: synthesized

<400> SEQUENCE: 90

```
gcccaagtgc tgacccagac tccatcgtcc gtgtctgcag ctgtgggagg cacagtcagc      60
atcagttgcc agtccagtca gagtgtttat agtaactggt tctcctggta tcagcagaaa     120
ccagggcagc ctcccaagct cctgatctat tctgcatcca ctctggcatc tggggtcccc     180
tcgcggttta aaggcagtgg atctgggaca cagttcactc tcaccatcag cgacctggag     240
tgtgacgatg ctgccactta ctactgtgca ggcggttaca atactgttat tgatactttt     300
gctttcggcg gaggcaccga ggtggagttc aaa                                  333
```

<210> SEQ ID NO 91
<211> LENGTH: 218
<212> TYPE: PRT
<213> ORGANISM: Artificial Sequence
<220> FEATURE:
<223> OTHER INFORMATION: synthesized

<400> SEQUENCE: 91

```
Ala Gln Val Leu Thr Gln Thr Pro Ser Ser Val Ser Ala Ala Val Gly
1               5                   10                  15

Gly Thr Val Ser Ile Ser Cys Gln Ser Ser Gln Ser Val Tyr Ser Asn
            20                  25                  30

Trp Phe Ser Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Ile Asp Thr Phe Ala Phe Gly Gly Gly Thr Glu Val Glu Phe Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 92
<211> LENGTH: 111
<212> TYPE: PRT
<213> ORGANISM: Artificial Sequence
<220> FEATURE:
<223> OTHER INFORMATION: synthesized

<400> SEQUENCE: 92

Ala Gln Val Leu Thr Gln Thr Pro Ser Ser Val Ser Ala Ala Val Gly
1               5                   10                  15

Gly Thr Val Ser Ile Ser Cys Gln Ser Ser Gln Ser Val Tyr Ser Asn
            20                  25                  30

Trp Phe Ser Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Asn Thr Val
                85                  90                  95

Ile Asp Thr Phe Ala Phe Gly Gly Gly Thr Glu Val Glu Phe Lys
            100                 105                 110

<210> SEQ ID NO 93
<211> LENGTH: 1326
<212> TYPE: DNA
<213> ORGANISM: Artificial Sequence
<220> FEATURE:
<223> OTHER INFORMATION: synthesized

<400> SEQUENCE: 93
cagtcgttgg aggagtccgg gggagacctg gtcaagcctg ggcatccct gacactcacc      60
tgcacagcct ctggaatcga cttcagtagg agatactaca tgtgctgggt ccgccaggct    120
ccagggaagg gctggagtg atcgcatgc atatatactg gtagccgcga tactcctcac     180
tacgcgagct gggcgaaagg ccgattcacc atctcccaaa cctcgtcgac cacggtgact   240
ctgcaaatga ccagtctgac agccgcggac acggccacct atttctgtgc gagagaaggt   300
agcctgtggg gccagggcac cctggtcacc gtctcgagcg ctagcaccaa gggcccatcg   360
gtcttccccc tggcaccctc ctccaagagc acctctgggg gcacagcggc cctgggctgc   420
ctggtcaagg actacttccc cgaaccggtg acggtgtcgt ggaactcagg cgccctgacc   480
agcggcgtgc acaccttccc ggctgtccta cagtcctcag gactctactc cctcagcagc   540
gtggtgaccg tgccctccag cagcttgggc acccagacct acatctgcaa cgtgaatcac   600

```
aagcccagca acaccaaggt ggacaagaga gttgagccca atcttgtga caaaactcac      660 acatgcccac cgtgcccagc acctgaagcc gcgggggcac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg tgtggtcagc      900
gtcctcaccg tcctgcacca ggactggctg aatggcaagg agtacaagtg cgcggtctcc      960
aacaaagccc tcccagcccc catcgagaaa accatctcca aagccaaagg gcagccccga     1020
gaaccacagg tgtacaccct gcccccatcc cgggatgagc tgaccaagaa ccaggtcagc     1080
ctgacctgcc tggtcaaagg cttctatccc agcgacatcg ccgtggagtg ggagagcaat     1140
gggcagccgg agaacaacta caagaccacg cctcccgtgc tggactccga cggctccttc     1200
ttcctctata gcaagctcac cgtggacaag agcaggtggc agcaggggaa cgtcttctca     1260
tgctccgtga tgcatgaggc tctgcacaac cactacacgc agaagagcct ctccctgtct     1320
ccgggt                                                                 1326
```

<210> SEQ ID NO 94
<211> LENGTH: 339
<212> TYPE: DNA
<213> ORGANISM: Artificial Sequence
<220> FEATURE:
<223> OTHER INFORMATION: synthesized

<400> SEQUENCE: 94

```
cagtcgttgg aggagtccgg gggagacctg gtcaagcctg ggcatccct gacactcacc        60 tgcacagcct ctggaatcga cttcagtagg agatactaca tgtgctgggt ccgccaggct      120
ccagggaagg ggctggagtg gatcgcatgc atatatactg gtagccgcga tactcctcac      180
tacgcgagct gggcgaaagg ccgattcacc atctcccaaa cctcgtcgac cacggtgact      240
ctgcaaatga ccagtctgac agccgcggac acggccacct atttctgtgc gagagaaggt      300
agcctgtggg gccagggcac cctggtcacc gtctcgagc                            339
```

<210> SEQ ID NO 95
<211> LENGTH: 442
<212> TYPE: PRT
<213> ORGANISM: Artificial Sequence
<220> FEATURE:
<223> OTHER INFORMATION: synthesized

<400> SEQUENCE: 95

```
Gln Ser Leu Glu Glu Ser Gly Gly Asp Leu Val Lys Pro Gly Ala Ser
1               5                   10                  15

Leu Thr Leu Thr Cys Thr Ala Ser Gly Ile Asp Phe Ser Arg Arg Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Ser Arg Asp Thr Pro His Tyr Ala Ser Trp
    50                  55                  60

Ala Lys Gly Arg Phe Thr Ile Ser Gln Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Gly Ser Leu Trp Gly Gln Gly Thr Leu Val Thr Val Ser
            100                 105                 110
```

```
Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Arg Val Glu Pro Lys Ser Cys Asp Lys Thr His Thr Cys Pro Pro
    210                 215                 220

Cys Pro Ala Pro Glu Ala Ala Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
            435                 440
```

<210> SEQ ID NO 96
<211> LENGTH: 113
<212> TYPE: PRT
<213> ORGANISM: Artificial Sequence
<220> FEATURE:
<223> OTHER INFORMATION: synthesized

<400> SEQUENCE: 96

```
Gln Ser Leu Glu Glu Ser Gly Gly Asp Leu Val Lys Pro Gly Ala Ser
1               5                   10                  15

Leu Thr Leu Thr Cys Thr Ala Ser Gly Ile Asp Phe Ser Arg Arg Tyr
            20                  25                  30
```

Tyr Met Cys Trp Val Arg Gln Ala Pro Gly Lys Gly Leu Glu Trp Ile
            35                  40                  45

Ala Cys Ile Tyr Thr Gly Ser Arg Asp Thr Pro His Tyr Ala Ser Trp
 50                  55                  60

Ala Lys Gly Arg Phe Thr Ile Ser Gln Thr Ser Thr Thr Val Thr
 65              70                  75                  80

Leu Gln Met Thr Ser Leu Thr Ala Ala Asp Thr Ala Thr Tyr Phe Cys
                85                  90                  95

Ala Arg Glu Gly Ser Leu Trp Gly Gln Gly Thr Leu Val Thr Val Ser
            100                 105                 110

Ser

<210> SEQ ID NO 97
<211> LENGTH: 651
<212> TYPE: DNA
<213> ORGANISM: Artificial Sequence
<220> FEATURE:
<223> OTHER INFORMATION: synthesized

<400> SEQUENCE: 97
gcgcaagtgc tgacccagac tccatcgcct gtgtctgcag ctgtgggagg cacagtcacc      60
atcaattgcc agtccagtca gagtgtttat agtaacagct tcttatcctg gtatcagcag     120
aaaccagggc agcctcccaa gcgcctgatc tattctgcat ccgatctggc atctggggtc     180
ccatcgcggt tcaaaggcag tggatctggg acacagttca ctctcaccat cagcgacctg     240
gagtgtgacg atgctgccac ttactactgt gcaggcgttt atagtgataa tacttatgtt     300
ttcggcggag gcaccgaggt ggagttcaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651

<210> SEQ ID NO 98
<211> LENGTH: 330
<212> TYPE: DNA
<213> ORGANISM: Artificial Sequence
<220> FEATURE:
<223> OTHER INFORMATION: synthesized

<400> SEQUENCE: 98
gcgcaagtgc tgacccagac tccatcgcct gtgtctgcag ctgtgggagg cacagtcacc      60
atcaattgcc agtccagtca gagtgtttat agtaacagct tcttatcctg gtatcagcag     120
aaaccagggc agcctcccaa gcgcctgatc tattctgcat ccgatctggc atctggggtc     180
ccatcgcggt tcaaaggcag tggatctggg acacagttca ctctcaccat cagcgacctg     240
gagtgtgacg atgctgccac ttactactgt gcaggcgttt atagtgataa tacttatgtt     300
ttcggcggag gcaccgaggt ggagttcaaa                                      330

<210> SEQ ID NO 99
<211> LENGTH: 217
<212> TYPE: PRT
<213> ORGANISM: Artificial Sequence
<220> FEATURE:
<223> OTHER INFORMATION: synthesized

<400> SEQUENCE: 99

Ala Gln Val Leu Thr Gln Thr Pro Ser Pro Val Ser Ala Ala Val Gly
1               5                   10                  15

Gly Thr Val Thr Ile Asn Cys Gln Ser Ser Gln Ser Val Tyr Ser Asn
                20                  25                  30

Ser Phe Leu Ser Trp Tyr Gln Gln Lys Pro Gly Gln Pro Pro Lys Arg
            35                  40                  45

Leu Ile Tyr Ser Ala Ser Asp Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Val Tyr Ser Asp
                85                  90                  95

Asn Thr Tyr Val Phe Gly Gly Thr Glu Val Glu Phe Lys Arg Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 100
<211> LENGTH: 110
<212> TYPE: PRT
<213> ORGANISM: Artificial Sequence
<220> FEATURE:
<223> OTHER INFORMATION: synthesized

<400> SEQUENCE: 100

Ala Gln Val Leu Thr Gln Thr Pro Ser Pro Val Ser Ala Ala Val Gly
1               5                   10                  15

Gly Thr Val Thr Ile Asn Cys Gln Ser Ser Gln Ser Val Tyr Ser Asn
                20                  25                  30

Ser Phe Leu Ser Trp Tyr Gln Gln Lys Pro Gly Gln Pro Pro Lys Arg
            35                  40                  45

Leu Ile Tyr Ser Ala Ser Asp Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Val Tyr Ser Asp
                85                  90                  95

Asn Thr Tyr Val Phe Gly Gly Thr Glu Val Glu Phe Lys
                100                 105                 110

<210> SEQ ID NO 101
<211> LENGTH: 1329
<212> TYPE: DNA

<213> ORGANISM: Artificial Sequence
<220> FEATURE:
<223> OTHER INFORMATION: synthesized

<400> SEQUENCE: 101

```
cagtcggtgg aggagtccgg cggtcgcctg gtaaagcctg acgaatccct gacactcacc    60
tgcacagcct ctggattctc cctcagtcac tactggatga cttgggtccg acaggctcca   120
gggaagggac tggaatacat cggattcatt aatgttggtg gtgacacatc ttacgcgagc   180
tggtcgaaag gccgattcac catctccaag gcctcgacca cggtggatct gaagatcagt   240
agtctgacaa ccgaggacac ggccacctat ttctgtggca gaggtggtct gacttttggt   300
tgggacttgt ggggcccagg gaccctcgtc accgtctcga gcgctagcac caagggccca   360
tcggtcttcc ccctggcacc ctcctccaag agcacctctg ggggcacagc ggccctgggc   420
tgcctggtca aggactactt ccccgaaccg gtgacggtgt cgtggaactc aggcgccctg   480
accagcggcg tgcacacctt cccggctgtc ctacagtcct caggactcta ctccctcagc   540
agcgtggtga ccgtgccctc agcagcttg gcacccaga cctacatctg caacgtgaat   600
cacaagccca gcaacaccaa ggtggacaag agagttgagc ccaaatcttg tgacaaaact   660
cacacatgcc caccgtgccc agcacctgaa gccgcggggg gaccgtcagt cttcctcttc   720
ccccccaaaac ccaaggacac cctcatgatc tcccggaccc ctgaggtcac atgcgtggtg   780
gtggacgtga gccacgaaga ccctgaggtc aagttcaact ggtacgtgga cggcgtggag   840
gtgcataatg ccaagacaaa gccgcgggag gagcagtaca acagcacgta ccgtgtggtc   900
agcgtcctca ccgtcctgca ccaggactgg ctgaatggca aggagtacaa gtgcgcggtc   960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct atagcaagct caccgtggac aagagcaggt ggcagcaggg gaacgtcttc  1260
tcatgctccg tgatgcatga ggctctgcac aaccactaca cgcagaagag cctctccctg  1320
tctccgggt                                                          1329
```

<210> SEQ ID NO 102
<211> LENGTH: 342
<212> TYPE: DNA
<213> ORGANISM: Artificial Sequence
<220> FEATURE:
<223> OTHER INFORMATION: synthesized

<400> SEQUENCE: 102

```
cagtcggtgg aggagtccgg cggtcgcctg gtaaagcctg acgaatccct gacactcacc    60
tgcacagcct ctggattctc cctcagtcac tactggatga cttgggtccg acaggctcca   120
gggaagggac tggaatacat cggattcatt aatgttggtg gtgacacatc ttacgcgagc   180
tggtcgaaag gccgattcac catctccaag gcctcgacca cggtggatct gaagatcagt   240
agtctgacaa ccgaggacac ggccacctat ttctgtggca gaggtggtct gacttttggt   300
tgggacttgt ggggcccagg gaccctcgtc accgtctcga gc                      342
```

<210> SEQ ID NO 103
<211> LENGTH: 444
<212> TYPE: PRT
<213> ORGANISM: Artificial Sequence
<220> FEATURE:
<223> OTHER INFORMATION: synthesized

<400> SEQUENCE: 103

```
Gln Ser Val Glu Glu Ser Gly Gly Arg Leu Val Lys Pro Asp Glu Ser
1               5                   10                  15

Leu Thr Leu Thr Cys Thr Ala Ser Gly Phe Ser Leu Ser His Tyr Trp
            20                  25                  30

Met Thr Trp Val Arg Gln Ala Pro Gly Lys Gly Leu Glu Tyr Ile Gly
        35                  40                  45

Phe Ile Asn Val Gly Gly Asp Thr Ser Tyr Ala Ser Trp Ser Lys Gly
    50                  55                  60

Arg Phe Thr Ile Ser Lys Ala Ser Thr Thr Val Asp Leu Lys Ile Ser
65                  70                  75                  80

Ser Leu Thr Thr Glu Asp Thr Ala Thr Tyr Phe Cys Gly Arg Gly Gly
                85                  90                  95

Leu Thr Phe Gly Trp Asp Leu Trp Gly Pro Gly Thr Leu Val Thr Val
            100                 105                 110

Ser Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400
```

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
        435                 440

<210> SEQ ID NO 104
<211> LENGTH: 114
<212> TYPE: PRT
<213> ORGANISM: Artificial Sequence
<220> FEATURE:
<223> OTHER INFORMATION: synthesized

<400> SEQUENCE: 104

Gln Ser Val Glu Glu Ser Gly Gly Arg Leu Val Lys Pro Asp Glu Ser
1               5                   10                  15

Leu Thr Leu Thr Cys Thr Ala Ser Gly Phe Ser Leu Ser His Tyr Trp
            20                  25                  30

Met Thr Trp Val Arg Gln Ala Pro Gly Lys Gly Leu Glu Tyr Ile Gly
        35                  40                  45

Phe Ile Asn Val Gly Gly Asp Thr Ser Tyr Ala Ser Trp Ser Lys Gly
    50                  55                  60

Arg Phe Thr Ile Ser Lys Ala Ser Thr Thr Val Asp Leu Lys Ile Ser
65                  70                  75                  80

Ser Leu Thr Thr Glu Asp Thr Ala Thr Tyr Phe Cys Gly Arg Gly Gly
                85                  90                  95

Leu Thr Phe Gly Trp Asp Leu Trp Gly Pro Gly Thr Leu Val Thr Val
            100                 105                 110

Ser Ser

<210> SEQ ID NO 105
<211> LENGTH: 654
<212> TYPE: DNA
<213> ORGANISM: Artificial Sequence
<220> FEATURE:
<223> OTHER INFORMATION: synthesized

<400> SEQUENCE: 105
gatgttgtga tgacccagac tccagcctcc gtgtctgaac ctgtgggagg cacagtcacc    60
atcaagtgcc aggccagtca gaacattagg acttacttat cctggtatca gcagaaacca   120
gggcagcgtc ccaagctcct gatctatgct gcagccaatc tggcatctgg ggtcccatcg   180
cggttcagtg gcagtagatc tgggacagag ttcactctca ccatcagcga cctggagtgt   240
gccgatgctg ccacttacta ttgtcagtgt acctatcttg gtactgatta tgttggcggt   300
gctttcggcg gaggcaccga ggtggagttc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600 acccatcagg gcctgagctc gcccgtcaca aagagcttca caggggaga gtgt           654

<210> SEQ ID NO 106
<211> LENGTH: 333
<212> TYPE: DNA

<213> ORGANISM: Artificial Sequence
<220> FEATURE:
<223> OTHER INFORMATION: synthesized

<400> SEQUENCE: 106

```
gatgttgtga tgacccagac tccagcctcc gtgtctgaac ctgtgggagg cacagtcacc      60
atcaagtgcc aggccagtca gaacattagg acttacttat cctggtatca gcagaaacca     120
gggcagcgtc ccaagctcct gatctatgct gcagccaatc tggcatctgg ggtcccatcg     180
cggttcagtg gcagtagatc tgggacagag ttcactctca ccatcagcga cctggagtgt     240
gccgatgctg ccacttacta ttgtcagtgt acctatcttg gtactgatta tgttggcggt     300
gctttcggcg gaggcaccga ggtggagttc aaa                                   333
```

<210> SEQ ID NO 107
<211> LENGTH: 218
<212> TYPE: PRT
<213> ORGANISM: Artificial Sequence
<220> FEATURE:
<223> OTHER INFORMATION: synthesized

<400> SEQUENCE: 107

```
Asp Val Val Met Thr Gln Thr Pro Ala Ser Val Ser Glu Pro Val Gly
  1               5                  10                  15

Gly Thr Val Thr Ile Lys Cys Gln Ala Ser Gln Asn Ile Arg Thr Tyr
             20                  25                  30

Leu Ser Trp Tyr Gln Gln Lys Pro Gly Gln Arg Pro Lys Leu Leu Ile
         35                  40                  45

Tyr Ala Ala Ala Asn Leu Ala Ser Gly Val Pro Ser Arg Phe Ser Gly
     50                  55                  60

Ser Arg Ser Gly Thr Glu Phe Thr Leu Thr Ile Ser Asp Leu Glu Cys
 65                  70                  75                  80

Ala Asp Ala Ala Thr Tyr Tyr Cys Gln Cys Thr Tyr Leu Gly Thr Asp
                 85                  90                  95

Tyr Val Gly Gly Ala Phe Gly Gly Thr Glu Val Glu Phe Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 108
<211> LENGTH: 111
<212> TYPE: PRT
<213> ORGANISM: Artificial Sequence
<220> FEATURE:
<223> OTHER INFORMATION: synthesized

<400> SEQUENCE: 108

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Arg Thr Tyr
            20                  25                  30

Leu Ser Trp Tyr Gln Lys Pro Gly Gln Arg Pro Lys Leu Leu Ile
        35                  40                  45

Tyr Ala Ala Asn Leu Ala Ser Gly Val Pro Ser Arg Phe Ser Gly
    50                  55                  60

Ser Arg Ser Gly Thr Glu Phe Thr Leu Thr Ile Ser Asp Leu Glu Cys
65              70                  75                  80

Ala Asp Ala Ala Thr Tyr Tyr Cys Gln Cys Thr Tyr Leu Gly Thr Asp
                85                  90                  95

Tyr Val Gly Gly Ala Phe Gly Gly Gly Thr Glu Val Glu Phe Lys
        100                 105                 110

<210> SEQ ID NO 109
<211> LENGTH: 1329
<212> TYPE: DNA
<213> ORGANISM: Artificial Sequence
<220> FEATURE:
<223> OTHER INFORMATION: synthesized

<400> SEQUENCE: 109
cggtcgctgg aggagtccgg gggtcgcctg gtcacgcctg gacacccct gacactcacc      60 tgcacagcct ctggattcac catcagtagc taccacatgc agtgggtccg ccaggctcca    120
gggaaggggc tggaatacat cggaaccatt agtagtggtg gtaatgtata ctacgcgagc    180
tgggcgagag gccgattcac catctccaga ccctcgtcga ccacggtgga tctgaagatg    240
accagtctga aaccgaggac acggccacc tatttctgtg ccagagactc tggttatagt     300
gatcctatgt ggggcccggg caccctggtc accgtctcga gcgctagcac caagggccca    360
tcggtcttcc ccctggcacc ctcctccaag agcacctctg gggcacagc ggccctgggc     420 tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc agcagcttg gcacccaga cctacatctg caacgtgaat      600
cacaagccca gcaacaccaa ggtggacaag agagttgagc ccaaatcttg tgacaaaact    660
cacacatgcc caccgtgccc agcacctgaa gccgcggggg gaccgtcagt cttcctcttc    720
cccccaaaac ccaaggacac cctcatgatc tcccggaccc ctgaggtcac atgcgtggtg    780
gtggacgtga gccacgaaga ccctgaggtc aagttcaact ggtacgtgga cggcgtggag    840
gtgcataatg ccaagacaaa gccgcgggag gagcagtaca acagcacgta ccgtgtggtc    900
agcgtcctca ccgtcctgca ccaggactgg ctgaatggca aggagtacaa gtgcgcggtc    960
tccaacaaag ccctcccagc ccccatcgag aaaaccatct ccaaagccaa agggcagccc   1020
cgagaaccac aggtgtacac cctgcccca tcccgggatg agctgaccaa gaaccaggtc    1080
agcctgacct gcctggtcaa aggcttctat cccagcgaca tcgccgtgga gtgggagagc    1140
aatgggcagc cggagaacaa ctacaagacc acgcctcccg tgctggactc cgacggctcc    1200
ttcttcctct atagcaagct caccgtggac aagagcaggt ggcagcaggg gaacgtcttc    1260
tcatgctccg tgatgcatga ggctctgcac aaccactaca cgcagaagag cctctccctg    1320
tctccgggt                                                            1329

```
<210> SEQ ID NO 110
<211> LENGTH: 342
<212> TYPE: DNA
<213> ORGANISM: Artificial Sequence
<220> FEATURE:
<223> OTHER INFORMATION: synthesized

<400> SEQUENCE: 110
cggtcgctgg aggagtccgg gggtcgcctg gtcacgcctg ggacacccct gacactcacc    60
tgcacagcct ctggattcac catcagtagc taccacatgc agtgggtccg ccaggctcca   120
gggaaggggc tggaatacat cggaaccatt agtagtggtg gtaatgtata ctacgcgagc   180
tgggcgagag gccgattcac catctccaga ccctcgtcga ccacggtgga tctgaagatg   240
accagtctga aaccgagga cacggccacc tatttctgtg ccagagactc tggttatagt   300
gatcctatgt ggggcccggg caccctggtc accgtctcga gc                      342

<210> SEQ ID NO 111
<211> LENGTH: 443
<212> TYPE: PRT
<213> ORGANISM: Artificial Sequence
<220> FEATURE:
<223> OTHER INFORMATION: synthesized

<400> SEQUENCE: 111

Arg Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Trp Ala Arg Gly
    50                  55                  60

Arg Phe Thr Ile Ser Arg Pro Ser Ser Thr Val Asp Leu Lys Met
65                  70                  75                  80

Thr Ser Leu Thr Thr Glu Asp Thr Ala Thr Tyr Phe Cys Ala Arg Asp
            85                  90                  95

Ser Gly Tyr Ser Asp Pro Met Trp Gly Pro Gly Thr Leu Val Thr Val
        100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
        180                 185                 190

Gln Thr Tyr Ile Cys Asn Val Asn His Lys Pro Ser Asn Thr Lys Val
    195                 200                 205

Asp Lys Arg Val Glu Pro Lys Ser Cys Asp Lys Thr His Thr Cys Pro
210                 215                 220

Pro Cys Pro Ala Pro Glu Ala Ala Gly Ala Pro Ser Val Phe Leu Phe
225                 230                 235                 240

Pro Pro Lys Pro Lys Asp Thr Leu Met Ile Ser Arg Thr Pro Glu Val
            245                 250                 255
```

Thr Cys Val Val Asp Val Ser His Glu Asp Pro Glu Val Lys Phe
            260             265             270

Asn Trp Tyr Val Asp Gly Val Glu Val His Asn Ala Lys Thr Lys Pro
        275             280             285

Arg Glu Glu Gln Tyr Asn Ser Thr Tyr Arg Val Val Ser Val Leu Thr
    290             295             300

Val Leu His Gln Asp Trp Leu Asn Gly Lys Glu Tyr Lys Cys Ala Val
305             310             315             320

Ser Asn Lys Ala Leu Pro Ala Pro Ile Glu Lys Thr Ile Ser Lys Ala
            325             330             335

Lys Gly Gln Pro Arg Glu Pro Gln Val Tyr Thr Leu Pro Pro Ser Arg
        340             345             350

Asp Glu Leu Thr Lys Asn Gln Val Ser Leu Thr Cys Leu Val Lys Gly
    355             360             365

Phe Tyr Pro Ser Asp Ile Ala Val Glu Trp Glu Ser Asn Gly Gln Pro
    370             375             380

Glu Asn Asn Tyr Lys Thr Thr Pro Pro Val Leu Asp Ser Asp Gly Ser
385             390             395             400

Phe Phe Leu Tyr Ser Lys Leu Thr Val Asp Lys Ser Arg Trp Gln Gln
            405             410             415

Gly Asn Val Phe Ser Cys Ser Val Met His Glu Ala Leu His Asn His
        420             425             430

Tyr Thr Gln Lys Ser Leu Ser Leu Ser Pro Gly
            435             440

<210> SEQ ID NO 112
<211> LENGTH: 114
<212> TYPE: PRT
<213> ORGANISM: Artificial Sequence
<220> FEATURE:
<223> OTHER INFORMATION: synthesized

<400> SEQUENCE: 112

Arg Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Trp Ala Arg Gly
    50                  55                  60

Arg Phe Thr Ile Ser Arg Pro Ser Ser Thr Thr Val Asp Leu Lys Met
65                  70                  75                  80

Thr Ser Leu Thr Thr Glu Asp Thr Ala Thr Tyr Phe Cys Ala Arg Asp
            85                  90                  95

Ser Gly Tyr Ser Asp Pro Met Trp Gly Pro Gly Thr Leu Val Thr Val
            100                 105                 110

Ser Ser

<210> SEQ ID NO 113
<211> LENGTH: 654
<212> TYPE: DNA
<213> ORGANISM: Artificial Sequence
<220> FEATURE:
<223> OTHER INFORMATION: synthesized

<400> SEQUENCE: 113

```
gcagccgtgc tgacccagac accatcgccc gtgtctgcag ctgtgggagg cacagtcacc    60
atcagttgcc agtccagtca gagtgtttat agtaacaacc aattatcctg gtttcagcag   120
aaatcagggc agcctcccaa gctcctgatc tatgatgcat ccaatctggc atctggggtc   180
ccatcacggt tcagcggcag tggatctggg acacagttca ctctcaccat cagcagcgtg   240
cagtgtgacg atgctgccac ttaccactgt ctaggcggta gtgatgatga tggtgatatt   300
gctttcggcg gaggcaccga ggtggtgttc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600 acccatcagg gcctgagctc gcccgtcaca aagagcttca caggggaga gtgt            654
```

<210> SEQ ID NO 114
<211> LENGTH: 333
<212> TYPE: DNA
<213> ORGANISM: Artificial Sequence
<220> FEATURE:
<223> OTHER INFORMATION: synthesized

<400> SEQUENCE: 114

```
gcagccgtgc tgacccagac accatcgccc gtgtctgcag ctgtgggagg cacagtcacc    60
atcagttgcc agtccagtca gagtgtttat agtaacaacc aattatcctg gtttcagcag   120
aaatcagggc agcctcccaa gctcctgatc tatgatgcat ccaatctggc atctggggtc   180
ccatcacggt tcagcggcag tggatctggg acacagttca ctctcaccat cagcagcgtg   240
cagtgtgacg atgctgccac ttaccactgt ctaggcggta gtgatgatga tggtgatatt   300
gctttcggcg gaggcaccga ggtggtgttc aaa                                 333
```

<210> SEQ ID NO 115
<211> LENGTH: 218
<212> TYPE: PRT
<213> ORGANISM: Artificial Sequence
<220> FEATURE:
<223> OTHER INFORMATION: synthesized

<400> SEQUENCE: 115

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Ser Asn
            20                  25                  30

Asn Gln Leu Ser Trp Phe Gln Gln Lys Ser Gly Gln Pro Pro Lys Leu
        35                  40                  45

Leu Ile Tyr Asp Ala Ser Asn Leu Ala Ser Gly Val Pro Ser Arg Phe
    50                  55                  60

Ser Gly Ser Gly Ser Gly Thr Gln Phe Thr Leu Thr Ile Ser Ser Val
65                  70                  75                  80

Gln Cys Asp Asp Ala Ala Thr Tyr His Cys Leu Gly Gly Ser Asp Asp
                85                  90                  95

Asp Gly Asp Ile Ala Phe Gly Gly Gly Thr Glu Val Val Phe Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 116
<211> LENGTH: 111
<212> TYPE: PRT
<213> ORGANISM: Artificial Sequence
<220> FEATURE:
<223> OTHER INFORMATION: synthesized

<400> SEQUENCE: 116

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Ser Asn
            20                  25                  30

Asn Gln Leu Ser Trp Phe Gln Gln Lys Ser Gly Gln Pro Pro Lys Leu
        35                  40                  45

Leu Ile Tyr Asp Ala Ser Asn Leu Ala Ser Gly Val Pro Ser Arg Phe
    50                  55                  60

Ser Gly Ser Gly Ser Gly Thr Gln Phe Thr Leu Thr Ile Ser Ser Val
65                  70                  75                  80

Gln Cys Asp Asp Ala Ala Thr Tyr His Cys Leu Gly Gly Ser Asp Asp
                85                  90                  95

Asp Gly Asp Ile Ala Phe Gly Gly Gly Thr Glu Val Val Phe Lys
            100                 105                 110

<210> SEQ ID NO 117
<211> LENGTH: 1323
<212> TYPE: DNA
<213> ORGANISM: Artificial Sequence
<220> FEATURE:
<223> OTHER INFORMATION: synthesized

<400> SEQUENCE: 117
cagtcactgg aggagtccgg gggtcgcctg gtcacgcctg ggacacccct gacactcacc      60
tgcacagcct ctggattctc cctcagtagc tactacatga gctgggtccg ccaggctcca     120
gggaagggac tggaatggat cggaagtatt tatggtagtg gtgccgcata ctacgcgagc     180
tgggcgaaag gccgattcac catctccaga acgtcgacca cggtggatct gaaaatgacc     240
agtctgacag ccgcggacac ggccacctat ttctgtgcca gagatcctat taacaatgcc     300
atgtggggcc aggcaccct ggtcaccgtc tcgagcgcta gcaccaaggg cccatcggtc     360
ttccccctgg cacctcctc caagagcacc tctggggca gcggccct gggctgcctg        420 gtcaaggact acttccccga accggtgacg gtgtcgtgga actcaggcgc cctgaccagc     480
ggcgtgcaca ccttcccggc tgtcctacag tcctcaggac tctactccct cagcagcgtg     540
gtgaccgtgc cctccagcag cttgggcacc cagacctaca tctgcaacgt gaatcacaag     600
cccagcaaca ccaaggtgga caagagagtt gagcccaaat cttgtgacaa aactcacaca     660

```
tgcccaccgt gcccagcacc tgaagccgcg ggggcaccgt cagtcttcct cttcccccca    720
aaacccaagg acaccctcat gatctcccgg acccctgagg tcacatgcgt ggtggtggac    780
gtgagccacg aagaccctga ggtcaagttc aactggtacg tggacggcgt ggaggtgcat    840
aatgccaaga caaagccgcg ggaggagcag tacaacagca cgtaccgtgt ggtcagcgtc    900
ctcaccgtcc tgcaccagga ctggctgaat ggcaaggagt acaagtgcgc ggtctccaac    960
aaagccctcc cagcccccat cgagaaaacc atctccaaag ccaagggcag ccccgagaa    1020 ccacaggtgt acaccctgcc cccatcccgg gatgagctga ccaagaacca ggtcagcctg    1080
acctgcctgg tcaaaggctt ctatcccagc gacatcgccg tggagtggga gagcaatggg    1140
cagccggaga acaactacaa gaccacgcct cccgtgctgg actccgacgg ctccttcttc    1200
ctctatagca agctcaccgt ggacaagagc aggtggcagc aggggaacgt cttctcatgc    1260
tccgtgatgc atgaggctct gcacaaccac tacacgcaga gagcctctc cctgtctccg    1320 ggt    1323
```

<210> SEQ ID NO 118
<211> LENGTH: 336
<212> TYPE: DNA
<213> ORGANISM: Artificial Sequence
<220> FEATURE:
<223> OTHER INFORMATION: synthesized

<400> SEQUENCE: 118

```
cagtcactgg aggagtccgg gggtcgcctg gtcacgcctg ggacacccct gacactcacc     60
tgcacagcct ctggattctc cctcagtagc tactacatga gctgggtccg ccaggctcca    120
gggaagggac tggaatggat cggaagtatt tatggtagtg gtgccgcata ctacgcgagc    180
tgggcgaaag gccgattcac catctccaga acgtcgacca cggtggatct gaaaatgacc    240
agtctgacag ccgcggacac ggccacctat ttctgtgcca gagatcctat taacaatgcc    300
atgtggggcc aggcacccct ggtcaccgtc tcgagc                              336
```

<210> SEQ ID NO 119
<211> LENGTH: 441
<212> TYPE: PRT
<213> ORGANISM: Artificial Sequence
<220> FEATURE:
<223> OTHER INFORMATION: synthesized

<400> SEQUENCE: 119

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Ser Ile Tyr Gly Ser Gly Ala Ala Tyr Tyr Ala Ser Trp Ala Lys Gly
    50                  55                  60

Arg Phe Thr Ile Ser Arg Thr Ser Thr Val Asp Leu Lys Met Thr
65                  70                  75                  80

Ser Leu Thr Ala Ala Asp Thr Ala Thr Tyr Phe Cys Ala Arg Asp Pro
            85                  90                  95

Ile Asn Asn Ala Met Trp Gly Pro Gly Thr Leu Val Thr Val Ser Ser
        100                 105                 110

Ala Ser Thr Lys Gly Pro Ser Val Phe Pro Leu Ala Pro Ser Ser Lys
```

```
            115                 120                 125
Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
    210                 215                 220

Pro Ala Pro Glu Ala Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Ala Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 120
<211> LENGTH: 112
<212> TYPE: PRT
<213> ORGANISM: Artificial Sequence
<220> FEATURE:
<223> OTHER INFORMATION: synthesized

<400> SEQUENCE: 120

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Ser Trp Val Arg Gln Ala Pro Gly Lys Gly Leu Glu Trp Ile Gly
```

```
            35                  40                  45
Ser Ile Tyr Gly Ser Gly Ala Ala Tyr Tyr Ala Ser Trp Ala Lys Gly
        50                  55                  60

Arg Phe Thr Ile Ser Arg Thr Ser Thr Thr Val Asp Leu Lys Met Thr
65                  70                  75                  80

Ser Leu Thr Ala Ala Asp Thr Ala Thr Tyr Phe Cys Ala Arg Asp Pro
                85                  90                  95

Ile Asn Asn Ala Met Trp Gly Pro Gly Thr Leu Val Thr Val Ser Ser
            100                 105                 110

<210> SEQ ID NO 121
<211> LENGTH: 657
<212> TYPE: DNA
<213> ORGANISM: Artificial Sequence
<220> FEATURE:
<223> OTHER INFORMATION: synthesized

<400> SEQUENCE: 121
gcccttgtga tgacccagac tccagcctcc gtgtctgcag ctgtgggagg cacagtcacc      60
atcaattgcc aggccagtga ggacattgat aactatttag cctggtatca gcagaaacca     120
gggcagcctc ccaagctcct gatcttttat gcatccgatc tggcatctgg ggtcccatcg     180
cggttctcag gcagtggatc tgggacacag ttcactctca ccatcagcgg tgtgcagtgt     240
gacgatgctg ccacttacta ctgtcaaggc ggttactata ctagtagtac tgatacgagg     300
ggtgctttcg gcggaggcac cgaggtggtg gtcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

<210> SEQ ID NO 122
<211> LENGTH: 336
<212> TYPE: DNA
<213> ORGANISM: Artificial Sequence
<220> FEATURE:
<223> OTHER INFORMATION: synthesized

<400> SEQUENCE: 122
gcccttgtga tgacccagac tccagcctcc gtgtctgcag ctgtgggagg cacagtcacc      60
atcaattgcc aggccagtga ggacattgat aactatttag cctggtatca gcagaaacca     120
gggcagcctc ccaagctcct gatcttttat gcatccgatc tggcatctgg ggtcccatcg     180
cggttctcag gcagtggatc tgggacacag ttcactctca ccatcagcgg tgtgcagtgt     240
gacgatgctg ccacttacta ctgtcaaggc ggttactata ctagtagtac tgatacgagg     300
ggtgctttcg gcggaggcac cgaggtggtg gtcaaa                               336

<210> SEQ ID NO 123
<211> LENGTH: 219
<212> TYPE: PRT
<213> ORGANISM: Artificial Sequence
<220> FEATURE:
<223> OTHER INFORMATION: synthesized

<400> SEQUENCE: 123

Ala Leu Val Met Thr Gln Thr Pro Ala Ser Val Ser Ala Ala Val Gly
```

```
            1               5                  10                 15
Gly Thr Val Thr Ile Asn Cys Gln Ala Ser Glu Asp Ile Asp Asn Tyr
                20                  25                 30

Leu Ala Trp Tyr Gln Gln Lys Pro Gly Gln Pro Lys Leu Leu Ile
            35                  40                 45

Phe Tyr Ala Ser Asp Leu Ala Ser Gly Val Pro Ser Arg Phe Ser Gly
        50                  55                 60

Ser Gly Ser Gly Thr Gln Phe Thr Leu Thr Ile Ser Gly Val Gln Cys
65                  70                 75                  80

Asp Asp Ala Ala Thr Tyr Tyr Cys Gln Gly Gly Tyr Tyr Thr Ser Ser
                85                 90                  95

Thr Asp Thr Arg Gly Ala Phe Gly Gly Gly Thr Glu Val Val Val Lys
                100                105                110

Arg Thr Val Ala Ala Pro Ser Val Phe Ile Phe Pro Pro Ser Asp Glu
                115                120                125

Gln Leu Lys Ser Gly Thr Ala Ser Val Val Cys Leu Leu Asn Asn Phe
        130                 135                140

Tyr Pro Arg Glu Ala Lys Val Gln Trp Lys Val Asp Asn Ala Leu Gln
145                 150                 155                160

Ser Gly Asn Ser Gln Glu Ser Val Thr Glu Gln Asp Ser Lys Asp Ser
                165                 170                175

Thr Tyr Ser Leu Ser Ser Thr Leu Thr Leu Ser Lys Ala Asp Tyr Glu
                180                 185                190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 124
<211> LENGTH: 112
<212> TYPE: PRT
<213> ORGANISM: Artificial Sequence
<220> FEATURE:
<223> OTHER INFORMATION: synthesized

<400> SEQUENCE: 124

Ala Leu Val Met Thr Gln Thr Pro Ala Ser Val Ser Ala Ala Val Gly
1               5                  10                 15

Gly Thr Val Thr Ile Asn Cys Gln Ala Ser Glu Asp Ile Asp Asn Tyr
                20                  25                 30

Leu Ala Trp Tyr Gln Gln Lys Pro Gly Gln Pro Pro Lys Leu Leu Ile
            35                  40                 45

Phe Tyr Ala Ser Asp Leu Ala Ser Gly Val Pro Ser Arg Phe Ser Gly
        50                  55                 60

Ser Gly Ser Gly Thr Gln Phe Thr Leu Thr Ile Ser Gly Val Gln Cys
65                  70                 75                  80

Asp Asp Ala Ala Thr Tyr Tyr Cys Gln Gly Gly Tyr Tyr Thr Ser Ser
                85                 90                  95

Thr Asp Thr Arg Gly Ala Phe Gly Gly Gly Thr Glu Val Val Val Lys
                100                105                110

<210> SEQ ID NO 125
<211> LENGTH: 1344
<212> TYPE: DNA
<213> ORGANISM: Artificial Sequence
<220> FEATURE:
<223> OTHER INFORMATION: synthesized
```

<400> SEQUENCE: 125

```
cagtcattgg aggaggccgg gggagacctg gtcaagcctg gggcatccct gacactcacc      60
tgcacagcct ctggcttctc cttcactagc agctactaca tgtgctgggt ccgccaggct     120
ccagggaagg ggctggagtg gatcgcatgc atttatactg gtagtagtgg tagcacttac     180
tacgcgaact gggcgaaagg ccgattcacc atctccaaaa cctcgtcgac cacggtgact     240
ctgcaaatga ccagtctgac agccgcggac acggccacct atttctgtgc gagagatagt     300
agtagttatt atatgtttaa cttgtggggc cagggcaccc tcgtcaccgt ctcgagcgct     360
agcaccaagg gcccatcggt cttccccctg gcacctcct ccaagagcac ctctgggggc      420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagccgc ggggggcaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgcg cggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggt                                          1344
```

<210> SEQ ID NO 126
<211> LENGTH: 357
<212> TYPE: DNA
<213> ORGANISM: Artificial Sequence
<220> FEATURE:
<223> OTHER INFORMATION: synthesized

<400> SEQUENCE: 126

```
cagtcattgg aggaggccgg gggagacctg gtcaagcctg gggcatccct gacactcacc      60
tgcacagcct ctggcttctc cttcactagc agctactaca tgtgctgggt ccgccaggct     120
ccagggaagg ggctggagtg gatcgcatgc atttatactg gtagtagtgg tagcacttac     180
tacgcgaact gggcgaaagg ccgattcacc atctccaaaa cctcgtcgac cacggtgact     240
ctgcaaatga ccagtctgac agccgcggac acggccacct atttctgtgc gagagatagt     300
agtagttatt atatgtttaa cttgtggggc cagggcaccc tcgtcaccgt ctcgagc        357
```

<210> SEQ ID NO 127
<211> LENGTH: 448
<212> TYPE: PRT
<213> ORGANISM: Artificial Sequence
<220> FEATURE:
<223> OTHER INFORMATION: synthesized

```
<400> SEQUENCE: 127

Gln Ser Leu Glu Glu Ala Gly Gly Asp Leu Val Lys Pro Gly Ala Ser
1               5                   10                  15

Leu Thr Leu Thr Cys Thr Ala Ser Gly Phe Ser Phe Thr Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Ser Ser Gly Ser Thr Tyr Tyr Ala Asn Trp
50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ser Ser Tyr Tyr Met Phe Asn Leu Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 128
<211> LENGTH: 119
<212> TYPE: PRT
<213> ORGANISM: Artificial Sequence
<220> FEATURE:
<223> OTHER INFORMATION: synthesized

<400> SEQUENCE: 128

Gln Ser Leu Glu Glu Ala Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Ser Ser Gly Ser Thr Tyr Tyr Ala Asn Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ser Ser Ser Tyr Tyr Met Phe Asn Leu Trp Gly Gln Gly
            100                 105                 110

Thr Leu Val Thr Val Ser Ser
        115

<210> SEQ ID NO 129
<211> LENGTH: 654
<212> TYPE: DNA
<213> ORGANISM: Artificial Sequence
<220> FEATURE:
<223> OTHER INFORMATION: synthesized

<400> SEQUENCE: 129
gcagccgtgc tgacccagac tccatcttcc acgtctgcag ctgtgggagg cacagtcacc      60
atcagttgcc agtccagtca gagtgtttat aataacaatg ctttagcctg gtatcagaaa     120
aaaccaggac agcctcccaa gctcctgatc tatttggctt ccactctggc atctggggtc     180
ccatcgcggt tcagcggcag tggatctggg acacagttca ctctcaccat cagcgacctg     240
gagtgtgacg atgctgccac ttattattgt ctaggtgttt ataatgatga tgttgataat     300
ggtttcggcg gaggcaccga ggtggtgttc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540 agcacccctga cgctgagcaa agcagactac gagaaacaca agtctacgc ctgcgaagtc     600 acccatcagg gcctgagctc gcccgtcaca aagagcttca caggggagag tgt            654

<210> SEQ ID NO 130
<211> LENGTH: 333
<212> TYPE: DNA
<213> ORGANISM: Artificial Sequence
<220> FEATURE:

<223> OTHER INFORMATION: synthesized

<400> SEQUENCE: 130

```
gcagccgtgc tgacccagac tccatcttcc acgtctgcag ctgtgggagg cacagtcacc    60
atcagttgcc agtccagtca gagtgtttat aataacaatg ctttagcctg gtatcagaaa   120
aaaccaggac agcctcccaa gctcctgatc tatttggctt ccactctggc atctggggtc   180
ccatcgcggt tcagcggcag tggatctggg acacagttca ctctcaccat cagcgacctg   240
gagtgtgacg atgctgccac ttattattgt ctaggtgttt ataatgatga tgttgataat   300
ggtttcggcg gaggcaccga ggtggtgttc aaa                                333
```

<210> SEQ ID NO 131
<211> LENGTH: 218
<212> TYPE: PRT
<213> ORGANISM: Artificial Sequence
<220> FEATURE:
<223> OTHER INFORMATION: synthesized

<400> SEQUENCE: 131

```
Ala Ala Val Leu Thr Gln Thr Pro Ser Ser Thr Ser Ala Ala Val Gly
1               5                   10                  15
Gly Thr Val Thr Ile Ser Cys Gln Ser Ser Gln Ser Val Tyr Asn Asn
            20                  25                  30
Asn Ala Leu Ala Trp Tyr Gln Lys Pro Gly Gln Pro Pro Lys Leu
        35                  40                  45
Leu Ile Tyr Leu Ala Ser Thr Leu Ala Ser Gly Val Pro Ser Arg Phe
    50                  55                  60
Ser Gly Ser Gly Ser Gly Thr Gln Phe Thr Leu Thr Ile Ser Asp Leu
65                  70                  75                  80
Glu Cys Asp Asp Ala Ala Thr Tyr Tyr Cys Leu Gly Val Tyr Asn Asp
                85                  90                  95
Asp Val Asp Asn Gly Phe Gly Gly Gly Thr Glu Val Val Phe Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 132
<211> LENGTH: 111
<212> TYPE: PRT
<213> ORGANISM: Artificial Sequence
<220> FEATURE:
<223> OTHER INFORMATION: synthesized

<400> SEQUENCE: 132

```
Ala Ala Val Leu Thr Gln Thr Pro Ser Ser Thr Ser Ala Ala Val Gly
```

```
                1               5                  10                   15
              Gly Thr Val Thr Ile Ser Cys Gln Ser Ser Gln Ser Val Tyr Asn Asn
                             20                  25                  30

Asn Ala Leu Ala Trp Tyr Gln Lys Lys Pro Gly Gln Pro Pro Lys Leu
                         35                  40                  45

Leu Ile Tyr Leu Ala Ser Thr Leu Ala Ser Gly Val Pro Ser Arg Phe
                     50                  55                  60

Ser Gly Ser Gly Ser Gly Thr Gln Phe Thr Leu Thr Ile Ser Asp Leu
              65                  70                  75                  80

Glu Cys Asp Asp Ala Ala Thr Tyr Tyr Cys Leu Gly Val Tyr Asn Asp
                                 85                  90                  95

Asp Val Asp Asn Gly Phe Gly Gly Gly Thr Glu Val Val Phe Lys
                             100                 105                 110
```

<210> SEQ ID NO 133
<211> LENGTH: 1332
<212> TYPE: DNA
<213> ORGANISM: Artificial Sequence
<220> FEATURE:
<223> OTHER INFORMATION: synthesized

<400> SEQUENCE: 133

```
cagtcgctgg aggagtccgg gggtcgcctg gtcacgcctg gaggatccct gacactcacc      60
tgcaccgtct ctggattctc cctcaataac aatgcaataa gctgggtccg ccaggctcca     120
gggaaggggc tggaatgggt tgcaatcata caaaatactg gtaccacaga ctacgcgagg     180
tgggcgaaag gccgattcac catctccaaa acctcgacca cggtggattt gaaaatcaac     240
agtccgacaa ccgaggacac ggccacctat ttctgtggca gagggtatgg ttttgagtcg     300
gagcttgtca tctggggccc gggcaccctg gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggcaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagccctccc agcccccatc gagaaaacca tctccaaagc caagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                        1332
```

<210> SEQ ID NO 134
<211> LENGTH: 345

<212> TYPE: DNA
<213> ORGANISM: Artificial Sequence
<220> FEATURE:
<223> OTHER INFORMATION: synthesized

<400> SEQUENCE: 134

```
cagtcgctgg aggagtccgg gggtcgcctg gtcacgcctg gaggatccct gacactcacc    60
tgcaccgtct ctggattctc cctcaataac aatgcaataa gctgggtccg ccaggctcca   120
gggaaggggc tggaatgggt tgcaatcata caaaatactg gtaccacaga ctacgcgagg   180
tgggcgaaag gccgattcac catctccaaa acctcgacca cggtggattt gaaaatcaac   240
agtccgacaa ccgaggacac ggccacctat ttctgtggca gagggtatgg ttttgagtcg   300
gagcttgtca tctggggccc gggcaccctg gtcaccgtct cgagc                   345
```

<210> SEQ ID NO 135
<211> LENGTH: 444
<212> TYPE: PRT
<213> ORGANISM: Artificial Sequence
<220> FEATURE:
<223> OTHER INFORMATION: synthesized

<400> SEQUENCE: 135

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Asn Asn Asn Ala
            20                  25                  30

Ile Ser Trp Val Arg Gln Ala Pro Gly Lys Gly Leu Glu Trp Val Ala
        35                  40                  45

Ile Ile Gln Asn Thr Gly Thr Thr Asp Tyr Ala Arg Trp Ala Lys Gly
    50                  55                  60

Arg Phe Thr Ile Ser Lys Thr Ser Thr Val Asp Leu Lys Ile Asn
65                  70                  75                  80

Ser Pro Thr Thr Glu Asp Thr Ala Thr Tyr Phe Cys Gly Arg Gly Tyr
                85                  90                  95

Gly Phe Glu Ser Glu Leu Val Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 136
<211> LENGTH: 115
<212> TYPE: PRT
<213> ORGANISM: Artificial Sequence
<220> FEATURE:
<223> OTHER INFORMATION: synthesized

<400> SEQUENCE: 136

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Asn Asn Asn Ala
            20                  25                  30

Ile Ser Trp Val Arg Gln Ala Pro Gly Lys Gly Leu Glu Trp Val Ala
        35                  40                  45

Ile Ile Gln Asn Thr Gly Thr Thr Asp Tyr Ala Arg Trp Ala Lys Gly
    50                  55                  60

Arg Phe Thr Ile Ser Lys Thr Ser Thr Val Asp Leu Lys Ile Asn
65                  70                  75                  80

Ser Pro Thr Thr Glu Asp Thr Ala Thr Tyr Phe Cys Gly Arg Gly Tyr
                85                  90                  95

Gly Phe Glu Ser Glu Leu Val Ile Trp Gly Pro Gly Thr Leu Val Thr
            100                 105                 110

Val Ser Ser
        115

<210> SEQ ID NO 137
<211> LENGTH: 657
<212> TYPE: DNA
<213> ORGANISM: Artificial Sequence
<220> FEATURE:
<223> OTHER INFORMATION: synthesized

<400> SEQUENCE: 137
gacgttgtga tgacccagtc tccatcttcc gtgtctgcat ctgtaggaga cagagtcacc        60

```
atcacctgtc aggccagtca gagcattggt gctgatttag cctggtatca gcagaaacca    120
gggaaagccc ctaagctcct gatctatagg gcatccactc tggcctctgg ggtcccatca    180
aggttcagcg gcagtggatc tgggacagat ttcactctca ccatcagcag cctgcagcct    240
gaagattttg caacttacta ttgtcaagct atttattatg gtactgatga tgtcatatac    300
catactttcg gcggagggac caaggtggag atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 138
<211> LENGTH: 336
<212> TYPE: DNA
<213> ORGANISM: Artificial Sequence
<220> FEATURE:
<223> OTHER INFORMATION: synthesized

<400> SEQUENCE: 138

```
gacgttgtga tgacccagtc tccatcttcc gtgtctgcat ctgtaggaga cagagtcacc     60
atcacctgtc aggccagtca gagcattggt gctgatttag cctggtatca gcagaaacca    120
gggaaagccc ctaagctcct gatctatagg gcatccactc tggcctctgg ggtcccatca    180
aggttcagcg gcagtggatc tgggacagat ttcactctca ccatcagcag cctgcagcct    240
gaagattttg caacttacta ttgtcaagct atttattatg gtactgatga tgtcatatac    300
catactttcg gcggagggac caaggtggag atcaaa                              336
```

<210> SEQ ID NO 139
<211> LENGTH: 219
<212> TYPE: PRT
<213> ORGANISM: Artificial Sequence
<220> FEATURE:
<223> OTHER INFORMATION: synthesized

<400> SEQUENCE: 139

```
Asp Val Val Met Thr Gln Ser Pro Ser Ser Val Ser Ala Ser Val Gly
1               5                   10                  15

Asp Arg Val Thr Ile Thr Cys Gln Ala Ser Gln Ser Ile Gly Ala Asp
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ile Tyr Tyr Gly Thr Asp
                85                  90                  95

Asp Val Ile Tyr His Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 140
<211> LENGTH: 112
<212> TYPE: PRT
<213> ORGANISM: Artificial Sequence
<220> FEATURE:
<223> OTHER INFORMATION: synthesized

<400> SEQUENCE: 140

Asp Val Val Met Thr Gln Ser Pro Ser Ser Val Ser Ala Ser Val Gly
1               5                   10                  15

Asp Arg Val Thr Ile Thr Cys Gln Ala Ser Gln Ser Ile Gly Ala Asp
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ile Tyr Tyr Gly Thr Asp
                85                  90                  95

Asp Val Ile Tyr His Thr Phe Gly Gly Gly Thr Lys Val Glu Ile Lys
            100                 105                 110

<210> SEQ ID NO 141
<211> LENGTH: 1341
<212> TYPE: DNA
<213> ORGANISM: Artificial Sequence
<220> FEATURE:
<223> OTHER INFORMATION: synthesized

<400> SEQUENCE: 141
gaggtgcagc tggtggagtc tgggggaggc ttggtccagc ctggggggtc cctgagactc      60
tcctgtgcag cctctggatt caccatcagt agccaccaca tgatctgggt ccgccaggct     120
ccagggaagg gctgcaata catcggattc attaatgatg gtgactatac atactacacg      180
aactccgcaa aggcagatt caccatctcc agagacaatt ccaagaacac gctgtatctt      240
caaatgaaca gcctgagagc cgaggacacg gctgtgtatt actgtgcgag aggggttgat      300
ggtactagtt atcctggctt gtggggccag ggaaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca gagagttga gcccaaatct      660

```
tgtgacaaaa ctcacacatg cccaccgtgc ccagcacctg aagccgcggg ggcaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcgcgg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg t                                             1341
```

<210> SEQ ID NO 142
<211> LENGTH: 354
<212> TYPE: DNA
<213> ORGANISM: Artificial Sequence
<220> FEATURE:
<223> OTHER INFORMATION: synthesized

<400> SEQUENCE: 142

```
gaggtgcagc tggtggagtc tgggggaggc ttggtccagc ctggggggtc cctgagactc     60
tcctgtgcag cctctggatt caccatcagt agccaccaca tgatctgggt ccgccaggct    120
ccagggaagg ggctgcaata catcggattc attaatgatg gtgactatac atactacacg    180
aactccgcaa aaggcagatt caccatctcc agagacaatt ccaagaacac gctgtatctt    240
caaatgaaca gcctgagagc cgaggacacg gctgtgtatt actgtgcgag agggggttgat    300 ggtactagtt atcctggctt gtggggccag ggaaccctgg tcaccgtctc gagc          354
```

<210> SEQ ID NO 143
<211> LENGTH: 447
<212> TYPE: PRT
<213> ORGANISM: Artificial Sequence
<220> FEATURE:
<223> OTHER INFORMATION: synthesized

<400> SEQUENCE: 143

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser His
            20                  25                  30

His Met Ile Trp Val Arg Gln Ala Pro Gly Lys Gly Leu Gln Tyr Ile
        35                  40                  45

Gly Phe Ile Asn Asp Gly Asp Tyr Thr Tyr Thr Asn Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Val Asp Gly Thr Ser Tyr Pro Gly Leu Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 144
<211> LENGTH: 118
<212> TYPE: PRT
<213> ORGANISM: Artificial Sequence
<220> FEATURE:
<223> OTHER INFORMATION: synthesized

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser His
            20                  25                  30

His Met Ile Trp Val Arg Gln Ala Pro Gly Lys Gly Leu Gln Tyr Ile
        35                  40                  45

-continued

```
Gly Phe Ile Asn Asp Gly Asp Tyr Thr Tyr Tyr Thr Asn Ser Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Val Asp Gly Thr Ser Tyr Pro Gly Leu Trp Gly Gln Gly Thr
            100                 105                 110

Leu Val Thr Val Ser Ser
        115
```

<210> SEQ ID NO 145
<211> LENGTH: 657
<212> TYPE: DNA
<213> ORGANISM: Artificial Sequence
<220> FEATURE:
<223> OTHER INFORMATION: synthesized

<400> SEQUENCE: 145

```
gacatccaga tgacccagtc tccatcctcc ctgtctgcat ctgtaggaga cagagtcacc    60
atcacttgcc aggccagtca gagcatttac agcaatttag cctggtatca gcagaaacca   120
gggaaagttc ctaagctcct gatctattct acatccactc tggcatctgg ggtcccatct   180
cggttcagtg gcagtggatc tgggacagat ttcactctca ccatcagcag cctgcagcct   240
gaagatgttg caacttatta ctgtcaaaac tattatggta gtagtactga tagttatggg   300
aatcctttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 146
<211> LENGTH: 336
<212> TYPE: DNA
<213> ORGANISM: Artificial Sequence
<220> FEATURE:
<223> OTHER INFORMATION: synthesized

<400> SEQUENCE: 146

```
gacatccaga tgacccagtc tccatcctcc ctgtctgcat ctgtaggaga cagagtcacc    60
atcacttgcc aggccagtca gagcatttac agcaatttag cctggtatca gcagaaacca   120
gggaaagttc ctaagctcct gatctattct acatccactc tggcatctgg ggtcccatct   180
cggttcagtg gcagtggatc tgggacagat ttcactctca ccatcagcag cctgcagcct   240
gaagatgttg caacttatta ctgtcaaaac tattatggta gtagtactga tagttatggg   300
aatcctttcg gcggagggac caaggtggag atcaaa                              336
```

<210> SEQ ID NO 147
<211> LENGTH: 219
<212> TYPE: PRT
<213> ORGANISM: Artificial Sequence
<220> FEATURE:
<223> OTHER INFORMATION: synthesized

<400> SEQUENCE: 147

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Val Pro Lys Leu Leu Ile
        35                  40                  45

Tyr Ser Thr Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Tyr Gly Ser Ser Thr
                85                  90                  95

Asp Ser Tyr Gly Asn Pro Phe Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 148
<211> LENGTH: 112
<212> TYPE: PRT
<213> ORGANISM: Artificial Sequence
<220> FEATURE:
<223> OTHER INFORMATION: synthesized

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Val Pro Lys Leu Leu Ile
        35                  40                  45

Tyr Ser Thr Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Tyr Gly Ser Ser Thr
                85                  90                  95

Asp Ser Tyr Gly Asn Pro Phe Gly Gly Thr Lys Val Glu Ile Lys
            100                 105                 110

<210> SEQ ID NO 149
<211> LENGTH: 1350
<212> TYPE: DNA
<213> ORGANISM: Artificial Sequence
```

<220> FEATURE:
<223> OTHER INFORMATION: synthesized

<400> SEQUENCE: 149

```
gaggtgcagc tggtggagtc tgggggaggc ttggtccagc ctgggggtc cctgagactc      60
tcctgtgcag cctctggaat cgacttcagt agcaactaca tgtgctgggt ccgccaggct    120
ccagggaagg ggctggagtg gatcgcatgc atttatggtg atagtagtga taatagttac    180
tccgcgagct ccgctaaagg cagattcacc atctccagag acaattccaa gaacacgctg    240
tatcttcaaa tgaacagcct gagagccgag gacacggctg tgtattactg tgcgagatct    300
ggttatagct atttaggcta ctttaacttg tggggccagg gaaccctggt caccgtctcg    360
agcgctagca ccaagggccc atcggtcttc cccctggcac cctcctccaa gagcacctct    420
gggggcacag cggccctggg ctgcctggtc aaggactact ccccgaacc ggtgacggtg     480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga gccgcgggg    720
gcaccgtcag tcttcctctt ccccccaaaa cccaaggaca cctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcgcggt ctccaacaaa gccctcccag ccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tatagcaagc tcaccgtgga caagagcagg   1260
tggcagcagg ggaacgtctt ctcatgctcc gtgatgcatg aggctctgca caaccactac   1320
acgcagaaga gcctctccct gtctccgggt                                    1350
```

<210> SEQ ID NO 150
<211> LENGTH: 363
<212> TYPE: DNA
<213> ORGANISM: Artificial Sequence
<220> FEATURE:
<223> OTHER INFORMATION: synthesized

<400> SEQUENCE: 150

```
gaggtgcagc tggtggagtc tgggggaggc ttggtccagc ctgggggtc cctgagactc      60
tcctgtgcag cctctggaat cgacttcagt agcaactaca tgtgctgggt ccgccaggct    120
ccagggaagg ggctggagtg gatcgcatgc atttatggtg atagtagtga taatagttac    180
tccgcgagct ccgctaaagg cagattcacc atctccagag acaattccaa gaacacgctg    240
tatcttcaaa tgaacagcct gagagccgag gacacggctg tgtattactg tgcgagatct    300
ggttatagct atttaggcta ctttaacttg tggggccagg gaaccctggt caccgtctcg    360
agc                                                                  363
```

<210> SEQ ID NO 151
<211> LENGTH: 450
<212> TYPE: PRT

<213> ORGANISM: Artificial Sequence
<220> FEATURE:
<223> OTHER INFORMATION: synthesized

<400> SEQUENCE: 151

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Ile | Asp | Phe | Ser | Ser | Asn |
| | | | 20 | | | | | 25 | | | | | 30 | | |
| Tyr | Met | Cys | Trp | Val | Arg | Gln | Ala | Pro | Gly | Lys | Gly | Leu | Glu | Trp | Ile |
| | | 35 | | | | | 40 | | | | | 45 | | | |
| Ala | Cys | Ile | Tyr | Gly | Asp | Ser | Ser | Asp | Asn | Ser | Tyr | Ser | Ala | Ser | Ser |
| | 50 | | | | | 55 | | | | | 60 | | | | |
| Ala | Lys | Gly | Arg | Phe | Thr | Ile | Ser | Arg | Asp | Asn | Ser | Lys | Asn | Thr | Leu |
| 65 | | | | | 70 | | | | | 75 | | | | | 80 |
| Tyr | Leu | Gln | Met | Asn | Ser | Leu | Arg | Ala | Glu | Asp | Thr | Ala | Val | Tyr | Tyr |
| | | | | 85 | | | | | 90 | | | | | 95 | |
| Cys | Ala | Arg | Ser | Gly | Tyr | Ser | Tyr | Leu | Gly | Tyr | Phe | Asn | Leu | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | 195 | | | | | 200 | | | | | 205 | | | |
| Lys | Pro | Ser | Asn | Thr | Lys | Val | Asp | Lys | Arg | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Ala | Ala | Gly |
| 225 | | | | | 230 | | | | | 235 | | | | | 240 |
| Ala | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Ala | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Asp | Glu | Leu | Thr | Lys | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | 370 | | | | | 375 | | | | | 380 | | | | |
| Trp | Glu | Ser | Asn | Gly | Gln | Pro | Glu | Asn | Asn | Tyr | Lys | Thr | Thr | Pro | Pro |

```
                385                 390                 395                 400
Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 152
<211> LENGTH: 121
<212> TYPE: PRT
<213> ORGANISM: Artificial Sequence
<220> FEATURE:
<223> OTHER INFORMATION: synthesized

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Ser Asn
            20                  25                  30

Tyr Met Cys Trp Val Arg Gln Ala Pro Gly Lys Gly Leu Glu Trp Ile
        35                  40                  45

Ala Cys Ile Tyr Gly Asp Ser Asp Asn Ser Tyr Ser Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Gly Tyr Ser Tyr Leu Gly Tyr Phe Asn Leu Trp Gly
            100                 105                 110

Gln Gly Thr Leu Val Thr Val Ser Ser
        115                 120

<210> SEQ ID NO 153
<211> LENGTH: 651
<212> TYPE: DNA
<213> ORGANISM: Artificial Sequence
<220> FEATURE:
<223> OTHER INFORMATION: synthesized

<400> SEQUENCE: 153
gacatccaga tgacccagtc tccatcctcc ctgtctgcat ctgtaggaga cagagtcacc      60
atcacttgcc agtccagtca gactgtttat aataacaact tgttatcctg gtatcagcag    120
aaaccaggga agttcctaa gctcctgatc tattatgcat ccactctggc atttggggtc     180
ccatctcggt tcagtggcag tggatctggg acagatttca ctctcaccat cagcagcctg    240
cagcctgaag atgttgcaac ttattactgt caaggcggtt atagtggttg gatttatgtt    300
ttcggcggag ggaccaaggt ggagatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 154
<211> LENGTH: 330
<212> TYPE: DNA
<213> ORGANISM: Artificial Sequence
<220> FEATURE:
<223> OTHER INFORMATION: synthesized

<400> SEQUENCE: 154

```
gacatccaga tgacccagtc tccatcctcc ctgtctgcat ctgtaggaga cagagtcacc    60
atcacttgcc agtccagtca gactgtttat aataacaact tgttatcctg gtatcagcag   120
aaaccaggga agttcctaa gctcctgatc tattatgcat ccactctggc atttggggtc   180
ccatctcggt tcagtggcag tggatctggg acagatttca ctctcaccat cagcagcctg   240
cagcctgaag atgttgcaac ttattactgt caaggcggtt atagtggttg gatttatgtt   300
ttcggcggag ggaccaaggt ggagatcaaa                                    330
```

<210> SEQ ID NO 155
<211> LENGTH: 217
<212> TYPE: PRT
<213> ORGANISM: Artificial Sequence
<220> FEATURE:
<223> OTHER INFORMATION: synthesized

<400> SEQUENCE: 155

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Thr Val Tyr Asn Asn
            20                  25                  30

Asn Leu Leu Ser Trp Tyr Gln Gln Lys Pro Gly Lys Val Pro Lys Leu
        35                  40                  45

Leu Ile Tyr Tyr Ala Ser Thr Leu Ala Phe Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Gln Gly Gly Tyr Ser Gly
                85                  90                  95

Trp Ile Tyr Val Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 156
<211> LENGTH: 110
<212> TYPE: PRT

<213> ORGANISM: Artificial Sequence
<220> FEATURE:
<223> OTHER INFORMATION: synthesized

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Thr Val Tyr Asn Asn
            20                  25                  30

Asn Leu Leu Ser Trp Tyr Gln Gln Lys Pro Gly Lys Val Pro Lys Leu
        35                  40                  45

Leu Ile Tyr Tyr Ala Ser Thr Leu Ala Phe Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Gln Gly Gly Tyr Ser Gly
                85                  90                  95

Trp Ile Tyr Val Phe Gly Gly Gly Thr Lys Val Glu Ile Lys
            100                 105                 110

<210> SEQ ID NO 157
<211> LENGTH: 1329
<212> TYPE: DNA
<213> ORGANISM: Artificial Sequence
<220> FEATURE:
<223> OTHER INFORMATION: synthesized

<400> SEQUENCE: 157

| | | | | | |
|---|---|---|---|---|---|
| cagtcgctgg | tggagtctgg | gggaggcttg | gtccagcctg | gggggtccct | gagactctcc | 60 |
| tgtgcagcct | ctggattctc | cctcagtaac | tactacatga | actgggtccg | ccaggctcca | 120 |
| gggaagggc | tggagtacat | cggaatcatt | agtagtagtg | gtagcgcata | ctacgcgagc | 180 |
| tccgctaaag | gcagattcac | catctccaga | gacaattcca | agaacacgct | gtatcttcaa | 240 |
| atgaacagcc | tgagagccga | ggacacggct | gtgtattact | gtgcgagagg | ggactacggc | 300 |
| atggacctct | ggggccaggg | aaccctggtc | accgtctcga | gcgctagcac | caagggccca | 360 |
| tcggtcttcc | ccctggcacc | ctcctccaag | agcacctctg | gggcacagc | ggccctgggc | 420 |
| tgcctggtca | aggactactt | ccccgaaccg | gtgacggtgt | cgtggaactc | aggcgccctg | 480 |
| accagcggcg | tgcacacctt | cccggctgtc | ctacagtcct | caggactcta | ctccctcagc | 540 |
| agcgtggtga | ccgtgccctc | agcagcttg | ggcacccaga | cctacatctg | caacgtgaat | 600 |
| cacaagccca | gcaacaccaa | ggtggacaag | agagttgagc | ccaaatcttg | tgacaaaact | 660 |
| cacacatgcc | caccgtgccc | agcacctgaa | gccgcggggg | gaccgtcagt | cttcctcttc | 720 |
| cccccaaaac | ccaaggacac | cctcatgatc | tcccggaccc | ctgaggtcac | atgcgtggtg | 780 |
| gtggacgtga | gccacgaaga | ccctgaggtc | aagttcaact | ggtacgtgga | cggcgtggag | 840 |
| gtgcataatg | ccaagacaaa | gccgcgggag | gagcagtaca | acagcacgta | ccgtgtggtc | 900 |
| agcgtcctca | ccgtcctgca | ccaggactgg | ctgaatggca | aggagtacaa | gtgcgcggtc | 960 |
| tccaacaaag | ccctcccagc | ccccatcgag | aaaaccatct | ccaaagccaa | agggcagccc | 1020 |
| cgagaaccac | aggtgtacac | cctgccccca | tcccgggatg | agctgaccaa | gaaccaggtc | 1080 |
| agcctgacct | gcctggtcaa | aggcttctat | cccagcgaca | tcgccgtgga | gtgggagagc | 1140 |
| aatgggcagc | cggagaacaa | ctacaagacc | acgcctcccg | tgctggactc | cgacggctcc | 1200 |
| ttcttcctct | atagcaagct | caccgtggac | aagagcaggt | ggcagcaggg | gaacgtcttc | 1260 |

```
tcatgctccg tgatgcatga ggctctgcac aaccactaca cgcagaagag cctctccctg    1320
tctccgggt                                                            1329
```

<210> SEQ ID NO 158
<211> LENGTH: 342
<212> TYPE: DNA
<213> ORGANISM: Artificial Sequence
<220> FEATURE:
<223> OTHER INFORMATION: synthesized

<400> SEQUENCE: 158

```
cagtcgctgg tggagtctgg gggaggcttg gtccagcctg gggggtccct gagactctcc     60
tgtgcagcct ctggattctc cctcagtaac tactacatga actgggtccg ccaggctcca    120
gggaaggggc tggagtacat cggaatcatt agtagtagtg gtagcgcata ctacgcgagc    180
tccgctaaag gcagattcac catctccaga gacaattcca agaacacgct gtatcttcaa    240
atgaacagcc tgagagccga ggacacggct gtgtattact gtgcgagagg ggactacggc    300
atggacctct ggggccaggg aaccctggtc accgtctcga gc                       342
```

<210> SEQ ID NO 159
<211> LENGTH: 443
<212> TYPE: PRT
<213> ORGANISM: Artificial Sequence
<220> FEATURE:
<223> OTHER INFORMATION: synthesized

<400> SEQUENCE: 159

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Asn Tyr Tyr
            20                  25                  30

Met Asn Trp Val Arg Gln Ala Pro Gly Lys Gly Leu Glu Tyr Ile Gly
        35                  40                  45

Ile Ile Ser Ser Ser Gly Ser Ala Tyr Tyr Ala Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Asp Tyr Gly Met Asp Leu Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Ala Ala Gly Ala Pro Ser Val Phe Leu Phe 225                 230                 235                 240
Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 160
<211> LENGTH: 114
<212> TYPE: PRT
<213> ORGANISM: Artificial Sequence
<220> FEATURE:
<223> OTHER INFORMATION: synthesized

<400> SEQUENCE: 160

Gln Ser Leu Val Glu Ser Gly Gly Leu Val Gln Pro Gly Gly Ser
1               5                   10                  15

Leu Arg Leu Ser Cys Ala Ala Ser Gly Phe Ser Leu Ser Asn Tyr Tyr
            20                  25                  30

Met Asn Trp Val Arg Gln Ala Pro Gly Lys Gly Leu Glu Tyr Ile Gly
        35                  40                  45

Ile Ile Ser Ser Ser Gly Ser Ala Tyr Tyr Ala Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Asp Tyr Gly Met Asp Leu Trp Gly Gln Gly Thr Leu Val Thr Val
            100                 105                 110

Ser Ser

<210> SEQ ID NO 161
<211> LENGTH: 657
<212> TYPE: DNA
<213> ORGANISM: Artificial Sequence
<220> FEATURE:
<223> OTHER INFORMATION: synthesized

<400> SEQUENCE: 161

```
gacgttgtga tgacccagtc tccatcttcc gtgtctgcat ctgtaggaga cagagtcacc    60
atcacctgtc aggccagtca gagcattggt agtgatttag cctggtatca gcagaaacca   120
gggaaagccc ctaagctcct gatctatagg gcatccactc tggcatctgg ggtcccatca   180
aggttcagcg gcagtggatc tgggacagat ttcactctca ccatcagcag cctgcagcct   240
gaagattttg caacttacta ttgtcaatcc atttattatg gtagtgatga tgtcatatac   300
catactttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa    480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 162
<211> LENGTH: 336
<212> TYPE: DNA
<213> ORGANISM: Artificial Sequence
<220> FEATURE:
<223> OTHER INFORMATION: synthesized

<400> SEQUENCE: 162

```
gacgttgtga tgacccagtc tccatcttcc gtgtctgcat ctgtaggaga cagagtcacc    60
atcacctgtc aggccagtca gagcattggt agtgatttag cctggtatca gcagaaacca   120
gggaaagccc ctaagctcct gatctatagg gcatccactc tggcatctgg ggtcccatca   180
aggttcagcg gcagtggatc tgggacagat ttcactctca ccatcagcag cctgcagcct   240
gaagattttg caacttacta ttgtcaatcc atttattatg gtagtgatga tgtcatatac   300
catactttcg gcggagggac caaggtggag atcaaa                              336
```

<210> SEQ ID NO 163
<211> LENGTH: 219
<212> TYPE: PRT
<213> ORGANISM: Artificial Sequence
<220> FEATURE:
<223> OTHER INFORMATION: synthesized

<400> SEQUENCE: 163

```
Asp Val Val Met Thr Gln Ser Pro Ser Ser Val Ser Ala Ser Val Gly
1               5                   10                  15

Asp Arg Val Thr Ile Thr Cys Gln Ala Ser Gln Ser Ile Gly Ser Asp
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ile Tyr Tyr Gly Ser Asp
                85                  90                  95

Asp Val Ile Tyr His Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 164
<211> LENGTH: 112
<212> TYPE: PRT
<213> ORGANISM: Artificial Sequence
<220> FEATURE:
<223> OTHER INFORMATION: synthesized

<400> SEQUENCE: 164

```
Asp Val Val Met Thr Gln Ser Pro Ser Ser Val Ser Ala Ser Val Gly
1               5                   10                  15

Asp Arg Val Thr Ile Thr Cys Gln Ala Ser Gln Ser Ile Gly Ser Asp
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ile Tyr Tyr Gly Ser Asp
                85                  90                  95

Asp Val Ile Tyr His Thr Phe Gly Gly Gly Thr Lys Val Glu Ile Lys
            100                 105                 110
```

<210> SEQ ID NO 165
<211> LENGTH: 1341
<212> TYPE: DNA
<213> ORGANISM: Artificial Sequence
<220> FEATURE:
<223> OTHER INFORMATION: synthesized

<400> SEQUENCE: 165

| | | |
|---|---|---|
| gaggtgcagc tggtggagtc tgggggaggc ttggtccagc ctggggggtc cctgagactc | 60 |
| tcctgtgcag cctctggatt cactatcaat agctaccaca tgatctgggt ccgccaggct | 120 |
| ccagggaagg ggctggagta catcggattc attaatgatg gtggtttcac atactacgcg | 180 |
| agctccgcta aaggcagatt caccatctcc agagacaatt ccaagaacac gctgtatctt | 240 |
| caaatgaaca gcctgagagc cgaggacacg gctgtgtatt actgtgcgag aggggttgat | 300 |
| ggtactagtt atcctgactt atggggccag ggaaccctgg tcaccgtctc gagcgctagc | 360 |
| accaagggcc catcggtctt ccccctggca ccctcctcca agagcacctc tgggggcaca | 420 |
| gcggccctgg gctgcctggt caaggactac ttccccgaac cggtgacggt gtcgtggaac | 480 |

```
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca agagagttga gcccaaatct    660
tgtgacaaaa ctcacacatg cccaccgtgc ccagcacctg aagccgcggg ggcaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcgcgg tctccaacaa agccctccca gcccccatcg agaaaccat ctccaaagcc    1020 aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 166
<211> LENGTH: 354
<212> TYPE: DNA
<213> ORGANISM: Artificial Sequence
<220> FEATURE:
<223> OTHER INFORMATION: synthesized

<400> SEQUENCE: 166

```
gaggtgcagc tggtggagtc tgggggaggc ttggtccagc ctgggggtc cctgagactc     60 tcctgtgcag cctctggatt cactatcaat agctaccaca tgatctgggt ccgccaggct    120
ccagggaagg ggctggagta catcggattc attaatgatg gtggtttcac atactacgcg    180
agctccgcta aaggcagatt caccatctcc agagacaatt ccaagaacac gctgtatctt    240
caaatgaaca gcctgagagc cgaggacacg gctgtgtatt actgtgcgag aggggttgat    300
ggtactagtt atcctgactt atggggccag ggaaccctgg tcaccgtctc gagc          354
```

<210> SEQ ID NO 167
<211> LENGTH: 447
<212> TYPE: PRT
<213> ORGANISM: Artificial Sequence
<220> FEATURE:
<223> OTHER INFORMATION: synthesized

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ser Tyr
            20                  25                  30

His Met Ile Trp Val Arg Gln Ala Pro Gly Lys Gly Leu Glu Tyr Ile
        35                  40                  45

Gly Phe Ile Asn Asp Gly Gly Phe Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Gly Val Asp Gly Thr Ser Tyr Pro Asp Leu Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 168
<211> LENGTH: 118
<212> TYPE: PRT
<213> ORGANISM: Artificial Sequence
<220> FEATURE:
<223> OTHER INFORMATION: synthesized

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ser Tyr
            20                  25                  30

His Met Ile Trp Val Arg Gln Ala Pro Gly Lys Gly Leu Glu Tyr Ile
        35                  40                  45

Gly Phe Ile Asn Asp Gly Gly Phe Thr Tyr Tyr Ala Ser Ser Ala Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Val Asp Gly Thr Ser Tyr Pro Asp Leu Trp Gly Gln Gly Thr
            100                 105                 110

Leu Val Thr Val Ser Ser
        115

<210> SEQ ID NO 169
<211> LENGTH: 654
<212> TYPE: DNA
<213> ORGANISM: Artificial Sequence
<220> FEATURE:
<223> OTHER INFORMATION: synthesized

<400> SEQUENCE: 169
gacatccaga tgacccagtc tccttccacc ctgtctgcat ctgtaggaga cagagtcacc    60
atcacttgcc aggccagtca gagcattggt agtaacttga actggtatca gcagaaacca   120
gggaaagccc ctaagctcct gatctattat gtatccactc tggcatctgg ggtcccatca   180
aggttcagcg gcagtggatc tgggacagaa ttcactctca ccatcagcag cctgcagcct   240
gatgattttg caacttatta ctgcctaggt gtttggaatt attggggtga tgacggtact   300
gctttcggcg agggaccaa ggtggagatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600 acccatcagg gcctgagctc gcccgtcaca aagagcttca caggggaga gtgt           654

<210> SEQ ID NO 170
<211> LENGTH: 333
<212> TYPE: DNA
<213> ORGANISM: Artificial Sequence
<220> FEATURE:
<223> OTHER INFORMATION: synthesized

<400> SEQUENCE: 170
gacatccaga tgacccagtc tccttccacc ctgtctgcat ctgtaggaga cagagtcacc    60
atcacttgcc aggccagtca gagcattggt agtaacttga actggtatca gcagaaacca   120
gggaaagccc ctaagctcct gatctattat gtatccactc tggcatctgg ggtcccatca   180
aggttcagcg gcagtggatc tgggacagaa ttcactctca ccatcagcag cctgcagcct   240
gatgattttg caacttatta ctgcctaggt gtttggaatt attggggtga tgacggtact   300
gctttcggcg agggaccaa ggtggagatc aaa                                 333

<210> SEQ ID NO 171
<211> LENGTH: 218

```
<212> TYPE: PRT
<213> ORGANISM: Artificial Sequence
<220> FEATURE:
<223> OTHER INFORMATION: synthesized

<400> SEQUENCE: 171

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Ser Asn
            20                  25                  30

Leu Asn Trp Tyr Gln Gln Lys Pro Gly Lys Ala Pro Lys Leu Leu Ile
        35                  40                  45

Tyr Tyr Val Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 172
<211> LENGTH: 111
<212> TYPE: PRT
<213> ORGANISM: Artificial Sequence
<220> FEATURE:
<223> OTHER INFORMATION: synthesized

<400> SEQUENCE: 172

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Ser Asn
            20                  25                  30

Leu Asn Trp Tyr Gln Gln Lys Pro Gly Lys Ala Pro Lys Leu Leu Ile
        35                  40                  45

Tyr Tyr Val Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Ala Phe Gly Gly Gly Thr Lys Val Glu Ile Lys
            100                 105                 110
```

<210> SEQ ID NO 173
<211> LENGTH: 1332
<212> TYPE: DNA
<213> ORGANISM: Artificial Sequence
<220> FEATURE:
<223> OTHER INFORMATION: synthesized

<400> SEQUENCE: 173

```
gaggtgcagc tggtggagtc tgggggaggc ttggtccagc ctgggggtc cctgagactc      60
tcctgtgcag cctctggatt ctccctcagt acctattata tgagctgggt ccgccaggct     120
ccagggaagg ggctggagtg gatcggaagt atttatgata gtggtgccgc atactacgcg     180
acctccgcga agggcagatt caccatctcc agagacaatt ccaagaacac gctgtatctt     240
caaatgaaca gcctgagagc cgaggacacg gctgtgtatt actgtgcgag agatcctatt     300
aataatgcca tctggggcca gggaaccctg gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggcaccgtc agtcttcctc      720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagccctccc agcccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                         1332
```

<210> SEQ ID NO 174
<211> LENGTH: 345
<212> TYPE: DNA
<213> ORGANISM: Artificial Sequence
<220> FEATURE:
<223> OTHER INFORMATION: synthesized

<400> SEQUENCE: 174

```
gaggtgcagc tggtggagtc tgggggaggc ttggtccagc ctgggggtc cctgagactc      60
tcctgtgcag cctctggatt ctccctcagt acctattata tgagctgggt ccgccaggct     120
ccagggaagg ggctggagtg gatcggaagt atttatgata gtggtgccgc atactacgcg     180
acctccgcga agggcagatt caccatctcc agagacaatt ccaagaacac gctgtatctt     240
caaatgaaca gcctgagagc cgaggacacg gctgtgtatt actgtgcgag agatcctatt     300
aataatgcca tctggggcca gggaaccctg gtcaccgtct cgagc                     345
```

<210> SEQ ID NO 175
<211> LENGTH: 444
<212> TYPE: PRT
<213> ORGANISM: Artificial Sequence
<220> FEATURE:
<223> OTHER INFORMATION: synthesized

<400> SEQUENCE: 175

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Tyr Met Ser Trp Val Arg Gln Ala Pro Gly Lys Gly Leu Glu Trp Ile
        35                  40                  45

Gly Ser Ile Tyr Asp Ser Gly Ala Ala Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Ala Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 176
<211> LENGTH: 115
<212> TYPE: PRT
<213> ORGANISM: Artificial Sequence
<220> FEATURE:
<223> OTHER INFORMATION: synthesized

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Tyr Met Ser Trp Val Arg Gln Ala Pro Gly Lys Gly Leu Glu Trp Ile
        35                  40                  45

Gly Ser Ile Tyr Asp Ser Gly Ala Ala Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Ala Ile Trp Gly Gln Gly Thr Leu Val Thr
            100                 105                 110

Val Ser Ser
        115

<210> SEQ ID NO 177
<211> LENGTH: 654
<212> TYPE: DNA
<213> ORGANISM: Artificial Sequence
<220> FEATURE:
<223> OTHER INFORMATION: synthesized

<400> SEQUENCE: 177
gacatccaga tgacccagtc tccttccacc ctgtctgcat ctgtaggaga cagagtcacc      60
atcacttgcc aggccagtca gagtattgct actaacttga actggtatca gcagaaacca     120
gggaaagccc ctaagctcct gatctattat acatccagtc tggcatctgg ggtcccatca     180
aggttcagcg gcagtggatc tgggacagaa ttcactctca ccatcagcag cctgcagcct     240
gatgattttg caacttatta ctgcctaggt gtttggaatt attggggtga tgatggtact     300
gctttcggcg agggaccaa ggtggagatc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600
```
acccatcagg gcctgagctc gcccgtcaca aagagcttca acaggggaga gtgt    654

<210> SEQ ID NO 178
<211> LENGTH: 333
<212> TYPE: DNA
<213> ORGANISM: Artificial Sequence
<220> FEATURE:
<223> OTHER INFORMATION: synthesized

<400> SEQUENCE: 178
gacatccaga tgacccagtc tccttccacc ctgtctgcat ctgtaggaga cagagtcacc    60
atcacttgcc aggccagtca gagtattgct actaacttga actggtatca gcagaaacca    120
gggaaagccc ctaagctcct gatctattat acatccagtc tggcatctgg ggtcccatca    180
aggttcagcg gcagtggatc tgggacagaa ttcactctca ccatcagcag cctgcagcct    240
gatgattttg caacttatta ctgcctaggt gtttggaatt attggggtga tgatggtact    300
gctttcggcg agggaccaa ggtggagatc aaa    333

<210> SEQ ID NO 179
<211> LENGTH: 218
<212> TYPE: PRT
<213> ORGANISM: Artificial Sequence
<220> FEATURE:
<223> OTHER INFORMATION: synthesized

<400> SEQUENCE: 179

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ala Thr Asn
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Ala Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 180
<211> LENGTH: 111

<212> TYPE: PRT
<213> ORGANISM: Artificial Sequence
<220> FEATURE:
<223> OTHER INFORMATION: synthesized

<400> SEQUENCE: 180

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ala Thr Asn
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Ala Phe Gly Gly Gly Thr Lys Val Glu Ile Lys
            100                 105                 110

<210> SEQ ID NO 181
<211> LENGTH: 1332
<212> TYPE: DNA
<213> ORGANISM: Artificial Sequence
<220> FEATURE:
<223> OTHER INFORMATION: synthesized

<400> SEQUENCE: 181
gaggtgcagc tggtggagtc tgggggaggc ttggtccagc ctggggggtc cctgagactc      60
tcctgtgcag cctctggatt ctccctcagt agctactaca tgagctgggt ccgccaggct     120
ccagggaagg ggctggagtg gatcggaagt atttatgcta gtggtagcgc atactacgcg     180
agttccgcga agggcagatt caccatctcc agagacaatt ccaagaacac gctgtatctt     240
caaatgaaca gcctgagagc cgaggacacg gctgtgtatt actgtgcgag agatcctatt     300
aacaatgaca tctggggcca gggaaccctg gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggcaccgtc agtcttcctc      720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagccctccc agcccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt    1332

<210> SEQ ID NO 182
<211> LENGTH: 345
<212> TYPE: DNA
<213> ORGANISM: Artificial Sequence
<220> FEATURE:
<223> OTHER INFORMATION: synthesized

<400> SEQUENCE: 182
gaggtgcagc tggtggagtc tgggggaggc ttggtccagc ctgggggtc cctgagactc     60 tcctgtgcag cctctggatt ctccctcagt agctactaca tgagctgggt ccgccaggct    120
ccagggaagg gctggagtg gatcggaagt atttatgcta gtggtagcgc atactacgcg    180
agttccgcga agggcagatt caccatctcc agagacaatt ccaagaacac gctgtatctt    240
caaatgaaca gcctgagagc cgaggacacg gctgtgtatt actgtgcgag agatcctatt    300
aacaatgaca tctggggcca gggaaccctg gtcaccgtct cgagc                    345

<210> SEQ ID NO 183
<211> LENGTH: 444
<212> TYPE: PRT
<213> ORGANISM: Artificial Sequence
<220> FEATURE:
<223> OTHER INFORMATION: synthesized

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Ser Ile Tyr Ala Ser Gly Ser Ala Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

```
Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
        435                 440

<210> SEQ ID NO 184
<211> LENGTH: 115
<212> TYPE: PRT
<213> ORGANISM: Artificial Sequence
<220> FEATURE:
<223> OTHER INFORMATION: synthesized

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Ser Ile Tyr Ala Ser Gly Ser Ala Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Asp Ile Trp Gly Gln Gly Thr Leu Val Thr
            100                 105                 110

Val Ser Ser
    115

<210> SEQ ID NO 185
<211> LENGTH: 654
```

<212> TYPE: DNA
<213> ORGANISM: Artificial Sequence
<220> FEATURE:
<223> OTHER INFORMATION: synthesized

<400> SEQUENCE: 185

```
gacatccaga tgacccagtc tccatcttcc gtgtctgcat ctgtaggaga cagagtcacc    60
atcacttgtc agtccagtcc gagtgtttat aagaacaacc aattagcctg gtatcagcag   120
aaaccaggga aagcccctaa gctcctgatc tatctggcat ctactctggc atctggggtc   180
ccatcaaggt tcagcggcag tggatctggg acagatttca ctctcaccat cagcagcctg   240
cagcctgaag attttgcaac ttactattgt gcaggcggtt atagtagtag tagtgatact   300
gctttcggcg agggaccaa ggtggagatc aaacgtacgg tggctgcacc atctgtcttc    360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600
acccatcagg gcctgagctc gcccgtcaca aagagcttca caggggaga gtgt            654
```

<210> SEQ ID NO 186
<211> LENGTH: 333
<212> TYPE: DNA
<213> ORGANISM: Artificial Sequence
<220> FEATURE:
<223> OTHER INFORMATION: synthesized

<400> SEQUENCE: 186

```
gacatccaga tgacccagtc tccatcttcc gtgtctgcat ctgtaggaga cagagtcacc    60
atcacttgtc agtccagtcc gagtgtttat aagaacaacc aattagcctg gtatcagcag   120
aaaccaggga aagcccctaa gctcctgatc tatctggcat ctactctggc atctggggtc   180
ccatcaaggt tcagcggcag tggatctggg acagatttca ctctcaccat cagcagcctg   240
cagcctgaag attttgcaac ttactattgt gcaggcggtt atagtagtag tagtgatact   300
gctttcggcg agggaccaa ggtggagatc aaa                                   333
```

<210> SEQ ID NO 187
<211> LENGTH: 218
<212> TYPE: PRT
<213> ORGANISM: Artificial Sequence
<220> FEATURE:
<223> OTHER INFORMATION: synthesized

<400> SEQUENCE: 187

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Tyr Lys Asn
            20                  25                  30

Asn Gln Leu Ala Trp Tyr Gln Gln Lys Pro Gly Lys Ala Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Ser Ser
                85                  90                  95
```

Ser Ser Asp Thr Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 188
<211> LENGTH: 111
<212> TYPE: PRT
<213> ORGANISM: Artificial Sequence
<220> FEATURE:
<223> OTHER INFORMATION: synthesized

<400> SEQUENCE: 188

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Tyr Lys Asn
            20                  25                  30

Asn Gln Leu Ala Trp Tyr Gln Gln Lys Pro Gly Lys Ala Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Ser Ser
                85                  90                  95

Ser Ser Asp Thr Ala Phe Gly Gly Gly Thr Lys Val Glu Ile Lys
            100                 105                 110

<210> SEQ ID NO 189
<211> LENGTH: 1270
<212> TYPE: DNA
<213> ORGANISM: Artificial Sequence
<220> FEATURE:
<223> OTHER INFORMATION: synthesized

<400> SEQUENCE: 189
tggaatcgac ctcagtgcct accacatgag ctgggtccgc caggctccag ggaaggggct    60
ggagtacatc gggatgattg tagtagtgg taccatacac tacgcgaact ccgcgaaagg   120
cagattcacc atctccaaag acaataccaa gaacacggtg gatcttcaaa tgaacagcct   180
gagagccgag gacacggctg tgtattactg tgcgagagac agtttataata gtgattatgc   240 ctttaactta tggggccagg gaaccctggt caccgtctcg agcgctagca ccaagggccc   300
atcggtcttc cccctggcac cctcctccaa gagcacctct ggggcacag cggcctggg   360 ctgcctggtc aaggactact tccccgaacc ggtgacggtg tcgtggaact caggcgccct   420

```
gaccagcggc gtgcacacct tcccggctgt cctacagtcc tcaggactct actccctcag    480
cagcgtggtg accgtgccct ccagcagctt gggcacccag acctacatct gcaacgtgaa    540
tcacaagccc agcaacacca aggtggacaa gagagttgag cccaaatctt gtgacaaaac    600
tcacacatgc ccaccgtgcc cagcacctga agccgcgggg gcaccgtcag tcttcctctt    660
ccccccaaaa cccaaggaca ccctcatgat ctcccggacc cctgaggtca catgcgtggt    720
ggtggacgtg agccacgaag accctgaggt caagttcaac tggtacgtgg acggcgtgga    780
ggtgcataat gccaagacaa agccgcggga ggagcagtac aacagcacgt accgtgtggt    840
cagcgtcctc accgtcctgc accaggactg gctgaatggc aaggagtaca agtgcgcggt    900
ctccaacaaa gccctcccag ccccatcga gaaaaccatc tccaaagcca agggcagcc     960 ccgagaacca caggtgtaca ccctgccccc atcccgggat gagctgacca agaaccaggt    1020
cagcctgacc tgcctggtca aaggcttcta tcccagcgac atcgccgtgg agtgggagag    1080
caatgggcag ccggagaaca actacaagac cacgcctccc gtgctggact ccgacggctc    1140
cttcttcctc tatagcaagc tcaccgtgga caagagcagg tggcagcagg ggaacgtctt    1200
ctcatgctcc gtgatgcatg aggctctgca caaccactac acgcagaaga gcctctccct    1260
gtctccgggt                                                            1270

<210> SEQ ID NO 190
<211> LENGTH: 357
<212> TYPE: DNA
<213> ORGANISM: Artificial Sequence
<220> FEATURE:
<223> OTHER INFORMATION: synthesized

<400> SEQUENCE: 190
gaggtgcagc tggtggagtc tgggggaggc ttggtccagc ctggggggtc cctgagactc    60
tcctgtacag cctctggaat cgacctcagt gcctaccaca tgagctgggt ccgccaggct    120
ccagggaagg gctggagta catcgggatg attggtagta gtggtaccat acactacgcg    180
aactccgcga aaggcagatt caccatctcc aaagacaata ccaagaacac ggtggatctt    240
caaatgaaca gcctgagagc cgaggacacg gctgtgtatt actgtgcgag agacagttat    300
aatagtgatt atgcctttaa cttatggggc cagggaaccc tggtcaccgt ctcgagc      357

<210> SEQ ID NO 191
<211> LENGTH: 448
<212> TYPE: PRT
<213> ORGANISM: Artificial Sequence
<220> FEATURE:
<223> OTHER INFORMATION: synthesized

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Thr Ala Ser Gly Ile Asp Leu Ser Ala Tyr
            20                  25                  30

His Met Ser Trp Val Arg Gln Ala Pro Gly Lys Gly Leu Glu Tyr Ile
        35                  40                  45

Gly Met Ile Gly Ser Ser Gly Thr Ile His Tyr Ala Asn Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95
```

Arg Asp Ser Tyr Asn Ser Asp Tyr Ala Phe Asn Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 192
<211> LENGTH: 119
<212> TYPE: PRT
<213> ORGANISM: Artificial Sequence
<220> FEATURE:
<223> OTHER INFORMATION: synthesized

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Thr Ala Ser Gly Ile Asp Leu Ser Ala Tyr
        20                  25                  30

His Met Ser Trp Val Arg Gln Ala Pro Gly Lys Gly Leu Glu Tyr Ile
            35                  40                  45

Gly Met Ile Gly Ser Ser Gly Thr Ile His Tyr Ala Asn Ser Ala Lys
 50                  55                  60

Gly Arg Phe Thr Ile Ser Lys Asp Asn Thr Lys Asn Thr Val Asp Leu
 65                  70                  75                  80

Gln Met Asn Ser Leu Arg Ala Glu Asp Thr Ala Val Tyr Tyr Cys Ala
                85                  90                  95

Arg Asp Ser Tyr Asn Ser Asp Tyr Ala Phe Asn Leu Trp Gly Gln Gly
            100                 105                 110

Thr Leu Val Thr Val Ser Ser
        115

<210> SEQ ID NO 193
<211> LENGTH: 653
<212> TYPE: DNA
<213> ORGANISM: Artificial Sequence
<220> FEATURE:
<223> OTHER INFORMATION: synthesized

<400> SEQUENCE: 193

| | | | | |
|---|---|---|---|---|
| gacatccaga | tgacccagtc | tccttccacc | ctgtctgcat | ctgtaggaga | cagagtcacc | 60 |
| atcacttgcc | agtccagtca | gagtgtttat | agtaactggt | atcctggta | tcagcagaaa | 120 |
| ccagggaaag | cccctaagag | actgatctat | tctgcatcca | ctctggcatc | tggggtccca | 180 |
| tcaaggttca | gcggcagtgg | atctgggaca | gaattcactc | tcaccatcag | cagcctgcag | 240 |
| cctgatgatt | ttgcaactta | ttactgcgca | ggcggttata | atactgttac | tgatactttt | 300 |
| gctttcggcg | agggaccaa | ggtggagatc | aaacgtacgg | tggctgcacc | atctgtcttc | 360 |
| atcttcccgc | catctgatga | gcagttgaaa | tctggaactg | cctctgttgt | gtgcctgctg | 420 |
| aataacttct | atcccagaga | ggccaaagta | cagtggaagg | tggataacgc | cctccaatcg | 480 |
| ggtaactccc | aggagagtgt | cacagagcag | gacagcaagg | acagcaccta | cagcctcagc | 540 |
| agcaccctga | cgctgagcaa | agcagactac | gagaaacaca | aagtctacgc | ctgcgaagtc | 600 |
| acccatcagg | gcctgagctc | gcccgtcaca | aagagcttca | caggggaga | gtg | 653 |

<210> SEQ ID NO 194
<211> LENGTH: 333
<212> TYPE: DNA
<213> ORGANISM: Artificial Sequence
<220> FEATURE:
<223> OTHER INFORMATION: synthesized

<400> SEQUENCE: 194

| | | | | | | |
|---|---|---|---|---|---|---|
| gacatccaga | tgacccagtc | tccttccacc | ctgtctgcat | ctgtaggaga | cagagtcacc | 60 |
| atcacttgcc | agtccagtca | gagtgtttat | agtaactggt | atcctggta | tcagcagaaa | 120 |
| ccagggaaag | cccctaagag | actgatctat | tctgcatcca | ctctggcatc | tggggtccca | 180 |
| tcaaggttca | gcggcagtgg | atctgggaca | gaattcactc | tcaccatcag | cagcctgcag | 240 |
| cctgatgatt | ttgcaactta | ttactgcgca | ggcggttata | atactgttac | tgatactttt | 300 |
| gctttcggcg | agggaccaa | ggtggagatc | aaa | | | 333 |

<210> SEQ ID NO 195
<211> LENGTH: 218

```
<212> TYPE: PRT
<213> ORGANISM: Artificial Sequence
<220> FEATURE:
<223> OTHER INFORMATION: synthesized

<400> SEQUENCE: 195

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Leu Ser Trp Tyr Gln Gln Lys Pro Gly Lys Ala Pro Lys Arg Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Thr Asp Thr Phe Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 196
<211> LENGTH: 111
<212> TYPE: PRT
<213> ORGANISM: Artificial Sequence
<220> FEATURE:
<223> OTHER INFORMATION: synthesized

<400> SEQUENCE: 196

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Leu Ser Trp Tyr Gln Gln Lys Pro Gly Lys Ala Pro Lys Arg Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Thr Asp Thr Phe Ala Phe Gly Gly Gly Thr Lys Val Glu Ile Lys
            100                 105                 110
```

<210> SEQ ID NO 197
<211> LENGTH: 1332
<212> TYPE: DNA
<213> ORGANISM: Artificial Sequence
<220> FEATURE:
<223> OTHER INFORMATION: synthesized

<400> SEQUENCE: 197

```
gaggtgcagc tgttggagtc tgggggaggc ttggtacagc ctgggggtc cctgagactc      60
tcctgtacag cctctggatt ctccttcagt agcaggcact acatgtgttg ggtccgccag    120
gctccaggga aggggctgga gtggatcgca tgcatttata ctggtagtag tggtactcct    180
cactacgcga gctccgcgaa aggccggttc accatctccc aagacaattc caagaacacg    240
gtgactctgc aaatgaacag cctgagagcc gaggacacgg ccgtatatta ctgtgcgaga    300
gaaggtaacc tgtggggcca gggaaccctg gtcaccgtct cgagcgctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaagccgcgg ggcaccgtc agtcttcctc    720
ttcccccccaa acccaaggda caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcgcg    960
gtctccaaca agccctccc agcccccatc gagaaaacca tctccaaagc caaagggcag   1020
ccccgagaac acaggtgta caccctgccc ccatcccggg atgagctgac caagaaccag   1080
gtcagcctga cctgcctggt caaaggcttc tatcccagcg catcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gt                                                      1332
```

<210> SEQ ID NO 198
<211> LENGTH: 345
<212> TYPE: DNA
<213> ORGANISM: Artificial Sequence
<220> FEATURE:
<223> OTHER INFORMATION: synthesized

<400> SEQUENCE: 198

```
gaggtgcagc tgttggagtc tgggggaggc ttggtacagc ctgggggtc cctgagactc      60
tcctgtacag cctctggatt ctccttcagt agcaggcact acatgtgttg ggtccgccag    120
gctccaggga aggggctgga gtggatcgca tgcatttata ctggtagtag tggtactcct    180
cactacgcga gctccgcgaa aggccggttc accatctccc aagacaattc caagaacacg    240
gtgactctgc aaatgaacag cctgagagcc gaggacacgg ccgtatatta ctgtgcgaga    300
gaaggtaacc tgtggggcca gggaaccctg gtcaccgtct cgagc                    345
```

<210> SEQ ID NO 199
<211> LENGTH: 444
<212> TYPE: PRT
<213> ORGANISM: Artificial Sequence
<220> FEATURE:
<223> OTHER INFORMATION: synthesized

<400> SEQUENCE: 199

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Ser Phe Ser Ser Arg
            20                  25                  30

His Tyr Met Cys Trp Val Arg Gln Ala Pro Gly Lys Gly Leu Glu Trp
        35                  40                  45

Ile Ala Cys Ile Tyr Thr Gly Ser Ser Gly Thr Pro His Tyr Ala Ser
    50                  55                  60

Ser Ala Lys Gly Arg Phe Thr Ile Ser Gln Asp Asn Ser Lys Asn Thr
65                  70                  75                  80

Val Thr Leu Gln Met Asn Ser Leu Arg Ala Glu Asp Thr Ala Val Tyr
                85                  90                  95

Tyr Cys Ala Arg Glu Gly Asn Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440

<210> SEQ ID NO 200
<211> LENGTH: 115
<212> TYPE: PRT
<213> ORGANISM: Artificial Sequence
<220> FEATURE:
<223> OTHER INFORMATION: synthesized

<400> SEQUENCE: 200

Glu Val Gln Leu Leu Glu Ser Gly Gly Gly Leu Val Gln Pro Gly Gly
1               5                   10                  15
Ser Leu Arg Leu Ser Cys Thr Ala Ser Gly Phe Ser Phe Ser Ser Arg
            20                  25                  30
His Tyr Met Cys Trp Val Arg Gln Ala Pro Gly Lys Gly Leu Glu Trp
        35                  40                  45
Ile Ala Cys Ile Tyr Thr Gly Ser Ser Gly Thr Pro His Tyr Ala Ser
    50                  55                  60
Ser Ala Lys Gly Arg Phe Thr Ile Ser Gln Asp Asn Ser Lys Asn Thr
65                  70                  75                  80
Val Thr Leu Gln Met Asn Ser Leu Arg Ala Glu Asp Thr Ala Val Tyr
                85                  90                  95
Tyr Cys Ala Arg Glu Gly Asn Leu Trp Gly Gln Gly Thr Leu Val Thr
            100                 105                 110
Val Ser Ser
        115

<210> SEQ ID NO 201
<211> LENGTH: 657
<212> TYPE: DNA
<213> ORGANISM: Artificial Sequence
<220> FEATURE:
<223> OTHER INFORMATION: synthesized

<400> SEQUENCE: 201
gcccttgtga tgacccagtc tccttccacc ctgtctgcat ctgtaggaga cagagtcacc    60
atcaattgcc aggccagtga ggacattgat acctatttag cctggtatca gcagaaacca   120
gggaaagccc ctaagctcct gatcttttat gcatccgatc tggcatctgg ggtcccatca   180
aggttcagcg gcagtggatc tgggacagaa ttcactctca ccatcagcag cctgcagcct   240
gatgattttg caacttatta ctgccaaggc ggttactata ctagtagtgc tgatacgagg   300
ggtgctttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
```
gtcacccatc agggcctgag ctcgcccgtc acaaagagct tcaacagggg agagtgt        657

<210> SEQ ID NO 202
<211> LENGTH: 336
<212> TYPE: DNA
<213> ORGANISM: Artificial Sequence
<220> FEATURE:
<223> OTHER INFORMATION: synthesized

<400> SEQUENCE: 202
gcccttgtga tgacccagtc tccttccacc ctgtctgcat ctgtaggaga cagagtcacc        60
atcaattgcc aggccagtga ggacattgat acctatttag cctggtatca gcagaaacca       120
gggaaagccc ctaagctcct gatcttttat gcatccgatc tggcatctgg ggtcccatca       180
aggttcagcg gcagtggatc tgggacagaa ttcactctca ccatcagcag cctgcagcct       240
gatgattttg caacttatta ctgccaaggc ggttactata ctagtagtgc tgatacgagg       300
ggtgctttcg gcggagggac caaggtggag atcaaa                                 336

<210> SEQ ID NO 203
<211> LENGTH: 219
<212> TYPE: PRT
<213> ORGANISM: Artificial Sequence
<220> FEATURE:
<223> OTHER INFORMATION: synthesized

<400> SEQUENCE: 203

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 204
<211> LENGTH: 112

```
<212> TYPE: PRT
<213> ORGANISM: Artificial Sequence
<220> FEATURE:
<223> OTHER INFORMATION: synthesized

<400> SEQUENCE: 204
```

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110

```
<210> SEQ ID NO 205
<211> LENGTH: 1347
<212> TYPE: DNA
<213> ORGANISM: Artificial Sequence
<220> FEATURE:
<223> OTHER INFORMATION: synthesized

<400> SEQUENCE: 205
```

| | | | | | |
|---|---|---|---|---|---|
| cagtcgctgg | tggagtctgg | gggaggcttg | gtacagcctg | gggggtccct | gagactctcc | 60 |
| tgtgcagcct | ctggattctc | cttcagtagc | aactactgga | tatgctgggt | ccgccaggct | 120 |
| ccagggaagg | ggctggagtg | gatcgcatgc | atttatgttg | gtagtagtgg | tgacacttac | 180 |
| tacgcgagct | ccgcgaaagg | ccggttcacc | atctccagag | acaattccaa | gaacacgctg | 240 |
| tatctgcaaa | tgaacagcct | gagagccgag | gacacggccg | tatattactg | tgcgagagat | 300 |
| agtagtagtt | attatatgtt | taacttgtgg | ggccagggaa | ccctggtcac | cgtctcgagc | 360 |
| gctagcacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagag | agttgagccc | 660 |
| aaatcttgtg | acaaaactca | cacatgccca | ccgtgcccag | cacctgaagc | cgcggggca | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcgggagga | gcagtacaac | 900 |
| agcacgtacc | gtgtggtcag | cgtcctcacc | gtcctgcacc | aggactggct | gaatggcaag | 960 |
| gagtacaagt | gcgcggtctc | caacaaagcc | ctcccagccc | ccatcgagaa | aaccatctcc | 1020 |
| aaagccaaag | ggcagccccg | agaaccacag | gtgtacaccc | tgcccccatc | ccgggatgag | 1080 |
| ctgaccaaga | accaggtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctat | agcaagctca | ccgtggacaa | gagcaggtgg | 1260 |

```
cagcagggga acgtcttctc atgctccgtg atgcatgagg ctctgcacaa ccactacacg   1320
cagaagagcc tctccctgtc tccgggt                                       1347

<210> SEQ ID NO 206
<211> LENGTH: 360
<212> TYPE: DNA
<213> ORGANISM: Artificial Sequence
<220> FEATURE:
<223> OTHER INFORMATION: synthesized

<400> SEQUENCE: 206
cagtcgctgg tggagtctgg gggaggcttg gtacagcctg gggggtccct gagactctcc    60
tgtgcagcct ctggattctc cttcagtagc aactactgga tatgctgggt ccgccaggct   120
ccagggaagg ggctggagtg gatcgcatgc atttatgttg gtagtagtgg tgacacttac   180
tacgcgagct ccgcgaaagg ccggttcacc atctccagag acaattccaa gaacacgctg   240
tatctgcaaa tgaacagcct gagagccgag gacacggccg tatattactg tgcgagagat   300
agtagtagtt attatatgtt taacttgtgg ggccagggaa ccctggtcac cgtctcgagc   360

<210> SEQ ID NO 207
<211> LENGTH: 449
<212> TYPE: PRT
<213> ORGANISM: Artificial Sequence
<220> FEATURE:
<223> OTHER INFORMATION: synthesized

<400> SEQUENCE: 207

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 208
<211> LENGTH: 120
<212> TYPE: PRT
<213> ORGANISM: Artificial Sequence
<220> FEATURE:
<223> OTHER INFORMATION: synthesized

<400> SEQUENCE: 208

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Tyr Tyr Met Phe Asn Leu Trp Gly Gln
                100                 105                 110

Gly Thr Leu Val Thr Val Ser Ser
            115                 120

<210> SEQ ID NO 209
<211> LENGTH: 654
<212> TYPE: DNA
<213> ORGANISM: Artificial Sequence
<220> FEATURE:
<223> OTHER INFORMATION: synthesized

<400> SEQUENCE: 209

```
gacatccaga tgacccagtc tccttccacc ctgtctgcat ctgtaggaga cagagtcacc    60
atcacttgcc aggccagtca gagtgtttat agtaactggt tatcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgtaat tgatactttt   300
gctttcggcg agggaccaa ggtggagatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggaga gtgt          654
```

<210> SEQ ID NO 210
<211> LENGTH: 333
<212> TYPE: DNA
<213> ORGANISM: Artificial Sequence
<220> FEATURE:
<223> OTHER INFORMATION: synthesized

<400> SEQUENCE: 210

```
gacatccaga tgacccagtc tccttccacc ctgtctgcat ctgtaggaga cagagtcacc    60
atcacttgcc aggccagtca gagtgtttat agtaactggt tatcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgtaat tgatactttt   300
gctttcggcg agggaccaa ggtggagatc aaa                                 333
```

<210> SEQ ID NO 211
<211> LENGTH: 218
<212> TYPE: PRT
<213> ORGANISM: Artificial Sequence
<220> FEATURE:
<223> OTHER INFORMATION: synthesized

<400> SEQUENCE: 211

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Val Tyr Ser Asn
            20                  25                  30

Trp Leu Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
```

```
            85                  90                  95
Ile Asp Thr Phe Ala Phe Gly Gly Thr Lys Val Glu Ile Lys Arg
                100                 105                 110

Thr Val Ala Ala Pro Ser Val Phe Ile Phe Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215
```

<210> SEQ ID NO 212
<211> LENGTH: 111
<212> TYPE: PRT
<213> ORGANISM: Artificial Sequence
<220> FEATURE:
<223> OTHER INFORMATION: synthesized

<400> SEQUENCE: 212

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Val Tyr Ser Asn
                20                  25                  30

Trp Leu Ser Trp Tyr Gln Gln Lys Pro Gly Lys Ala Pro Lys Leu Leu
            35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys
                100                 105                 110
```

<210> SEQ ID NO 213
<211> LENGTH: 1332
<212> TYPE: DNA
<213> ORGANISM: Artificial Sequence
<220> FEATURE:
<223> OTHER INFORMATION: synthesized

<400> SEQUENCE: 213

```
gaggtgcagc tgttggagtc tgggggaggc ttggtacagc ctggggggtc cctgagactc      60
tcctgtgcag cctctggaat cgacttcagt agtagttact acatgtgctg ggtccgccag     120
gctccaggga aggggctgga gtggatcgca tgcatttata ctggtggtag tggtactcct     180
cactacgcga gctccgcgaa aggccggttc accatctcca gagacaattc caagaacacg     240
ctgtatctgc aaatgaacag cctgagagcc gaggacacgg ccgtatatta ctgtgcgaga     300
gaaggtagcc tgtggggcca gggaaccctg gtcaccgtct cgagcgctag caccaagggc     360
```

```
ccatcggtct tcccctggc accctcctcc aagagcacct ctggggggcac agcggccctg      420 ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaagccgcgg gggcaccgtc agtcttcctc      720
ttccccccaa acccaagga caccctcatg atctcccgga cccctgaggt cacatgcgtg       780
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcgcg      960
gtctccaaca aagccctccc agcccccatc gagaaaacca tctccaaagc caagggcag      1020 ccccgagaac acaggtgta caccctgccc ccatcccggg atgagctgac caagaaccag     1080
gtcagcctga cctgcctggt caaaggcttc tatcccagcg acatcgccgt ggagtgggag     1140
agcaatgggc agccggagaa caactacaag accacgcctc ccgtgctgga ctccgacggc      1200
tccttcttcc tctatagcaa gctcaccgtg gacaagagca ggtggcagca ggggaacgtc      1260
ttctcatgct ccgtgatgca tgaggctctg cacaaccact acacgcagaa gagcctctcc     1320
ctgtctccgg gt                                                         1332
```

<210> SEQ ID NO 214
<211> LENGTH: 345
<212> TYPE: DNA
<213> ORGANISM: Artificial Sequence
<220> FEATURE:
<223> OTHER INFORMATION: synthesized

<400> SEQUENCE: 214

```
gaggtgcagc tgttggagtc tgggggaggc ttggtacagc ctggggggtc cctgagactc       60
tcctgtgcag cctctggaat cgacttcagt agtagttact acatgtgctg ggtccgccag      120
gctccaggga aggggctgga gtggatcgca tgcatttata ctggtggtag tggtactcct      180
cactacgcga gctccgcgaa aggccggttc accatctcca gagacaattc caagaacacg      240
ctgtatctgc aaatgaacag cctgagagcc gaggacacgg ccgtatatta ctgtgcgaga      300
gaaggtagcc tgtggggcca gggaaccctg gtcaccgtct cgagc                      345
```

<210> SEQ ID NO 215
<211> LENGTH: 444
<212> TYPE: PRT
<213> ORGANISM: Artificial Sequence
<220> FEATURE:
<223> OTHER INFORMATION: synthesized

<400> SEQUENCE: 215

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ile Asp Phe Ser Ser Ser
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Gly Ser Gly Thr Pro His Tyr Ala Ser
    50                  55                  60

Ser Ala Lys Gly Arg Phe Thr Ile Ser Arg Asp Asn Ser Lys Asn Thr
```

```
                65                  70                  75                  80
Leu Tyr Leu Gln Met Asn Ser Leu Arg Ala Glu Asp Thr Ala Val Tyr
                    85                  90                  95

Tyr Cys Ala Arg Glu Gly Ser Leu Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 216
<211> LENGTH: 115
<212> TYPE: PRT
<213> ORGANISM: Artificial Sequence
<220> FEATURE:
<223> OTHER INFORMATION: synthesized
```

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Ser Ser
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Gly Ser Gly Thr Pro His Tyr Ala Ser
50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser
        115

<210> SEQ ID NO 217
<211> LENGTH: 654
<212> TYPE: DNA
<213> ORGANISM: Artificial Sequence
<220> FEATURE:
<223> OTHER INFORMATION: synthesized

<400> SEQUENCE: 217
gacatccaga tgacccagtc tccttccacc ctgtctgcat ctgtaggaga cagagtcacc    60
atcacttgcc agtccagtca gagtgtttat agtaactggt tctcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgtaac tgatactttt   300
gctttcggcg agggaccaa ggtggagatc aaacgtacgg tggctgcacc atctgtcttc    360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600
acccatcagg gcctgagctc gcccgtcaca aagagcttca caggggaga gtgt          654

<210> SEQ ID NO 218
<211> LENGTH: 333
<212> TYPE: DNA
<213> ORGANISM: Artificial Sequence
<220> FEATURE:
<223> OTHER INFORMATION: synthesized

<400> SEQUENCE: 218
gacatccaga tgacccagtc tccttccacc ctgtctgcat ctgtaggaga cagagtcacc    60
atcacttgcc agtccagtca gagtgtttat agtaactggt tctcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgtaac tgatactttt   300
gctttcggcg agggaccaa ggtggagatc aaa                                 333

<210> SEQ ID NO 219
<211> LENGTH: 218
<212> TYPE: PRT
<213> ORGANISM: Artificial Sequence
<220> FEATURE:
<223> OTHER INFORMATION: synthesized

<400> SEQUENCE: 219

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Thr Asp Thr Phe Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 220
<211> LENGTH: 111
<212> TYPE: PRT
<213> ORGANISM: Artificial Sequence
<220> FEATURE:
<223> OTHER INFORMATION: synthesized

<400> SEQUENCE: 220

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val 85                 90                 95
Thr Asp Thr Phe Ala Phe Gly Gly Gly Thr Lys Val Glu Ile Lys
               100                105                110

<210> SEQ ID NO 221
<211> LENGTH: 1332
<212> TYPE: DNA
<213> ORGANISM: Artificial Sequence
<220> FEATURE:
<223> OTHER INFORMATION: synthesized

<400> SEQUENCE: 221

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggaat | cgacttcagt | aggagatact | acatgtgctg | ggtccgccag | 120 |
| gctccaggga | aggggctgga | gtggatcgca | tgcatgtata | ctggtagccg | cgatactcct | 180 |
| cactacgcga | gctccgcgaa | aggccggttc | accatctcca | gagacaattc | caagaacacg | 240 |
| ctgtatctgc | aaatgaacag | cctgagagcc | gaggacacgg | ccgtatatta | ctgtgcgaga | 300 |
| gaaggtaacc | tgtggggcca | gggaaccctg | gtcaccgtct | cgagcgctag | caccaagggc | 360 |
| ccatcggtct | tccccctggc | accctcctcc | aagagcacct | ctggggggcac | agcggccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcaccc | agacctacat | ctgcaacgtg | 600 |
| aatcacaagc | ccagcaacac | caaggtggac | aagagagttg | agcccaaatc | ttgtgacaaa | 660 |
| actcacacat | gcccaccgtg | cccagcacct | gaagccgcgg | gggcaccgtc | agtcttcctc | 720 |
| ttccccccaa | aacccaagga | caccctcatg | atctcccgga | cccctgaggt | cacatgcgtg | 780 |
| gtggtggacg | tgagccacga | agaccctgag | gtcaagttca | actggtacgt | ggacggcgtg | 840 |
| gaggtgcata | atgccaagac | aaagccgcgg | gaggagcagt | acaacagcac | gtaccgtgtg | 900 |
| gtcagcgtcc | tcaccgtcct | gcaccaggac | tggctgaatg | gcaaggagta | caagtgcgcg | 960 |
| gtctccaaca | aagccctccc | agcccccatc | gagaaaacca | tctccaaagc | caaagggcag | 1020 |
| ccccgagaac | cacaggtgta | caccctgccc | ccatcccggg | atgagctgac | caagaaccag | 1080 |
| gtcagcctga | cctgcctggt | caaaggcttc | tatcccagcg | acatcgccgt | ggagtgggag | 1140 |
| agcaatgggc | agccggagaa | caactacaag | accacgcctc | ccgtgctgga | ctccgacggc | 1200 |
| tccttcttcc | tctatagcaa | gctcaccgtg | gacaagagca | ggtggcagca | ggggaacgtc | 1260 |
| ttctcatgct | ccgtgatgca | tgaggctctg | cacaaccact | acacgcagaa | gagcctctcc | 1320 |
| ctgtctccgg | gt | | | | | 1332 |

<210> SEQ ID NO 222
<211> LENGTH: 345
<212> TYPE: DNA
<213> ORGANISM: Artificial Sequence
<220> FEATURE:
<223> OTHER INFORMATION: synthesized

<400> SEQUENCE: 222

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggaat | cgacttcagt | aggagatact | acatgtgctg | ggtccgccag | 120 |
| gctccaggga | aggggctgga | gtggatcgca | tgcatgtata | ctggtagccg | cgatactcct | 180 |
| cactacgcga | gctccgcgaa | aggccggttc | accatctcca | gagacaattc | caagaacacg | 240 |

```
ctgtatctgc aaatgaacag cctgagagcc gaggacacgg ccgtatatta ctgtgcgaga    300
gaaggtaacc tgtggggcca gggaaccctg gtcaccgtct cgagc                   345
```

<210> SEQ ID NO 223
<211> LENGTH: 444
<212> TYPE: PRT
<213> ORGANISM: Artificial Sequence
<220> FEATURE:
<223> OTHER INFORMATION: synthesized

<400> SEQUENCE: 223

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Met Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Asn Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 224
<211> LENGTH: 115
<212> TYPE: PRT
<213> ORGANISM: Artificial Sequence
<220> FEATURE:
<223> OTHER INFORMATION: synthesized

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Met Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Asn Leu Trp Gly Gln Gly Thr Leu Val Thr
            100                 105                 110

Val Ser Ser
        115

<210> SEQ ID NO 225
<211> LENGTH: 654
<212> TYPE: DNA
<213> ORGANISM: Artificial Sequence
<220> FEATURE:
<223> OTHER INFORMATION: synthesized

<400> SEQUENCE: 225
gacatccaga tgacccagtc tccttccacc ctgtctgcat ctgtaggaga cagagtcacc    60
atcacttgcc agtccagtca gagtgtttat agtaactggt tctcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgttat tgatactttt   300
gctttcggcg gagggaccaa ggtggagatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480

```
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt           654
```

<210> SEQ ID NO 226
<211> LENGTH: 333
<212> TYPE: DNA
<213> ORGANISM: Artificial Sequence
<220> FEATURE:
<223> OTHER INFORMATION: synthesized

<400> SEQUENCE: 226

```
gacatccaga tgacccagtc tccttccacc ctgtctgcat ctgtaggaga cagagtcacc     60
atcacttgcc agtccagtca gagtgtttat agtaactggt tctcctggta tcagcagaaa   120
ccagggaaag cccctaagct cctgatctat tctgcatcca ctctggcatc tggggtccca   180
tcaaggttca gcggcagtgg atctgggaca gaattcactc tcaccatcag cagcctgcag   240
cctgatgatt ttgcaactta ttactgcgca ggcggttaca atactgttat tgatactttt   300
gctttcggcg agggaccaa ggtggagatc aaa                                   333
```

<210> SEQ ID NO 227
<211> LENGTH: 218
<212> TYPE: PRT
<213> ORGANISM: Artificial Sequence
<220> FEATURE:
<223> OTHER INFORMATION: synthesized

<400> SEQUENCE: 227

```
Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 228
<211> LENGTH: 111
<212> TYPE: PRT
<213> ORGANISM: Artificial Sequence
<220> FEATURE:
<223> OTHER INFORMATION: synthesized

<400> SEQUENCE: 228

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys
            100                 105                 110

<210> SEQ ID NO 229
<211> LENGTH: 1332
<212> TYPE: DNA
<213> ORGANISM: Artificial Sequence
<220> FEATURE:
<223> OTHER INFORMATION: synthesized

<400> SEQUENCE: 229

| | |
|---|---|
| gaggtgcagc tgttggagtc tgggggaggc ttggtacagc ctggggggtc cctgagactc | 60 |
| tcctgtgcag cctctggaat cgacttcagt aggagatact acatgtgctg ggtccgccag | 120 |
| gctccaggga aggggctgga gtggatcgca tgcatatata ctggtagccg cgatactcct | 180 |
| cactacgcga gctccgcgaa aggccggttc accatctcca gagacaattc caagaacacg | 240 |
| ctgtatctgc aaatgaacag cctgagagcc gaggacacgg ccgtatatta ctgtgcgaga | 300 |
| gaaggtagcc tgtggggcca gggaaccctg gtcaccgtct cgagcgctag caccaagggc | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagagagttg agcccaaatc ttgtgacaaa | 660 |
| actcacacat gcccaccgtg cccagcacct gaagccgcgg ggcaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgtgtg | 900 |
| gtcagcgtcc tcaccgtcct gcaccaggac tggctgaatg gcaaggagta caagtgcgcg | 960 |
| gtctccaaca aagccctccc agcccccatc gagaaaacca tctccaaagc caagggcag | 1020 |
| ccccgagaac acaggtgta cacctgcccc catcccggg atgagctgac caagaaccag | 1080 |
| gtcagcctga cctgcctggt caaaggcttc tatcccagcg acatcgccgt ggagtgggag | 1140 |

```
agcaatgggc agccggagaa caactacaag accacgcctc ccgtgctgga ctccgacggc    1200
tccttcttcc tctatagcaa gctcaccgtg acaagagca ggtggcagca ggggaacgtc    1260
ttctcatgct ccgtgatgca tgaggctctg cacaaccact acacgcagaa gagcctctcc    1320
ctgtctccgg gt                                                       1332

<210> SEQ ID NO 230
<211> LENGTH: 345
<212> TYPE: DNA
<213> ORGANISM: Artificial Sequence
<220> FEATURE:
<223> OTHER INFORMATION: synthesized

<400> SEQUENCE: 230
gaggtgcagc tgttggagtc tgggggaggc ttggtacagc ctgggggtc cctgagactc      60 tcctgtgcag cctctggaat cgacttcagt aggagatact acatgtgctg ggtccgccag    120
gctccaggga aggggctgga gtggatcgca tgcatatata ctggtagccg cgatactcct    180
cactacgcga gctccgcgaa aggccggttc accatctcca gagacaattc caagaacacg    240
ctgtatctgc aaatgaacag cctgagagcc gaggacacgg ccgtatatta ctgtgcgaga    300
gaaggtagcc tgtggggcca gggaaccctg gtcaccgtct cgagc                    345

<210> SEQ ID NO 231
<211> LENGTH: 444
<212> TYPE: PRT
<213> ORGANISM: Artificial Sequence
<220> FEATURE:
<223> OTHER INFORMATION: synthesized

<400> SEQUENCE: 231
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

```
Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225             230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305             310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385             390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 232
<211> LENGTH: 115
<212> TYPE: PRT
<213> ORGANISM: Artificial Sequence
<220> FEATURE:
<223> OTHER INFORMATION: synthesized

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65              70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser
        115
```

```
<210> SEQ ID NO 233
<211> LENGTH: 651
<212> TYPE: DNA
<213> ORGANISM: Artificial Sequence
<220> FEATURE:
<223> OTHER INFORMATION: synthesized

<400> SEQUENCE: 233
gacatccaga tgacccagtc tccttccacc ctgtctgcat ctgtaggaga cagagtcacc      60
atcacttgcc agtccagtca gagtgtttat agtaacagct tcttatcctg gtatcagcag     120
aaaccaggga aagcccctaa gctcctgatc tattctgcat ccgatctggc atctggggtc    180
ccatcaaggt tcagcggcag tggatctggg acagaattca ctctcaccat cagcagcctg    240
cagcctgatg attttgcaac ttattactgc gcaggcgttt atagtgataa tacttatgtt    300
ttcggcggag ggaccaaggt ggagatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651

<210> SEQ ID NO 234
<211> LENGTH: 330
<212> TYPE: DNA
<213> ORGANISM: Artificial Sequence
<220> FEATURE:
<223> OTHER INFORMATION: synthesized

<400> SEQUENCE: 234
gacatccaga tgacccagtc tccttccacc ctgtctgcat ctgtaggaga cagagtcacc     60
atcacttgcc agtccagtca gagtgtttat agtaacagct tcttatcctg gtatcagcag    120
aaaccaggga aagcccctaa gctcctgatc tattctgcat ccgatctggc atctggggtc    180
ccatcaaggt tcagcggcag tggatctggg acagaattca ctctcaccat cagcagcctg    240
cagcctgatg attttgcaac ttattactgc gcaggcgttt atagtgataa tacttatgtt    300
ttcggcggag ggaccaaggt ggagatcaaa                                     330

<210> SEQ ID NO 235
<211> LENGTH: 217
<212> TYPE: PRT
<213> ORGANISM: Artificial Sequence
<220> FEATURE:
<223> OTHER INFORMATION: synthesized

<400> SEQUENCE: 235

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Ser Phe Leu Ser Trp Tyr Gln Gln Lys Pro Gly Lys Ala Pro Lys Leu
        35                  40                  45

Leu Ile Tyr Ser Ala Ser Asp Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80
```

Gln Pro Asp Asp Phe Ala Thr Tyr Tyr Cys Ala Gly Val Tyr Ser Asp
                85                  90                  95

Asn Thr Tyr Val Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 236
<211> LENGTH: 110
<212> TYPE: PRT
<213> ORGANISM: Artificial Sequence
<220> FEATURE:
<223> OTHER INFORMATION: synthesized

<400> SEQUENCE: 236

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Ser Phe Leu Ser Trp Tyr Gln Gln Lys Pro Gly Lys Ala Pro Lys Leu
        35                  40                  45

Leu Ile Tyr Ser Ala Ser Asp Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Ala Gly Val Tyr Ser Asp
                85                  90                  95

Asn Thr Tyr Val Phe Gly Gly Gly Thr Lys Val Glu Ile Lys
            100                 105                 110

<210> SEQ ID NO 237
<211> LENGTH: 1338
<212> TYPE: DNA
<213> ORGANISM: Artificial Sequence
<220> FEATURE:
<223> OTHER INFORMATION: synthesized

<400> SEQUENCE: 237
gaggtgcagc tggtggagtc tgggggaggc ttggtacagc cagggccgtc cctgagactc      60
tcctgtacag cttctggatt ctccctcagt cactactgga tgacttgggt ccgccaggct     120
ccagggaagg ggctggagta catcggattc attaatgttg gtggtgacac atcttacgcg     180
agctctgtga aaggcagatt caccatctca agagatgatt ccaaaagcat cgcctatctg     240
caaatgaaca gcctgaaaac cgaggacaca gccgtgtatt actgtggcag aggtggtctg     300

```
acttttggtt gggacttgtg gggccaggga accctggtca ccgtctcgag cgctagcacc    360
aagggcccat cggtcttccc cctggcaccc tcctccaaga gcacctctgg ggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag ccgcgggggc accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcgcggtct ccaacaaagc cctcccagcc cccatcgaga aaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ctccgggt                                                  1338
```

<210> SEQ ID NO 238
<211> LENGTH: 351
<212> TYPE: DNA
<213> ORGANISM: Artificial Sequence
<220> FEATURE:
<223> OTHER INFORMATION: synthesized

<400> SEQUENCE: 238

```
gaggtgcagc tggtggagtc tgggggaggc ttggtacagc cagggccgtc cctgagactc    60
tcctgtacag cttctggatt ctccctcagt cactactgga tgacttgggt ccgccaggct   120
ccagggaagg ggctggagta catcggattc attaatgttg gtggtgacac atcttacgcg   180
agctctgtga aaggcagatt caccatctca agagatgatt ccaaaagcat cgcctatctg   240
caaatgaaca gcctgaaaac cgaggacaca gccgtgtatt actgtggcag aggtggtctg   300
acttttggtt gggacttgtg gggccaggga accctggtca ccgtctcgag c             351
```

<210> SEQ ID NO 239
<211> LENGTH: 446
<212> TYPE: PRT
<213> ORGANISM: Artificial Sequence
<220> FEATURE:
<223> OTHER INFORMATION: synthesized

<400> SEQUENCE: 239

```
Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Ser Leu Ser His Tyr
            20                  25                  30

Trp Met Thr Trp Val Arg Gln Ala Pro Gly Lys Gly Leu Glu Tyr Ile
        35                  40                  45

Gly Phe Ile Asn Val Gly Gly Asp Thr Ser Tyr Ala Ser Ser Val Lys
    50                  55                  60
```

```
Gly Arg Phe Thr Ile Ser Arg Asp Asp Ser Lys Ser Ile Ala Tyr Leu
 65                  70                  75                  80

Gln Met Asn Ser Leu Lys Thr Glu Asp Thr Ala Val Tyr Tyr Cys Gly
                 85                  90                  95

Arg Gly Gly Leu Thr Phe Gly Trp Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 240
<211> LENGTH: 117
<212> TYPE: PRT
<213> ORGANISM: Artificial Sequence
<220> FEATURE:
```

<223> OTHER INFORMATION: synthesized

<400> SEQUENCE: 240

Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Ser Leu Ser His Tyr
            20                  25                  30

Trp Met Thr Trp Val Arg Gln Ala Pro Gly Lys Gly Leu Glu Tyr Ile
        35                  40                  45

Gly Phe Ile Asn Val Gly Gly Asp Thr Ser Tyr Ala Ser Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Gly
                85                  90                  95

Arg Gly Gly Leu Thr Phe Gly Trp Asp Leu Trp Gly Gln Gly Thr Leu
            100                 105                 110

Val Thr Val Ser Ser
        115

<210> SEQ ID NO 241
<211> LENGTH: 654
<212> TYPE: DNA
<213> ORGANISM: Artificial Sequence
<220> FEATURE:
<223> OTHER INFORMATION: synthesized

<400> SEQUENCE: 241

```
gacgttgtga tgacccagtc tccatcttcc gtgtctgcat ctgtaggaga cagagtcacc    60
atcacctgtc aggccagtca gaacattagg acttacttat cctggtatca gcagaaacca   120
gggaaagccc ctaagctcct gatctatgct gcagccaatc tggcatctgg ggtcccatca   180
aggttcagcg gcagtggatc tgggacagat ttcactctca ccatcagcga cctggagcct   240
ggcgatgctg caacttacta ttgtcagtct acctatcttg gtactgatta tgttggcggt   300
gctttcggcg agggaccaa ggtggagatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc ctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggaga gtgt          654
```

<210> SEQ ID NO 242
<211> LENGTH: 333
<212> TYPE: DNA
<213> ORGANISM: Artificial Sequence
<220> FEATURE:
<223> OTHER INFORMATION: synthesized

<400> SEQUENCE: 242

```
gacgttgtga tgacccagtc tccatcttcc gtgtctgcat ctgtaggaga cagagtcacc    60
atcacctgtc aggccagtca gaacattagg acttacttat cctggtatca gcagaaacca   120
gggaaagccc ctaagctcct gatctatgct gcagccaatc tggcatctgg ggtcccatca   180
aggttcagcg gcagtggatc tgggacagat ttcactctca ccatcagcga cctggagcct   240
ggcgatgctg caacttacta ttgtcagtct acctatcttg gtactgatta tgttggcggt   300
```
gctttcggcg agggaccaa ggtggagatc aaa        333

<210> SEQ ID NO 243
<211> LENGTH: 218
<212> TYPE: PRT
<213> ORGANISM: Artificial Sequence
<220> FEATURE:
<223> OTHER INFORMATION: synthesized

<400> SEQUENCE: 243

Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
                85                  90                  95

Tyr Val Gly Gly Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 244
<211> LENGTH: 111
<212> TYPE: PRT
<213> ORGANISM: Artificial Sequence
<220> FEATURE:
<223> OTHER INFORMATION: synthesized

<400> SEQUENCE: 244

Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
            85                  90                  95

Tyr Val Gly Gly Ala Phe Gly Gly Gly Thr Lys Val Glu Ile Lys
100                 105                 110

<210> SEQ ID NO 245
<211> LENGTH: 1332
<212> TYPE: DNA
<213> ORGANISM: Artificial Sequence
<220> FEATURE:
<223> OTHER INFORMATION: synthesized

<400> SEQUENCE: 245

```
cggtcgctgg tggagtctgg ggaggcttg gtccagcctg ggggtccct gagactctcc      60
tgtacagcct ctggattcac catcagtagc taccacatgc agtgggtccg ccaggctcca    120
gggaagggc tggagtacat cggaaccatt agtagtggtg gtaatgtata ctacgcgagc    180
tccgcgagag gcagattcac catctccaga ccctcgtcca agaacacggt ggatcttcaa    240
atgaacagcc tgagagccga ggacacggct gtgtattact gtgcgagaga ctctggttat    300
agtgatccta gtggggcca gggaaccctg gtcaccgtct cgagcgctag caccaagggc    360
ccatcggtct tccccctggc accctcctcc aagagcacct ctggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaagccgcgg ggcaccgtc agtcttcctc    720
ttccccccaa acccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcgcg    960
gtctccaaca aagccctccc agcccccatc gagaaaacca tctccaaagc caaagggcag   1020
ccccgagaac cacaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gt                                                       1332
```

<210> SEQ ID NO 246
<211> LENGTH: 345
<212> TYPE: DNA
<213> ORGANISM: Artificial Sequence
<220> FEATURE:
<223> OTHER INFORMATION: synthesized

<400> SEQUENCE: 246

```
cggtcgctgg tggagtctgg ggaggcttg gtccagcctg ggggtccct gagactctcc      60
tgtacagcct ctggattcac catcagtagc taccacatgc agtgggtccg ccaggctcca    120
gggaagggc tggagtacat cggaaccatt agtagtggtg gtaatgtata ctacgcgagc    180
```

```
tccgcgagag gcagattcac catctccaga ccctcgtcca agaacacggt ggatcttcaa    240
atgaacagcc tgagagccga ggacacggct gtgtattact gtgcgagaga ctctggttat    300
agtgatccta tgtggggcca gggaaccctg gtcaccgtct cgagc                    345
```

<210> SEQ ID NO 247
<211> LENGTH: 444
<212> TYPE: PRT
<213> ORGANISM: Artificial Sequence
<220> FEATURE:
<223> OTHER INFORMATION: synthesized

<400> SEQUENCE: 247

```
Arg Ser Leu Val Glu Ser Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335
```

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 248
<211> LENGTH: 115
<212> TYPE: PRT
<213> ORGANISM: Artificial Sequence
<220> FEATURE:
<223> OTHER INFORMATION: synthesized

<400> SEQUENCE: 248

Arg Ser Leu Val Glu Ser Gly Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Ser
        115

<210> SEQ ID NO 249
<211> LENGTH: 654
<212> TYPE: DNA
<213> ORGANISM: Artificial Sequence
<220> FEATURE:
<223> OTHER INFORMATION: synthesized

<400> SEQUENCE: 249
gacatccaga tgacccagtc tccttccacc ctgtctgcat ctgtaggaga cagagtcacc     60
atcacttgcc aggccagtca gagcattagt actaacttga actggtatca gcagaaacca    120
gggaaagccc ctaagctcct gatctattat gcatccagtc tggcatctgg ggtcccatca    180
aggttcagcg gcagtggatc tgggacagaa ttcactctca ccatcagcag cctgcagcct    240
gatgattttg caacttatta ctgcctaggt gtttggaatt attggggtga tgatggtact    300
gatttcggcg gagggaccaa ggtggagatc aaacgtacgg tggctgcacc atctgtcttc    360
atcttcccgc catctgatga gcagttgaaa tctggaactg cctctgttgt gtgcctgctg    420

-continued

```
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca caggggaga gtgt           654
```

<210> SEQ ID NO 250
<211> LENGTH: 333
<212> TYPE: DNA
<213> ORGANISM: Artificial Sequence
<220> FEATURE:
<223> OTHER INFORMATION: synthesized

<400> SEQUENCE: 250

```
gacatccaga tgacccagtc tccttccacc ctgtctgcat ctgtaggaga cagagtcacc     60
atcacttgcc aggccagtca gagcattagt actaacttga actggtatca gcagaaacca    120
gggaaagccc ctaagctcct gatctattat gcatccagtc tggcatctgg ggtcccatca    180
aggttcagcg gcagtggatc tgggacagaa ttcactctca ccatcagcag cctgcagcct    240
gatgattttg caacttatta ctgcctaggt gtttggaatt attggggtga tgatggtact    300
gatttcggcg gagggaccaa ggtggagatc aaa                                 333
```

<210> SEQ ID NO 251
<211> LENGTH: 218
<212> TYPE: PRT
<213> ORGANISM: Artificial Sequence
<220> FEATURE:
<223> OTHER INFORMATION: synthesized

<400> SEQUENCE: 251

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Thr Asn
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Asp Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 252
<211> LENGTH: 111
<212> TYPE: PRT
<213> ORGANISM: Artificial Sequence
<220> FEATURE:
<223> OTHER INFORMATION: synthesized

<400> SEQUENCE: 252

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Thr Asn
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gly Val Trp Asn Tyr Trp Gly
                85                  90                  95

Asp Asp Gly Thr Asp Phe Gly Gly Gly Thr Lys Val Glu Ile Lys
            100                 105                 110

<210> SEQ ID NO 253
<211> LENGTH: 1332
<212> TYPE: DNA
<213> ORGANISM: Artificial Sequence
<220> FEATURE:
<223> OTHER INFORMATION: synthesized

<400> SEQUENCE: 253
gaggtgcagc tggtggagtc tgggggaggc ttggtccagc ctggggggtc cctgagactc      60
tcctgtgcag cctctggatt ctccctcagt agctactaca tgagctgggt ccgccaggct     120
ccagggaagg ggctggagtg gatcggaagt atttatggta gtggtgccgc atactacgcg     180
agctccgcta aaggcagatt caccatctcc agagacaatt ccaagaacac gctgtatctt     240
caaatgaaca gcctgagagc cgaggacacg gctgtgtatt actgtgcgag agatcctatt     300
aacaatgcca tgtggggcca gggaaccctg gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggcaccgtc agtcttcctc      720 ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagccctccc agcccccatc gagaaaacca tctccaaagc caagggcag    1020 ccccgagaac cacaggtgta caccctgccc ccatcccggg atgagctgac caagaaccag    1080

-continued

```
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg acaagagca ggtggcagca ggggaacgtc     1260
ttctcatgct ccgtgatgca tgaggctctg cacaaccact acacgcagaa gagcctctcc    1320
ctgtctccgg gt                                                         1332
```

<210> SEQ ID NO 254
<211> LENGTH: 345
<212> TYPE: DNA
<213> ORGANISM: Artificial Sequence
<220> FEATURE:
<223> OTHER INFORMATION: synthesized

<400> SEQUENCE: 254

```
gaggtgcagc tggtggagtc tgggggaggc ttggtccagc ctggggggtc cctgagactc     60
tcctgtgcag cctctggatt ctccctcagt agctactaca tgagctgggt ccgccaggct    120
ccagggaagg ggctggagtg gatcggaagt atttatggta gtggtgccgc atactacgcg    180
agctccgcta aaggcagatt caccatctcc agagacaatt ccaagaacac gctgtatctt    240
caaatgaaca gcctgagagc cgaggacacg gctgtgtatt actgtgcgag agatcctatt    300
aacaatgcca tgtggggcca gggaaccctg gtcaccgtct cgagc                     345
```

<210> SEQ ID NO 255
<211> LENGTH: 444
<212> TYPE: PRT
<213> ORGANISM: Artificial Sequence
<220> FEATURE:
<223> OTHER INFORMATION: synthesized

<400> SEQUENCE: 255

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Ser Ile Tyr Gly Ser Gly Ala Ala Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Ala Met Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 256
<211> LENGTH: 115
<212> TYPE: PRT
<213> ORGANISM: Artificial Sequence
<220> FEATURE:
<223> OTHER INFORMATION: synthesized

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Ser Ile Tyr Gly Ser Gly Ala Ala Tyr Tyr Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Ile Asn Asn Ala Met Trp Gly Gln Gly Thr Leu Val Thr
            100                 105                 110
```

Val Ser Ser
    115

<210> SEQ ID NO 257
<211> LENGTH: 657
<212> TYPE: DNA
<213> ORGANISM: Artificial Sequence
<220> FEATURE:
<223> OTHER INFORMATION: synthesized

<400> SEQUENCE: 257
gcccttgtga tgacccagtc tccttccacc ctgtctgcat ctgtaggaga cagagtcacc    60
atcaattgcc aggccagtga ggacattgat aactatttag cctggtatca gcagaaacca   120
gggaaagccc ctaagctcct gatctttat gcatccgatc tggcatctgg ggtcccatca   180
aggttcagcg gcagtggatc tgggacagaa ttcactctca ccatcagcag cctgcagcct   240
gatgattttg caacttatta ctgccaaggc ggttactata ctagtagtac tgatacgagg   300
ggtgctttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657

<210> SEQ ID NO 258
<211> LENGTH: 336
<212> TYPE: DNA
<213> ORGANISM: Artificial Sequence
<220> FEATURE:
<223> OTHER INFORMATION: synthesized

<400> SEQUENCE: 258
gcccttgtga tgacccagtc tccttccacc ctgtctgcat ctgtaggaga cagagtcacc    60
atcaattgcc aggccagtga ggacattgat aactatttag cctggtatca gcagaaacca   120
gggaaagccc ctaagctcct gatctttat gcatccgatc tggcatctgg ggtcccatca   180
aggttcagcg gcagtggatc tgggacagaa ttcactctca ccatcagcag cctgcagcct   240
gatgattttg caacttatta ctgccaaggc ggttactata ctagtagtac tgatacgagg   300
ggtgctttcg gcggagggac caaggtggag atcaaa                             336

<210> SEQ ID NO 259
<211> LENGTH: 219
<212> TYPE: PRT
<213> ORGANISM: Artificial Sequence
<220> FEATURE:
<223> OTHER INFORMATION: synthesized

<400> SEQUENCE: 259

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Asn Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gly Gly Tyr Tyr Thr Ser Ser
                 85                  90                  95

Thr Asp Thr Arg Gly Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 260
<211> LENGTH: 112
<212> TYPE: PRT
<213> ORGANISM: Artificial Sequence
<220> FEATURE:
<223> OTHER INFORMATION: synthesized

<400> SEQUENCE: 260

Ala Leu Val Met Thr Gln Ser Pro Ser Thr Leu Ser Ala Ser Val Gly
  1               5                  10                  15

Asp Arg Val Thr Ile Asn Cys Gln Ala Ser Glu Asp Ile Asp Asn Tyr
             20                  25                  30

Leu Ala Trp Tyr Gln Gln Lys Pro Gly Lys Ala Pro Lys Leu Leu Ile
         35                  40                  45

Phe Tyr Ala Ser Asp Leu Ala Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gly Gly Tyr Tyr Thr Ser Ser
                 85                  90                  95

Thr Asp Thr Arg Gly Ala Phe Gly Gly Gly Thr Lys Val Glu Ile Lys
            100                 105                 110
```

```
<210> SEQ ID NO 261
<211> LENGTH: 1347
<212> TYPE: DNA
<213> ORGANISM: Artificial Sequence
<220> FEATURE:
<223> OTHER INFORMATION: synthesized

<400> SEQUENCE: 261
cagtcgctgg tggagtctgg gggaggcttg gtacagcctg ggggtccct  gagactctcc    60 tgtgcagcct ctggattctc cttcactagc agctactaca tgtgctgggt ccgccaggct   120
ccagggaagg gctggagtg  gatcgcatgc atttatactg gtagtagtgg tagcacttac   180
tacgcgaact ccgcgaaagg ccggttcacc atctccagag acaattccaa gaacacgctg   240
```

```
tatctgcaaa tgaacagcct gagagccgag gacacggccg tatattactg tgcgagagat    300
agtagtagtt attatatgtt taacttgtgg ggccagggaa ccctggtcac cgtctcgagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaagc cgcggggcga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcgcggtctc caacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggt                                       1347

<210> SEQ ID NO 262
<211> LENGTH: 360
<212> TYPE: DNA
<213> ORGANISM: Artificial Sequence
<220> FEATURE:
<223> OTHER INFORMATION: synthesized

<400> SEQUENCE: 262
cagtcgctgg tggagtctgg gggaggcttg gtacagcctg gggggtccct gagactctcc     60
tgtgcagcct ctggattctc cttcactagc agctactaca tgtgctgggt ccgccaggct    120
ccagggaagg gctggagtg gatcgcatgc atttatactg gtagtagtgg tagcacttac    180
tacgcgaact ccgcgaaagg ccggttcacc atctccagag acaattccaa gaacacgctg    240
tatctgcaaa tgaacagcct gagagccgag gacacggccg tatattactg tgcgagagat    300
agtagtagtt attatatgtt taacttgtgg ggccagggaa ccctggtcac cgtctcgagc    360

<210> SEQ ID NO 263
<211> LENGTH: 449
<212> TYPE: PRT
<213> ORGANISM: Artificial Sequence
<220> FEATURE:
<223> OTHER INFORMATION: synthesized

<400> SEQUENCE: 263

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Thr Ser Ser Tyr
            20                  25                  30

Tyr Met Cys Trp Val Arg Gln Ala Pro Gly Lys Gly Leu Glu Trp Ile
        35                  40                  45
```

```
Ala Cys Ile Tyr Thr Gly Ser Ser Gly Ser Thr Tyr Tyr Ala Asn Ser
    50              55                  60

Ala Lys Gly Arg Phe Thr Ile Ser Arg Asp Asn Ser Lys Asn Thr Leu
65              70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100             105                 110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
130             135                 140

Leu Gly Cys Leu Val Lys Asp Tyr Phe Pro Glu Pro Val Thr Val Ser
145             150             155                 160

Trp Asn Ser Gly Ala Leu Thr Ser Gly Val His Thr Phe Pro Ala Val
                165             170                 175

Leu Gln Ser Ser Gly Leu Tyr Ser Leu Ser Ser Val Val Thr Val Pro
            180             185                 190

Ser Ser Ser Leu Gly Thr Gln Thr Tyr Ile Cys Asn Val Asn His Lys
            195             200             205

Pro Ser Asn Thr Lys Val Asp Lys Arg Val Glu Pro Lys Ser Cys Asp
210             215                 220

Lys Thr His Thr Cys Pro Pro Cys Pro Ala Pro Glu Ala Ala Gly Ala
225             230             235                 240

Pro Ser Val Phe Leu Phe Pro Pro Lys Pro Lys Asp Thr Leu Met Ile
                245             250                 255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
290             295             300

Val Val Ser Val Leu Thr Val Leu His Gln Asp Trp Leu Asn Gly Lys
305             310             315             320

Glu Tyr Lys Cys Ala Val Ser Asn Lys Ala Leu Pro Ala Pro Ile Glu
                325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly

<210> SEQ ID NO 264
```

<211> LENGTH: 120
<212> TYPE: PRT
<213> ORGANISM: Artificial Sequence
<220> FEATURE:
<223> OTHER INFORMATION: synthesized

<400> SEQUENCE: 264

Gln Ser Leu Val Glu Ser Gly Gly Gly Leu Val Gln Pro Gly Gly Ser
1               5                   10                  15
Leu Arg Leu Ser Cys Ala Ala Ser Gly Phe Ser Phe Thr Ser Ser Tyr
            20                  25                  30
Tyr Met Cys Trp Val Arg Gln Ala Pro Gly Lys Gly Leu Glu Trp Ile
        35                  40                  45
Ala Cys Ile Tyr Thr Gly Ser Ser Gly Ser Thr Tyr Tyr Ala Asn Ser
    50                  55                  60
Ala Lys Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Asp Ser Ser Ser Tyr Tyr Met Phe Asn Leu Trp Gly Gln
            100                 105                 110
Gly Thr Leu Val Thr Val Ser Ser
        115                 120

<210> SEQ ID NO 265
<211> LENGTH: 654
<212> TYPE: DNA
<213> ORGANISM: Artificial Sequence
<220> FEATURE:
<223> OTHER INFORMATION: synthesized

<400> SEQUENCE: 265
gacatccaga tgacccagtc tccatcctcc ctgtctgcat ctgtaggaga cagagtcacc        60
atcacttgcc agtccagtca gagtgtttat aataacaatg ctttagcctg gtatcagcag       120
aaaccaggga agttcctaa gctcctgatc tatttggctt ccactctggc atctggggtc       180
ccatctcggt tcagtggcag tggatctggg acagatttca ctctcaccat cagcagcctg       240
cagcctgaag atgttgcaac ttattactgt ctaggtgttt ataatgatga tgttgataat       300
ggtttcggcg agggaccaa ggtggagatc aaacgtacgg tggctgcacc atctgtcttc       360
atcttcccgc catctgatga gcagttgaaa tctggaactg cctctgttgt gtgcctgctg       420
aataacttct atcccagaga ggccaaagta cagtggaagg tggataacgc cctccaatcg       480
ggtaactccc aggagagtgt cacagagcag gacagcaagg acagcaccta cagcctcagc       540
agcaccctga cgctgagcaa agcagactac gagaaacaca agtctacgc ctgcgaagtc       600 acccatcagg gcctgagctc gcccgtcaca aagagcttca cagggagag tgt              654

<210> SEQ ID NO 266
<211> LENGTH: 333
<212> TYPE: DNA
<213> ORGANISM: Artificial Sequence
<220> FEATURE:
<223> OTHER INFORMATION: synthesized

<400> SEQUENCE: 266
gacatccaga tgacccagtc tccatcctcc ctgtctgcat ctgtaggaga cagagtcacc        60
atcacttgcc agtccagtca gagtgtttat aataacaatg ctttagcctg gtatcagcag       120
aaaccaggga agttcctaa gctcctgatc tatttggctt ccactctggc atctggggtc       180

```
ccatctcggt tcagtggcag tggatctggg acagatttca ctctcaccat cagcagcctg    240
cagcctgaag atgttgcaac ttattactgt ctaggtgttt ataatgatga tgttgataat    300
ggtttcggcg agggaccaa ggtggagatc aaa                                  333
```

<210> SEQ ID NO 267
<211> LENGTH: 218
<212> TYPE: PRT
<213> ORGANISM: Artificial Sequence
<220> FEATURE:
<223> OTHER INFORMATION: synthesized

<400> SEQUENCE: 267

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Ala Leu Ala Trp Tyr Gln Gln Lys Pro Gly Lys Val Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Leu Gly Val Tyr Asn Asp
                85                  90                  95

Asp Val Asp Asn Gly Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 268
<211> LENGTH: 111
<212> TYPE: PRT
<213> ORGANISM: Artificial Sequence
<220> FEATURE:
<223> OTHER INFORMATION: synthesized

<400> SEQUENCE: 268

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Ala Leu Ala Trp Tyr Gln Gln Lys Pro Gly Lys Val Pro Lys Leu
        35                  40                  45

Leu Ile Tyr Leu Ala Ser Thr Leu Ala Ser Gly Val Pro Ser Arg Phe
```

```
              50                  55                  60
Ser Gly Ser Gly Ser Gly Thr Asp Phe Thr Leu Thr Ile Ser Ser Leu
 65                  70                  75                  80

Gln Pro Glu Asp Val Ala Thr Tyr Tyr Cys Leu Gly Val Tyr Asn Asp
                 85                  90                  95

Asp Val Asp Asn Gly Phe Gly Gly Gly Thr Lys Val Glu Ile Lys
                100                 105                 110
```

<210> SEQ ID NO 269
<211> LENGTH: 1341
<212> TYPE: DNA
<213> ORGANISM: Artificial Sequence
<220> FEATURE:
<223> OTHER INFORMATION: synthesized

<400> SEQUENCE: 269

```
gaggtgcagc tggtggagtc tgggggaggc ttggtccagc ctggggggtc cctgagactc      60
tcctgtgcag cctctggatt ctccctcaat aacaatgcaa taagctgggt ccgccaggct     120
ccagggaagg gctggagtg ggttgcaatc atacaaaata ctggtaccac agactacgcg     180
aggtccgcta aaggcagatt caccatctcc agagacaatt ccaagaacac gctgtatctt     240
caaatgaaca gcctgagagc cgaggacacg gctgtgtatt actgtgcgag agggtatggt     300
tttgagtcgg agcttgtcat ctggggccag ggaaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca agagagttga gcccaaatct     660
tgtgacaaaa ctcacacatg cccaccgtgc ccagcacctg aagccgcggg ggcaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcgcgg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                             1341
```

<210> SEQ ID NO 270
<211> LENGTH: 354
<212> TYPE: DNA
<213> ORGANISM: Artificial Sequence
<220> FEATURE:
<223> OTHER INFORMATION: synthesized

<400> SEQUENCE: 270

```
gaggtgcagc tggtggagtc tgggggaggc ttggtccagc ctggggggtc cctgagactc      60
```

```
tcctgtgcag cctctggatt ctccctcaat aacaatgcaa taagctgggt ccgccaggct    120
ccagggaagg ggctggagtg ggttgcaatc atacaaaata ctggtaccac agactacgcg    180
aggtccgcta aaggcagatt caccatctcc agagacaatt ccaagaacac gctgtatctt    240
caaatgaaca gcctgagagc cgaggacacg gctgtgtatt actgtgcgag agggtatggt    300
tttgagtcgg agcttgtcat ctggggccag ggaaccctgg tcaccgtctc gagc          354
```

<210> SEQ ID NO 271
<211> LENGTH: 447
<212> TYPE: PRT
<213> ORGANISM: Artificial Sequence
<220> FEATURE:
<223> OTHER INFORMATION: synthesized

<400> SEQUENCE: 271

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Asn
            20                  25                  30

Ala Ile Ser Trp Val Arg Gln Ala Pro Gly Lys Gly Leu Glu Trp Val
        35                  40                  45

Ala Ile Ile Gln Asn Thr Gly Thr Thr Asp Tyr Ala Arg Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Phe Glu Ser Glu Leu Val Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 272
<211> LENGTH: 118
<212> TYPE: PRT
<213> ORGANISM: Artificial Sequence
<220> FEATURE:
<223> OTHER INFORMATION: synthesized

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Asn
            20                  25                  30

Ala Ile Ser Trp Val Arg Gln Ala Pro Gly Lys Gly Leu Glu Trp Val
        35                  40                  45

Ala Ile Ile Gln Asn Thr Gly Thr Thr Asp Tyr Ala Arg Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Phe Glu Ser Glu Leu Val Ile Trp Gly Gln Gly Thr
            100                 105                 110

Leu Val Thr Val Ser Ser
            115
```